US005138067A

United States Patent [19]

Kamata et al.

[11] Patent Number: 5,138,067

[45] Date of Patent: Aug. 11, 1992

[54] LIPID DERIVATIVES

[75] Inventors: Susumu Kamata; Tatsuo Tsuri, both of Hyogo; Nobuhiro Haga; Takeaki Matsui, both of Osaka; Morio Kishi; Kimio Takahashi, both of Kyoto; Sanji Hagishita, Nara; Kaoru Seno, Hyogo, all of Japan

[73] Assignee: Shionogi & Co. Ltd., Osaka, Japan

[21] Appl. No.: 707,164

[22] Filed: May 29, 1991

Related U.S. Application Data

[62] Division of Ser. No. 284,590, Nov. 29, 1988, Pat. No. 5,047,540.

[51] Int. Cl.[5] .................. C07D 215/36; C07D 277/60; C07D 241/00; C07C 261/00

[52] U.S. Cl. .................................. 548/204; 546/172; 546/146; 546/335; 548/152; 548/341; 548/110; 548/253; 548/243; 544/336; 560/165; 564/95; 558/437

[58] Field of Search ............... 548/204, 152, 341, 110, 548/253, 243; 514/365, 311, 367, 399, 307, 255, 357, 381, 380, 314, 478, 601, 526, 527, 528; 546/172, 146, 335; 544/336; 560/165; 564/95; 558/437

[56] References Cited

U.S. PATENT DOCUMENTS 3,753,982 8/1973 Roffey et al. ....................... 548/204

*Primary Examiner*—Mary C. Lee
*Assistant Examiner*—Robert C. Whittenbaugh
*Attorney, Agent, or Firm*—Wenderoth, Lind & Ponack

[57] ABSTRACT

Lipid derivatives represented by the formula:

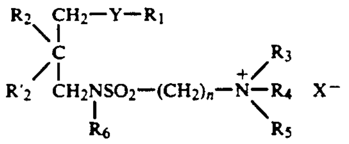

wherein $R_1$ is alkyl or alkylcarbamoyl; $R_2$ is lower alkyloxy, lower alkylcarbamoyloxy, lower alkylcarbonylamino, lower alkyloxycarbonylamino, lower alkylureido, lower alkyloxymethyl, lower alkylcarbonylmethyl, cyanomethyl, heterocyclic group, or heterocyclyloxy; $R_2'$ is hydrogen or $R_2$ and $R_2'$ taken together with $R_2$ form $-O(CH_2)_m-$ wherein m is an integer of 1 to 5; $R_3$, $R_4$, and $R_5$ each is hydrogen or lower alkyl or two or three of $R_3$, $R_4$, and $R_5$ taken together with the adjacent nitrogen atom form cyclic ammonio; $R_6$ is hydrogen or lower alkylcarbonyl; $X^-$ is a counter anion; Y is oxygen or sulfur; and n is an integer of 1 to 10, being useful as PAF antagonists, e.g., as antithrombotic, antivasoconstricting, antibronchoconstricting agent or antitumor agent.

17 Claims, No Drawings

LIPID DERIVATIVES

This application is a division of Ser. No. 07/284,590 filed Nov. 29, 1988, now U.S. Pat. No. 5,047,540.

BACKGROUND OF THE INVENTION

1. Field of the Invention

The present invention relates to lipid derivatives which may be used as PAF (Platelet Activating Factor) antagonist or antitumor agent in the field of medicine.

In more detail, the invention relates to the compounds represented by the following formula (I).

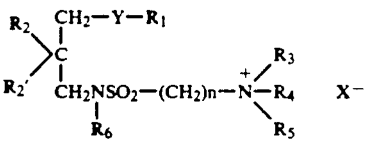

(I)

wherein $R_1$ is alkyl or alkylcarbamoyl; $R_2$ is lower alkyloxy, lower alkylcarbamoyloxy, lower alkylcarbonylamino, lower alkyloxycarbonylamino, lower alkylureido, lower alkyloxymethyl, lower alkylcarbonylmethyl, cyanomethyl, heterocyclic group, or heterocyclyloxy; $R_2'$ is hydrogen or taken together with $R_2$ forms $-O(CH_2)_m-$ wherein m is an integer of 1 to 5; $R_3$, $R_4$, and $R_5$ each is hydrogen or lower alkyl or two or three of $R_3$, $R_4$, and $R_5$ taken together with the adjacent nitrogen atom form cyclic ammonio; $R_6$ is hydrogen or lower alkylcarbonyl; $X^-$ is a counter anion; Y is oxygen or sulfur; and n is an integer of 1 to 10.

2. Prior Art

PAF which is represented by the following formula:

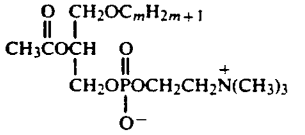

wherein m indicates 16 or 18 is generated from basocyte, neutrophile, acidocyte, macrophage, mast cell, platelet, human leukemia cell, or vascular endothelial cell through various stimulations.

In addition to the platelet activating action, PAF has been known to have the biological activities such as constriction of smooth muscle, decrease of coronary blood flow, inhibition of cardiac effect, increase of vascular permeability or hypotension. It is thought that PAF plays an important role in some physiological and pathological reaction, such as inflammation, asthma, thrombosis, anaphylactic shock, allergy, hypotension, ischemic heart disease, acute transplant rejection, nephritis, and gastric ulcer.

PAF antagonists are being developed as agents for the treatment of those diseases. [P. Braquet et al., Pharmacological Reviews, 39, 98-145, (1987)]. Some PAF antagonists which are structurally analogous to PAF are disclosed, for example, in JPN Kokai Nos. 57-67589, 60-243047, and 62-228088.

SUMMARY

Lipid derivatives represented by the formula:

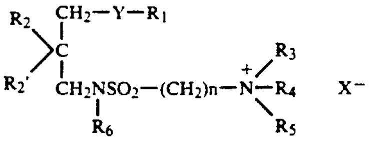

(I)

wherein $R_1$ is alkyl or alkylcarbamoyl; $R_2$ is lower alkyloxy, lower alkylcarbamoyloxy, lower alkylcarbonylamino, lower alkyloxycarbonylamino, lower alkylureido, lower alkyloxymethyl, lower alkylcarbonylmethyl, cyanomethyl, heterocyclic group, or heterocyclyloxy; $R_2'$ is hydrogen or taken together with $R_2$ forms $-O(CH_2)_m-$ wherein m is an integer of 1 to 5; $R_3$, $R_4$, and $R_5$ each is hydrogen or lower alkyl or two or three of $R_3$, $R_4$, and $R_5$ taken together with the adjacent nitrogen atom form cyclic ammonio; $R_6$ is hydrogen or lower alkylcarbonyl; $X^-$ is a counter anion; Y is oxygen or sulfur; and n is an integer of 1 to 10. These compounds may be useful as PAF antagonists, e.g., as antithrombotic, antivasoconstricting, antibronchoconstricting agent or antitumor agent.

DESCRIPTION OF THE PREFERRED EMBODIMENT

Though several PAF antagonists have been developed so far, they still have some problems; e.g., having no specific action to PAF receptor, possession of PAF-like action as well as PAF antagonistic effect, possession of side effect such as hemolysis, their metabolic unstability, and so on. These problems are desired to be solved.

The inventors of the present invention have studied hard to develop useful PAF antagonists or antitumor agents. They found that PAF could be converted into PAF antagonists or antitumor agents if its phosphate moiety would be substituted by sulfonamide. This invention is based on these findings.

The compounds of the present invention are represented by the following formula (I):

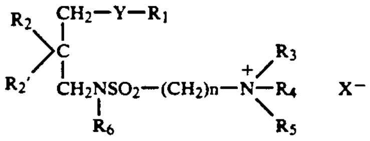

(I)

wherein $R_1$ is alkyl or alkylcarbamoyl; $R_2$ is lower alkyloxy, lower alkylcarbamoyloxy, lower alkylcarbonylamino, lower alkyloxycarbonylamino, lower alkylureido, lower alkyloxymethyl, lower alkylcarbonylmethyl, cyanomethyl, heterocyclic group, or heterocyclyloxy; $R_2'$ is hydrogen or taken together with $R_2$ forms $-O(CH_2)_m-$ wherein m is an integer of 1 to 5; $R_3$, $R_4$, and $R_5$ each is hydrogen or lower alkyl or two or three of $R_3$, $R_4$, and $R_5$ taken together with the adjacent nitrogen atom form cyclic ammonio; $R_6$ is hydrogen or lower alkylcarbonyl; $X^-$ is a counter anion; Y is oxygen or sulfur; and n is an integer of 1 to 10.

The following definitions are given for various terms used throughout this specification.

The term "lower alkyl" refers to straight or branched $C_1$ to $C_7$ alkyl, e.g., methyl, ethyl, propyl, isopropyl, butyl, isobutyl, tert-butyl, pentyl, hexyl, heptyl.

The term "alkyl" refers to straight $C_1$ to $C_{35}$ alkyl which may have a double bond or triple bond. Preferably, it refers to $C_{10}$ to $C_{30}$ higher alkyl, e.g., decyl, undecyl, dodecyl, tridecyl, tetradecyl, pentadecyl, hexadecyl, heptadecyl, octadecyl, nanodecyl, icosyl, henicosyl, docosyl, tricosyl, tetracosyl, pentacosyl, hexacosyl, heptacosyl, octacosyl, nonacosyl, triacontyl.

In the term "lower alkyloxy, lower alkylcarbamoyloxy, lower alkylcarbonyl, lower alkylcarbonylamino, lower alkyloxycarbonylamino, lower alkylureido, lower alkyloxymethyl, or lower alkylcarbonylmethyl", the lower alkyl moiety corresponds to the above mentioned lower alkyl.

The term "heterocyclic group" refers to 5- to 7-membered heterocyclic group, which may have one to four heteroatoms such as oxygen, sulfur, and/or nitrogen, optionally substituted by lower alkyl, lower alkyloxy, hydroxy, halogen, or lower alkyloxycarbonyl or a combination thereof. Those substituents on the heterocyclic group are sometimes referred to as "the substituent". Heterocyclic group includes, for example, 1H-pyrrol-1-yl, 2-methyl-1H-pyrrol-1-yl, 3-methyl-1H-pyrrol-1-yl, 1H-imidazol-1-yl, 2-methyl-1H-imidazol-1-yl, 2,4-dimethyl-1H-imidazol-1-yl, 1H-pyrazol-1-yl, 5-methyl-1H-pyrazol-1-yl, 3,5-dimethyl-1H-pyrazol-1-yl, 1H-1,2,3-triazol-1-yl, 4-methyl-1H-1,2,3-triazol-1-yl, 4-methyl-2H-1,2,3-triazol-2-yl, 4-methyl-3H-1,2,3-triazol-3-yl, 3-methyl-1H-1,2,4-triazol-1-yl, 3-methyl-2H-1,2,4-triazol-2-yl, 3-methyl-4H-1,2,4-triazol-4-yl, 2H-tetrazol-2-yl, 1H-tetrazol-1-yl, 5-methyl-1H-tetrazol-1-yl, and 5-methyl-2H-tetrazol-2-yl.

The term "heterocyclyloxy" refers to hydroxy substituted by the heterocyclic group and includes, e.g., 3-isoxazolyloxy, 3-isothiazolyloxy, 3-pyrazolyloxy, 3-(4-methylisoxazolyl)oxy, 4-(1,2,3-triazolyl)oxy, and 4-(5-methyl-1,2,3-triazolyl)oxy.

The term "cyclic ammonio" refers to 5 or 6 membered mono-, bi-, or tricyclic ammonio which may contain heteroatoms and optionally be substituted by lower alkyl, carboxyl, lower alkyloxycarbonyl, hydroxy, lower alkyloxy, acyloxy, lower alkylamino, amino, carbamoyl, ureido or the like. Cyclic ammonio includes, e.g., N-methyl-1-pyrrolinio, N-methyl-1-pyrrolidinio, 3-oxazolio, 2-isoxazolio, 3-thiazolio, 4-methyl-3- thiazolio, 5-hydroxyethyl-4-methyl-3-thiazolio, 3-imidazolio, 1- pyridinio, 3-carboxy-1-pyridinio, N-methyl-1-piperidinio, N-methyl-4-morpholio, 1-pyrimidinio, 1-pyrazinio, N-methyl-1-piperazinio, 1-triazinio, 3-benzoxazolio, 3-benzothiazolio, 1-quinolinio, 6-methoxy-1-quinolinio, 5,6,7,8-tetrahydro-1-quinolinio, 2-isoquinolinio, 1-quinoxalinio, azirinio, or the like.

The term "counter anion" refers to a pharmacologically acceptable anion such as halogen anion (e.g., chlorine, bromine, iodine), acetate anion, methylsulfonate anion, sulfate anion, nitrate anion, or phosphate anion. When the substituent on the cyclic ammonio can be an anion, it may form an inner salt with ammonium cation.

In the above definition of $R_1$, $C_{12}$ to $C_{20}$ higher alkyl, e.g., dodecyl, tridecyl, tetradecyl, pentadecyl, hexadecyl, heptadecyl, octadecyl, nonadecyl, and icosyl, are preferable examples for the alkyl and, especially, $C_{16}$ to $C_{18}$ alkyl, e.g., hexadecyl, heptadecyl, octadecyl, and the like are more desirable.

When $R_1$ is alkylcarbamoyl, the alkyl moiety corresponds to the above mentioned alkyl, that is, dodecylcarbamoyl, tridecylcarbamoyl, tetradecylcarbamoyl, pentadecylcarbamoyl, hexadecylcarbamoyl, heptadecylcarbamoyl, octadecylcarbamoyl, nonadecylcarbamoyl, and icosylcarbamoyl are preferable examples for the alkylcarbamoyl and, especially, hexadecylcarbamoyl, heptadecylcarbamoyl, octadecylcarbamoyl, and the like are more desirable.

Especially preferable lower alkyloxy for $R_2$ is methoxy, ethoxy, or propoxy; lower alkylcarbamoyloxy for $R_2$ is methylcarbamoyloxy, ethylcarbamoyloxy, or propylcarbamoyloxy; lower alkylcarbonylamino for $R_2$ is methylcarbonylamino, ethylcarbonylamino, or propylcarbonylamino; lower alkyloxycarbonylamino for $R_2$ is methoxycarbonylamino, ethoxycarbonylamino, or propoxycarbonylamino; lower alkylureido for $R_2$ is methylureido, ethylureido, or propylureido; lower alkyloxymethyl for $R_2$ is methoxymethyl, ethoxymethyl, or propoxymethyl; and lower alkylcarbonylmethyl for $R_2$ is methylcarbonylmethyl, ethylcarbonylmethyl, or propylcarbonylmethyl. Especially preferable heterocyclic group for $R_2$ is N-containing 5 or 6 membered heterocyclic group which may contain oxygen or sulfur and optionally have the substituent, e.g. 3-methyl-2H-1,2,4-triazol-2-yl, 3H-1,2,3,4-tetrazol-3-yl, 5H-1,2,3,4-tetrazol-5-yl, 5-methyl-1H-tetrazol-1-yl, 5-methyl-2H-tetrazol-2-yl. Heterocyclyloxy for $R_2$ refers to hydroxy substituted by the 5 or 6 membered heterocyclic which may contain one to four heteroatoms such as oxygen, sulfur, or nitrogen and optionally have the substituent, e.g., 3-isoxazolyloxy, or 3-(4-methylisoxazolyl)oxy.

The most desirable $R_2$ is methoxy, methylcarbamoyloxy, acetamido, methoxycarbonylamino, methylureido, methoxymethyl, acetylmethyl, cyanomethyl, 3-methyl-2H-1,2,4-triazol-2-yl, 5-methyl-1H-tetrazol-1-yl, 5-methyl-2H-tetrazol-2-yl, or 3-isoxazolyloxy.

$R_2$ and $R_2'$ taken together may form $-O(CH_2)m-$. Preferable m is an integer of 1 to 5, more desirably m is an integer, 4 or 5, and most desirably an integer, 4.

Especially preferable lower alkyl for $R_3$, $R_4$ and $R_5$ lower alkyl is methyl, ethyl or propyl and the most desirable lower alkyl is methyl.

Especially preferable cyclic ammonio is N-methyl-1-pyrrolinio, N-methyl-1-pyrrolidinio, 3-oxazolio, 2-isoxazolio, 3-thiazolio, 4-methyl-3-thiazolio, 5-hydroxyethyl-4-methyl-3-thiazolio, 1-N-methyl-3-imidazolio, 1-pyridinio, 3-carboxy-1-pyridinio, N-methyl-1-piperidinio, N-methyl-4-morpholio, 1-pyrimidinio, 1-pyrazinio, 1-methyl-1-piperadinio, 1- triazinio, 3-benzoxazolio, 3-benzothiazolio, 1-quinolinio, 6-methoxy-1-quinolinio, 5,6,7,8-tetrahydro-1-quinolinio, 2- isoquinolinio, or 1-quinoxalinio.

Especially preferable alkylcarbonyl for $R_6$ is acetyl, propionyl, or butyryl and the most desirable $R_6$ is acetyl.

Preferable n is an integer of 1 to 10, more desirably n is an integer, 1 to 5, and most desirably an integer, 2 to 4.

The preferable lower alkyl for $R_7$ is above mentioned $C_1$ to $C_7$ alkyl, especially preferable lower alkyl for $R_7$ is methyl or ethyl, or propyl and most desirable lower alkyl for $R_7$ is methyl.

Prot-OH refers to an ordinally used hydroxy protecting group such as benzyl, triarylmethyl, e.g., triphenylmethyl (trityl), trialkylsilyl, e.g., trimethylsilyl, tert-butyldimethylsilyl, tetrahydropyranyl, acetyl, benzoyl, p-nitrobenzoyl, or the like.

Prot-$NH_2$ refers to an amino protecting group such as acetyl, benzoyl, benzoyloxycarbonyl, tert-butoxycarbonyl, trityl, or the like.

Illustrative of the compounds (I) of the invention are:

2-methoxy-1-octadecylcarbamoyloxy-3-(3-trimethylammoniopropylsulfonylamino)propane chloride, 2-methoxy-1-octadecylcarbamoyloxy-3-(3-thiazoliopropylsulfonylamino)propane iodide,
2-methoxy-1-octadecylcarbamoyloxy-3-(3-pyridiniopropylsulfonylamino)propane iodide,
2-methoxy-3-(3-N-methylmorphoriniopropylsulfonylamino)-1-octadecylcarbamoyloxypropane iodide,
2-methoxy-3-[3-(4-methylthiazolinio)propylsulfonylamino]-1-octadecylcarbamoyloxypropane iodide,
2-methoxy-1-octadecylcarbamoyloxy-3-(3-pyraziniopropylsulfonylamino)propane iodide,
2-methoxy-1-octadecylcarbamoyloxy-3-(3-quinoliniopropylsulfonylamino)propane iodide,
2-methyoxy-3-[3-(6-methoxyquinolinio)propylsulfonylamino]-1-octadecylcarbamoyloxypropane iodide,
1-hexadecylthio-2-methoxy-3-(3-trimethylammoniopropylsulfonylamino)propane iodide,
1-hexadecylthio-2-methoxy-3-(3-thiazoliopropylsulfonylamino)propane iodide,
1-hexadecyloxy-2-methoxy-3-(3-trimethylammoniopropylsulfonylamino)propane iodide,
1-hexadecyloxy-2-methoxy-3-(3-thiazoliopropylsulfonylamino)propane iodide,
2-methoxy-1-octadecylcarbamoyloxy-3-(2-thiazolioethylsulfonylamino)propane iodide,
2-methoxy-1-octadecylcarbamoyloxy-3-(4-thiazoliobutylsulfonylamino)propane iodide,
2-methoxy-1-octadecylcarbamoyloxy-3-(4-quinoliniobutylsulfonylamino)propane iodide,
3-(4-benzothiazoliobutylsulfonylamino)-2-methoxy-1-octadecylcarbamoyloxypropane iodide,
3-(4-isoquinoliniobutylsulfonylamino)-2-methoxy-1-octadecylcarbamoyloxypropane iodide,
2-methoxy-3-(4-N-methylimidazoliobutylsulfonylamino)-1-octadecylcarbamoyloxypropane iodide,
2-methoxy-1-octadecylcarbamoyloxy-3-(4-quinoliniobutylsulfonylamino)propane chloride,
3-(4-benzothiazoliobutylsulfonylamino)-2-methoxy-1-octadecylcarbamoyloxypropane chloride,
3-(4-isoquinoliniobutylsulfonylamino)-2-methoxy-1-octadecylcarbamoyloxypropane chloride,
3-(4-N-methylimidazoliobutylsulfonylamino)-2-methoxy-1-octadecylcarbamoyloxypropane chloride,
1-hexadecyloxy-2-methoxy-3-[3-(4-methylthiazolio)-propylsulfonylamino]propane iodide,
1-hexadecyloxy-2-methoxy-3-(3-pyraziniopropylsulfonylamino)propane iodide,
2-methoxy-3-(3-N-methylimidazoliopropylsulfonylamino)-1-octadecylcarbamoylthiopropane iodide,
2-methoxy-1-octadecylcarbamoylthio-3-(4-quinoliniopropylsulfonylamino)propane iodide,
2-methoxy-1-octadecylcarbamoylthio-3-(3-thiazoliopropylsulfonylamino)propane iodide,
2-methoxy-1-octadecylcarbamoylthio-3-(4-quinoliniopropylsulfonylamino)propane chloride,
2-methoxy-1-octadecylcarbamoyloxy-3-[4-{3-carboxylate pyridinio}butylsulfonylamino]propane,
2-hexadecylthiomethyl-2-(3-trimethylammoniopropylsulfonylaminomethyl)tetrahydrofuran,
2-octadecylcarbamoyloxymethyl-2-(3-quinoliniopropylsulfonylaminomethyl)tetrahydrofuran iodide,
1-hexadecylthio-2-methylcarbamoyloxy-3-(3-quinoliniopropylsulfonylamino)propane iodide,
1-hexadecylthio-2-methylcarbamoyloxy-3-(3-trimethylammoniopropylsulfonylamino)propane iodide,
2-methylcarbamoyloxy-1-octadecylcarbamoyloxy-3-(3-quinoliniopropylsulfonylamino)propane iodide,
2-methylcarbamoyloxy-1-octadecylcarbamoyloxy-3-(3-trimethylammoniopropylsulfonylamino)propane iodide,
1-octadecylcarbamoyloxy-2-methoxycarbonylamino-3-(3-trimethylammoniopropylsulfonylamino)propane iodide,
2-tert-butoxycarbonylamino-1-octadecylcarbamoyloxy-3-(3-trimethylammoniopropylsulfonylamino)propane iodide,
2-acetamido-1-octadecylcarbamoyloxy-3-(3-trimethylammoniopropylsulfonylamino)propane iodide,
1-octadecylcarbamoyloxy-2-(3-methylureido)-3-(3-trimethylammoniopropylsulfonylamino)propane iodide,
1-hexadecylthio-2-methoxycarbonylamino-3-(3-trimethylammoniopropylsulfonylamino)propane iodide,
2-tert-butoxycarbonylamino-1-hexadecylthio-3-(3-trimethylammoniopropylsulfonylamino)propane iodide,
2-acetamido-1-hexadecylthio-3-(3-trimethylammoniopropylsulfonylamino)propane iodide,
1-hexadecylthio-2-(3-methylureido)-3-(3-trimethylammoniopropylamino)propane iodide,
2-acetamido-3-(N-acetyl-3-trimethylammoniopropylsulfonylamino)-1-octadecylcarbamoyloxypropane iodide,
1-octadecylcarbamoyloxy-2-methoxycarbonylamino-3-(3-quinoliniopropylsulfonylamino)propane iodide,
2-butoxycarbonylamino-1-octadecylcarbamoyloxy-3-(3-quinoliniopropylsulfonylamino)propane iodide,
2-acetamido-1-octadecylcarbamoyloxy-3-(3-quinoliniopropylsulfonylamino)propane iodide,
1-octadecylcarbamoyloxy-2-(3-methylureido)-3-(3-quinoliniopropylsulfonylamino)propane iodide,
1-hexadecylthio-2-methoxycarbonylamino-3-(3-quinoliniopropylsulfonylamino)propane iodide,
2-tert-butoxycarbonylamino-1-hexadecylthio-3-(3-quinoliniopropylsulfonylamino)propane iodide,
2-acetamido-1-hexadecylthio-3-(3-quinoliniopropylsulfonylamino)propane iodide,
1-hexadecylthio-2-(3-methylureido)-3-(3-quinoliniopropylamino)propane iodide,
2-acetamido-3-(N-acetyl-3-quinoliniopropylsulfonylamino)-1-octadecylcarbamoyloxypropane iodide,
1-hexadecylthio-2-(3-methyl-2H-1,2,4-triazol-2-yl)-3-(3-trimethylammoniopropylsulfonylamino)propane iodide,
2-(3-methyl-2H-1,2,4-triazol-2-yl)-1-octadecylcarbamoyloxy-3-(3-quinoliniopropylsulfonylamino)propane iodide,
2-(3-methyl-1H-1,2,4-triazol-1-yl)-1-octadecylcarbamoyloxy-3-(3-quinoliniopropylsulfonylamino)propane iodide,
2-(5-methyl-1H-triazol-1-yl)-1-octadecylcarbamoyloxy-3-(3-trimethylammoniopropylsulfonylamino)propane iodide,
2-(5-methyl-1H-tetrazol-1-yl)-1-octadecylcarbamoyloxy-3-(3-quinoliniopropylsulfonylamino)propane iodide,
1-hexadecylthio-2-(5-methyl-2H-tetrazol-2-yl)-3-(3-trimethylammoniopropylsulfonylamino)propane iodide, 2-(5-methyl-2H-tetrazol-2-yl)-1-octadecylcarbamoyloxy-3-(3-quinoliniopropylsulfonylamino)propane iodide,
2-(3-isoxazolyloxy)-1-hexadecylthio-3-(3-trimethylammoniopropylsulfonylamino)propane iodide,
2-(3-isoxazolyloxy)-1-octadecylcarbamoyloxy-3-(3-trimethylammoniopropylsulfonylamino)propane iodide,
2-(3-isoxazolyloxy)-1-octadecylcarbamoyloxy-3-(3-quinoliniopropylsulfonylamino)propane iodide,
3-(N-acetyl-3-trimethylammoniopropylsulfonylamino)-2-methoxymethyl-1-hexadecyloxypropane iodide,
1-hexadecyloxy-2-methoxymethyl-3-(3-trimethylammoniopropylsulfonylamino)propane iodide,
1-hexadecyloxy-2-methoxymethyl-3-(3-quinoliniopropylsulfonylamino)propane iodide,
1-hexadecylthio-2-methoxymethyl-3-(3-trimethylammoniopropylsulfonylamino)propane iodide,
1-octadecylcarbamoyloxy-2-methoxymethyl-3-(3-quinoliniopropylsulfonylamino)propane iodide,
3-(N-acetyl-3-quinoliniopropylsulfonylamino)-2-methoxymethyl-1-octadecylcarbamoyloxypropane iodide,
1-octadecylcarbamoyloxy-2-(2-oxopropyl)-3-(3-quinoliniopropylsulfonylamino)propane iodide,
2-cyanomethyl-1-hexadecyloxy-3-(3-trimethylammoniopropylsulfonylamino)propane iodide,
2-cyanomethyl-1-hexadecyloxy-3-(3-quinoliniopropylsulfonylamino)propane iodide,
2-cyanomethyl-1-octadecylcarbamoyloxy-3-(3-quinoliniopropylsulfonylamino)propane iodide, and
1-hexadecylthio-2-(2-oxopropyl)-3-(3-trimethylammoniopropylsulfonylamino)propane iodide.

The following abbreviations are used throughout this specification.

Me: methyl,
Et: ethyl,
tBu: tert-butyl,
Ph: phenyl
Tr: triphenylmethyl (trityl),
Ac: acetyl,
DEAD: diethyl azodicarboxylate,
THF: tetrahydrofuran, and
MEK: methyl ethyl ketone.

The compound (I) contains two stereoisomers, i.e., those of R- and S-configuration.

This invention includes each enantiomer, their mixture, and racemate thereof.

The compound (I) of the present invention is prepared by the following process, for example.

Reaction Scheme

Process I

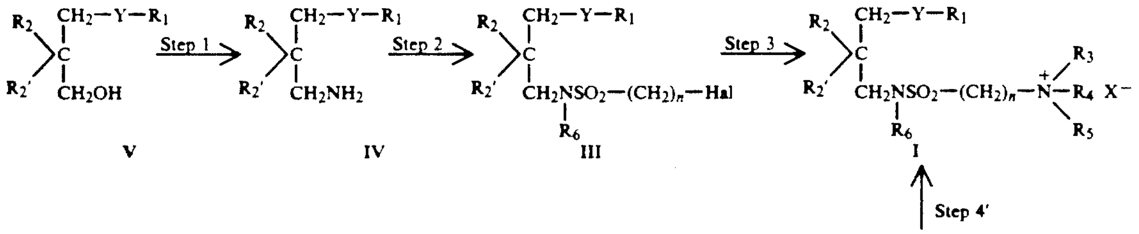

V IV III I

Process II

III

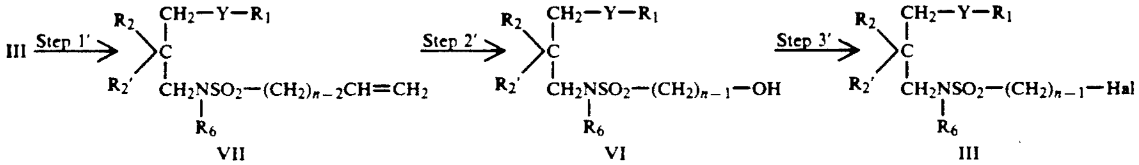

VII VI III (wherein Hal is chlorine, bromine, or iodine; $R_1$, $R_2$, $R_2'$, $R_3$, $R_4$, $R_5$, $R_6$ n, Y and X each has the same meaning as defined before.)

PROCESS I

(Step 1)

In this step, the hydroxy of the compound V is converted into the amino.

This step can be carried out by hydrolysis of the N-substituted succinimide or N-substituted phthalimide derivative of the compound V.

The reaction to prepare the N-substituted succinimide or N-substituted phthalimide derivatives of the compound V is carried out by reacting succinimide or phthalimide in the presence of triphenylphosphine and diethyl azodicarboxylate in a solvent such as tetrahydrofuran, benzene, or dimethylformamide (DMF) at room temperature for a period of several hours to several tens of hours.

The hydrolysis is carried out in the presence of hydrazine in a solvent such as alcohol (e.g., methanol, ethanol) at room temperature or under reflux condition for several hours.

As an alternative method, the hydroxy of the compound V may be converted into the amino by allowing to react the methanesulfonyloxy or benzenesulfonyloxy derivatives of V with sodium azide or lithium azide, followed by the reduction of the azide-compound with a reduceing agent such as triphenylphosphine.

(Step 2)

In this step, the compound IV is sulfonylated with a haloalkanesulfonyl halide represented by the formula Hal' $-SO_2(CH_2)n-$Hal wherein Hal and Hal' each is halogen, and n is the same as defined above to give the sulfonamide derivative III.

As the said sulfonyl halide, 3-chloropropanesulfonyl chloride, 3-chloropropanesulfonyl bromide, 4-chlorobutansulfonyl chloride, 4-chlorobutanesulfonyl bromide, 5-chloropentanesulfonyl chloride, 6-bromohexanesulfonyl chloride, 7-bromoheptanesulfonyl bromide, 8-chlorooctanesulfonyl chloride, 9-bromononanesulfonyl bromide, 10-chlorodecanesulfonyl chloride, or the like is exemplified.

The reaction is carried out in the presence of a base such as triethylamine, pyridine, sodium hydroxide in a solvent such as chlorinated hydrocarbon (e.g., chloroform, dichloromethane), ether (e.g., ethyl ether, tetrahydrofuran) or aromatic hydrocarbon (e.g., benzene) under cooling or at room temperature for a period of several hours to several tens of hours.

Dimethylaminopyridine may be added as a catalyst, if necessary.

In such a case where the compound prepared by this step is a chloride, it can be further converted into other halides such as bromide or iodide by the treatment with sodium bromide or sodium iodide, respectively, in a usual manner.

When the compound wherein $R_6$ is alkylcarbonyl is required, the compound previously prepared by this step may be allowed to react with an acylating reagent in the presence of a base such as triethylamine, pyridine, N,N-diisopropylethylamine in a chlorinated hydrocarbon, e.g., dichloromethane, chloroform under cooling or at room temperature.

The acylating reagent such as acid halide, e.g., acetyl chloride, propionyl chloride, butyryl chloride, isobutylryl chloride, valeryl chloride, isovaleryl chloride, pivaloyl chloride, pentanoyl chloride, hexanoyl chloride, heptanoyl chloride or acid anhydride. e.g., acetic anhydride, propionic anhydride, butyric anhydride, isobutyric anhydride, valeric anhydride, isovaleric anhydride, pivalic anhydride, hentanoic anhydride, hexanoic anhydride, heptanoic anhydride is exemplified.

(Step 3)

In this step, the compound III is converted into an ammonium compound to give the compound (I) of the present invention.

As an amine forming an ammonium compound, alkylamine (e.g., trimethylamine, triethylamine) or 5 to 6-membered mono-, bi-, or tricyclic amine which may contain heteroatom and/or have substituent (e.g., N-methylpyrrole, N-methylpyrrolidine, oxazole, isoxazole, thiazole, 4-methylthiazole, N-methylimidazole, pyridine, 3-carboxypyridine, N-methylpiperidine, N-methylmorpholine, pyrimidine, pyrazine, N-methylpiperazine, triazine, benzoxazole, benzothiazole, quinoline, isoquinoline, quinoxaline, azirine) is exemplified.

The reaction is carried out using an amine itself as a solvent or in a solvent such as alcohol (e.g., methanol, ethanol), aromatic hydrocarbon (e.g., benzene, toluene), ether (e.g., ethyl ether, tetrahydrofuran, dioxane) or dimethylformamide at room temperature or under heating for a period of several hours to several tens of hours.

As an alternative method, in such a case where the halogen substituent of the compound III is chloride, the chloride is substituted by bromide or iodide and the resulting compound is allowed to react with several kinds of amines to give an ammonium bromide or iodide which may be further treated with hydrochloric acid to give chloride.

PROCESS II (Step 1′)

In this step, a hydrogen halide is eliminated from the compound III to give the compound VII.

This step is carried out by oxidation of the phenylselenide compound or phenylthio compound, which can be prepared by substitution of the halogen of the compound III to phenylselenium anion or phenylthio anion, with a peroxide followed by heating the resulting compound to eliminate benzeneselenic acid or benzenesulfenic acid.

The reaction to prepare the phenylselenyl compound or phenylthio compound is carried out using the reagents obtained by the reduction of diphenyldiselenide or diphenylsulfide with sodium borohydride in a solvent such as an alcohol (e.g., methanol, ethanol, isopropanol), an ether (e.g., ethyl ether, tetrahydrofuran) or dioxane at room temperature or under heating for several hours.

The oxidation is carried out using a peroxide such as an aqueous hydrogen peroxide, m-chloroperbenzoic acid, peracetic acid, tert-butyl hydroperoxide, or the like in a solvent such as an alcohol (e.g., methanol, ethanol) or a chlorinated hydrocarbon (e.g., dichloromethane, chloroform) at room temperature for several hours.

The reaction to eliminate the oxide by heating is carried out in a solvent such as an aromatic hydrocarbone (e.g., benzene, toluene) or a chlorinated hydrocarbon (e.g., dichloromethane, chloroform) under heating.

(Step 2′)

In this step, the double bond of the compound VII is cleaved oxidatively to give the aldehyde which is then reduced to the compound VI.

The aldehyde is prepared by reductive decomposition of the ozonide which is obtained by the ozonization of the compound VII.

The ozonization is carried out in a solvent such as a chlorinated hydrocarbon (e.g., dichloromethane, chloroform, carbon tetrachloride), an alcohol (e.g., methanol, ethanol), benzene, or ethyl acetate under cooling for several hours; if necessary, the solvent may be used in combination.

The reductive decomposition of the ozonide is carried out using a reducing agent such as zinc dust in acetic acid, or triphenylphosphite trimethylphosphite, dimethylsulfide, sodium idodide, sulfur dioxide, sodium hydrogensulfite, tin(II) chloride, or iron(II) sulfate, or by catalytic reduction using a catalyst such as platinium, palladium, nickel, palladium on calcium carbonate.

The reduction converting the aldehyde to the alcohol is carried out using reducing agent such as metal hydride (e.g., lithium aluminum hydride, lithium borohydride, sodium borohydride, lithium trimethoxyaluminohydride, lithium tri-tert-butoxyaluminohydride) in a solvent such as an alcohol (e.g., methanol, ethanol) or ether (e.g., ethyl ether, tetrahydrofuran) at room temperature or under heating for several hours.

(Step 3′)

In this step, the hydroxy of the compound VI is halogenated.

The halogenation is achieved by direct halogenation of the hydroxy using halogenating agent such as phosphorus halide (e.g., phosphorus trichloride, phosphorus pentachloride, phosphorus tribromide, phosphorus pentabromide) or thionyl halide (e.g., thionyl chloride, thionyl bromide) or indirect halogenation through an intermediate to which a leaving group is attached.

The reaction for introducing a leaving group is carried out with a compound forming the leaving group such as a substituted sulfonyl chloride (e.g., methanesulfonyl chloride, benzenesulfonyl chloride, p-toluenesulfonyl chloride) in the presence of a base such as triethylamine, pyridine, or the like in the usual manner. Then, the resulting compound is allowed to react with an alkali metal halide such as lithium chloride, sodium bromide, or sodium idodide.

The reaction is carried out, depending on the property of the halogenating agent, in a solvent such as a chlorinated hydrocarbon (e.g., dichloromethane, chloroform, carbon tetrachloride), a ketone (e.g., acetone, methyl ethyl ketone), or dimethylformamide in accordance with the usual manner.

(Step 4')

In this step, the halogen of the compound III' is substituted with an amine to give the compound (I) of the present invention. This step may be carried out in accordance with Step 3.

If necessary, the anions of the compounds of the present invention which are prepared in Step 3 or this step may be exchanged with other desired anions.

PROCESS (i)

When —Y—$R_1$ is alkylcarbamoylthio, the compound Va can be prepared by the following manner.

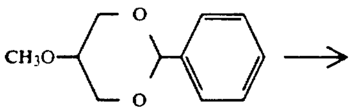

X6

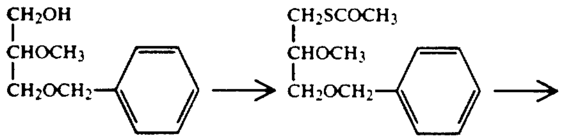

IX6 VIII6

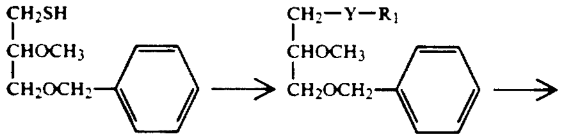

VII6 VIA

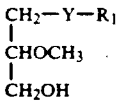

VA wherein $R_1$ is alkylcarbamoylthio, Y is sulfur.

The compound X6 is reductively cleaved to give the compound IX6 and the hydroxy of the compound IX6 is converted into the mercapto to give the compound VII6 which is then allowed to react with an isocyanate having the desired alkyl to give the compound VIA. The compound VA is prepared by removing the benzyl of the compound VIA.

The reaction to prepare the compound IX6 from the compound X6 is carried out by using lithium aluminium hydride-aluminium chloride as a reducing agent.

The step to prepare the compound VII6 from compound IX6 is achieved as follows.

The hydroxy of the compound IX6 is converted into the leaving group by reaction with a compound which forms a leaving group, such as methanesulfonyl chloride, benzenesulfonyl chloride, p-toluenesulfonyl chloride, or the like in the presence of a base such as triethylamine according to the usual manner prior to the reaction with potassium thioacetate or sodium thioacetate to give the thioacetate VII6, which is then hydrolyzed with a base to give the mercapto derivative VII6. Then, the prepared compound VII6 is allowed to react with an isocyanate having a desired $C_{12}$ to $C_{20}$ alkyl such as dodecylisocyanate, hexadecylisocyanate, or octadecylisocyanate in a solvent such as pyridine to give the compound VIA.

The compound VA is prepared by cleaving the benzyl ether of the compound VIA with trimethylsilyl iodide or aluminium chloride-sodium iodide in acetonitrile under a neutral condition at temperatures of 0° C. to room temperature.

PROCESS (ii)

When $R_2$ is alkylcarbamoyloxy, the compound Vc can be prepared by the following manner.

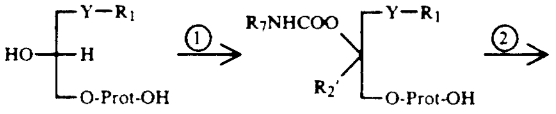

C1 C2

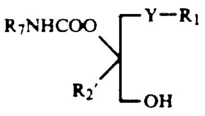

VC wherein $R_7$ is lower alkyl, Prot-OH is hydroxy protecting group, and $R_1$, $R_2'$, and Y each has the same meaning as defined before.

① In this step, an alcohol C1 is attached to an alkylisocyanate.

As the alkylisocyanate, methyl isocyanate, ethyl isocyanate, propyl isocyanate, isopropyl isocyanate, butyl isocyanate, tert-butyl isocyanate, or the like is exemplified.

The reaction is carried out in a solvent such as chlorinated hydrocarbon, e.g., dichloromethane, chloroform or dimethylformamide at room temperature or under heating for a period of several hours to several tens hours.

A catalyst such as an acid, e.g., boron trifluoride etherate, hydrochloric acid, aluminum chloride or a base, e.g., triethylamine, pyridine, 4-dimethylaminopyridine, 4-methylpiperidine may be used, if necessary.

② In this step, the 3-hydroxy protecting group is removed.

The deprotection, of which condition depends on the protecting group, is carried out in the presence of an acid, e.g., (1) trifluoroacetic acid, (2) acetic acid, (3) hydrogen bromide/acetic acid, (4) hydrochloric acid/-chloroform. The reaction may be carried out by catalytic hydrogenolysis in the presence of a palladium catalyst.

PROCESS (iii)

When —Y—$R_1$ is alkylcarbamoyloxy and $R_2$ is alkoxycarbonylamino, the compound VE can be prepared by the following manner.

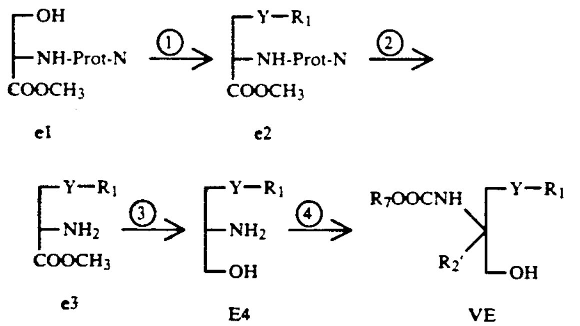

e1 e2 e3 E4 VE wherein $R_1$ is alkylcarbamoyl, Y is oxygen, and Prot-N is amino protecting group, and $R_2'$, $R_7$ each has the same meaning as defined before.

① In this step, a $C_{12}$-$C_{20}$ alkyl isocyanate is condensed to the alcohol E1.

As the alkyl isocyanate used for this step, dodecyl isocyanate, tridecyl isocyanate, tetradecyl isocyanate, pentadecyl isocyanate, hexadecyl isocyanate, heptadecyl isocyanate, octadecyl isocyanate, nonadecyl isocyanate, icosanyl isocyanate or the like is exemplified. The reaction is carried out in the same manner as described in Process (ii)-①.

② In this step, the amino protecting group is removed.

The deprotection, the conditions depend of which on the protecting group, is carried out in the usual manner such as by catalytic hydrogenolysis (with palladium catalyst under atmospheric hydrogen at room temperature in methanol, methanol-acetic acid, or glacial acetic acid) or by mild acid treatment (aqueous acetic acid at 30° C. or aqueous trifluoroacetic acid at −5° C.).

③ In this step, the methoxycarbonyl of the compound E3 is reduced into the hydroxymethyl. As a reducing agent, an metal hydride complex, e.g., lithium aluminumhydride, lithium borohydride, sodium borohydride, lithium trimethoxyaluminohydride, lithium tri-tert-butoxyaluminohydride, calcium borohydride resulted from calcium chloride and sodium borohydride is exemplified.

The reaction is carried out in a solvent such as alcohol, e.g., methanol, ethanol, propanol or ether, e.g., ethyl ether, tetrahydrofuran, glyme, diglyme under cooling for several hours.

④ In this step, the amino of the compound E4 is converted into the alkyloxycarbonylamino.

The reagent for alkyloxycarbonylaminolation such as alkyl haloformate, e.g., methyl chloroformate, methyl bromoformate, ethyl chloroformate, propylchloroformate, isopropyl chloroformate, butyl chloroformate, isobutyl bromoformate, tert-butyl chloroformate, pentyl chloroformate, hexyl chloroformate, heptyl chloroformate or dialkyl dicarbonate, e.g., dimethyl dicarbonate, diethyl dicarbonate, dipropyl dicarbonate, diisopropyl dicarbonate, dibutyl dicarbonate, di-tert-butyl dicarbonate, dipentyl dicarbonate, dihexyl dicarbonate, diheptyl dicarbonate is exemplified.

The reaction is carried out in a solvent such as ether, e.g., ethyl ether, tetrahydrofuran or ketone, e.g., acetone at room temperature for several hours.

PROCESS (iv)

When —Y—$R_1$ is alkylthio and $R_2$ is alkoxycarbonylamino, the compound IV E2 can be prepared by the following manner.

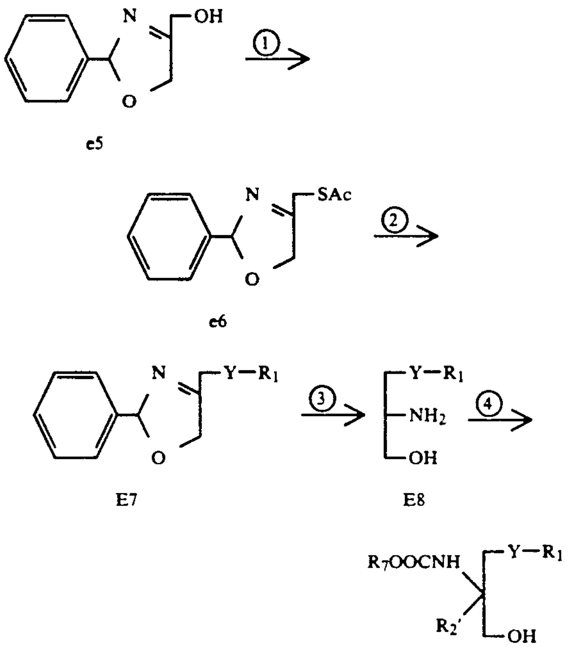

e5 e6 E7 E8 VE2 wherein $R_1$ is alkyl, Y is oxygen, and $R_2'$ and $R_7$ each has the same meaning as defined before.

① In this step, the alcohol e5 is converted into the thioacetate e6.

This step can be carried out by the same procedure to prepare the compound VII 6 from the compound IX 6 in Process (i), that is, the alcohol e5 is converted into a sulfonate or halide which is then converted into the thioacetate with potassium thioacetate or sodium thioacetate.

② In this step, acetyl of the compound e6 is converted into the desired alkyl.

The thioacetate e6 is hydrolyzed with a base to give the thiol which is treated with sodium hydroxide to give the thiolate anion which is allowed to react with $C_{12}$-$C_{20}$ alkyl halide, e.g., dodecyl bromide, tridecyl bromide, tetradecyl bromide, pentadecyl bromide, pentadecyl chloride, hexadecyl bromide, pentadecyl bromide, heptadecyl bromide, octadecyl bromide, octadecyl chloride, nonadecyl bromide, isosanyl bromide to give the compound E7.

This step can be carried out by using $C_{12}$-$C_{20}$ alkylisocyanate in the same manner as described in Process (i).

③ In this step, the amino and hydroxy protecting group of the compound E7 is removed.

The reaction is carried out in the presence of an acid such as dilute hydrochloric acid or dilute sulfuric acid.

④ In this step, the amino of the compound E8 is converted into the alkyloxycarbonylamino.

This step can be carried out in the same manner as described in Process (iii)-④.

PROCESS (v)

When $R_2$ is alkylureido or alkanoylamino, the compound III F or III G is prepared by the following manner.

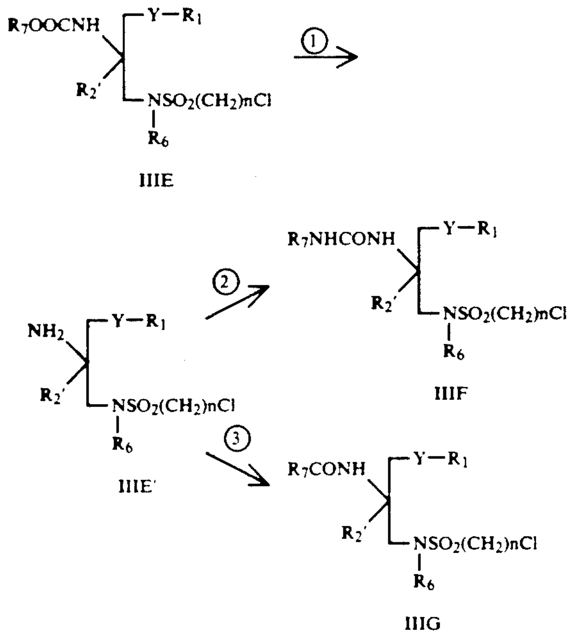

wherein $R_1'$, $R_2'$, $R_6$, $R_7$, Y, and n each has the same meaning as defined before.

① In this step, the alkoxycarbonyl of the compound III E which is prepared from compound VE1 or VE2 by allowing to reaction in the same manner described in Process I, Steps 1 and 2 is cleaved to give the compound III E'.

This step is carried out in the usual manner for removing the urethane type amino protecting group, for example, hydrogen bromide or hydrochloric acid treatment in acetic acid, hydrochloric acid treatment in ethyl ether, ethyl acetate or nitromethane, or trifluoroacetic acid treatment.

② In this step, the compound III F is prepared by the addition of an alkylisocyanate to the amine III E'.

The reaction is carried out using the $C_1$-$C_7$ alkylisocyanate, e.g., methyl isocyanate, ethyl isocyanate, propyl isocyanate, isopropyl isocyanate, butyl isocyanate, tert-butyl isocyanate, pentyl isocyanate, hexyl isocyanate, heptyl isocyanate in an inactive solvent such as aromatic hydrocarbon, e.g., benzene, toluene, chlorobenzene, chlorinated hydrocarbon, e.g., chloroform, dichloromethane, ether, e.g., tetrahydrofuran, or acetone.

③ In this step, the amine III E' is converted into the acid amide III G.

The acylating reagent such as acid halide, e.g., acetyl chloride, propionyl chloride, butyryl chloride, isobutylryl chloride, valeryl chloride, isovaleryl chloride, pivaloyl chloride, pentanoyl chloride, hexanoyl chloride, heptanoyl chloride or acid anhydride, e.g., acetic anhydride, propionic anhydride, butyric anhydride, isobutyric anhydride, valeric anhydride, isovaleric anhydride, pivalic anhydride, pentanoic anhydride, hexanoic anhydride, heptanoic anhydride is exemplified.

The reaction is carried out by heating without solvent or in an inactive solvent such as ethyl ether, benzene or the like. A base such as pyridine or an acid such as sulfuric acid may be added, if necessary.

PROCESS (vi)

When $R_2$ is heterocyclic group or heterocyclyloxy, the compound V HIJ can be prepared by the following manner.

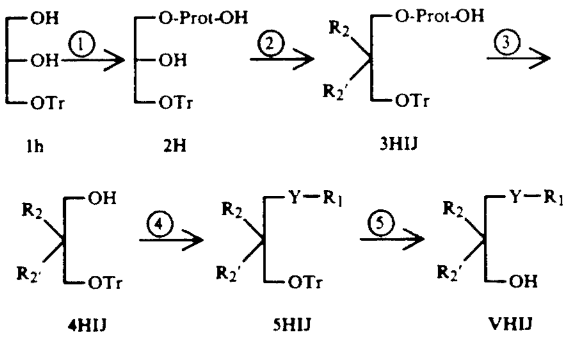

wherein $R_2$ is heterocyclic group or heterocyclyloxy and $R_1$, $R_2'$, Y and Prot-OH each has the same meaning as defined before.

① In this step, the hydroxy at 1 position is selectively protected.

The protecting group selectively attached to the primary hydroxy such as tert-butyldimethylsilyl is used. The reaction is carried out using tert-butyldimethylchlorosilane in the presence of a base such as imidazole.

② In this step, the desired heterocyclic group or heterocyclyloxy is introduced to 2H to give the compound 3HIJ.

The reaction is achieved according to the manner described in O. Mitsunobu, SYNTHESIS, 1, (1981).

The reaction is carried out using the desired heterocycle such as pyrrole, 2-methylpyrrole, 3-methylpyrrole, imidazole, 2-methylimidazole, 2,4-dimethylimidazole, pyrazole, 5-methylpyrazole, 3,5-dimethylpyrazole, 1,2,3-triazole, 4-methyl-1,2,3-triazole, 3-methyl-1,2,4-triazole, 3,5-dimethyl-1,2,4-triazole, tetrazole, or 5-methyltetrazole or 3-hydroxyisoxazole, 3-hydroxyisothiazole, 3-hydroxypyrazole, 3-hydroxy-4-methylisoxazole, 4-hydroxy-1,2,3-triazole or 4-hydroxy-5-methyl-1,2,3-triazole in the presence of triphenylphosphine and diethyl azodicarboxylate in a dry ether solvent such as ethyl ether, tetrahydrofuran, or benzene.

③ In this step, the hydroxy protecting group at 1 position is removed selectively.

The deprotection is carried out in the usual manner such as the acetic acid treatment at room temperature or tetra-n-butylammonium fluoride treatment in tetrahydrofuran.

④ In this step, the hydroxy of the compound 4HIJ is converted into the desired side chain.

This step can be carried out in the same manner as described in Processes (i), (ii)-①, or (iv)-①, ②.

⑤ In this step, the hydroxy protecting group at 3 position of the compound 5HIJ is removed.

The deprotection is carried out in the usual manner using an agent such as acetic acid, hydrochloric acid/chloroform, hydrobromic acid/acetic acid, p-toluenesulfonic acid or the like.

PROCESS (vii)

When $R_2$ is alkaloylmethyl, the compound III M can be prepared by the following manner.

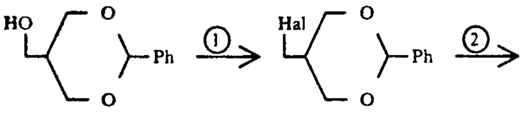

m1 M2

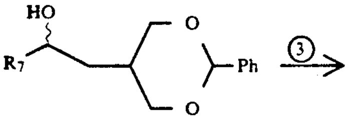

M3

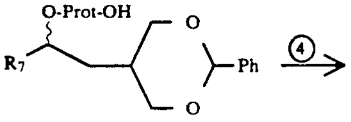

M4

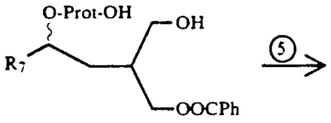

M5

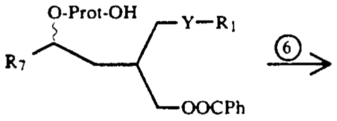

M6

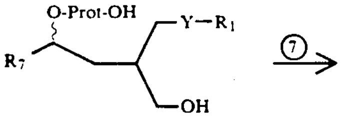

M7

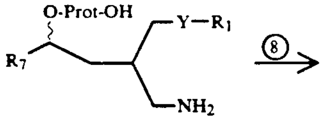

M8

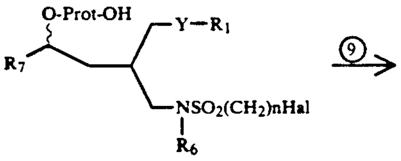

M9

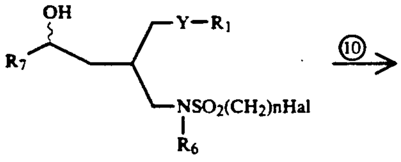

M10

-continued

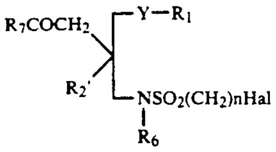

IIIM wherein $R_1$, $R_2'$, $R_6$, $R_7$, Y, n, Hal, and Prot-OH each has the same meaning as defined before.

(1) In this step, the hydroxy of the compound m1 is halogenated.

This step can be carried out in the same manner as described in Process II, Step 3'.

(2) In this step, an aldehyde is condensed additionally to the compound M2 to give the compound M3.

This step can be carried out in the usual manner of Grignard reaction.

The aldehyde such as $C_2$-$C_8$ aldehyde, e.g., acetoaldehyde, propionaldehyde, butyraldehyde, isobutyraldehyde, valeraldehyde, isovaleraldehyde, pivaloaldehyde, hexanol, heptanol, octanol is exemplified.

(3) In this step, the hydroxy of the compound M3 is protected. The ordinally used hydroxy protecting group can be used. In the case when triarylmethyl (e.g., trityl) or aroyl (e.g., benzoyl) is introduced, the corresponding halide such as trityl chloride, trityl bromide, or benzoyl chloride is allowed to react in the presence of base such as pyridine, triethylamine.

In the case when trialkylsilyl (e.g., trimethylsilyl, tert-butyldimethysilyl) is introduced, trialkylsilane such as trimethylchlorosilane or tert-butyldimethylchlorosilane is allowed to react in the presence of base such as imidazole.

(4) In this step, the compound M4 is cleaved to the compound M5.

The reaction is carried out by treatment with an aqueous suspension of N-bromosuccinimide containing a trace of hydrobromic acid.

(5) In this step, the hydroxy of the compound M5 is converted into the desired side chain.

This step is carried out in the same manner as described in Processes (i), (ii)-(1), or (iv)-(1), (2).

(6) In this step, the compound M6 is hydrolyzed with a base to give the compound M7.

The reaction is carried out in the usual manner with a base such as sodium hydroxide, potassium hydroxide, barium hydroxide, or the like in water or in an alcohol (e.g., methanol, ethanol).

(7) In this step, the hydroxy of the compound M7 is converted into the amino.

This step can be carried in the same manner as described in Process I Step 1.

(8) In this step, the compound M8 is sulfonylated to give the sulfonamide derivative M9.

This step can be carried out in the same manner as described in process I Step 2.

(9) In this step, the hydroxy protecting group of the compound M9 is removed.

The deprotection is carried out as follows. When protecting group is triarylmethyl, it is cleaved by treatment with acid, when protecting group is trialkylsilyl, it is cleaved by treatment with acetic acid or with tetra-n-butyl-ammonium fluoride in tetrahydrofuran, and when protecting group is aroyl, it is cleaved by hydrolysis with a base such as sodium methoxide.

⑩ In this step, the hydroxy of the compound M10 is oxidized into the carbonyl.

As an oxidizing agent, chromate-type agent such as Jones' reagent, Collins' reagent, pyridinium chlorochromate or pyridinium dichromate, or dimethylsulfoxide combined with sulfur trioxide, trifluoroacetic anydride, methanesulfonic anhydride, thionyl chloride or oxalyl chloride or the like may be used. In a case where dimethylsulfoxide is used as an oxidizing agent, a tertiary amine such as triethylamine or pyridine may be used as a decomposing agent. As a solvent, according to the property of the agent a chlorinated hydrocarbon such as chloroform or dichloromethane, ether such as diethyl ether, tetrahydrofuran, or dimethylsulfoxide may be used. The reaction may be carried out under cooling or at room temperature within several hours.

PROCESS (vii)

When $R_2$ is cyanomethyl, the compound VN can be prepared in the following manner.

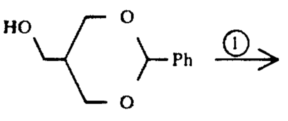

n1

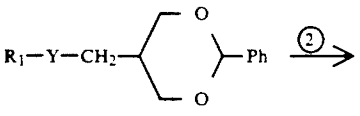

N2

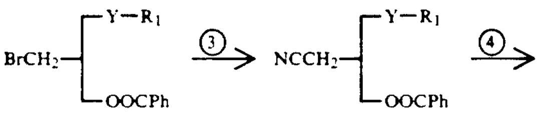

N3 N4

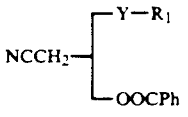

VN wherein $R_1$ and Y each has the same meaning as defined before.

① In this step, the hydroxy of the compound n1 is converted to the desired side chain.

This step can be carried out in the same manner as described in Process (i), (ii)-①, or (iv)-①, ②.

② In this step, the acetal N2 is cleaved into the compound N3.

This step is carried out by using N-bromosuccinimide in a solvent such as chlorinated hydrocarbon (e.g., carbon tetrachloride, chloroform, dichloromethane) by heating for several hours.

③ In this step, the compound N3 is cyanolated to give the compound N4.

This step can be carried out using metal cyanine such as sodium cyanide, potassium cyanide, copper(I) cyanide or the like in a solvent such as acetone, acetonitrile, pyridine, ethyl ether, benzene, dimethylsulfoxide, dimethylformamide under heating. A phase transfer catalyst such as crown ether, e.g., 18-crown-6 or tetraethylammonium cyanide may be used, if necessary.

④ In this step, the benzoate N4 is hydrolyzed to the alcohol.

This step can be carried out in the same manner, the usual manner of the hydrolysis with a base, as described in Process (vii)-⑥.

The following examples are included to explain the embodiments of the present invention in more detail, but these are not intended to limit the scope of the invention.

The following compounds may be used as starting materials.

2-Methoxy-3-octadecylcarbamoyloxypropylamine (Japan Kokai No. 85-243047),
3-hexadecylthio-2-methoxypropanol (Ger. Offen. DE 3,204,735),
3-hexadecyloxy-2-methoxypropanol [Shimazu et al., Chem. Pharm. Bull., 30, 3260, (1982)],
β-methyl-αγ-benzylidenglycol [P. E. Verkade, et al., Recl. Trav. Chim. Pays.-Bas., 61, 831, (1942)],
2-hexadecylthiomethyl-2-hydroxymethyltetrahydrofuran (U.S. Pat. No. 792,095),
2-hydroxymethyl-2-octadecylcarbamoylmethyltetrahydrofuran (U.S. Pat. No. 792,095),
1-hexadecylthio-3-trityloxy-2-propanol [J. Med. Chem., 31, 410 (1988)],
1-octadecylcarbamoyloxy-3-trityloxy-2-propanol, [J. Med. Chem., 31, 410 (1988)],
N-tritylserine methyl ester [Tetrahedron Letters. 22, 491, (1981)],
4-hydroxymethyl-2-phenyl-2-oxazoline [J. Org. Chem., 48, 1197 (1983)],
3-trityloxy-1,2-propandiol [Chem. Ber., 94, 812, (1961)],
3-hexadecyloxy-2-methoxymethylpropanol [JP Kokai Pub. No. 83-10592],
3-hexadecylthio-2-methoxymethylpropylamine [JP Kokai Pub. No. 82-98291],
2-methoxymethyl-3-octadecylcarbamoyloxypropanol [JP Kokai Pub. No. 83-10592] and
5-hydroxymethyl-2-phenyl-1,3-dioxane [Lipids, 22(11), 947-951 (1987)].

(1) Preparation of 3-(3-chloropropylsulfonylamino)-2-methoxy-1-octadecylcarbamoyloxypropane III a1

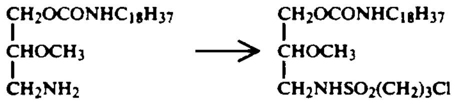

IVa1 IIIa1

To a solution of 1.2 g (3 mM) of 2-methoxy-3-octadecylcarbamoyloxypropylamine IV a1 (described in JP Kokai No. 60-243047) in 24 ml of dichloromethane and 0.54 ml (3.9 mM) of triethylamine is added 0.401 ml (3.3 mM) of 3-chloropropanesulfonyl chloride with ice-cooling and the mixture is stirred at room temperature overnight. The product is isolated by dichloromethane extraction and dichloromethane layer is washed with saturated aqueous sodium hydrogencarbonate and saturated aqueous sodium chloride, dried over anhydrous magnesium sulfate, and evaporated. The residue is purified by the column chromatography on silica gel with a n-hexane-ethyl acetate (3:2) mixture as an eluent. The product is recrystallized from chloroform-n-hexane mixture to give 1.386 g (2.56 mM) of 3-(3-chloropropylsulfonylamino)-2-methoxy-1-octadecylcarbamoyloxypropane III a1 as colorless crystals in 85% yield.

NMR: δ ppm($CDCl_3$) 0.86(t,3H), 1.24(s,30H), 1.58(m,2H), 2.1~2.5 (m,2H), 2.9~3.6(m,7H), 3.44(s,3H), 3.67(t,2H,J=6.0 Hz), 4.18(m,2H), 4.87(m,1H), 5.10(m,1H).

IR: νmax($CHCl_3$) 3445, 2920, 2850, 1715, 1510, 1460, 1330, 1220, 1145 $cm^{-1}$.

Anal. Calcd. (%) for $C_{26}H_{53}O_5N_2SCl$: C 57.70, H 9.87, N 5.18, S 5.92, Cl 6.55, Found (%) C 57.51, H 9.84, N 5.34, S 5.95, Cl 6.82.

MS: 540($M^+$, $Cl^{35}$).

Mp.: 64.5°~66° C.

(2) Preparation of 3-(3-iodopropylsulfonylamino)-2-methoxy-1-octadecylcarbamoyloxypropane II a1

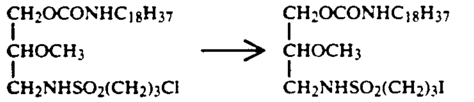

IIIa1 IIa1

To a solution of 972 mg (1.8 mM) of 3-(3-chloropropylsulfonylamino)-2-methoxy-1-octadecylcarbamoyloxypropane III a1 in 10 ml of methyl ethyl ketone is added 500 mg (3.38 mM) of sodium iodide and the mixture is refluxed for 3 hours with stirring. After the solvent is evaporated, the residue is purified by the column chromatography on silica gel with a n-hexane - ethyl acetate (1:1) mixture as an eluent. The product is recrystallized from chloroform-n-hexane to give 972 mg (1.54 mM) of 3-(3-iodopropylsulfonylamino)-2-methoxy-1-octadecylcarbamoyloxypropane II a1 in 86% yield.

NMR: δ ppm($CDCl_3$) 0.88(t,3H), 1.26(s,30H), 1.5(m,2H), 2.25~2.40(m,2H), 3.1~3.3(m,4H), 3.31(t,2H,J=6.6 Hz), 3.46(s,3H), 3.50(m, 1H), 4.05~4.30(m,2H), 4.83(m,1H), 5.00(t,1H,J=6 Hz).

IR: νmax($CHCl_3$) 3450, 2940, 2855, 1725, 1510, 1470, 1335, 1230, 1145 $cm^{-1}$.

Anal. Calcd. (%) for $C_{26}H_{53}O_5N_2SI$: C 49.12, H 8.44, N 4.56, S 5.34, I 20.08, Found (%) C 49.36, H 8.44, N 4.43, S 5.07, I 20.10.

MS: $505(M-I)^+$.

mp.: 61.5°~62.5° C.

EXAMPLE 1

Preparation of 2-methoxy-1-octadecylcarbamoyloxy-3-(3-trimethylammoniosulfonylamino)propane chloride Ia1

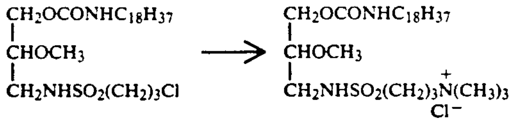

IIIa1 Ia1

A solution of 420 mg (0.776 mM) of 3-(3-chloropropylsulfonylamino)-2-methoxy-1-octadecylcarbamoyloxypropane III a1 in 10 ml mixture of trimethylamine-toluene (10 ml/25 ml) is heated at 120° C. in a sealed tube for 24 hours. The solvent is evaporated and the residue which is washed with acetone-ether several times is purified by column chromatography on HP-20 to give 50 mg of 2-methoxy-1-octadecylcarbamoyloxy-3-(3-trimethylammoniosulfonylamino)propane chloride Ia1 in 11% yield.

NMR: δ ppm ($CDCl_3$) 0.86(t,3H), 1.25(s,30H), 1.4~1.6(m,2H), 2.0~2.5(m,2H), 3.20(s,3H), 3.0~3.4(m,6H), 3.46(s,3H), 3.4~3.8(m, 3H), 4.15(m,2H).

IR: νmax($CHCl_3$) 3450, 2925, 2850, 1710, 1460, 1320, 1220, 1140 $cm^{-1}$.

Anal. Calcd. (%) for $C_{29}H_{62}O_5N_3SCl.1.5H_2O$: C 55.52, H 10.44, N 6.70, S 5.11, Cl 5.65, Found (%) C 55.49, H 10.42, N 6.78, S 4.85, Cl 5.78.

mp.: 60°~62° C.

EXAMPLE 2

Preparation of 2-methoxy-1-octadecylcarbamoyloxy-3-(3-thiazoliopropylsulfonylamino)propane iodide Ia2

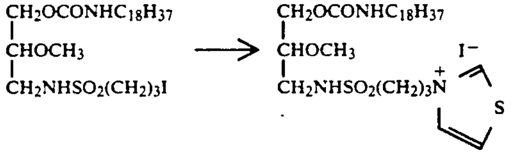

IIa1 Ia2

A solution of 240 mg (0.38 mM) of 3-(3-iodopropylsulfonylamino)-2-methoxy-1-octadecylcarbamoyloxypropane in 2 ml of thiazole is stirred at 50° C. overnight. After thiazole is evaporated, the residue is recrystallized from dichloromethaneacetone to give 150 mg (0.209 mM) of 2-methoxy-1-octadecylcarbamoyloxy-3-(3-thiazoliopropylsulfonylamino)propane iodide Ia2 in 55% yield.

NMR: δ ppm ($d_6$DMSO) 0.86(t,3H), 1.24(s,30H), 1.36(m,2H), 2.2~2.4(m,2H), 2.9~3.2(m,6H), 3.32(s,3H), 3.3~3.45(m,1H), 3.80~4.15(m, 2H), 4.67(t,2H,J=7.2 Hz), 7.15(t,1H,J=5.6 Hz), 7.33(t,1H,J=5.8 Hz), 8.35~8.42(m,1H), 8.60(d,1H,J=3.8 Hz), 10.20(s,1H).

IR: νmax(KBr) 3360, 2925, 2855, 1685, 1565, 1470, 1310, 1280, 1145, 1130 $cm^{-1}$.

Anal. Calcd. (%) for $C_{29}H_{56}O_5N_3S_2I.0.2H_2O$: C 48.28, H 7.88, N 5.82, S 8.89, I 17.59, Found (%) C 48.37, H 7.88, N 6.00, S 9.22, I 17.38.

mp.: 116°~118° C. (Decompose)

EXAMPLES 3 to 7

The compounds shown in Table 1 are prepared from the compound II a1 by the same procedure as described in Example 2.

In Example 4, the residue resulting from evaporating an amine is washed with n-hexane and in Examples 5 and 6, the said residue is washed with ethyl ether.

TABLE 1

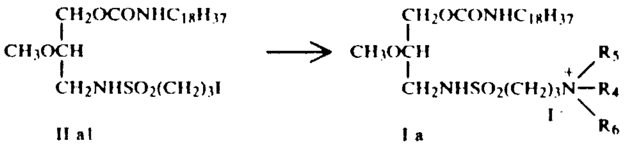

| Ex. No. | Cpd. No. | S.M. II 1 [mg] | 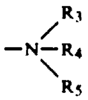 | Amine | Reaction Tempt. | Reaction Time | Purification | Yd. [mg] [%] | NMR: δ ppm | IRν max: [cm⁻¹] mp. [°C.] | Analysis Calcd. (%) Found (%) |
|---|---|---|---|---|---|---|---|---|---|---|---|
| 3 | I a3 | 260 | 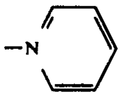 | Pyridine (2 ml) | 1) room temperature 2) 50° C. | 1) Overnight 2) 1 hour | Recrystallization (Acetic acid/ethyl acetate/water = 4/1/1) | 120 41% | (d6-DMSO) 0.85(t, 3H), 1.23 (s, 30H), 1.36(m, 2H), 2.32(m, 2H), 2.9~3.4(m, 10H), 3.30 (s, 3H), 3.8~4.2(m, 2H), 4.71(t, 2H, J = 7.3Hz), 7.18(t, 1H, J = 6Hz), 7.35(m, 1H), 8.19 (t, 2H, J = 6.8Hz), 8.63(t, 1H, J = 7.6Hz), 9.08(d, 1H, J = 5.4Hz). | ($CHCl_3$) 3450, 2930, 2850, 1710, 1510, 1320, 1220, 1140. 80~81 (Decompd.) | ($C_{31}H_{58}O_5N_3SI.0.5H_2O$) C 51.65, H 8.25, N 5.83, S 4.45, I 17.61, C 51.57, H 8.20, N 5.83, S 4.73, I 17.33. |
| 4 | I a4 | 233 | 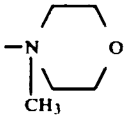 | N-Methylmorpholine (4 ml) | Room temperature | Overnight | Recrystallization (Acetone/n-hexane) | 160 56% | ($CDCl_3$+$CD_3OD$) 0.88(t, 3H), 1.26(s, 30H), 1.5(m, 2H), 2.25~2.45(m, 2H), 3.12(t, 2H, J = 7Hz), 3.2~3.4(m, 6H), 3.47 (s, 3H), 3.5~3.7(m, 5H), 3.73 (s, 3H), 3.8~3.9(m, 2H), 4.0~4.1(m, 2H), 4.1~4.2(m, 2H). | ($CHCl_3$) 3450, 2930, 2850, 1715, 1510, 1470, 1330, 1230, 1150. 61~62 (Decmpd.) | ($C_{31}H_{64}O_6N_3SI.1.0H_2O$) C 49.52, H 8.85, N 5.59, S 4.26, I 16.88, C 49.44, H 8.79, N 5.71, S 4.47, I 16.90. |
| 5 | I a5 | 420 | 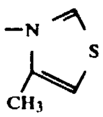 | 4-Methylthiazole (3 ml) | 60° C. | 4 hrs | Recrystallization (Dichloromethane/ethyl ether) | 150 31% | ($CDCl_3$) 0.88(t, 3H), 1.25 (s, 30H), 1.5(m, 2H), 2.55(m, 2H), 2.71(s, 3H), 3.05~3.20 (m, 2H), 3.20~3.35(m, 2H), 3.35~3.50(m, 2H), 3.44(s, 3H), 3.6(m, 1H), 4.0~4.3(m, 2H), 4.89(t, 2H, J = 7.6Hz), 5.27(t, 1H, J = 6Hz), 6.18(t, 1H, J = 5.6Hz), 7.8(m, 1H), 10.78 (d, 1H, J = 2.6Hz). | ($CHCl_3$) 3450, 2930, 2850, 1710, 1510, 1465, 1440, 1325, 1230, 1140. 60~62 | ($C_{30}H_{58}O_5N_3S_2I.0.2H_2O$) C 49.00, H 8.00, N 5.71, S 8.72, I 17.26, C 48.92, H 7.93, N 5.71, S 8.63, I 17.27. |
| 6 | I a6 | 440 | 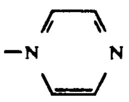 | Pyradine (4 ml) | 60° C. | 4 hrs | Recrystallization (Dichloromethane/acetone) | 276 56% | ($d^6$-DMSO) 0.86(t, 3H), 1.24 (s, 30H), 1.34(m, 2H), 2.36(m, 2H), 2.95(m, 2H), 3.05(m, 2H), 3.21(m, 2H), 3.40(m, 2H), 3.8~4.2(m, 2H), 4.02(s, 3H), 4.78(t, 2H, J = 7.2Hz), 7.13(t, 1H, J = 5Hz), 7.35(t, 1H, J = 6Hz), 9.24(m, 2H), 9.55(m, 2H). | ($CHCl_3$) 3450, 2930, 2850, 1710, 1520, 1445, 1320, 1220, 1145. 113.5~115 | ($C_{30}H_{57}O_6N_4SI.0.1H_2O$) C 50.43, H 8.07, N 7.84, S 4.49, I 17.76, C 50.27, H 7.98, N 7.83, S 4.79, I 17.75. |

TABLE 1-continued
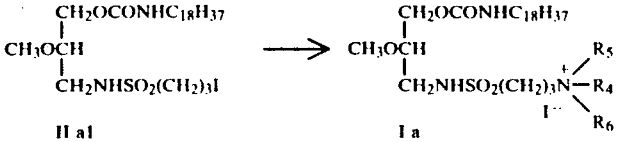
II a1 → I a
| Ex. No. | Cpd. No. | S.M. II 1 [mg] | 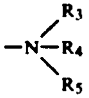 | Amine | Reaction Tempt. | Reaction Time | Purification | Yd. [mg] [%] | NMR: δ ppm | IR ν max: [$cm^{-1}$] mp. [°C.] | Analysis Calcd. (%) Found (%) |
|---|---|---|---|---|---|---|---|---|---|---|---|
| 7 | Ia7 | 1300 | 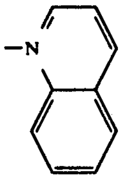 | Quinoline (2 ml) | 60° C. | overnight | recryst. $Et_2O$ | 850 54% | ($CDCl_3$) 0.88(t, 3H), 1.25 (s, 30H), 1.5(m, 2H), 2.60 ~ 2.85(m, 2H), 3.0 ~ 3.2(m, 2H), 3.2 ~ 3.4(m, 2H), 3.5 ~ 3.7(m, 3H), 3.41(s, 3H), 4.0 ~ 4.2(m, 2H), 5.32(t, 1H, J = 6Hz), 5.60(t, 2H, J = 8.1Hz), 6.06(t, 1H, J = 6Hz), 7.97(t, 1H, J = 8Hz), 8.1 ~ 8.4(m, 3H), 8.71(d, 1H, J = 9.2Hz), 9.03(d, 1H, J = 8.2Hz), 10.27(d, 1H, J = 5.4Hz). | ($CHCl_3$) 3445, 2920, 2850, 1710, 1520, 1460, 1320, 1230, 1140. 56.5 ~ 58 (dec.) | ($C_{36}H_{60}O_5N_3SI.0.75H_2O$) C 54.22, H 7.99 N 5.42 S 4.13, I 16.37, C 54.18, H 7.92, N 5.50, S 4.26, I 16.65 |

(3) Preparation of 3-hexadecylthio-2-methoxypropylamine IV a2

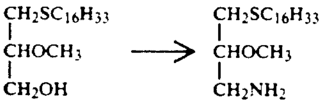

Va2 IVa2

To a solution of 4.356 g (12.57 mM) of 3-hexadecylthio-2-methoxypropanol Va2 (described in Ger. Offen. DE 3,204,735), 3.7 g (25.14 mM) of phthalimide, and 6.59 g (25.14 mM) of triphenylphosphine in 150 ml of tetrahydrofuran is added dropwise 4.37 g (25.14 mM) of diethyl azodicarboxylate with ice-cooling and the mixture is stirred at room temperature for 3 days. After the solvent is evaporated, the residue is purified by column chromatography on silica gel with a n-hexane-ethyl acetate-chloroform (9:1:1) mixture as an eluent. The product is recrystallized from dichloromethane-n-hexane to give 4.9 g (10.23 mM) of the phthalimide compound in 82% yield.

To a solution of 4.678 g (9.83 mM) of the phthalimide compound in 100 ml of methanol is added 0.54 g (10.79 mM) of hydrazine monohydrate and the mixture is stirred for 5 hours under refluxing. After the solvent is evaporated, the residue is dissolved in chloroform and filtered through Celit to remove the insoluble material. The filtrated is evaporated and the residue is purified by the column chromatography on silica gel with a chloroform-methanol (20:1 to 9:1) (0.2% triethylamine) mixture as an eluent to give 2.98 g (8.622 mM) of 3-hexadecylthio-2-methoxypropylamine IV a2 in 88% yield.

NMR: δ ppm($CDCl_3$) 0.88(t,3H), 1.26(s,26H), 1.6(m,2H), 2.5~3.0 (m,6H), 3.30(m,1H), 3.43(s,3H).

IR: νmax($CHCl_3$) 3380, 2930, 2850, 1465, 1380, 1230, 1110 $cm^{-1}$.

MS: 346($MH^+$).

(4) Preparation of 3-(3-chloropropylsulfonylamino)-1-hexadecylthio-2-methoxypropane III a2

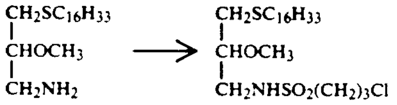

IVa2 IIIa2

To a solution of 1.018 g (2.95 mM) of 3-hexadecylthio-2-methoxypropylamine IV a2 in 15 ml of dichloromethane and 0.534 ml (3.83 mM) of triethylamine is added 0.563 mg (3.24 mM) of 3-chloropropanesulfonyl chloride with ice-cooling and the mixture is stirred at 0° C. for 3 hours. After the solvent is evaporated, the residue is purified by the column chromatography on silica gel with a n-hexane-ethyl acetate (4:1) mixture as an eluent. The product is recrystallized from chloroform-n-hexane to give 1.275 g (2.62 mM) of 3-(3-chloropropylsulfonylamino)-1-hexadecylthio-2-methoxypropane III a2 as a colorless powder in 89% yield.

NMR: δ ppm($CDCl_3$) 0.88(t,3H), 1.26(s,26H), 1.6(m,2H), 2.2~2.4 (m,2H), 2.55(t,2H,J=7.4 Hz), 2.53~2.80(m,2H), 3.10~3.30(m,3H), 3.42(s,3H), 3.4~3.6(m,2H), 3.69(t,2H,J=6.2 Hz), 4.70(t,1H,J=6 Hz).

IR: νmax($CHCl_3$) 3380, 2930, 2850, 1470, 1410, 1330, 1150, 1095 $cm^{-1}$.

Anal. Calcd. (%) for $C_{23}H_{48}O_3NS_2Cl$: C 56.82, H 9.95, N 2.88, S 13.19, Cl 7.29, Found (%): C 56.76, H 9.89, N 3.18, S 12.94, Cl 7.18.

MS: 485($M^+$, $Cl^{35}$).

mp.: 49°~50° C.

(5) Preparation of 1-hexadecylthio-3-(3-iodopropylsulfonylamino)-2-methoxypropane II a2

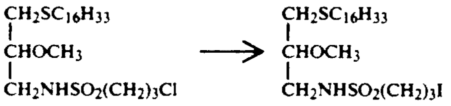

IIIa2 IIa2

To a solution of 1.03 g (2.12 mM) of 3-(3-chloropropylsulfonylamino)-1-hexadecylthio-2-methoxypropane III a2 in 20 ml of methyl ethyl ketone is added 636 mg (4.24 mM) of sodium iodide and the mixture is refluxed or 3 hours with stirring. After the solvent is evaporated, the residue is purified by the column chromatography on silica gel with a n-hexane-ethyl acetate (4:1) mixture as an eluent to give 1.06 g (1.835 mM) of 1-hexadecylthio-3-(3-iodopropylsulfonylamino)-2-methoxypropane II a2 as an oil in 87% yield.

NMR: δ ppm($CDCl_3$) 0.88(t,3H), 1.26(s,26H), 1.6(m,2H), 2.22~2.40(m,2H), 2.55(t,2H,J=7.4 Hz), 2.53~2.81(m,2H), 3.11~3.26 (m,3H), 3.31(t,2H,J=6.6 Hz), 3.43(s,3H), 3.41~3.56(m,1H), 4.65(t,1H, J=6 Hz).

IR: νmax($CHCl_3$) 3370, 2920, 2850, 1460, 1405, 1325, 1145, 1090 $cm^{-1}$.

Anal. Calcd. (%) for $C_{23}H_{48}O_3NS_2I$: C 47.82, H 8.38, N 2.42, S 11.10, I 21.97, Found(%): C 47.62, H 8.28, N 2.50, S 11.09, I 22.18.

MS: 577($M^+$).

EXAMPLE 8

Preparation of 1-hexadecylthio-2-methoxy-3-(3-trimethylammoniopropylsulfonylamino)propane iodide Ia8

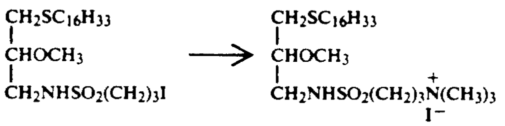

IIa2 Ia8

A solution of 500 mg (0.866 mM) of 1-hexadecylthio-3-(3-iodopropylsulfonylamino)-2-methoxypropane II a2 in 10 ml of mixture of trimethylamine-toluene (10 ml/25 ml) is allowed to react at room temperature in a sealed tube for 24 hours. After the solvent is evaporated, the residue is purified by the column chromatography on silica gel with a chloroform-methanol (5:1 to 3:1) mixture as an eluent. The product is recrystallized from dichloromethane-n-hexane to give 330 mg (0.518 mM) of 1-hexadecylthio-3-(3-trimethylammoniopropylsulfonylamino)-2-methoxypropane Ia8 in 60% yield.

NMR: δ ppm($CDCl_3$) 0.88(t,3H), 1.26(s,26H), 1.58(m,2H), 2.3~2.5 (m,2H), 2.56(t,2H,J=7.2 Hz), 2.72(d,2H,J=5.8 Hz), 3.20~3.65(m,5H), 3.43(s,9H), 3.45(s,3H), 3.85~3.93(m,2H), 6.20(t,1H,J=6 Hz).

IR: νmax($CHCl_3$) 3375, 2925, 2850, 1470, 1330, 1230, 1150, 1090, 1055, 1030 $cm^{-1}$.

mp.: 69°~71° C.

Anal. Calcd. for $C_{26}H_{57}O_3N_2S_2I.0.4H_2O$: C 48.49, H 9.05, N 4.35, S 9.96, I 19.71, Found(%): C 48.66, H 8.85, N 4.47, S 10.19, I 19.47.

EXAMPLE 9

Preparation of 1-hexadecylthio-2-methoxy-3-(3-thiazoliopropylsulfonylamino)propane iodide Ia9

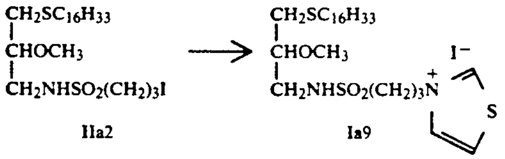

IIa2 Ia9

A solution of 600 mg (1.04 mM) of 1-hexadecylthio-3-(3-iodopropylsulfonylamino)-2-methoxypropane II a2 in 5 ml of thiazole is stirred at 60° C. for 6 hours. After thiazole is evaporated, the residue is washed with ether and recrystallized from acetone to give 387 mg (0.584 mM) of 1-hexadecylthio-2-methoxy-3-(3-thiazoliopropylsulfonylamino)propane iodide Ia9 in 56% yield.

NMR: δ ppm($CDCl_3$) 0.88(t,3H), 1.26(s,26H), 1.58(m,2H), 2.55 (t,2H,J=7.3 Hz), 2.70(d,2H,J=5.6 Hz), 2.5~2.7(m,2H), 3.1~3.5(m,4H), 3.43(s,3H), 3.55(m,1H), 5.04(t,2H,J=7.4 Hz), 6.26(t,1H,J=6 Hz), 8.29~8.32(m,1H), 8.72~8.75(m,1H), 10.59~10.60(m,1H).

IR: νmax($CHCl_3$) 3375, 2930, 2850, 1460, 1325, 1220, 1140, 1090 $cm^{-1}$.

Anal. Calcd. (%) for $C_{26}H_{51}O_3N_3S_3I.0.1H_2O$: C 46.99, H 7.76, N 4.21, S 14.47, I 19.10, Found (%): C 46.79, H 7.71, N 4.25, S 14.42, I 19.01.

mp.: 70°~73° C.

(6) Preparation of 3-hexadecyloxy-2-methoxypropylamine IV a3

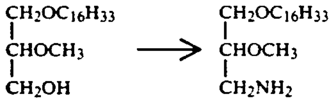

Va3 IVa3

To a solution of 8.26 g (25 mM) of 3-hexadecyloxy-2-methoxypropanol Va3 [described in Shimazu et al., Chem. Pharm. Bull. 30, 3260, (1982)], 7.35 g (50 mM) of phthalimide, and 13.1 g (50 mM) of triphenylphosphine in 300 ml of tetrahydrofuran is added dropwise 8.7 g (50 mM) of diethyl azodicarboxylate with ice-cooling, and the mixture is stirred at room temperature for 3 days. After the solvent is evaporated, the residue is purified by the column chromatography on silica gel with a n-hexane-ethyl acetate-chloroform (9:1:1) mixture as an eluent. The product is recrystallized from n-hexane to give 10.142 g (22.06 mM) of the phthalimide compound in 88% yield.

To a solution of 10.142 g (22.06 mM) of the phthalimide compound in 200 ml of methanol is added 1.47 g (29.4 mM) of hydrazine monohydrate and the mixture is refluxed for 5 hours with stirring. After the solvent is evaporated, the residue to which is added chloroform is passed through Celite to remove the insoluble material. The filtrate is evaporated and the residue is purified by column chromatography on silica gel with a chloform-methanol (5:1) (0.2% triethylamine) as an eluent to give 5.523 g (16.76 mM) of 3-hexadecyloxy-2-methoxypropylamine IV a3 in 76% yield.

NMR: δ ppm($CDCl_3$) 0.88(t,3H), 1.26(s,26H), 1.58(m,2H), 2.70~2.96(m,6H), 3.33(m,1H), 3.45(s,3H), 3.40~3.60(m,6H).

IR: νmax($CHCl_3$) 3380, 2920, 2845, 1580, 1465, 1360, 1240, 1115, 860 $cm^{-1}$.

MS: 330 ($MH^+$).

(7) Preparation of 3-(3-chloropropylsulfonylamino)-1-hexadecyloxy-2-methoxypropane III a3

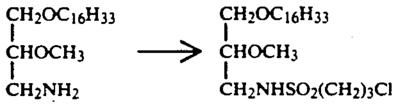

IVa3 IIIa3

To a solution of 3.368 g (10.22 mM) of 3-hexadecyloxy-2-methoxypropylamine IV a3 in 35 ml of dichloromethane and 1.85 ml (13.29 mM) of triethylamine is added 1.99 g (11.24 mM) of 3-chloropropanesulfonyl chloride with ice-cooling and the mixture is stirred at room temperature for 4 hours and then heated for 30 minutes with stirring. After the solvent is evaporated, the residue is purified by the column chromatography on silica gel with a n-hexane-ethyl acetate (3:1) mixture as an eluent. The product is recrystallized form methanol to give 4.15 g (8.827 mM) of 3-(3-chloropropylsulfonylamino)-1-hexadecyloxy-2-methoxypropane III a3 as a colorless powder in 86% yield.

NMR: δ ppm($CDCl_3$) 0.88(t,3H), 1.26(s,26H), 1.56(m,2H), 2.20~2.38(m,2H), 3.15~3.60(m,9H), 3.44(s,3H), 3.68(t,2H,J=6.2 Hz), 4.79 (t,1H,J=6 Hz).

IR: νmax($CHCl_3$) 3375, 2920, 2845, 1465, 1335, 1410, 1265, 1145 $cm^{-1}$.

mp.: 49°~50° C.

Anal. Calcd. (%) for $C_{23}H_{48}O_4NSCl$: C 58.76, H 10.29, N 2.98, S 6.82, Cl 7.54, Found (%) C 58.63, H 10.20, N 3.00, S 6.72, Cl 7.47.

MS: 469 ($M^+$, $Cl^{35}$).

(8) Preparation of 1-hexadecyloxy-3-(3-iodopropylsulfonylamino)-2-methoxypropane II a3

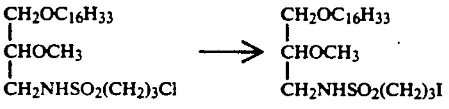

IIIa3 IIa3

To a solution of 3.845 (8.18 mM) of 3-(3-chloropropylsulfonylamino)-1-hexadecyloxy-2-methoxypropane III a3 in 30 ml of methyl ethyl ketone is added 2.45 g (16.36 mM) of sodium iodide and the mixture is refluxed for 3 hours with stirring. After the solvent is evaporated, the residue is purified by the column chromatography on silica gel with a n-hexane-ethyl acetate (4:1) mixture as an eluent. The product is recrystallied from methanol to give 3.556 g (6.332 mM) of 1-hexadecyloxy-3-(3-iodopropylsulfonylamino)-2-methoxypropane II a3 in 77% yield.

NMR: δ ppm($CDCl_3$) 0.88(t,3H), 1.26(s,26H), 1.58(m,2H), 2.25~2.40(m,2H), 3.10~3.60(m,9H), 3.30(t,2H,J=6.6 Hz), 3.44(s,3H), 4.81 (t,1H,J=6 Hz).

IR: νmax($CHCl_3$) 3380, 2930, 2855, 1470, 1410, 1335, 1270, 1150 $cm^{-1}$.

Anal. Calcd. (%) for $C_{23}H_{48}O_4NSI$: C 49.19, H 8.61, N 2.49, S 5.71, I 22.60, Found (%) C 49.11, H 8.54, N 2.53, S 6.00, I 22.48.

MS: 562 ($M^+$).

mp.: 46°~47° C.

EXAMPLE 10

Preparation of 1-hexadecyloxy-2-methoxy-3-(3-trimethylammoniopropylsulfonylamino)propane iodide I a10

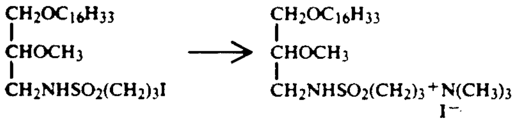

IIa3 Ia10

A solution of 600 mg (1.068 mM) of 1-hexadecyloxy-3-(3-iodopropylsulfonylamino)-2-methoxypropane II a3 in 10 ml of trimethylamine-toluene (10 ml/25 ml) mixture is allowed to react at room temperature in a sealed tube for 24 hours. After the solvent is evaporated, the residue is washed with ether to give 577 mg of 1-hexadecyloxy-2-methoxy-3-(3-trimethylammoniopropylsulfonyamino)propane iodide I a10 in 87% yield.

NMR: δ ppm($CDCl_3$) 0.88(t,3H), 1.26(s,26H), 1.58(m,2H), 2.3~2.5(m,2H), 3.15~3.65(m,9H), 3.42(s,9H), 3.47(s,3H), 3.80~3.95(m, 2H), 6.3(t,1H,J=6 Hz).

IR: νmax($CHCl_3$) 3380, 2925, 2850, 1470, 1325, 1230, 1145 $cm^{-1}$.

Anal. Calcd. (%) for $C_{26}H_{57}O_3N_2SI$: C 50.31, H 9.26, N 4.51, S 5.17, I 20.44, Found (%): C 50.20, H 9.25, N 4.63, S 5.29, I 20.48.

mp. 80.5°~82.5° C.

EXAMPLE 11

Preparation of 1-hexadecyloxy-2-methoxy-3-(3-thiazoliopropylsulfonylamino)propane iodide I a11

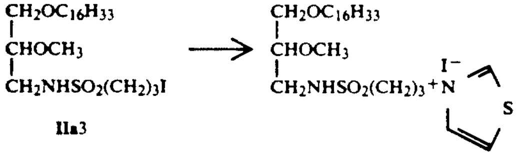

IIa3 Ia11

A solution of 600 mg (1.07 mM) of 1-hexadecyloxy-3-(3-iodopropylsulfonylamino)-2-methoxypropane in 5 ml of thiazole is stirred at 50° C. for 6 hours. After thiazole is evaporated, the residue is purified by the column chromatography on silica gel with a chloroform-methanol (5:1 to 3:1) mixture as an eluent. The product is recrystallized from ether-dichloromethane to give 450 mg (0.70 mM) of 1-hexadecyloxy-2-methoxy-3-(3-thiazoliopropylsulfonylamino)propane iodide I a11 in 66% yield.

NMR: δ ppm(DMSO) 0.85(t,3H), 1.24(s,26H), 1.48(m,2H), 2.2~2.4(m,2H), 3.31(s,3H), 2.9~3.5(m,9H), 4.65(t,2H,J=7 Hz), 7.26(t,1H, J=6 Hz), 8.36~8.39(m,1H), 8.57~8.60(m,1H), 10.17~10.20(m,1H).

IR: νmax($CHCl_3$) 3400, 2930, 2850, 1460, 1320, 1220, 1140 $cm^{-1}$.

mp. 52°~53° C.

(9) Preparation of 2-methoxy-1-octadecylcarbamoyloxy-3-(3-phenylselenylpropylsulfonylamino)propane II a1'

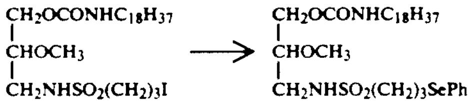

IIa1 IIa'1

To a solution of 1.52 g (4.9 mM) of diphenyl diselenide in 25 ml of dry ethanol is added 370 mg (9.78 mM) of sodium borohydride with ice-cooling and the mixture is stirred for 30 minutes. To the above mixture are added 0.56 ml (9.78 mM) of acetic acid and a solution of 1.03 g (1.63 mM) of 3-(3-iodopropylsulfonylamino)-2-methoxy-1-octadecylcarbamoyloxypropane in 10 ml of tetrahydrofuran and the mixture is stirred at room temperature for 1.5 hours. The product is extracted with ethyl acetate, and the organic layer is washed with 1N-hydrochloric acid, saturated aqueous sodium hydrogencarbonate, and saturated aqueous sodium chloride, dried over anhydrous magnesium sulfate, and evaporated. The residue is purified by the column chromatography on silica gel with a n-hexane-ethyl acetate (2:1) eluent to give 1.06 g (1.60 mM) of 2-methoxy-1-octadecylcarbamoyloxy-3-(3-phenylselenylpropylsulfonylamino)propane II a1' as a colorless powder in 98% yield.

NMR: δ ppm($CDCl_3$) 0.88(t,3H), 1.26(s,30H), 1.5(m,2H), 2.1~2.24 (m,2H), 3.01(t,2H,J=7 Hz), 3.08~3.32(m,6H), 3.42(s,3H), 3.46(m, 1H), 4.00~4.28(m,2H), 4.73~4.90(m,2H), 7.24~7.34(m,3H), 7.45~7.57(m,2H).

IR: νmax($CHCl_3$) 3450, 2930, 2850, 1720, 1515, 1460, 1330, 1220, 1145 $cm^{-1}$.

MS: M+662 ($Se^{80}$).

(10) Preparation of 2-methoxy-1-octadecylcarbamoyloxy-3-(3-propensulfonylamino)propane VII a4

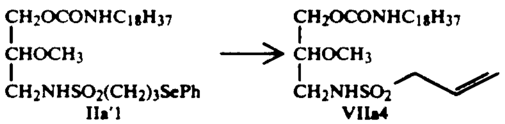

IIa'1 VIIa4

To a solution of 1.028 g (1.553 mM) of 2-methoxy-1-octadecylcarbamoyloxy-3-(3-phenylselenylpropylsulfonylamino)propane in 30 ml of mixture of methanol-dichloromethane (5:1) are added 0.25 ml (3.16 mM) of pyridine and 2 ml of 30% hydrogen peroxide with ice-cooling and the mixture is warmed to room temperature and stirred for 5 hours. the product is isolated by ethyl acetate extraction and the organic layer is washed with an aqueous sodium chloride, dried over anhydrous magunesium sulfate, and evaporated. To the residue are added 30 ml of benzene and 0.25 ml of pyridine and the mixture is heated at 45° C. to 50° C. for an hour. After the solvent is evaporated, the residue is purified by the column chromatography on silica gel with a n-hexane-ethyl acetate (2:1 to 1:1) mixture as an eluent. The product is recrystallized from dichloromethane-n-hexane to give 624 mg (1.24 mM) of 2-methoxy-1-octadecylcarbamoyloxy-3-(3-propenesulfonylamino)propane VII a4 as colorless crystals in 80% yield.

NMR: δ ppm($CDCl_3$) 0.88(t,3H), 1.26(s,30H), 1.5(m,2H), 3.1~3.4(m,4H), 3.74~3.82(m,2H), 3.45(s,3H), 3.50(m,1H), 4.05~4.30(m,2H), 4.8(m,1H), 4.93(t,1H,J=6 Hz), 5.35~5.50(m,2H), 5.82~6.04(m,1H).

IR: νmax($CHCl_3$) 3460, 2930, 2850, 1725, 1520, 1475, 1340, 1240, 1150 $cm^{-1}$.

Anal. Calcd. (%) for $C_{26}H_{52}O_5N_2S$: C 61.87, H 10.38, N 5.55, S 6.35, Found (%): C 61.68, H 10.34, N 5.73, S 6.20.

mp.: 74°~75.5° C.

(11) Preparation of 2-methoxy-1-octadecylcarbamoyloxy-3-(2-hydroxyethylsulfonylamino)propane VI a4

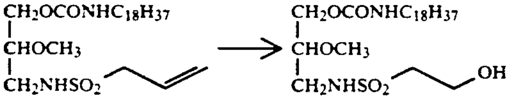

VIIa4 VIa4

A solution of 600 mg (1.19 mM) of 2-methoxy-1-octadecylcarbamoyloxy-3-(3-propenesulfonylamino)-propane VII a4 in 22 ml of methanol-dichloromethane (1:10) mixture is ozonized at −78° C. The resulting ozonide is decomposed with 0.5 ml of dimethylsulfide. After the solvent is evaporated, 300 mg (7.93 mM) of sodium borohydride is added with ice-cooling to the residue in methanol. The mixture is warmed up to room temperature and stirred for 2 hours. The product is isolated by ethyl acetate extraction and the organic layer is washed with an aqueous solution of sodium chloride, dried over anhydrous magnesium sulfate, and evaporated. The residue is purified by the column chromatography on silica gel with a n-hexane-ethyl acetate mixture as an eluent to give 300 mg (0.59 mM) of 2-methoxy-1-octadecylcarbamoyloxy-3-(2-hydroxyethylsulfonylamino)propane VI a4 as a colorless powder in 50% yield.

NMR: δ ppm($CDCl_3$) 0.88(t,3H), 1.26(s,30H), 1.5(m,2H), 2.05 (br.,1H), 3.05~3.35(m,6H), 3.45(s,3H), 3.51(m,1H), 4.02~4.12(m, 2H), 4.12~4.27(m,2H), 4.89(m,1H), 5.19(m,1H).

IR: νmax($CHCl_3$) 3450, 2920, 2850, 1710, 1510, 1465, 1330, 1220, 1135 $cm^{-1}$.

MS: 509 ($MH^+$).

(12) Preparation of 2-methoxy-1-octadecylcarbamoyloxy-3-(2-methanesulfonyloxyethylsulfonylamino)propane VI a4'

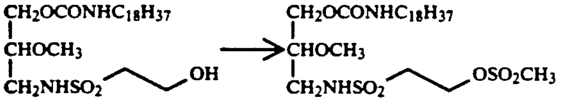

VIa4 VIa4'

To a solution of 298 mg (0.586 mM) of 2-methoxy-1-octadecylcarbamoyloxy-3-(2-hydroxyethylsulfonylamino)propane VI a4 in 6 ml of dichloromethane and 2 ml of tetrahydrofuran are added 50 μl (0.645 mM)

of methanesulfonyl chloride and 0.106 ml of triethylamine with ice-cooling and the mixture is stirred at room temperature for 2 hours. After the solvent is evaporated, the residue is purified by the column chromatography on silica gel with a n-hexane-ethyl acetate (1:1 to 1:2) mixture as an eluent to give 287 mg (0.489 mM) of 2-methoxy-1-octadecylcarbamoyloxy-3-(2-methanesulfonylamino)propane VI a4' as an colorless powder in 83% yield.

NMR: δ ppm($CDCl_3$) 0.88(t,3H), 1.26(s,30H), 1.5(m,2H), 3.11(s,3H), 3.10~3.42(m,4H), 3.45(s,3H), 3.50(t,2H,J=6 Hz), 4.15~4.28(m,2H), 4.61(t,2H,J=6 Hz), 4.91(m,1H), 5.19(t,1H,J=6.2 Hz).

IR: νmax($CHCl_3$) 3460, 2930, 2850, 1725, 1520, 1470, 1345, 1235, 1180, 1155, 1000, 970 $cm^{-1}$.

(13) Preparation of 3-(2-iodoethylsulfonylamino)-2-methoxy-1-octadecylcarbamoyloxypropane II a4

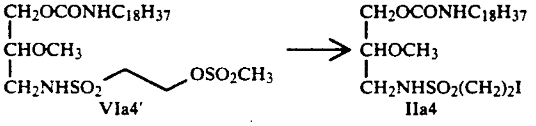

VIa4' IIa4

To a solution of 200 mg (0.341 mM) of 2-methoxy-1-octadecylcarbamoyloxy-3-(2-methanesulfonyloxyethylsulfonylamino)propane VI a4' in 5 ml of acetone is added 200 mg (1.33 mM) of sodium iodide and the mixture is refluxed with stirring for 5 hours. After the solvent is evaporated, the residue is purified by the column chromatography on silica gel with a n-hexane-ethyl acetate (2:1) mixture as an eluent to give 188 mg (0.296 mM) of 3-(2-iodoethylsulfonylamino)-2-methoxy-1-octadecylcarbamoyloxypropane II a4 in 87% yield.

NMR: δ ppm($CDCl_3$) 0.88(t,3H), 1.26(s,30H), 1.5(m,2H), 3.10~3.30(m,4H), 3.46(s,3H), 3.30~3.60(m,5H), 4.1~4.3(m,2H), 4.83(m,1H), 5.10(t,1H,J=6.3 Hz).

IR: νmax($CHCl_3$) 3450, 2935, 2855, 1720, 1515, 1460, 1410, 1335, 1220, 1145, 1090, 1050 $cm^{-1}$.

EXAMPLE 12

Preparation of 2-methoxy-1-octadecylcarbamoyloxy-3-(2-thiazolioethylsulfonylamino)propane iodide I a12

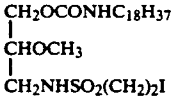

IIa4

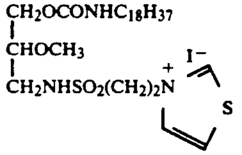

Ia12

A solution of 188 mg (0.296 mM) of 3-(2-iodoethylsulfonylamino)-2-methoxy-1-octadecylcarbamoyloxypropane in 2 ml of thiazole is stirred at 60° C. for 12 hours. After thiazole is evaporated, the residue is purified by the column chromatography on silica gel with a chloroform-methanol (5:1) mixture as an eluent. The product is recrystallized from ether-dichloromethane-acetone to give 30 mg (0.043 mM) of 2-methoxy-1- octadecylcarbamoyloxy-3-(2-thazolioethylsulfonylamino)propane iodide I a12 in 14% yield.

NMR: δ ppm($CDCl_3+CD_3OD$) 0.88(t,3H), 1.25(s,30H), 1.5(m,2H), 3.05~3.20(m,2H), 3.20~3.40(m,2H), 3.46(s,3H), 3.60(m,1H), 3.94(m, 2H), 4.0~4.3(m,2H), 5.2~5.4(m,2H), 5.55(m,1H), 6.82(m,1H), 8.17(d, 1H,J=3.8 Hz), 8.70(d,1H,J=3.8 Hz), 10.60~10.65(m,1H).

IR: νmax(KBr) 3360, 2920, 2850, 1700, 1535, 1460, 1335, 1255, 1150 $cm^{-1}$.

(14) Preparation of 3-(4-chlorobutylsulfonylamino)-2-methoxy-1-octadecylcarbamoyloxypropane III a5

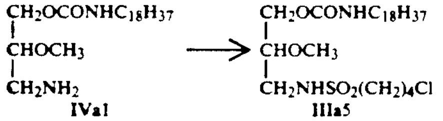

IVa1 IIIa5

To a solution of 1.2 g (3 mM) of 2-methoxy-3-octadecylcarbamoyloxypropylamine IV a1 in 24 ml of dichloromethane and 0.5 ml (3.6 mM) of triethylamine is added 0.75 g (3.93 mM) of 4-chlorobutanesulfonyl chloride with ice-cooling and the mixture is stirred at room temperature overnight. The product is isolated with dichloromethane extraction and dichloromethane layer is washed with saturated aqueous sodium hydrogencarbonate and saturated aqueous sodium chloride, dried over anhydrous magnesium sulfate, and evaporated. The residue is purified by the column chromatography on silica gel with a n-hexane-ethyl acetate (3:2) mixture as an eluent. The product is recrystallized from dichloromethane-n-hexane to give 1.28 g (2.305 mM) of 3-(4-chlorobutylsulfonylamino)-2-methoxy-1-octadecylcarbamoyloxypropane III a5 as colorless crystals in 77% yield.

NMR: δ ppm($CDCl_3$) 0.88(t,3H), 1.25(s,30H), 1.48(m,2H), 1.8~2.1(m,4H), 3.0~3.4(m,6H), 3.45(s,3H), 3.4~3.55(m,1H), 3.58(t,2H, J=6.0 Hz), 4.05~4.3(m,2H), 4.8(br,1H), 4.94 (t,1H,J=6 Hz).

IR: νmax($CHCl_3$) 3450, 2930, 2850, 1720, 1510, 1330, 1225, 1140, 1040 $cm^{-1}$.

Anal. Calcd. (%) for $C_{27}H_{55}O_5N_2SCl$: C 58.4, H 9.98, N 5.05, S 5.77, Cl 6.38, Found (%) C 58.15, H 9.91, N 5.16, S 5.89, Cl 6.71.

MS: 554($M^+$, $Cl^{35}$).

mp.: 57.5°~58.5° C.

(15) Preparation of 3-(4-iodobutylsulfonylamino)-2-methoxy-1-octadecylcarbamoyloxypropane II a5

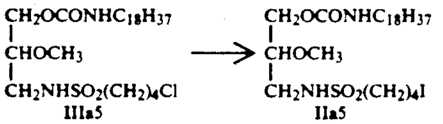

IIIa5 IIa5

To a solution of 1.23 g (2.22 mM) of 3-(4-chlorobutylsulfonylamino)-2-methoxy-1-octadecylcarbamoyloxypropane III a5 in 20 ml of methyl ethyl ketone is added 0.67 g (4.44 mM) of sodium iodide and the mixture is heated for 3 hours with stirring. After the solvent is evaporated, the residue is purified by the column chromatography on silica gel with a n-hexane-ethyl acetate (1:1) mixture as an eluent. The product is recrystallized from chloroform-n-hexane to give 1.16 g (1.79 mM) of 3-(4-iodobutylsulfonylamino)-2-methoxy-1-octadecylcarbamoyloxypropane II a5 in 81% yield.

NMR: δ ppm($CDCl_3$) 0.88(t,3H), 1.26(s,30H), 1.5(m,2H), 1.9~2.0(m,4H), 3.0~3.4(m,10H), 3.46(s,3H), 3.50(m,1H), 4.1~4.3(m,2H), 4.7(br,1H), 4.87(t,1H,J=6.6 Hz).

IR: νmax($CHCl_3$) 3450, 2925, 2850, 1720, 1510, 1330, 1230, 1140 $cm^{-1}$.

mp.: 71°~72° C.

Anal. Calcd. (%) for $C_{27}H_{55}O_5N_2SI$: C 50.15, H 8.57, N 4.33, S 4.96, I 19.62, Found (%) C 50.09, H 8.45, N 4.41, S 5.26, I 19.33.

MS: 647($M^+$).

EXAMPLE 13

Preparation of 2-methoxy-1-octadecylcarbamoyloxy-3-(4-thiazoliobutylsulfonylamino)propane iodide I a13

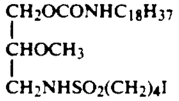

IIa5

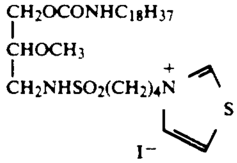

Ia13

A solution of 300 mg (0.464 mM) of 3-(4-idodobutylsulfonylamino)-2-methoxy-1-octadecylcarbamoyloxypropane in 3 ml of thiazole is stirred at 60° C. for 6 hours. After thiazole is evaporated, the residue is washed with ether and recrystallized from ether-dichloromethane to give 140 mg (0.191 mM) of 2-methoxy-1-octadecylcarbamoyloxy-3-(4-thiazoliobutylsulfonylamino)propane iodide I a13 in 41% yield.

NMR: δ ppm($CDCl_3$) 0.88(t,3H), 1.25(s,30H), 1.5(m,2H), 1.8~2.05(m,2H), 2.05~2.40(m,2H), 3.00~3.40(m,6H), 3.44(s,3H), 3.60(m,1H), 4.0~4.3(m,2H), 4.85(m,2H), 5.38(br,1H), 6.16(br,1H), 8.3~8.4(m,1H), 8.6~8.7(m,1H), 10.55(s,1H).

IR: νmax($CHCl_3$) 3400, 2930, 2850, 1715, 1465, 1430, 1320, 1235, 1140 $cm^{-1}$.

Anal. Calcd. (%) for $C_{30}H_{58}O_5N_3S_2I.0.5H_2O$: C 48.64, H 8.03, N 5.67, S 8.66, I 17.13, Found (%) C 48.46, H 7.99, N 5.77, S 8.87, I 17.02.

mp.: 59.5°~61.5° C.

EXAMPLES 14 TO 17

The compounds of the present invention shown in the following Table 2 are prepared from the compound II a5 by the same procedure as described in Example 2.

TABLE 2

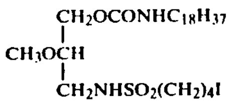
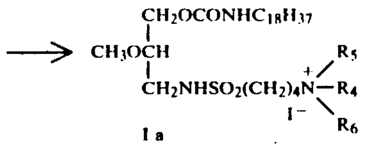

II a5 I a

| Ex. No. | Cpd. No. | S.M. II 5 [mg] | 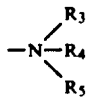 | Amine | Reaction Tempt. | Reaction Time | Purification | Yd. [mg] [%] | NMR: δ ppm | IRν max: [cm⁻¹] mp. [°C.] | Analysis Calcd. (%) Found (%) |
|---|---|---|---|---|---|---|---|---|---|---|---|
| 14 | Ia 14 | 650 | 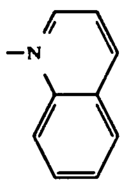 | Quinoline (3 ml) | 45° C. | 2 Days | The product dissolved in chlorofrom-methanol is washed with 5.7% HI and water. The solvent is evaporated and the residue is recrystallized from acetone. | 490 63% | ($CDCl_3$) 0.88(t, 3H), 1.25(s, 30H), 1.48(m, 2H), 2.0~2.5(m, 4H), 3.0~3.2(m, 2H), 3.2~3.4 (m, 4H), 3.42(s, 3H), 3.54(m, 1H), 4.0~4.3(m, 2H), 5.28(t, 1H, J=5.5Hz), 5.46(t, 2H, J=7.6 Hz), 5.85(t, 1H, J=6Hz), 7.97 (t, 1H, J=8.0Hz), 8.05~8.40(m, 3H), 8.68(d, 1H, J=9.6Hz), 9.01(d, 1H, J=8.2Hz), 10.25(d, 1H, J=5.4Hz). | ($CHCl_3$) 3450, 2925, 2850, 1715, 1520, 1460, 1325, 1220, 1140. 56.0~59.0 | ($C_{36}H_{62}O_5N_3SI.0.5H_2O$) C 55.09, H 8.09, N 5.35 S 4.08, I 16.17, C 54.88, H 7.95, N 5.41 S 4.33, I 16.25. |
| 15 | Ia 15 | 688 | 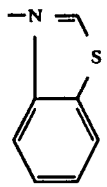 | Benzothiazole (2 ml) | 60° C. | Overnight | The product obtained by trituration with ether is recrystallized from acetone - ether. | 555 67% | ($CDCl_3$) 0.88(t, 3H), 1.25(s, 30H), 1.48(m, 2H), 2.0~2.25 (m, 2H), 2.25~2.50(m, 2H), 3.0~3.2(m, 2H), 3.2~3.4(m, 4H), 3.40(s, 3H), 3.57(m, 1H), 4.0~4.3(m, 2H), 5.10~5.35(m, 3H), 5.98(t, 1H, J=6Hz), 7.8~8.0(m, 2H), 8.3~8.45(m, 2H), 11.35(s, 1H). | ($CHCl_3$) 3450, 2930, 2850, 1715, 1510, 1460, 1430, 1330, 1220, 1140. 59.0~61.0 | ($C_{34}H_{60}O_6N_3S_2I.0.5H_2O$) C 51.63, H 7.77, N 5.31 S 8.10, I 16.05, C 51.43, H 7.83, N 5.38 S 8.39, I 16.02. |
| 16 | Ia 16 | 600 | 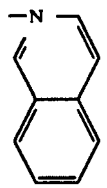 | Isoquinoline (2 ml) | 60° C. | Overnight | 1) Column chromatography on silica gel (Eluent:chloroform-methanol=5:1) 2) Recrystallization (Acetone - ether) | 542 75% | ($CDCl_3$) 0.88(t, 3H), 1.25 (s, 30H), 1.48(m, 2H), 1.95~2.15(m, 2H), 2.30~2.50(m, 2H), 3.0~3.2(m, 2H), 3.2~3.4(m, 4H), 3.41(s, 3H), 3.57(m, 1H), 4.0~4.3(m, 2H), 5.13(t, 2H, J=7.6Hz), 5.32(t, 1H, J=6Hz), 5.90(t, 1H, J=6Hz), 7.9~8.1(m, 1H), 8.1~8.2(m, 2H), 8.37(d, 1H, J=6.8Hz), 8.65(d, 1H, J=8.4 Hz), 8.86~8.98(m, 1H), 10.69 (s, 1H). | ($CHCl_3$) 3450, 2930, 2850, 1715, 1460, 1320, 1220, 1140. 59.0~60.0 (Decompose) | ($C_{36}H_{62}O_5N_3SI.0.1H_2O$) C 55.60, H 8.06, N 5.40 S 4.12, I 16.32, C 55.35, H 8.04, N 5.58 S 4.47, I 16.16. |

TABLE 2-continued
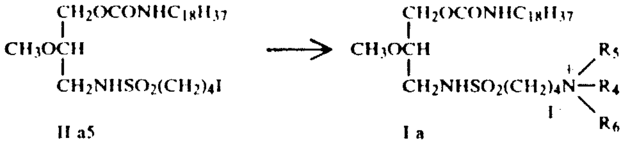
II a5 → I a
| Ex. No. | Cpd. No. | S.M. II 5 [mg] | 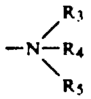 | Amine | Reaction Tempt. | Reaction Time | Purification | Yd. [mg] [%] | NMR: δ ppm | IRν max: [cm⁻¹] mp. [°C.] | Analysis Calcd. (%) Found (%) |
|---|---|---|---|---|---|---|---|---|---|---|---|
| 17 | Ia 17 | 650 | 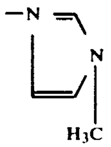 | N-methylimidazole (1.5 ml) | 25° C. | Overnight | After precipitated from acetone as a powder, the product is washed with ether. | 501 69% | ($CDCl_3$) 0.88(t, 3H), 1.25 (s, 30H), 1.49(m, 2H), 1.75 ~ 2.00(m, 2H), 2.0 ~ 2.2(m, 2H), 3.0 ~ 3.5(m, 6H), 3.44(s, 3H), 3.59(m, 1H), 4.06(s, 3H), 4.0 ~ 4.3(m, 2H), 4.47(t, 2H, J = 6.7Hz), 5.21(t, 1H, J = 6Hz), 5.93(t, 1H, J = 6Hz), 7.38(s, 1H), 7.62(s, 1H), 9.71(s, 1H). | ($CHCl_3$) 3450, 2920, 2850, 1715, 1460, 1325, 1220, 1140. | ($C_{31}H_{62}O_5N_4SI$) C 51.09, H 8.44, N 7.69 S 4.40, I 17.41, C 50.79, H 8.36, N 7.67 S 4.71, I 17.41. |

EXAMPLE 18

Preparation of 2-methoxy-1-octadecylcarbamoyloxy-3-(4-quinoliobutylsulfonylamino)propane chloride I a18

IIa5

Ia18

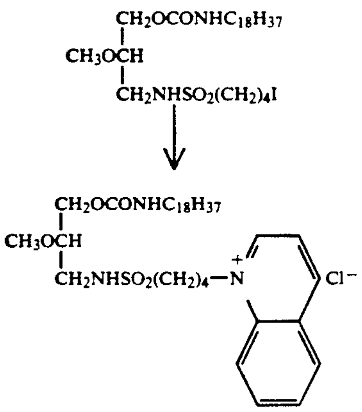

A solution of 1.57 g (2.43 mM) of 3-(4-iodobutylsulfonylamino)-2-methoxy-1-octadecylcarbamoyloxypropane in 3 ml of quinoline is stirred at 40° C. for 3 days. The product is isolated by extraction with a chloroform-methanol mixture and the organic layer is washed with 1N-hydrochloric acid twice. After the solvent is evaporated, the residue is recrystallized from acetone to give 1.07 g (1.56 mM) of 2-methoxy-1-octadecylcarbamoyloxy-3-(4-quinoliobutylsulfonylamino)propane chloride I a18 in 64% yield.

NMR: δ ppm($CDCl_3$) 0.88(t,3H), 1.25(s,30H), 1.48(m,2H), 2.0~2.3(m,2H), 2.3~2.5(m,2H), 3.0~3.2(m,2H), 3.2~3.4(m,4H), 3.39(s, 3H), 3.58(m,1H), 4.0~4.3(m,2H), 5.40~5.65(m,3H), 6.85(t,1H,J=7 Hz), 7.93(t,1H,J=7.2 Hz), 8.0~8.4(m,3H), 8.65(d,1H,J=9 Hz), 9.01(d,1H, J=8.2 Hz), 10.35(d,1H,J=5.2 Hz).

IR: νmax($CHCl_3$) 3450, 2925, 2850, 1715, 1520, 1465, 1320, 1220, 1140.

mp.: 57.0°~59.0° C.

Anal. Calcd. (%) for $C_{36}H_{62}O_5N_3SCl.1.5H_2O$: C 60.78, H 9.21, N 5.91, S 4.51, Cl 4.98, Found (%): C 60.94, H 9.02, N 5.91, S 4.78, Cl 4.58.

mp. 57° C. to 59° C.

EXAMPLE 19

Preparation of 3-(4-benzothiazoliobutylsulfonylamino)-2-methoxy-1-octadecylcarbamoyloxypropane chloride I a19

Ia15

Ia19

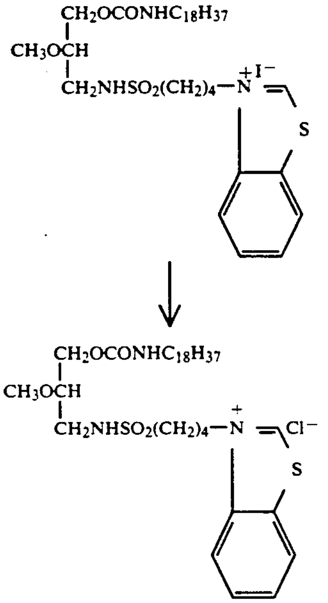

A solution of 300 mg (0.384 mM) of 3-(4-benzothiazoliobutylsulfonylamino)-2-methoxy-1-octadecylcarbamoyloxypropane iodide I a15 in a chloroform-methanol mixture is washed with aqueous 1N-hydrochloric acid twice and with water once and the solvent is evaporated. The residue is recrystallized from dichloromethane-acetone to give 65 mg (0.0941 mM) of 3-(4-benzothiazoliobutylsulfonylamino)-2-methoxy-1-octadecylcarbamoyloxypropane chloride I a19 in 25% yield.

NMR δ ppm($CDCl_3$): 0.88(t,3H), 1.25(s,30H), 2.2~2.4(m,1H), 2.0~2.2(m,2H), 2.2~2.4(m,2H), 3.0~3.2(m,2H), 3.2~3.4(m,4H), 3.38(s, 3H), 3.55(m,1H), 4.0~4.3(m,2H), 5.25(m,2H), 5.52(br,1H), 6.80(br, 1H), 7.70~7.95(m,2H), 8.2~8.4(m,2H), 11.80(s,1H).

IR νmax($CHCl_3$): 3450, 2940, 2855, 1715, 1515, 1465, 1435, 1330, 1220, 1140 $cm^{-1}$.

mp.: 57.0°~59.0° C.

Anal. Calcd. (%) for $C_{36}H_{62}O_5N_3SCl.1.5H_2O$: C 56.92, H 8.85, N 5.86, S 8.94, Cl 4.94, Found (%) C 56.72, H 8.71, N 6.05, S 8.97, Cl 4.68.

EXAMPLES 20 TO 21

The compounds shown in Table 3 are prepared in the same manner as in Example 19.

TABLE 3

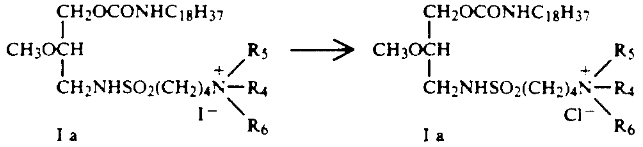

| Ex. No. | Cpd. No. | 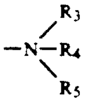 | Yd. | NMR: δ ppm | IRν max [cm⁻¹] mp. [°C.] | Analysis Calcd. (%) Found (%) |
|---|---|---|---|---|---|---|
| 20 | Ia 20 | 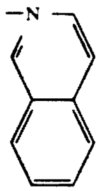 | 59% | ($CDCl_3$) 0.88(t, 3H), 1.25(s, 30H), 1.46(m, 2H), 1.95~2.15(m, 2H), 2.25~2.45(m, 2H), 3.0~3.2(m, 2H), 3.2~3.4(m, 4H), 3.37(s, 3H), 3.55(m, 1H), 4.0~4.3 (m, 2H), 5.16(t, 2H, J=7.5Hz), 5.63(br, 1H), 6.9(br, 1H), 7.85~8.0(m, 1H), 8.0~8.16(m, 2H), 8.30(d, 1H, J=6.8Hz), 8.64(d, 1H, J=7.8Hz), 8.94(d, 1H, J=6.8Hz), 10.76(s, 1H). | ($CHCl_3$) 3450, 2920, 2845, 1710, 1510, 1460, 1320, 1220, 1135. 56.0~57.0 | ($C_{36}H_{62}O_6N_3SCl.1.5H_2O$) C 60.78, H 9.21, N 5.91, S 4.51, Cl 4.98, C 60.80, H 9.11, N 5.99, S 4.51, Cl 4.98. |
| 21 | Ia 21 | 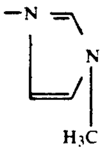 | 43% | ($CDCl_3$) 0.88(t, 3H), 1.25(s, 30H), 1.48(m, 2H), 1.8~2.0(m, 2H), 2.0~2.2(m, 2H), 3.0~3.3(m, 6H), 3.42(s, 3H), 3.59(m, 1H), 4.04(s, 3H), 4.0~4.28(m, 2H), 4.45 (t, 2H, J=6.6Hz), 5.50(t, 1H, J=6Hz), 6.96(t, 1H, J=7Hz), 7.41(s, 1H), 7.61(s, 1H), 10.01(s, 1H). | ($CHCl_3$) 3450, 2920, 2850, 1710, 1460, 1320, 1220, 1135. 58.5~59.5 | ($C_{31}H_{62}O_5N_4SCl.2.3H_2O$) C 54.85, H 9.74, N 8.25, S 4.72, Cl 5.22, C 54.67, H 9.50, N 8.28, S 5.01, Cl 5.47. |

EXAMPLES 22 to 23

The compounds shown in Table 4 are prepared by the same procedure as described in Example 9.

TABLE 4

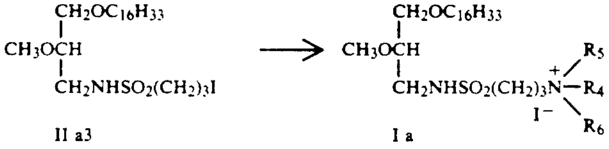

| Ex. No. | Cpd. No. | 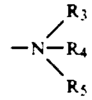 | Amine | NMR: δ ppm | IRν max [cm⁻¹] |
|---|---|---|---|---|---|
| 22 | Ia 22 | 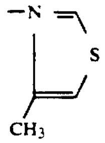 | | ($CDCl_3$) 0.88(t, 3H), 1.26(s, 26H), 1.55(m, 2H), 2.45~2.65(m, 2H), 2.70(s, 3H), 3.15~3.60(m, 9H), 3.45(s, 3H), 4.92(t, 2H, J=8.0Hz), 5.88(t, 1H, J=6Hz), 7.78~7.82(m, 1H), 10.90(d, 1H, J=2.8Hz). | ($CHCl_3$) 3370, 2925, 2850, 1465, 1440, 1325, 1210, 1140. |
| 23 | Ia 23 | 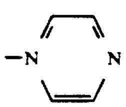 | | ($CDCl_3$) 0.88(t, 3H), 1.26(s, 26H), 1.56(m, 2H), 2.55~2.80(m, 2H), 3.0~3.6(m, 9H), 3.44(s, 3H), 5.18(t, 2H, J=7.6Hz), 6.26(t, 1H, J=6Hz), 9.54(s, 4H). | ($CHCl_3$) 2925, 2850, 1440, 1320, 1210, 1135, 720. |

(16) Preparation of 3-benzyloxy-1-hydroxy-2-methoxypropane IX 6

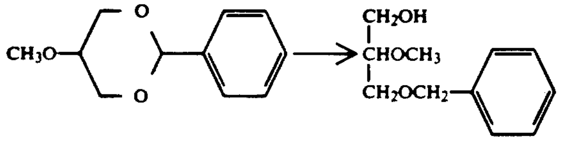

X6 IX6

To a suspension of 18.98 g (0.5 mol) of lithium aluminumhydride in 400 ml of ether is added dropwise a solution of 66.69 g (0.5 mol) of aluminium chloride in 250 ml of ether at −40° C. and the mixture is stirred at −20° C. for 30 minutes. To the reaction mixture is added a solution of β-methyl-αγ-benzilideneglycol X 6 [described in P. E. Verkade, et al., Recl. Trav. Chim. Pays. Bas., 61, 831, (1942)] in 200 ml of dichloromethane at such a rate that the reaction temperature is kept below −20° C. After warming up to room temperature gradually, the mixture is stirred for 2 hours. A saturated aqueous solution of sodium sulfate is added to the reaction mixture with ice-cooling and the resulting white percipitate is removed by the filtration. The filtrate is concentrated under reduced pressure and the residue is distilled under reduced pressure to give 47.1 g of the titled compound IX 6 in 96% yield as a distilate at 133° C. (2 to 3 mm Hg).

NMR: δ ppm ($CDCl_3$) 2.44(s,1H), 3.38~3.52(m,1H), 3.45(s,3H), 3.53~3.83(m,4H), 4.53(s,2H), 7.32(s,5H).

(17) Preparation of 1-acetylthio-3-benzlyoxy-2-methoxypropane VII 6

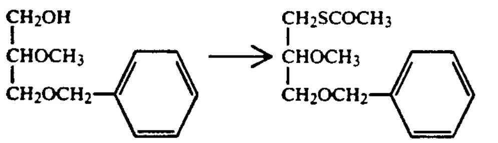

IX6 VIII6

To a solution of 14.7 g (75 mM) of dl-3-benzyloxy-2-methoxypropylalcohol IX 6 and 12.53 ml (90 mM) of triethylamine in 150 ml of dichloromethane is added 6.08 ml (78.75 mM) of methanesulfonyl chloride with ice-cooling and the mixture is stirred at room temperature for an hour. The product is isolated by dichloromethane extraction and the dichloromethane layer is washed with water, dried, and evaporated to give the crude mesylate IX 6'. To a solution of the above crude mesylate IX 6' in 200 ml of acetonitrile is added 8.994 g (78.75 mM) of potassium thioacetate and the mixture is heated under reflux for 15 hours. After cooling, the reaction mixture is poured into water and the product is isolated by ethyl acetate extraction. The ethyl acetate layer is washed with water, dried, and evaporated. The oily residue is distilled under reduced pressure to give 16.92 g (67 mM) of the titled compound, 1-acetylthio-3-benzyloxy-2-methoxypropane VII 6 as a distillates of bp. 130° C. to 137° C. (2 mmHg) in 89% yield.

NMR δ ppm ($CDCl_3$): 2.34(s,3H), 3.13(d,2H,J=5.6 Hz), 3.43~3.58(m, 3H), 4.55(s,2H), 7.33(s,5H).

IR ν max ($CHCl_3$): 3000, 2930, 2850, 2820, 1685, 1450, 1355, 1100 $cm^{-1}$.

(18) Preparation of 3-benzyloxy-2-methoxypropylthioalcohol VII 6

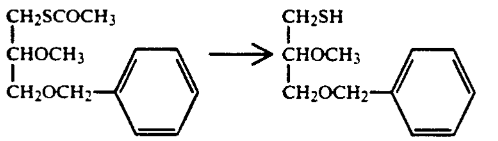

VIII6 VII6

To a solution of 14.028 g (55 mM) of acetylthio-3-benzyloxy-2-methoxypropane VII 6 in 300 ml of methanol is added dropwise 11.24 ml (58.3 mM) of 28 weight % solution of sodium methoxide in methanol at −10° C. After the mixture is stirred at −10° C. to 0° C. for 2 hours, 3.58 ml of methanesulfonic acid is added. The reaction mixture is poured into water and the product is isolated by ethyl acetate extraction. The ethyl acetate layer is washed with water, dried, and evaporated. The oily residue is purified by column chromatography on silica gel using an ether-n-hexane (3:97) mixture as an eluent to give 8.85 g (41.7 mM) of the titled compound, 3-benzyloxy-2-methoxypropylthioalcohol VII 6 as an oil.

NMR δ ppm ($CDCl_3$): 1.49(t,1H,J=8.5 Hz), 2.58~2.87(m,2H), 3.40~3.53(m,1H), 3.44(s,3H), 3.56~3.63(m,2H), 4.55(s,2H), 7.34(s,5H).

IR ν max ($CHCl_3$): 3000, 2940, 2860, 2820, 1455, 1365, 1100 $cm^{-1}$.

(19) Preparation of 3-benzyloxy-2-methoxy-1-octadecylcarbamoylthiopropane VI 6

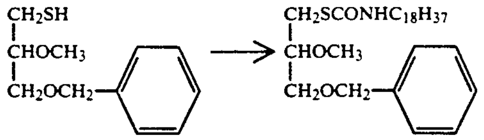

VII6 VI6

A solution of 7.258 g (34.2 mM) of 3-benzyloxy-2-methoxypropylthioalcohol VII 6 and 11.65 g (39.4 mM) of octadecylisocyanate in 100 ml of pyridine is heated under reflux for 1 hour. The reaction mixture is concentrated and the residue is purified by column chromatography on silica gel using a toluene-ethyl acetate (9:1 to 4:1) mixture as an eluent to give 17.027 g (33.6 mM) of the titled compound, 3-benzyloxy-2-methoxy-1-octadecylcarbamoylthiopropane VI 6 as a solid in 98% yield.

NMR δ ppm ($CDCl_3$): 0.88(t,3H), 1.25(s,30H), 1.40~1.60(m,2H), 3.10~3.19(m,2H), 3.19~3.34(m,2H), 3.46(s,3H), 3.50~3.62(m,3H), 4.56(s,2H), 5.37~5.50(broad,1H), 7.33(s,5H).

mp. 40°~41° C.

Anal. Calcd. (%) for $C_{30}H_{53}O_3NS$: C 70.96, H 10.52, N 2.76, S 6.31, Found (%): C 70.90, H 10.50, N 2.76, S 6.31, Found (%): C 70.90, H 10.50, N 2.91, S 5.99.

(20) Preparation of 3-octadecylcarbamoylthio-2-methoxypropylalcohol V a6

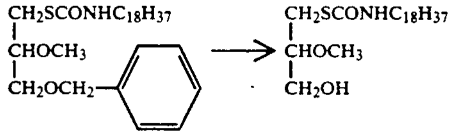

VI6 Va6

To a solution of 1.02 g (2 mM) of 3-benzyloxy-2-methoxy-1-octadcylcarbamoylthiopropane VI a6 in 80 ml of acetonitrile is added 0.4 ml (2.81 mM) of trimethylsilyl iodide with ice-cooling and the mixture is allowed to stand at room temperature for 15 hours. To the reaction mixture is added 50 ml of 10% aqueous solution of sodium thiosulfate and the product is isolated with dichloromethane extraction. The dichloromethane layer is washed with water, dried, and evaporated. The residue is purified by column chromatography on silica gel using a n-hexane-ethyl acetate (2:1) mixture as an eluent to give 480 mg (1.15 mM) of the titled compound, 3-octadecylcarbamoylthio-2-methoxypropylalcohol V a6 as a solid in 57% yield.

NMR δ ppm ($CDCl_3$): 0.88(t,3H), 1.26(s,30H), 1.42~1.60(m,2H), 2.75~2.97(broad,1H), 2.98~3.38(m,1H), 3.44(s,3H), 3.38~3.52(m,1H), 3.52~3.75(m,2H), 5.42~5.63(broad, 1H).

mp. 62°~63° C.

IR ν max ($CHCl_3$) 3430, 2920, 2850, 1655, 1500, 1465, 1190, 1100, 1045 $cm^{-1}$ Anal. Calcd. (%) for $C_{23}H_{47}NSO_3$: C 66.14, H 11.34, N 3.35, S 7.68, Found (%): C 65.78, H 11.34, N 3.31, S 7.50.

(21) Preparation of 2-methoxy-3-octadecylcarbamoylthiopropylamine IV a6

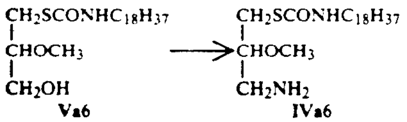

Va6 IVa6

To a solution of 417.7 mg (1 mM) of 2-methoxy-3-octadecylcarbamoylthiopropylalcohol V a6, 229.2 mg (1.5 mM) of phthalimide, and 408.6 mg (1.5 mM) of triphenylphophine in 15 ml of tetrahydrofuran, which is cooled to −30° C., is added dropwise 271.2 mg (1.5 mM) of diethyl azodicarboxylate and the mixture is stirred for 30 minutes, and at room temperature for additional 2 hours. After the solvent is evaporated, the residue is purified by the column chromatography on silica gel with a benzene-ethyl acetate (9:1) mixture as an eluent to give 400 mg (0.732 mM) of the phthalimide-compound in 73% yield.

To a solution of 1.091 g (1.864 mM) of the phthalimide-compound in 30 ml of ethanol and 10 ml of tetrahydrofuran is added 2.5 ml of hydrazine monohydrate and the mixture is stirred at room temperature for 3 hours. After the solvent is evaporated, the residue is purified by the column chromatography on silica gel with a chloroform-methanol (5:1) mixture as an (0.2% triethylamine) eluent to give 418.3 mg (1.003 mM) of 2-methoxy-3-octadecylcarbamoylthiopropylamine IV a6 in 54% yield.

NMR δ ppm ($CDCl_3+CD_3OD$): 0.88(t,3H), 1.26(s,30H), 1.40~1.62(m, 2H), 2.65~2.94(m,2H), 2.95~3.17(m,1H), 3.17~3.30(m,2H), 3.30~3.42(m,1H), 3.45(s,3H).

IR ν max ($CHCl_3$): 3425, 2930, 2850, 1665, 1500, 1190, 1100 $cm^{-1}$.

(22) Preparation of 3-(3-chloropropylsulfonylamino)-2-methoxy-1-octadecylcarbamoylthiopropane III a6

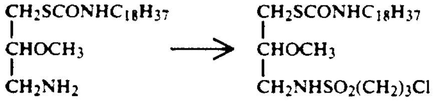

IVa6 IIIa6

To a solution of 93 mg (0.223 mM) of 2-methoxy-3-octadecylcarbamoylthiopropylamine IV a6 and 40.4 μl (3.9 mM) of triethylamine in 5 ml of dichloromethane and 2 ml of tetrahydrofuran is added 29.8 μl (3.3 mM) of 3-chloropropanesulfonyl chloride with ice-cooling, and the mixture is stirred for 2 hours and at room temperature for an additional 30 minutes. The product is isolated by dichloromethane extraction and the dichloromethane layer is washed with an aqueous sodium hydrogencarbonate and a saturated aqueous solution of sodium chloride, dried over anhydrous magnesium sulfate, and evaporated. The residue is purified by the column chromatography on silica gel with a benzene-ethyl acetate (4:1) mixture as an eluent to give 83 mg (0.149 mM) of 3-(3-chloropropylsulfonylamino)-2-methoxy-1-octadecylcarbamoylthiopropane III a6 as a colorless powder in 67% yield.

NMR: δ ppm ($CDCl_3$) 0.88(t,3H), 1.26(s,30H), 1.40~1.60(m,2H), 2.20~2.37(m,2H), 2.93~3.40(m,8H), 3.40~3.55(m,1H), 3.43(s,3H), 3.69(t,J=5.3 Hz,2H), 5.17~5.35(broad,1H), 5.37~5.54(broad,1H).

IR: ν max ($CHCl_3$) 3420, 2930, 2850, 1670, 1495, 1460, 1335, 1185, 1150, 1090 $cm^{-1}$.

(23) Preparation of 3-(3-iodopropylsulfonylamino)-2-methoxy-1-octadecylcarbamoylthiopropane II a6

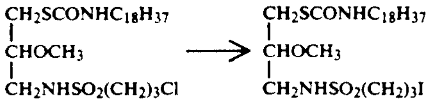

IIIa6 IIa6

To a solution of 197 mg (0.354 mM) of 3-(3-chloropropylsulfonylamino)-2-methoxy-1-octadecylcarbamoylthiopropane III a6 in 7 ml of methyl ethyl ketone is added 265 mg (1.77 mM) of sodium iodide and the mixture is heated under refluxing for 3 hours with stirring. After the solvent is evaporated, the residue is purified by the column chromatography on silica gel with a n-hexane-ethyl acetate (3:1) mixture as an eluent to give 197 mg (0.304 mM) of 3-(3-iodopropylsulfonylamino)-2-methoxy-1-octadecylcarbamoylthiopropane II a6 in 86% yield.

NMR: δ ppm ($CDCl_3$) 0.88(t,3H), 1.26(s,30H), 1.42~1.62(m,2H), 2.25~2.42(m,2H), 2.95~3.50(m,8H), 3.44(s,3H), 3.50~3.58(m,1H), 5.18~5.34(broad,1H), 5.38~5.57(broad,1H).

IR: ν max ($CHCl_3$) 3425, 2925, 2850, 1670, 1500, 1460, 1325, 1185, 1140, 1100 $cm^{-1}$.

EXAMPLE 24

Preparation of 2-methoxy-1-octadecylcarbamoylthio-3-(3-N-methylimidazoliniopropylsulfonylamino)propane iodide I a24

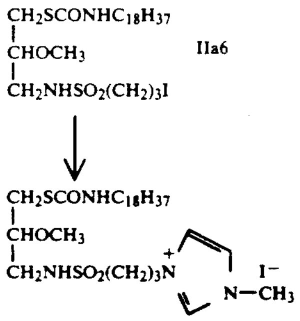

IIa6

Ia24

A solution of 100 mg of 3-(3-iodopropylsulfonylamino)-2-methoxy-1-octadecylcarbamoylthiopropane II a6 in 0.3 ml of N-methylimidazole is stirred at 25° C. overnight. After the solvent is evaporated, the residue is washed with water to give 102 mg of 2-methoxy-1-octadecylcarbamoylthio-3-(3-N-methylimidazoliniopropylsulfonylamino)propane iodide I a24 in 91% yield.

NMR: δ ppm($CDCl_3$) 0.88(t,3H), 1.26(s,30H), 1.45~1.65(m,2H), 2.40~2.63(m,2H), 2.93~3.40(m,8H), 3.43(s,3H), 3.45~3.60(m,1H), 4.06(s,3H), 4.63(m,2H), 5.96~6.24(broad,2H), 7.38(s,1H), 7.71(s,1H), 9.66(s,1H).

IR: ν max ($CHCl_3$) 3430, 3150, 2920, 2850, 1670, 1495, 1460, 1320, 1140, 1095 $cm^{-1}$.

EXAMPLE 25

Preparation of 2-methoxy-1-octadecylcarbamoylthio-3-(3-quinoliniopropylsulfonylamino)propane iodide I a25

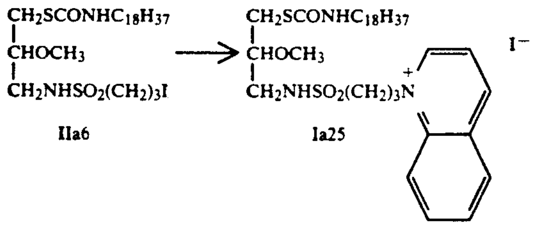

IIa6 Ia25

A solution of 88 mg (0.136 mM) of 3-(3-iodopropylsulfonylamino)-2-methoxy-1-octadecylcarbamoylthiopropane II a6 in 1 ml of quinoline is stirred at 45° C. for 2 days and the product is isolated by extraction with a mixture of chloroform-methanol and the organic layer is washed with 5.7% hydroiodic acid twice and with water once and the solvent is evaporated. The residue is recrystallized from acetone to give 2-methoxy-1-octadecylcarbamoylthio-3-(3-quinoliniopropylsulfonylamino)propane iodide I a25

NMR: δ ppm ($CDCl_3$) 0.88(t,3H), 1.25(s,30H), 1.40~1.62(m,2H), 2.62~2.85(m,2H), 2.90~3.65(m,9H), 3.39(s,3H), 5.56(t,2H,J=8.1 Hz), 5.80~6.25(broad,2H), 7.99(t,1H,J=7.4 Hz), 8.13~8.37(m,3H), 8.67(d,1H,J=8.8 Hz), 9.07(d,1H,J=8.2 Hz), 10.14(d,1H,J=5.2 Hz).

IR: ν max ($CHCl_3$) 3430, 2930, 2855, 1670, 1500, 1465, 1330, 1150 $cm^{-1}$.

EXAMPLE 26

Preparation of 2-methoxy-1-octadecylcarbamoylthio-3-(3-thiazoliniopropylsulfonylamino)propane iodide I a26

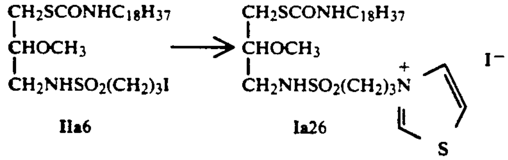

IIa6 Ia26

A solution of 76 mg of 3-(3-iodopropylsulfonylamino)-2-methoxy-1-octadecylcarbamoylthiopropane II a6 in 1 ml of thiazole is heated at 60° C. for 6 hours. After the solvent is evaporated, the residue is washed with ether and subsequently with acetonitrile to give 32 mg of 2-methoxy-1-octadecylcarbamoylthio-3-(3-thiazoliniopropylsulfonylamino)propane iodide I a26 in 37% yield.

NMR: δ ppm ($CDCl_3$) 0.88(t,3H), 1.25(s,30H), 1.40~1.62(2H), 2.50~2.75(m,2H), 2.95~3.60(m,9H), 3.42(s,3H), 4.95~5.20(m,2H), 6.07~6.29(m,2H), 8.20~8.30(m,1H), 9.70~9.80(m,1H), 10.20~10.32(m,1H).

IR: ν max ($CHCl_3$) 3420, 2925, 2850, 1670, 1500, 1465, 1330, 1150 $cm^{-1}$.

EXAMPLE 27

Preparation of 2-methoxy-1-octadecylcarbamoylthio-3-(4-quinoliniopropylsulfonyamino)propane chloride I a27

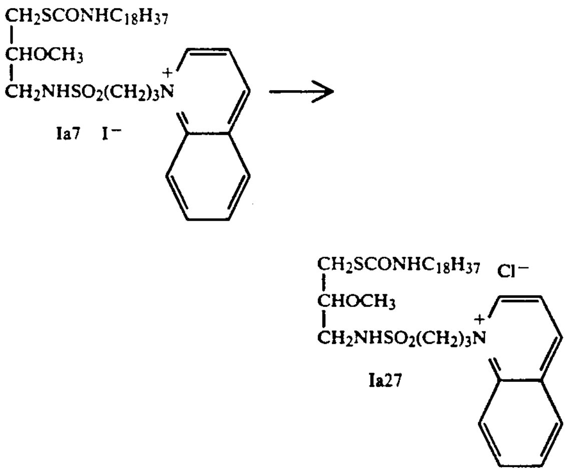

Ia7 Ia27

The titled compound is prepared in by the same procedure as described in Example 19.

NMR: δ ppm ($CDCl_3$) 0.88(t,3H), 1.25(s,30H), 1.48(m,2H), 2.15~2.35(m,2H), 3.0~3.2(m,2H), 3.2~3.35(m,2H), 3.37(s,3H), 3.35~3.50(m,1H), 3.50~3.70(m,2H), 4.00~4.30(m,2H), 5.55~5.80(m,3H), 7.75(t,1H,J=6 Hz), 7.94(t,1H, J=7.6 Hz), 8.15~8.40(m,3H), 8.74(d,1H, J=9.0 Hz), 8.97(d,1H,J=8.2 Hz), 10.48(d,1H,J=5.6 Hz).

IR: ν max ($CHCl_3$) 3455, 2930, 2855, 1715, 1530, 1470, 1325, 1220, 1140 $cm^{-1}$.

m.p. 57°~59° C.

Anal. Calcd. (%) for $C_{35}H_{60}O_5N_3SCl.1.2H_2O$: C 60.75, H 9.09, N 6.07, S 4.63, Cl 5.12, Found (%): C 60.66, H 9.09, N 6.23, S 4.51, Cl 4.89.

EXAMPLE 28

Preparation of 1-(N-n-octadecylcarbamoyloxy)-2-methoxy-3-[4-[3-carboxylatepyridinio]butylsulfonylamino]propane I a28

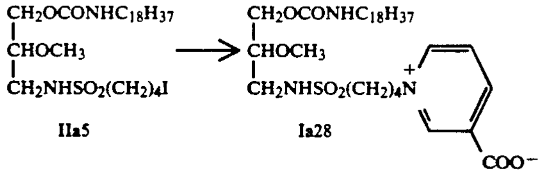

IIa5 Ia28

A solution of 600 mg (0.928 mmol) of 3-(4-iodobutylsulfonylamino)-2-methoxy-1-octadecylcarbamoyloxypropane and 230 mg (1.87 mmol) of nicotinic acid in 10 ml of dimethylsulfoxide is heated at 80° C. for 3 days. The product is isolated by dichloromethane extraction and dichloromethane layer is washed once with a 1N-hydrochloric acid, saturated aqueous solution of sodium hydrogencarbonate, and saturated aqueous solution of sodium chloride and evaporated. The residue is recrystallized from dichloromethane -acetone mixture to give 279 mg (0.435 mmol) of 1-(N-n-octadecylcarbamoyloxy)-2-methoxy-3-[4-[carboxylatepyridinio]-butylsulfonylamino]propane I a28 in 47% yield.

NMR: δ ppm ($CDCl_3$) 0.88(t,3H), 1.25(s,30H), 1.48(m,2H), 1.65~1.95(m, 2H), 1.95~2.25(m,2H), 2.9~3.3(m,6H), 3.36(s,3H), 3.50(m,1H), 3.9~4.3(m,2H), 4.6~4.9(m,2H), 5.65~5.80(m,1H), 7.20~7.50(m,1H), 7.90~8.10(m,1H), 8.70~8.90(m,1H), 8.90~9.10(m,1H), 9.25~9.50 (m,1H).

IR: ν max($CHCl_3$) 3450, 2920, 2850, 1710, 1640, 1615, 1510, 1460, 1360, 1210, 1135 $cm^{-1}$.

Anal. Calcd. (%) for $C_{33}H_{59}O_7N_3S.1.2H_2O$: C 59.74, H 9.33, N 6.33, S 4.83, ; Found (%): C, 59.61, H 9.36, N 6.26, S 4.63.

(23) Preparation of 2-aminomethyl-2-hexadecylthiomethyltetrahydrofuran IV b1

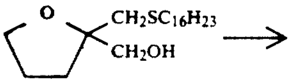

Vb1

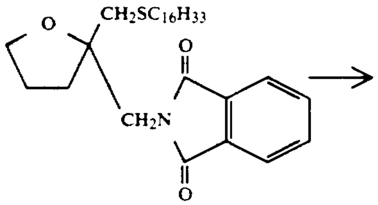

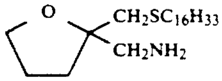

IVb1

2-Hexadecylthiomethyl-2-hydroxymethyltetrahydrofuran IV b1 is allowed to react and worked by the same procedure as described in (3), the summary of the experimental condition and the physical data of the product are listed in the Tables 5 and 6.

(24) Preparation of 2-(3-chloropropylsulfonylaminomethyl)-2-hexadecylthiomethyltetrahydrofuran III b1

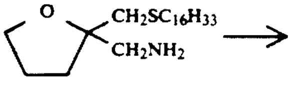

IVb1

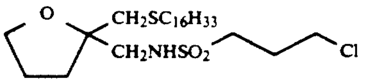

IIIb1

2-Aminomethyl-2-hexadecylthiomethyltetrahydrofuran IV b1 is allowed to react and worked by the same procedure as described in (4). m.p. 44.5° to 45.5° C. The summary of the experimental condition and the physical data of the product are listed in the Table 7.

(25) Preparation of 2-hexadecylthiomethyl-2-(iodopropylsulfonylmethyl)-tetrahydrofuran II b1

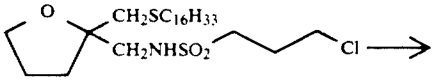

IIIb1

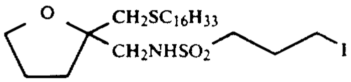

IIb1

2-(3-Chloropropylsulfonylaminomethyl)-2-hexadecylthiomethyltetrahydrofuran III b1 is allowed to react and worked by the same procedure as described in (5). m.p. 36° to 37° C. The summary of the experimental condition and the physical data of the product are listed in the Table 8.

EXAMPLE 29

Preparation of 2-hexadecylthiomethyl-2-(3-trimethylammoniopropylsulfonylaminomethyl)tetrahydrofuran I b1

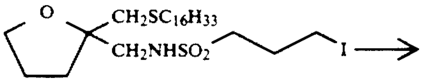

IIb1

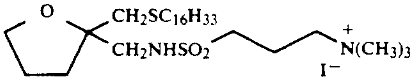

Ib1

2-hexadecylthiomethyl-2-(3-iodopropylsulfonylaminomethyl)tetrahydrofuran is allowed to react and worked by the same procedure as described in Example 8. The summary of the experimental condition and the physical data of the product are listed in the Table 9.

(26) Preparation of 2-aminomethyl-2-octadecylcarbamoyloxymethyltetrafuran IV b2

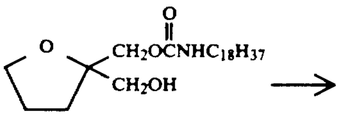

Vb2

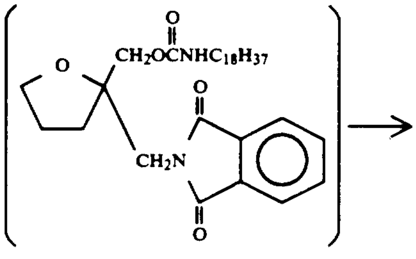

-continued

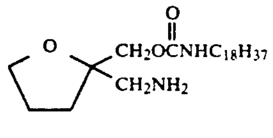

IVb2

2-Hydroxymethyl-2-octadecylcarbamoyloxymethyl-tetrahydrofuran is allowed to react and worked by the same procedure as described in (3). m.p. (The phthalimido compound) 91° to 92° C. The summary of the experimental condition and the physical data of the product are listed in the Tables 5 and 6.

(27) Preparation of 2-(3-chloropropylsulfonylaminomethyl)-2-octadecylcarbamoyloxymethyltetrahydrofuran III b2

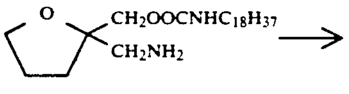

IVb2

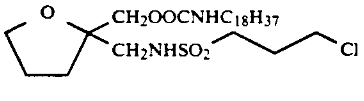

IIIb2

2-Aminomethyl-2-octadecylcarbamoyloxymethyltetrahydrofuran IV b2 is allowed to react and worked by the same procedure as described in (4). The summary of the experimental condition and the physical data of the product are listed in the Table 7.

(28) Preparation of 2-(3-iodopropylsulfonylaminomethyl)-2-octadecylcarbamoyloxymethyltetrahydrofuran II b2

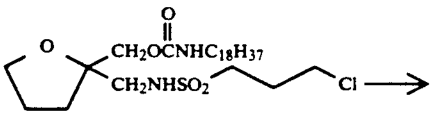

IIIb2

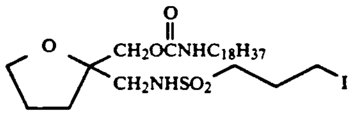

IIb2

2-(3-Chloropropylsulfonylaminomethyl)-2-octadecylcarbamoylmethyltetahydrofuran is allowed to react and worked by the same procedure as described in (5). m.p. 66.5° to 67.5° C. The summary of the experimental condition and the physical data of the product are listed in the Table 8.

EXAMPLE 30

Preparation of 2-octadecylcarbamoyloxymethyl-2-(3-qunolinioproylsulfonylaminomethyl)tetrahydrofuran iodido I b2

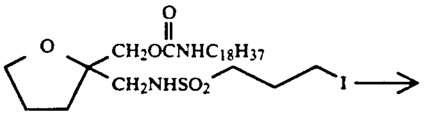

IIb2

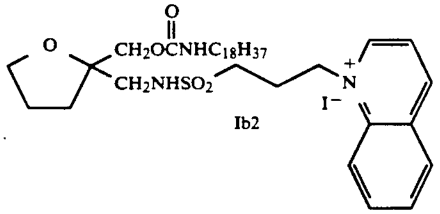

Ib2

2-(3-iodopropylsulfonylaminomethyl)-2-octadecylcarbamoyloxymethyltetrahydrofuran II b2 is allowed to react and worked by the same procedure as described in Example 25. The summary of the experimental condition and the physical data of the product are listed in the Table 10.

(29) Preparation of 3-hexadecylthio-2-methylcarbamoyloxypropanol V c1

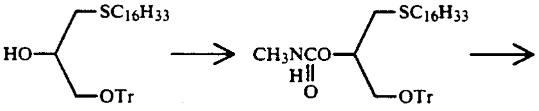

c1 c2

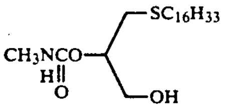

Vc1

To a solution of 1-hexadecylthio-3-trityloxy-2-propanol c1 4.6 g (8.0 mmol) in dichloromethane 100 ml are added 4-dimethylaminopyridine 1.17 g (9.6 mmol) and methyl isocyanate 4.72 ml (80 mmol). The solution is allowed to stand at room temperature for 72 hr and concentrated. The residue is chromatographed on $SiO_2$ (46 g) and eluted with ethyl acetate:hexane (1:5) to give 1-hexadecylthio-2-methylcarbamoyloxy-3-trityloxypropane c2 as a crude oil (5.6 g). The oil is dissolved in dichloromethane 100 ml and boron trifluoride-methanol complex 1.68 ml (15.5 mmol) is added under cooling. The resulting yellow solution is stirred at 0° C. for 15 min and then at room temperature for 1 hr. Sodium carbonate aq solution is added to neutralize the reaction mixture and an organic layer is separated. The organic layer is subjected to $SiO_2$ (80 g) column chromatography and eluted with ethyl acetate:hexane (1:1) to afford crude crystals 2.07 g. The crystals are triturated and washed with pentane to yield the titled compound V c1 1.205 g. The mother liquor is purified by Lobar column chromatography with the same solvent as described above to give additional V c1 0.321 g (49% total yield), mp. 53°-55° C.

NMR:δ($CDCl_3$) 0.80~1.70 (m, 31H), 2.22 (br.s, 1H), 2.50~2.75 (m, 4H), 2.80 (d, J=5 Hz, 3H), 3.82 (m, 2H), 4.85 (br.m, 2H).

(30) Preparation of 3-hexadecylthio-2-methylcarbamoyloxypropylamine IV c1

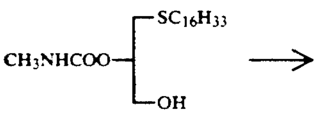

Vc1

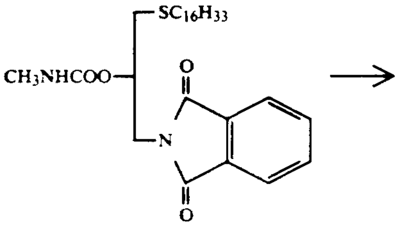

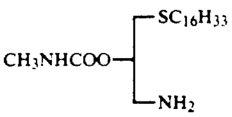

IVc1

3-Hexadecylthio-2-methylcarbamoyloxypropanol is allowed to react and worked up by the same procedure as described in (3). The summary of the experimental condition and the physical data of the product are listed in the Tables 5 and 6.

The crude phthalimide compound is recrystallizied from methanol-dichloromethane (10:1).

(31) Preparation of 3-(3-chloropropylsulfonylamino)-1-hexadecylthio-2-methylcarbamoyloxypropane III c1.

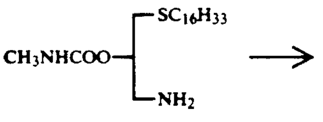

IVc1

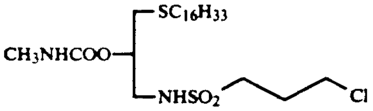

IIIc1

3-Hexadecylthio-2-methylcarbamoyloxypropylamine IV c1 is allowed to react and worked up by the same procedure as described in (4). m.p. 84.5°-85.5° C. The summary of the experimental condition and the physical data of the product are listed in the Table 7.

(32) Preparation of 1-hexadecylthio-3-(3-iodopropylsulfonylamino)-2-methylcarbamoyloxypropane II c1

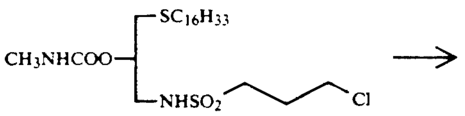

IIIc1

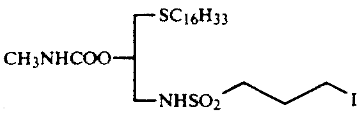

IIc1

3-(3-Chloropropylsulfonylamino)-1-hexadecylthio-2-methylcarbamoyloxypropan III c1 is allowed to react and worked up by the same procedure as described in (5). The summary of the experimental condition and the physical data of the product are listed in the Table 8.

EXAMPLE 31

Preparation of 1-hexadecylthio-2-methylcarbamoyloxy-3-(3-quinoliniopropylsulfonylamino)propane iodide I c1

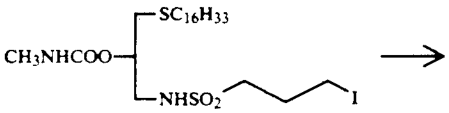

IIc1

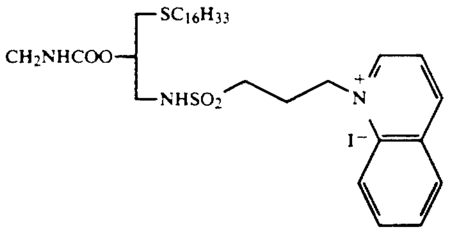

Ic1

1-Hexadecylthio-3-(3-iodopropylsulfonylamino)-2-methylcarbamoyloxypropane II c1 is allowed to react and worked up by the same procedure as described in Example 25. The summary of the experimental condition and the physical data of the product are listed in the Table 10.

EXAMPLE 32

Preparation of 1-hexadecylthio-2-methylcarbamoyloxy-3-(3-trimethylammoniopropylsulfonylamino)propane iodide I c2

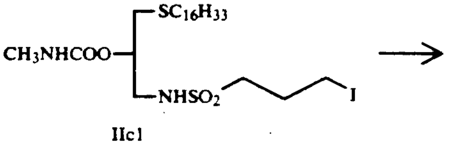

IIc1

-continued

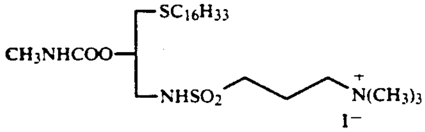

Ic2

1-Hexadecylthio-3-(3-iodopropylsulfonylamino)-2-methylcarbamoyloxypropane II c1 is allowed to react worked up by the same procedure as described in Example 8. The summary of the experimental condition and the physical data of the product are listed in the Table 9.

(33) Preparation of 2-methylcarbamoyloxy-1-octadecylcarbamoyloxy-3-trityloxypropane c4

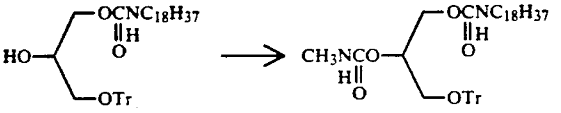

c3 c4

1-octadecylcarbamoyloxy-3-trityloxy-2-propanol c3 1.26 g (2.0 mmol) obtained above is dissolved in dichloromethane 20 ml and 4-dimethylaminopyridine 0.293 g (2.4 mmol) and methylisocyanate 1.18 ml (20 mmol) are added. The solution is stirred at room temperature for 24 hr and evaporated. The residue is purified by $SiO_2$ column chromatography with ethyl acetate:hexane (1:1) to yield the titled compound c4 0.789 g (59% yield). mp. 89°-91° C.

NMR: δ ($CDCl_3$) 0.86(t,J=6 Hz,3H), 1.28(br.s,32H), 2.74(d,J=6 Hz, 3H), 2.90~3.45(m,4H), 4.24(d,J=6 Hz,2H), 4.70(m,2H), 5.10(m,1H), 7.15~7.65(m,15H).

(34) Preparation of 2-methylcarbamoyloxy-3-octadecylcarbamoyloxy-propanol V c2.

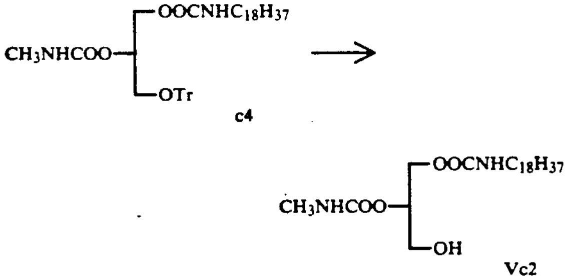

c4

Vc2

The compound c4 4.5 g (6.68 mmol) obtained above is dissolved in dichloromethane 45 ml and boron trifluoride-methanol complex 1.08 ml (9.96 mmol) is added at 0° C. The solution is stirred at room temperature for 4 hr and washed with sodium hydrogen carbonate aq solution. The organic layer is dried over anhydrous sodium sulfate and evaporated. The residual crystals are recrystallized from methanol-ether to yield the titled compound V c2 2.04 g (69% yield). mp. 92°-93° C.

NMR: δ ($CDCl_3$), 0.86(t,J=6 Hz,3H), 1.26(br.s,32H), 2.75(d,J=6 Hz, 3H), 2.80~3.45(m,3H), 3.68(m,2H), 4.25(d,J=6 Hz,2H), 4.75~5.25(m, 3H).

IR: σmax(Nujol) 3340, 3290, 1685, 1520, 1375, 1285, 1150, 1065 $cm^{-1}$.

(35) Preparation of 2-methylcarbamoyloxy-3-octadecylcarbamoyloxy-propylamine IV c2

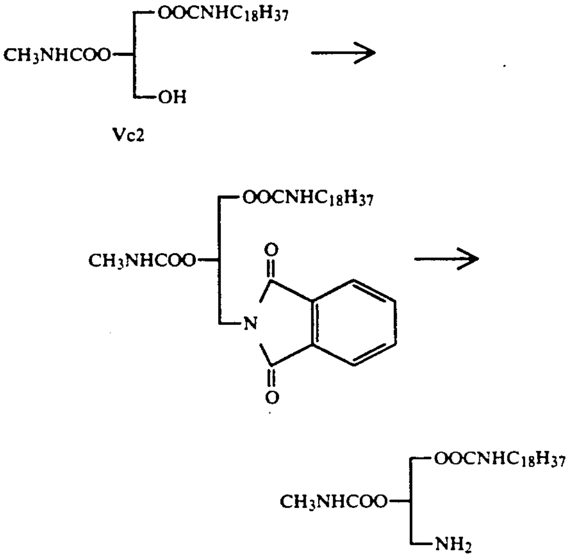

Vc2

IVc2

2-Methylcarbamoyloxy-3-octadecylcarbamoyloxy-propanol V c2 is allowed to react and worked up by the same procedure as described in (3) to give an amine IV c2 of m.p. 91°-92° C. The summary of the experimental condition and the physical data of the product are listed in the Table 5 and 6.

(36) Preparation of 3-(3-chloropropylsulfonylamino)-2-methylcarbamoyloxy-1-octadecylcarbamoyloxypropane III c2

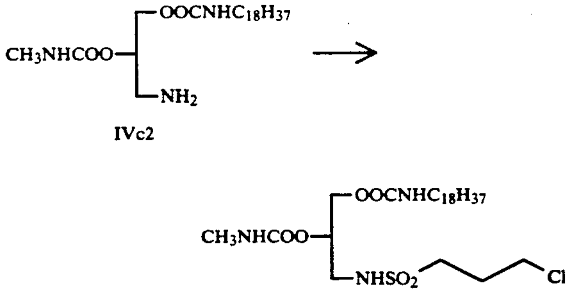

IVc2

IIIc2

2-Methylcarbamoyloxy-3-octadecylcarbamoyloxy-propylamine IV c2 is allowed to react and worked up by the same procedure as described in (4). m.p. 102°-104° C. The summary of the experimental condition and the physical data of the product are listed in the Table 7.

(37) Preparation of 3-(3-iodopropylsulfonylamino)-2-methylcarbamoyloxy-1-octadecylcarbamoyloxypropane II c2

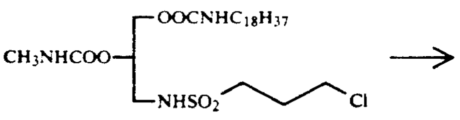

IIIc2

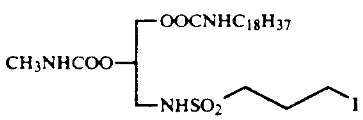

IIc2

3-(3-Chloropropylsulfonylamino)-2-methylcarbamoyloxy-1-octadecylcarbamoyloxypropane III c2 is allowed to react and worked up by the same procedure as described in (5). m.p. 97°-99° C. The summary of the experimental condition and the physical data of the product are listed in the Table 8.

EXAMPLE 33

Preparation of 2-methylcarbamoyloxy-1-octadecylcarbamoyloxy-3(3-quinoliniopropylsulfonylamino)propane iodide I c3

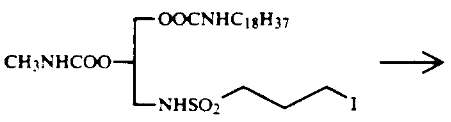

IIc2

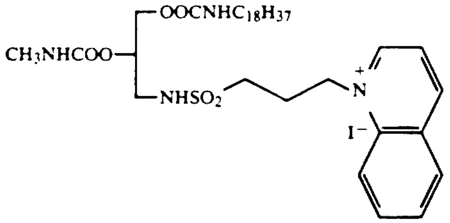

Ic3

3-(3-Iodopropylsulfonylamino)-2-methylcarbamoyloxy-1-octadecylcarbamoyloxypropane II c2 is allowed to react and worked up by the same procedure as described in Example 25. The summary of the experimental condition and the physical data of the product are listed in the Table 10.

EXAMPLE 34

Preparation of 2-methylcarbamoyloxy-1-octadecylcarbamoyloxy-3-(3-trimethylammoniopropylsulfonylamino)propane iodine I c4

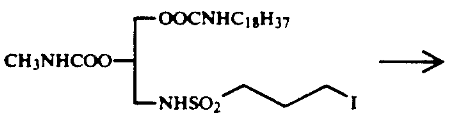

IIc2

-continued

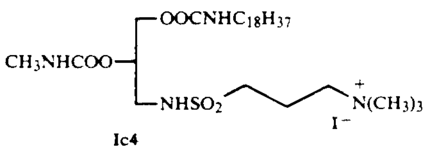

Ic4

3-(3-Iodopropylsulfonylamino)-2-methylcarbamoyloxy-1-octadecylcarbamoyloxypropane II c2 is allowed to react and worked up by the same procedure as described in Example 8. The summary of the experimental condition and the physical data of the product are listed in the Table 9.

(38) Preparation of O-octadecylcarbamoyl-N-triphenylmethylserine methyl ester e2

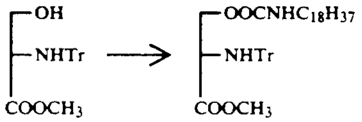

e1 e2

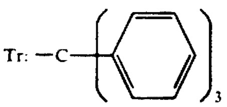

A solution of 1.67 g of N-triphenylmethylserine methyl ester and 2.0 g of stearylisocyanate in 10 ml of N,N-dimethyl-formamide is heated at 85° C. for 16 h, poured to ice-water and extracted with ethyl acetate. The extracts are washed with water, dried over anhydrous sodium sulfate and concentrated under reduced pressure. The residue is subjected to flash chromatography on silica gel in hexane:ethyl acetate (3:2) to give 2.46 g (82.6% yield) of the titled compound e2.

NMR($CDCl_3$) $\delta$ ppm: 0.88(3H,t,J=7 Hz), 1.25(30H,s), 1.46(2H,m), 2.78(1H,d,J=10 Hz), 3.16(2H,m), 3.19(3H,s), 3.58(1H,m), 4.21(1H,dd,J=11,6 Hz), 4.37(1H,dd,J=11,5 Hz), 4.69(1H,t,J=11 Hz), 7.1-7.3(9H,m), 7.45-7.6(6H,m).

(39) Preparation of O-octadecylcarbamoylserine methyl ester e3.

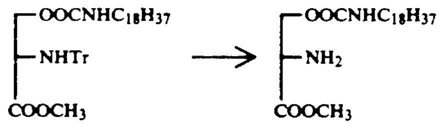

e2 e3

To a solution of 573 mg of e2 in 15 ml of acetone is added 5 ml of 10% hydrochloric acid. The mixture is allowed to stand at room temperature overnight, made alkaline with aqueous sodium carbonate and extracted with ethyl acetate. The extracts are washed with water, dried over anhydrous sodium sulfate and concentrated under reduced pressure. The residue is subjected to flash chromatography on silica gel in ethyl acetate:methanol (9:1) and recrystallized from ethyl acetate-hexane to give 276 mg (74.9% yield) of the title compound 3e. mp. 70°-71° C.

NMR: ($CDCl_3$) δ ppm 0.89(3H,t,J=6 Hz), 1.26(30H,s), 1.49(2H,m), 1.78(2H,s), 3.16(2H,m), 3.73(1H,m), 3.76(3H,s), 4.31(2H,d,J=5 Hz), 4.76(1H,s).

(40) Preparation of 2-amino-3-octadecylcarbamoyloxypropanol e4

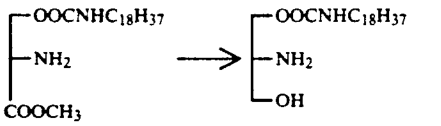

e3 e4

To a mixture of 760 mg of sodium borohydride in 30 ml of ethanol is added 1.11 g of calcium chloride at −40° C. The mixture is stirred at −20° C. for 1 h. A solution of 2.08 g of e3 in 50 ml of ethanol is added dropwise to the mixture at −20° C. The mixture is stirred at −20° C. for 3 h. Water is added. The mixture is extracted with ethyl acetate. The extracts are washed with water, dried over anhydrous sodium sulfate and concentrated under reduced pressure. The residue is subjected to flash chromatography on silica gel in chloroform:methanol (9:1) and then recrystallized from hexane to give 1.57 g (80.9% yield) of the titled compound e4. mp. 103°-105° C.

NMR: ($CDCl_3$) δ ppm 0.88(3H,t,J=6 Hz), 1.26(30H,s), 1.49(2H,m), 1.73(3H,s), 3.06(1H,m), 3.17(2H,m), 3.51(2H,m), 4.08(2H,d,J=5 Hz), 4.75(1H,s).

(41) Preparation of 2-methoxycarbonylamino-3-octadecylcarbamoyloxypropanol V e1

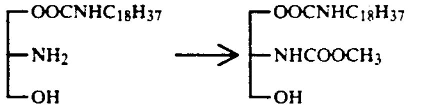

e4 Ve1

A solution of 117 mg of methyl chloroformate in 8 ml of acetone is added dropwise to a suspension of 120 mg of e4 in 3 ml of 3.3% aqueous sodium carbonate. The mixture is stirred for 6 h and extracted with ethyl acetate. The extracts are washed with water, dried over anhydrous sodium sulfate and concentrated under reduced pressure. The residue is subjected to flash chromatography on silica gel in ethyl acetate and recrystallized from hexane to give 115 mg (82.3% yield) of the titled compound Ve1. mp. 84°-85° C.

NMR($CDCl_3$) δ ppm 0.89(3H,t,J=6 Hz), 1.26(30H,s), 1.50(2H, m), 1.61(1H,s), 3.07(1H,br.s), 3.18(2H,m), 3.69(3H,s), 3.86(1H, br.s), 4.20(2H,d,J=5 Hz), 4.83(1H,s), 5.23(1H, d,J=7 Hz).

(42) Preparation of 2-tert-butoxycarbonylamino-3-octadecylcarbamoyloxypropanol V e2

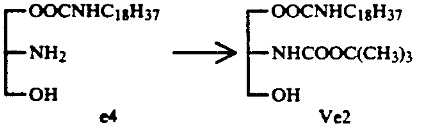

e4 Ve2

2-tert-Butoxycarbonylamino-3-octadecylcarbamoyloxypropanol V e2 is prepared by the same manner as described in (41) by using tert-butyldicarbonate instead of methyl chloroformate.

Yield 93.4%. mp. 73°-75° C.

NMR: ($CDCl_3$) δ ppm 0.87(3H,t,J=5 Hz), 1.26(30H,s), 1.44(9H,s), 1.56(2H,m), 3.18(2H,m), 3.63(2H,m), 3.81(1H,br.s), 4.18(2H,d,J=5 Hz), 4.78(1H,br.s), 5.20(1H, br.s).

(43) Preparation of 2-methyoxycarbonylamino-3-octadecylcarbamoyloxypropylamine IV e1

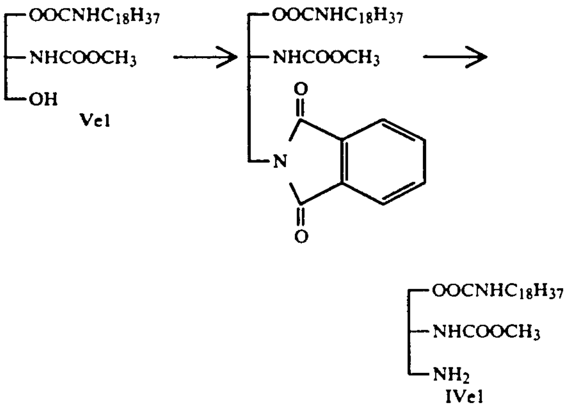

Ve1

IVe1

2-Methoxycarbamoyl-3-octadecylcarbamoyloxypropanol V e1 is allowed to react and worked up by the same procedure as described in (3). The phthalimide derivative: m.p. 128°-129° C., the amine derivative: 85°-86° C. The summary of the experimental condition and the physical data of the product are listed in Tables 5 and 6.

(44) Preparation of 2-tert-butyoxycarbonylamino-3-octadecylcarbonyloxypropylamine IV e2

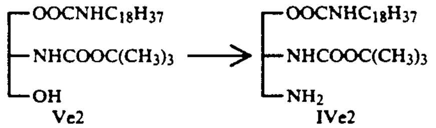

Ve2 IVe2

2-tert-Butoxycarbonylamino-3-octadecylcarbamoyloxypropane V e2 is allowed to react and worked up by the same procedure as described in (3). The phthalimide compound: m.p. 127°-129° C., The amino compound IV e2 69°-70° C. The summary of the experimental condition and the physical data of the product are listed in Tables 5 and 6.

(45) Preparation of 4-acetylthiomethyl-2-phenyl-2-oxazoline e6

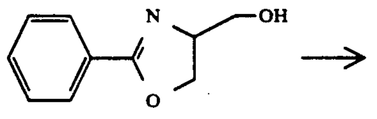

e5

-continued

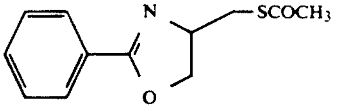

e6

4-Hydroxymethyl-2-phenyl-2-oxazoline e5 is allowed to react by the same procedure as described in (17). The extract is purified by the flash chromatography on silica gel eluted with hexane:ethyl acetate 2:1. The product is recrystallized from hexane to give the titled compound e6 as needle crystals. mp. 59°-60° C.

NMR ($CDCl_3$) δ ppm 2.37(3H,s), 3.23(2H,m), 4.11(1H,m), 4.33-4.62 (2H), 7.36-7.55(3H), 7.95(2H,m).

(46) Preparation of 4-hexadecylthiomethyl-2-phenyl-2-oxazoline e7

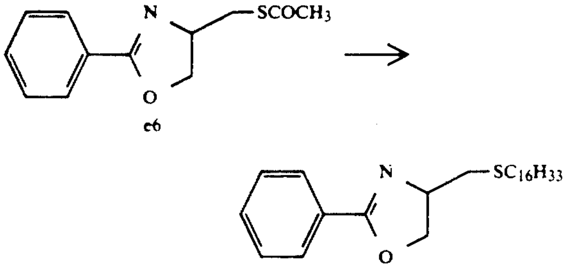

e6 e7

To a solution of 13.28 g of the thiolester e6 in 70 ml of methanol is added 60 ml of 10% aqueous sodium hydroxide at 0° C. The solution is stirred at room temperature for 2 h. Water is added. The mixture is extracted with ether. The extracts are washed with water, dried over anhydrous sodium sulfate and concentrated under reduced pressure to give 7.68 g (70.4% yield) of the crude thiol.

To a solution of the residue in 40 ml of dry tetrahydrofuran is added 1.6 g of 60% sodium hydride in small portions at room temperature. The mixture is stirred for 30 min. A solution of 12.22 g of 1-bromohexadecane in 10 ml of dry tetrahydrofuran is added. The mixture is stirred at room temperature overnight. Ether is added. The mixture is washed with water, dried over anhydrous sodium sulfate and concentrated under reduced pressure. The residue is subjected to flash chromatography on silica gel in hexane:ethyl acetate (4:1) and then recrystallized from hexane to give 14.68 g (62.3% yield) of the titled compound e7. mp. 39°-41° C.

NMR($CDCl_3$) δ ppm 0.88(3H,t,J=6.5 Hz), 1.25(26H,s), 1.59(2H,m), 2.53-2.67(3H), 2.99(1H,m), 4.30(1H,m), 4.43-4.59(2H), 7.36-7.54 (3H), 7.95(2H,m).

(47) Preparation of 2-amino-3-hexadecylthiopropanol e8

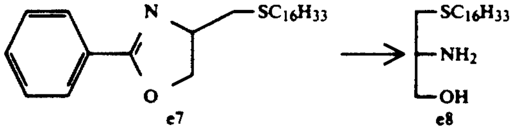

e7 e8

A suspension of 15.0 g of the oxazoline e7 in 55 ml of 6N-sulfuric acid is stirred at 105° C. for 24 h, made alkaline with 10% of aqueous sodium hydroxide and extracted with ethyl acetate. The extracts are washed with water, dried over anhydrous sodium sulfate and concentrated under reduced pressure. The residue is subjected to flash chromatography on silica gel in chloroform and then chloroform:methanol (10:1) and recrystallized from dichloromethane-hexane to give 11.16 g (93.7% yield) of the titled compound e8 as plates. mp. 70°-71° C.

NMR($CDCl_3$) δ ppm 0.88(3H,t,J=6.5 Hz), 1.26(26H,s), 1.58(2H,m), 1.85(3H,s), 2.46(1H,dd,J=8.2,13.3 Hz), 2.52(2H,t,J=7.3 Hz), 2.66 (1H,dd,J=4.8, 13.3 Hz), 3.02(1H,m), 3.42(1H,dd,J=6.5, 10.7 Hz), 3.67(1H,dd,J=4.1, 10.7 Hz).

(48) Preparation of 3-hexadecylthio-2-methoxycarbonylaminopropanol e9

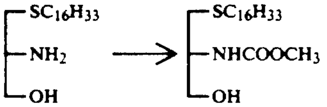

e8 e9

The compound e8 is allowed to react by the same procedure as described in (41). Yield 94.6%, m.p. 55°-56° C.

NMR($CDCl_3$) δ ppm: 0.88(3H,t,J=6.4 Hz), 1.26(26H,s), 1.58(2H,m), 2.55(2H,t,J=7.2 Hz), 2.73(2H,d, J=5.7 Hz), 3.69(3H,s), 3.67-3.88(3H), 5.21(br.s).

(49) Preparation of 3-hexadecylthio-2-tert-butoxycarbonylaminopropanol 12b

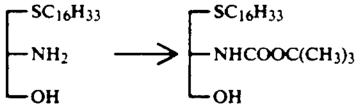

e8 e10

The compound e8 is allowed to react by the same procedure as described in (42). Yield 95.9%, m.p. 48°-50° C.

NMR($CDCl_3$) δ ppm: 0.88(3H,t,J=6.4 Hz), 1.26(26H,s), 1.45(9H,s), 1.58(2H,m), 1.96(1H,s), 2.55(2H,t, J=7.0 Hz), 2.71(2H,d,J=4.0 Hz), 3.69-3.82(3H), 5.02(1H, br.s).

(50) Preparation of 1-hexadecylthio-3-methanesulfonyloxy-2-methoxycarbonylaminopropane e11

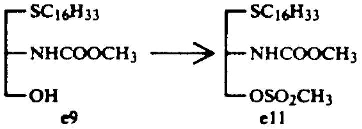

e9 e11

A solution of 0.96 g of methanesulfonyl chloride in 5 ml of dichloromethane is added dropwise to a solution of 2.727 g of the alcohol e9 in 35 ml of dichloromethane and 4 ml of triethylamine at −10° C. The mixture is stirred at −10° C. for 2 h. Ether is added. The mixture is washed with water, 10% hydrochloric acid, aqueous sodium hydrogencarbonate and water, dried over anhydrous sodium sulfate and concentrated under reduced pressure. The residue is recrystallized from benzene-hexane to give 3.133 g (95.7% yield) of the titled compound e11 as a powder. mp. 82°-83° C.

NMR($CDCl_3$) δ ppm: 0.88(3H,t,J=6.5 Hz), 1.26 (26H, s), 1.58(2H, m), 2.55(2H,t,J=7.2 Hz), 2.68(1H,dd,J=7.3,13.5 Hz), 2.78(1H,dd, J=5.2,13.5 Hz), 3.05(3H,s), 3.70(3H,s), 4.05(1H,m), 4.34(1H,dd, J=4.3,10.2 Hz), 4.45(1H,dd,J=4.2,10.2 Hz), 5.10(1H,d, J=8.0 Hz).

(51) Preparation of 2-tert-butoxycarbonylamino-1-hexadecylthio-3-methanesulfoxypropane e12

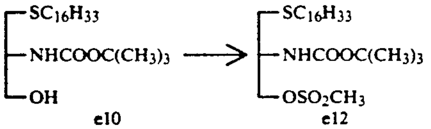

e10 e12

The compound e10 is allowed to react by the same procedure as in (50). Yield: 97.9%. mp. 90°-91° C.

NMR($CDCl_3$) δ ppm 0.88(3H, t, J=6.4 Hz), 1.26 (26H, s), 1.45(9H, s), 1.58(2H, m), 2.55(2H, t, J=7.1 Hz), 2.67(1H, dd, J=7.2, 13.5 Hz), 2.76 (1H, dd, J=5.6, 13.5 Hz), 3.05(3H, s), 4.00 (1H, m), 4.32(1H, dd, J=4.3, 10.2 Hz), 4.45 (1H, dd, J=4.1, 10.2 Hz), 4.90(1H, d, J=7.8 Hz).

(52) Preparation of 3-azido-1-hexadecylthio-2-methoxycarbonylaminopropane e13

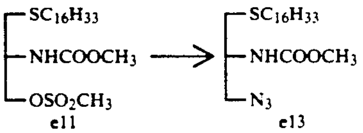

e11 e13

A mixture of 4.677 g of the mesylate e11 and 1 g of sodium azide in 25 ml of hexamethylphosphoric triamide is stirred at 50° C. for 4 h. Ether is added. The mixture is washed with water, dried over anhydrous sodium sulfate and concentrated under reduced pressure. The residue is subjected to flash chromatography on silica gel in hexane:ethyl acetate (8:1) and then recrystallized from hexane to give 3.925 g (94.6% yield) of the titled compound e13 as needles. mp. 44.5°-45.5° C.

NMR($CDCl_3$) δ ppm 0.88(3H, t, J=6.5 Hz), 1.26 (26H, s), 1.58(2H, m), 2.54(2H, t, J=7.3 Hz), 2.64(1H, dd, J=7.3, 13.9 Hz), 2.73(1H, dd, J=6.0, 13.9 Hz), 3.52(1H, dd, J=5.0, 12.3 Hz), 3.65(1H, dd, J=4.5, 12.3 Hz), 3.69(3H, s), 3.91(1H, m), 4.98(1H, d, J=6.5 Hz).

(53) Preparation of 3-azido-2-tert-butoxycarbonylamino-1-hexadecylthiopropane e14

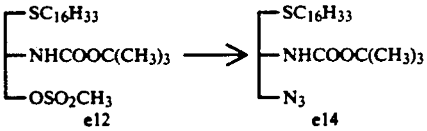

e12 e14

The compound e12 is allowed to react by the same procedure as described in (52). Yield: 93.6%, mp. 63°-64° C.

NMR($CDCl_3$) δ ppm 0.88(3H, t, J=6.4 Hz), 1.26 (26H, s), 1.45(9H, s), 1.58(2H, m), 2.54(2H, t, J=7.3 Hz), 2.63(1H, dd, J=7.4, 14.0 Hz), 2.71 (1H, dd, J=6.1, 14.0 Hz), 3.50(1H, dd, J=5.1, 12.2 Hz), 3.64(1H, dd, J=4.2, 12.2 Hz), 3.86 (1H, m), 4.81(1H, d, J=6.5 Hz).

(54) Preparation of 3-hexadecylthio-2-methoxycarbonylaminopropylamine IV e3

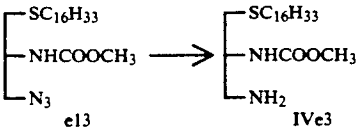

e13 IVe3

A solution of 3.875 g of the azide e13 and 3.19 g of triphenylphosphine in 40 ml of tetrahydrofuran is stirred for 20 h and 10 ml of water is added. The mixture is heated under reflux for 30 min. Ether is added. The mixture is washed with water, dried over anhydrous sodium sulfate and concentrated under reduced pressure. The residue is subjected to flash chromatography on silica gel in chloroform and then chloroform:methanol (25:2) and then recrystallized from hexane to give 3.532 g (97.2% yield) of the titled compound IV e3 as crystalline powders. mp. 49°-50.5° C.

NMR($CDCl_3$) δ ppm 0.88(3H, t, J=6.4 Hz), 1.26 (26H, s), 1.45(2H, s), 1.58(2H, m), 2.54(2H, t, J=7.3 Hz), 2.62(1H, dd, J=6.9, 13.2 Hz), 2.74 (1H, dd, J=5.7, 13.2 Hz), 2.87(2H, d, J=5.5 Hz), 3.68(3H, s), 3.76(1H, m), 5.14(1H, d, J=7.6 Hz).

(55) Preparation of 3-hexadecylthio-2-tert-butoxycarbonyl aminopropylamine IV e4

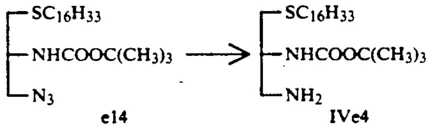

e14 IVe4

The compound e14 is allowed to react by the same manner as described in (54). Yield: 95.3%. mp. 46°-47° C.

NMR($CDCl_3$) δ ppm 0.88(3H, t, J=6.4 Hz), 1.26 (26H, s), 1.45(9H, s), 1.50-1.66(4H), 2.54 (2H, t, J=7.3 Hz), 2.62(1H, dd, J=6.7, 13.1 Hz), 2.72(1H, dd, J=5.5, 13.1 Hz), 2.86(2H, d, J=5.1 Hz), 3.71(1H, m), 4.94(1H, d, J=7.5 Hz).

(56) Preparation of 3-(3-chloropropylsulfonylamino)-2-methoxycarbonylamino-1-octadecylcarbamoyloxypropane III e1

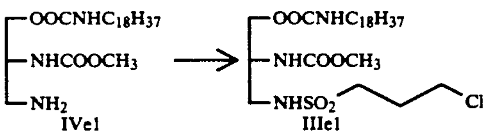

IVe1 IIIe1

2-Methoxycarbonylamino-3-octadecylcarbamoyloxypropylamine IV e1 is allowed to react and worked up by the same procedure as described in (4). mp. 99°-101° C. The summary of the experimental condition and the physical data of the product are listed in Table 7.

(57) Preparation of 2-tert-butoxycarbonylamino-3-(3-chloropropylsulfonylamino)-1-octadecylcarbamoyloxypropane III e2

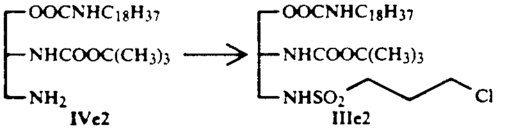

IVe2 IIIe2

2-tert-Butoxycarbonylamino-3-octadecylcarbamoyloxypropylamine IV e2 is allowed to react by the same procedure as described in (4). m.p. 112°-115° C. The summary of the experimental condition and the physical data of the product are listed in Table 7.

(58) Preparation of 3-(3-chloropropylsulfonylamino)-1-hexadecylthio-2-methoxycarbonylaminopropane III e3

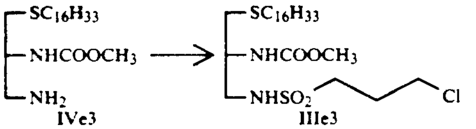

IVe3 IIIe3

3-Hexadecylthio-2-methoxycarbonylaminopropylamine IV e3 is allowed to react and worked up by the same procedure as described in (4). m.p. 67°-69° C. The summary of the experimental condition and the physical data of the product are listed in Table 7.

(59) Preparation of 2-tert-butoxycarbonylamino-3-(3-chloropropylsulfonylamino)-1-hexadecylthiopropane III e4

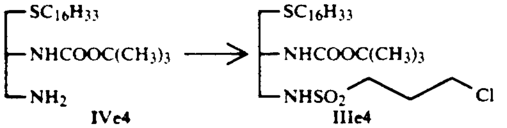

IVe4 IIIe4

3-Hexadecylthio-2-tert-butoxycarbonylaminopropylamine IV e4 is allowed to react and worked up by the same procedure as described in (4). m.p. 100.5°-101.5° C. The summary of the experimental condition and the physical data of the product are listed in Table 7.

(60) Preparation of 2-amino-3-(3-chloropropylsulfonylamino)-1-octadecylcarbamoyloxypropane III e1'

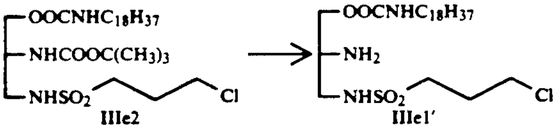

IIIe2 IIIe1'

A solution of 0.5 ml of trifluoroacetic acid in 2 ml of dichloromethane is added dropwise to a suspension of 252 mg of the BOC derivative III e2 in 5 ml dichloromethane at room temperature. The mixture is stirred at room temperature for 2 h and made alkaline with aqueous sodium hydrogencarbonate. The organic phase is separated and the aqueous phase is extracted with dichloromethane. The combined organic phases are washed with water, dried over anhydrous sodium sulfate and concentrated under reduced pressure. The residue is subjected to flash chromatography on silica gel in chloroform:methane (9:1) and recrystallized from ethyl acetate-hexane to give 190 mg (89.7% yield) of the titled compound III e1' as crystalline powders. mp. 86°-88° C.

NMR($CDCl_3$) δ ppm 0.88(3H, t, J=5 Hz), 1.26 (30H, s), 1.50(2H, m), 2.20(2H, br.s), 2.30 (2H, m), 3.69(2H, t, J=6 Hz), 4.09 (3H, br.s), 4.88 (1H, br.s).

(61) Preparation of 2-amino-3-(3-chloropropylsulfonylamino)-1-hexadecylthiopropane III e2'

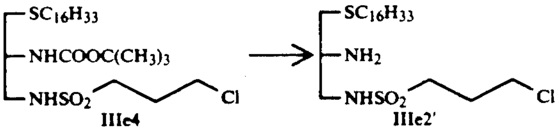

IIIe4 IIIe2'

The compound III e4 is allowed to react by the same manner as described in (60). Yield 98.4%. m.p. 76°77° C.

NMR($CDCl_3$) δ ppm 0.88(3H, t, J=6.4 Hz), 1.26 (26H, s), 1.58(2H, m), 2.20(3H, br.s), 2.30 (2H, m), 2.44-2.55(3H), 2.65(1H, dd, J=5.0, 13.3 Hz), 2.97(1H, dd, J=7.5, 11.8 Hz), 3.07 (1H, m), 3.19-3.33(3H), 3.70(2H, t, J=6.2 Hz).

(62) Preparation of 2-acetamido-3-(3-chloropropylsulfonylamino)-1-octadecylcarbamoyloxypropane III g1

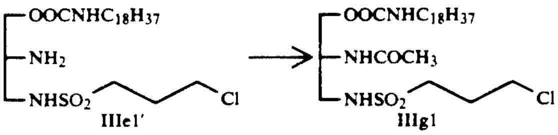

IIIe1' IIIg1

A solution of 0.77 ml of pyridine in 2 ml of dichloromethane is added to a solution of 501 mg of the amine III e1' and 194 mg of acetic anhydride in 15 ml of dichloromethane. The mixture is stirred at room temperature for 2 h, washed with dilute hydrochloric acid, aqueous sodium hydrogencarbonate and water, dried over anhydrous sodium sulfate and concentrated under reduced pressure. The residue is subjected to flash chromatography on silica gel in chloroform:methanol (10:1) and recrystallized from ethyl acetate to give 459 mg of the titled compound III III g1. mp. 110°-112° C.

NMR($CDCl_3$) δ ppm 0.88(3H, t, J=6 Hz), 1.26 (30H, s), 1.50(2H, m), 2.02(3H, s), 2.28(2H, m), 3.1-3.3(6H), 3.69(2H, t, J=6 Hz), 4.1-4.3 (3H), 4.91(1H, t, J=6 Hz), 5.72(1H, br.s), 6.48(1H, d, J=6 Hz).

(63) Preparation of 3-(3-chloropropylsulfonylamino)-2-(3-methylureido)-1-octadecylcarbamoyloxypropane III f1

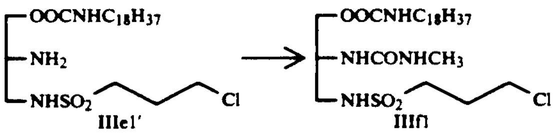

IIIe1' IIIf1

To a solution of 480 mg of the amine III e1' in 5 ml of N,N-dimethylformamide is added 0.2 ml of methylisocyanate. The mixture is stirred at room temperature for 1 h, poured to water and extracted with ethyl acetate. The extracts are dried over anhydrous sodium sulfate and concentrated under reduced pressure. The residue is subjected to flash chromatography on silica gel in chloroform:methanol (9:1) and recrystallized from ethyl acetate to give 469 mg (88.0% yield) of the titled compound. mp. 87°-90° C.

NMR($CDCl_3$) δ ppm 0.88(3H, t, J=6 Hz), 1.26 (30H, s), 1.50(2H, m), 2.28(2H, m), 2.77(3H, s), 3.1-3.3(6H), 3.68(2H, t, J=7 Hz), 4.05 (1H, br.s), 4.15(2H, m), 5.04(1H, br.s), 5.51 (1H, br.s), 6.11(1H, br.s).

(64) Preparation of 2-acetamido-3-(3-chloropropylsulfonylamino)-1-hexadecylthiopropane III g2

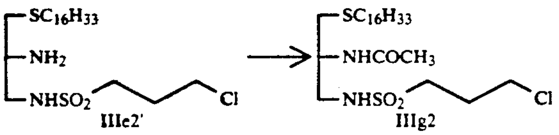

IIIe2' IIIg2

A solution of 161.5 mg (2.042 mmol) of the amine III e2' in 2 ml of dichloromethane is added dropwise to a solution of 962 mg (2.042 mmol) of the amine III e2' and 0.5 ml of acetic anhydride in 20 ml of dichloromethane at room temperature. The mixture stirred for 1 h. The volatile materials are removed by distillation under reduced pressure and the residue is subjected to flash chromatography on silica gel in chloroform and then chloroform:methanol (20:1) and recrystallized from hexane to give 924 mg (88.2% yield) of the titled compound III g2. mp. 86°-88° C.

NMR($CDCl_3$) δ ppm 0.88(3H, t, J=6.5 Hz), 1.26 (26H, s), 1.58(2H, m), 2.03(3H, s), 2.28(2H, m), 2.54(2H, t, J=7.3 Hz), 2.65(1H, dd, J=7.0, 13.5 Hz), 2.76(1H, dd, J=5.9, 13.5 Hz), 3.18-3.37(4H), 3.69(2H, t, J=6.2 Hz), 4.13 (1H, m), 5.36(1H, t, J=6.1 Hz), 6.23(1H, d, J=7.9 Hz).

(65) Preparation of 3-(3-chloropropylsulfonylamino)-1-hexadecylthio-2-(3-methylureido)-propane III f2

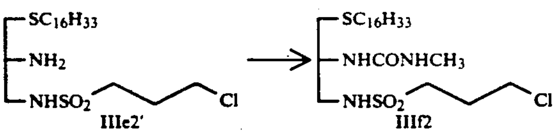

IIIe2' IIIf2

A solution of 0.2 ml of methyl isocyanate in 2 ml of N,N-dimethylformamide is added to a solution of 1.01 g (2.143 mmol) of the amine III e2' in 20 ml of N,N-dimethylformamide. The solution is stirred at room temperature for 3 h and ethyl acetate is added. The mixture is washed with water, dried over anhydrous sodium sulfate and concentrated under reduced pressure. The residue is recrystallized from hexane to give 1.107 g (97.8% yield) of the titled compound III f2. mp. 79°-80° C.

NMR($CDCl_3$) δ ppm:0.88(3H, t, J=6.4 Hz), 1.26(26H, s), 1.57(2H, m), 1.88(1H, br.s), 2.28(2H, m), 2.54(2H, t, J=7.0 Hz), 2.70(2H, m), 2.78(3H, s), 3.17-3.41(4H), 3.68(2H, t, J=6.2 Hz), 3.99(1H, m), 5.12(1H, br.s), 5.78 (1H, br.s).

(66) Preparation of 3-(N-acetyl-3-chloropropylsulfonylamino)-2-acetamido-1-octadecylcarbamoyloxypropane III g3

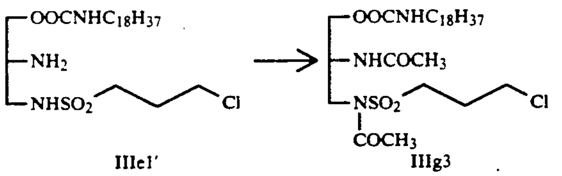

IIIe1' IIIg3

A solution of 0.5 ml of acetic anhydride in 2 ml of dichloromethane is added to a solution of 361 mg of the amine III e1' in 2 ml of triethylamine and 10 ml of dichloromethane. The mixture is allowed to stand at room temperature overnight, washed with dilute hydrochloric acid, aqueous sodium hydrogencarbonate and water dried over anhydrous sodium sulfate and concentrated under reduced pressure. The residue is subjected to flash chromatography on silica gel in chloroform:methanol (20:1) and recrystallized from ethyl acetate to give 342 mg (81.7% yield) of the titled compound III g3. mp. 116°-117° C.

NMR($CDCl_3$) δppm 0.88 (3H, t, J=5 Hz), 1.26 (30H, s), 1.50 (2H, m), 1.99 (3H, s), 2.33 (2H, m), 2.46 (3H, s), 3.17 (2H, m), 3.58 (2H, t, J=7 Hz), 3.69 (2H, t, J=7 Hz), 3.90 (2H, m), 4.10 (1H, dd, J=12.5 Hz), 4.22 (1H, dd, J=12.5 Hz), 4.47 (1H, m), 4.81 (1H, t, J=5 Hz), 6.08 (1H, d, J=7 Hz).

(67) Preparation of 3-(3-iodopropylsulfonylamino)-2-methoxycarbonylamino-1-octadecylcarbamoyloxypropane II e1

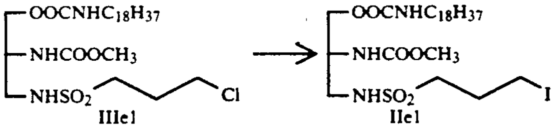

IIIe1 IIe1

3-(3-Chloropropylsulfonylamino)-2-methoxycarbonylamino-1-octadecylcarbamoyloxypropane III e1 is allowed to react and worked up by the same procedure as described in (5). m.p. 97° C. The summary of the experimental condition and the physical data of the product are listed in Table 8.

(68) Preparation of 2-butoxycarbonylamino-3-(3-iodopropylsulfonylamino)-1-octadecylcarbamoyloxypropane II e2

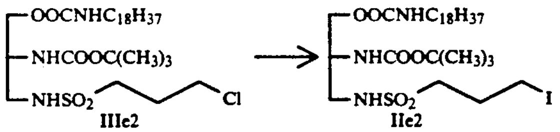

IIIe2 IIe2

2-Butoxycarbonylamino-3-(3-chloropropylsulfonylamino)-1-octadecylcarbamoyloxypropane III e2 is allowed to react and worked up by the same procedure as described in (5). m.p. 96°-98° C. The summary of the experimental condition and the physical data of the product are listed in Table 8.

(69) Preparation of 2-acetamido-3-(3-iodopropylsulfonylamino)-1-octadecylcarbamoyloxypropane II g1

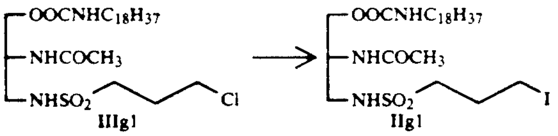

IIIg1 IIg1

2-acetamido-3-(3-chloropropylsulfonylamino)-1-octadecylcarbamoyloxypropane III g1 is allowed to react and worked up by the same procedure as described in (5). m.p. 101°-102° C. The summary of the experimental condition and the physical data of the product are listed in Table 8.

(70) Preparation of 3-(3-iodopropylsulfonylamino)-2-(3-methylureido)-1-octadecylcarbamoyloxypropane II f1

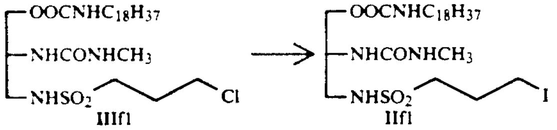

IIIf1 IIf1

3-(3-chloropropylsulfonylamino)-2-(3-methylureido)-1-octadecylcarbamoyloxypropane III f1 is allowed to react and worked up by the same procedure as described in (5). m.p. 87°-89° C. The summary of the experimental condition and the physical data of the product are listed in Table 8.

(71) Preparation of 1-hexadecylthio-3-(3-iodopropylsulfonylamino)-2-methoxycarbonylaminopropane II e3

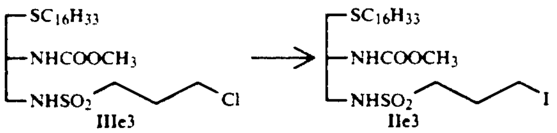

IIIe3 IIe3

3-(3-Chloropropylsulfonylamino)-1-hexadecylthio-2-methoxycarbonylaminopropane III e3 is allowed to react and worked up by the same procedure as described in (5). m.p. 79°-81° C. The summary of the experimental condition and the physical data of the product are listed in Table 8.

(72) Preparation of 2-butoxycarbonylamino-1-hexadecylthio-3-(3-iodopropylsulfonylamino)propane II e4

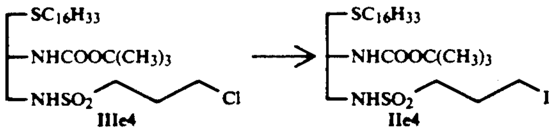

IIIe4 IIe4

2-Butoxycarbonylamino-3-(3-chloropropylsulfonylamino)-1-hexadecylthiopropane III e4 is allowed to react and worked up by the same procedure as described in (5). m.p. 82°-83° C. The summary of the experimental condition and the physical data of the product are listed in Table 8.

(73) Preparation of 2-acetamido-1-hexadecylthio-3-(3-iodopropylsulfonylamino)propane II g2

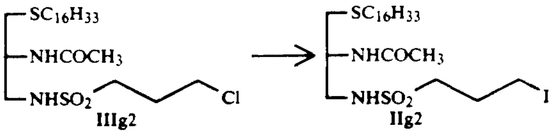

IIIg2 IIg2

2-Acetamido-3-(3-chloropropylsulfonylamino)-1-hexadecylthiopropane III g2 is allowed to react and worked up by the same procedure as described in (5). m.p. 75°-76° C. The summary of the experimental condition and the physical data of the product are listed in Table 8.

(74) Preparation of 1-hexadecylthio-3-(3-iodopropylsulfonylamino)-2-(3-methylureido)propane II f2

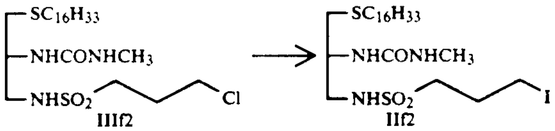

IIIf2 IIf2

3-(3-Chloropropylsulfonylamino)-1-hexadecylthio-2-(3-methylureido)propane III f2 is allowed to react and worked up by the same procedure as described in (5). m.p. 70°-71° C. The summary of the experimental condition and the physical data of the product are listed, in Table 8.

(75) Preparation of 3-(N-acetyl-3-iodopropylsulfonylamino)-2-acetamido-1-octadecylcarbamoyloxypropane II g3

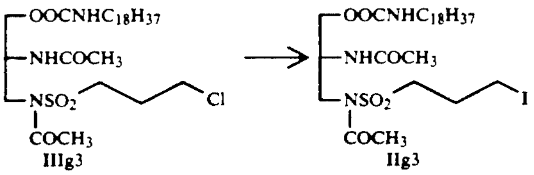

IIIg3 IIg3

3-(N-Acetyl-3-iodopropylsulfonylamino)-2-acetamido-1-octadecylcarbamoyloxypropane III g3 is allowed to react and worked up by the same procedure as described in (5). m.p. 118°-119° C. The summary of the experimental condition and the physical data of the product are listed in Table 8.

EXAMPLE 35

Preparation of 1-octadecylcarbamoyloxy-2-methoxycarbonylamino-3-(3-trimethylammoniopropylsulfonylamino)propane iodide I e1

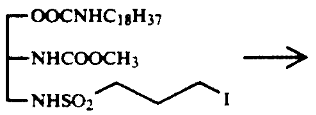

IIe1

-continued

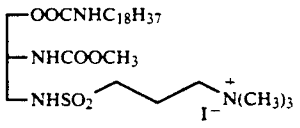

Ie1

3-(3-Iodopropylsulfonylamino)-2-methoxycarbonylamino-1-octadecylcarbamoyloxypropane II e1 is allowed to react and worked up by the same procedure as described in Example 8. The summary of the experimental condition and the physical data of the product are listed in Table 9.

EXAMPLE 36

2-tert-butoxycarbonylamino-1-octadecylcarbamoyloxy-3-(3-trimethylammoniopropylsulfonylamino)propane iodide I e2

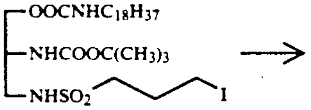

IIe2

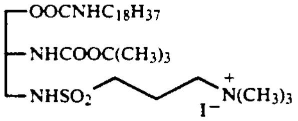

Ie2

2-tert-Butoxycarbonylamino-3-(3-iodopropylsulfonylamino)-1-octadecylcarbamoyloxypropane II e2 is allowed to react and worked up by the same procedure as described in Example 8. The summary of the experimental condition and the physical data of the product are listed in Table 9.

EXAMPLE 37

Preparation of 2-acetamido-1-octadecylcarbamoyloxy-3-(3-trimethylammoniopropylsulfonylamino)propane iodide I g1

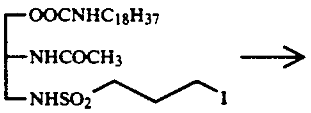

IIg1

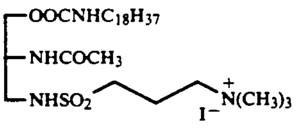

Ig1

2-Acetamido-3-(3-iodopropylsulfonylamino)-1-octadecylcarbamoyloxypropane II g1 is allowed to react and worked up by the same procedure as described in Example 8. The summary of the experimental condition and the physical data of the product are listed in Table 9.

EXAMPLE 38

Preparation of 1-octadecylcarbamoyloxy-2-(3-methylureido)-3-(3-trimethylammoniopropylsulfonylamino)propane iodide I f1

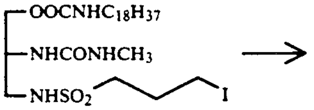

IIf1

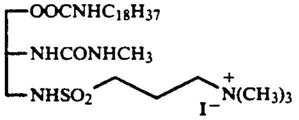

If1

3-(3-Iodopropylsulfonylamino)-2-(3-methylureido)-1-octadecylcarbamoyloxypropane II f1 is allowed to react and worked up by the same procedure as described in Example 8. The summary of the experimental condition and the physical data of the product are listed in Table 9.

EXAMPLE 39

Preparation of 1-hexadecylthio-2-methoxycarbonylamino-3-(3-trimethylammoniopropylsulfonylamino)propane iodide I e3

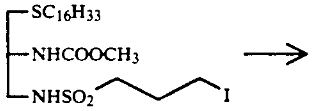

IIe3

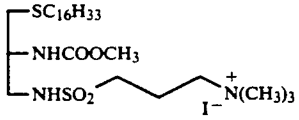

Ie3

1-Hexadecylthio-3-(3-iodopropylsulfonylamino)-2-methoxycarbonylamino propane II e3 is allowed to react and worked up by the same procedure as described in Example 8. The summary of the experimental condition and the physical data of the product are listed in Table 9.

EXAMPLE 40

Preparation of 2-tert-butoxycarbonylamino-1-hexadecylthio-3-(3-trimethylammoniopropylsulfonylamino)propane iodide I e4

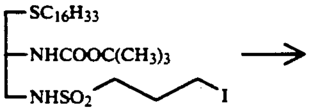

IIe4

-continued

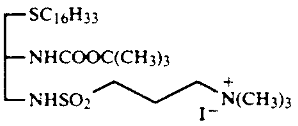

Ie4

2-tert-Butoxycarbonylamino-1-hexadecylthio-3-(3-iodopropylsulfonylamino)propane II e4 is allowed to react and worked up by the same procedure as described in Example 8. The summary of the experimental condition and the physical data of the product are listed in Table 9.

EXAMPLE 41

Preparation of 2-acetamido-1-hexadecylthio-3-(3-trimethylammoniopropylsulfonylamino)propane iodide I g2

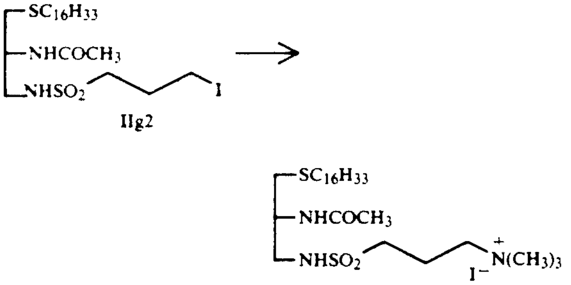

IIg2

Ig2

2-Acetamido-1-hexadecylthio-3-(3-iodopropylsulfonylamino)propane II g2 is allowed to react and worked up by the same procedure as described in Example 8. The summary of the experimental condition and the physical data of the product are listed in Table 9.

EXAMPLE 42

Preparation of 1-hexadecylthio-2-(3-methylureido)-3-(3-trimethylammoniopropylamino)propane iodide I f2

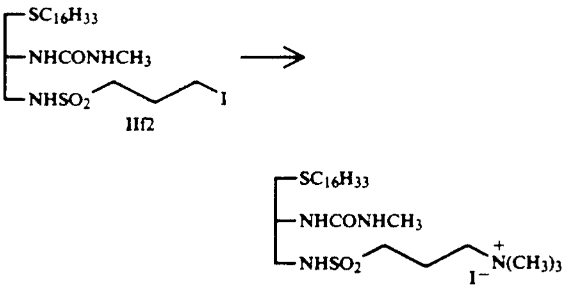

IIf2

If2

1-Hexadecylthio-3-(3-iodopropylsulfonylamino)-2-(3-methylureido)propane II f2 is allowed to react and worked up by the same procedure as described in Example 8. The summary of the experimental condition and the physical data of the product are listed in Table 9.

EXAMPLE 43

Preparation of 3-(N-acetyl-3-trimethylammoniopropylsulfonylamino)-2-acetamido-1-octadecylcarbamoyloxypropane iodide I g3

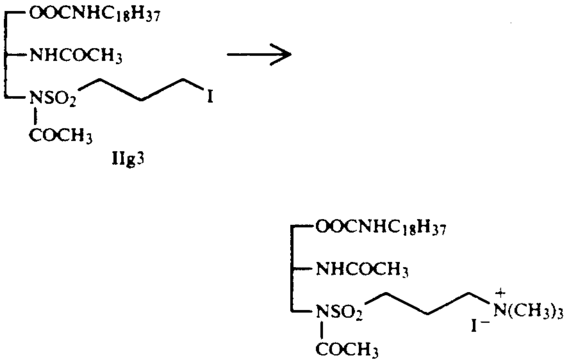

IIg3

Ig3

3-(N-Acetyl-3-iodopropylsulfonylamino)-2-acetamido-1-octadecylcarbamoyloxypropane II g3 is allowed to react and worked up by the same procedure as described in Example 8. The summary of the experimental condition and the physical data of the product are listed in Table 9.

EXAMPLE 44

Preparation of 1-octadecylcarbamoyloxy-2-methoxycarbonylamino-3-(3-quinoliniopropylsulfonylamino)propane iodide I e5

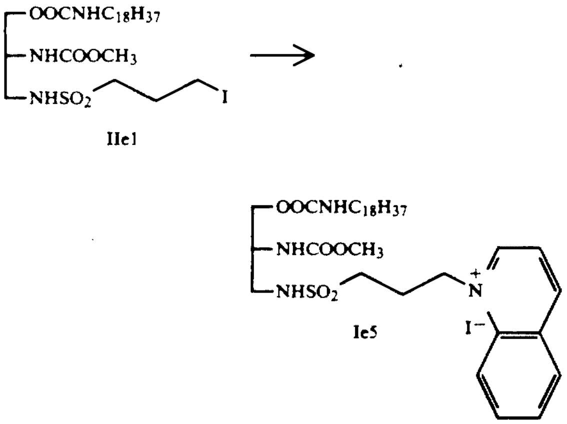

IIe1

Ie5

3-(3-Iodopropylsulfonylamino)-2-methoxycarbonylamino-1-octadecylcarbamoyloxypropane II e1 is allowed to react and worked up by the same procedure as described in Example 25. The summary of the experimental condition and the physical data of the product are listed in Table 10.

EXAMPLE 45

Preparation of 2-tert-butoxycarbonylamino-1-octadecylcarbamoyloxy-3-(3-quinoliniopropylsulfonylamino)propane iodide Ie6

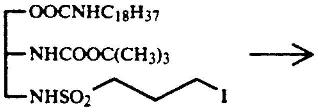

IIe2

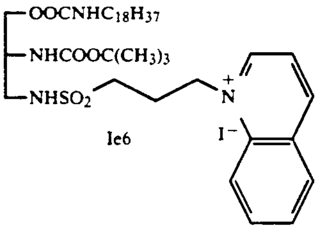

Ie6

2-tert-Butoxycarbonylamino-3-(3-iodopropylsulfonylamino)-1-octadecylcarbamoyloxypropane IIe2 is allowed to react and worked up by the same procedure as described in Example 25. The summary of the experimental condition and the physical data of the product are listed in Table 10.

EXAMPLE 46

Preparation of 2-acetamido-1-octadecylcarbamoyloxy-3-(3-quinoliniopropylsulfonylamino)propane iodide I g4

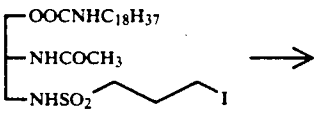

IIg1

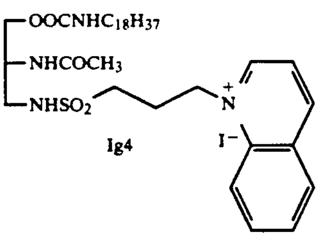

Ig4

2-Acetamido-3-(3-iodopropylsulfonylamino)-1-octadecylcarbamoyloxy propane II g1 is allowed to react and worked up by the same procedure as described in Example 25. The summary of the experimental condition and the physical data of the product are listed in Table 10.

EXAMPLE 47

Preparation of 1-octadecylcarbamoyloxy-2-(3-methylureido)-3-(3-quinoliniopropylsulfonylamino)propane iodide I f3

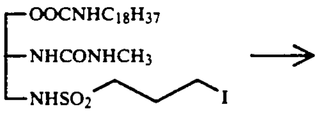

IIf1

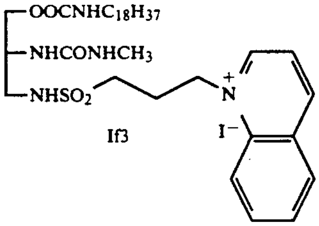

If3

3-(3-Iodopropylsulfonylamino)-2-(3-methylureido)-1-octadecylcarbamoyloxypropane II f1 is allowed to react and worked up by the same procedure as described in Example 25. The summary of the experimental condition and the physical data of the product are listed in Table 10.

EXAMPLE 48

Preparation of 1-hexadecylthio-2-methoxycarbonylamino-3-(3-quinoliniopropylsulfonylamino)propane iodide I e7

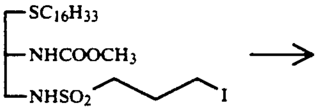

IIe3

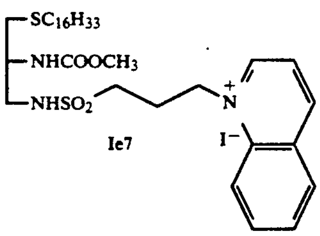

Ie7

1-Hexadecylthio-3-(3-iodopropylsulfonylamino)-2-methoxycarbonylaminopropane II e3 is allowed to react and worked up by the same procedure as described in Example 25. The summary of the experimental condition and the physical data of the product are listed in Table 10.

EXAMPLE 49

Preparation of 2-tert-butoxycarbonylamino-1-hexadecylthio-3-(3-quinoliniopropylsulfonylamino)propane iodide I e8

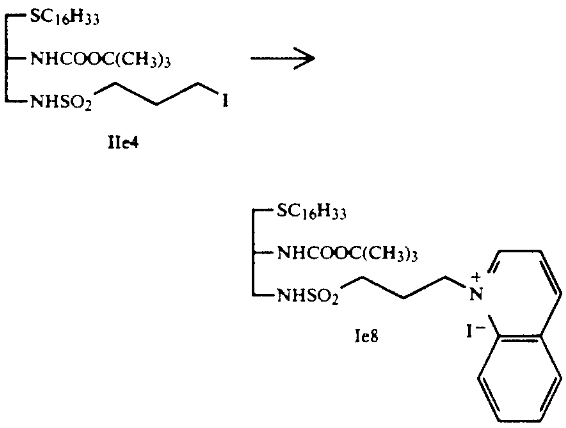

IIe4 Ie8

2-tert-Butoxycarbonylamino-1-hexadecylthio-3-(3-iodopropylsulfonylamino)propane II e4 is allowed to react and worked up by the same procedure as described in Example 25. The summary of the experimental condition and the physical data of the product are listed in Table 10.

EXAMPLE 50

Preparation of 2-acetamido-1-hexadecylthio-3-(3-quinoliniopropylsulfonylamino)propane iodide I g5

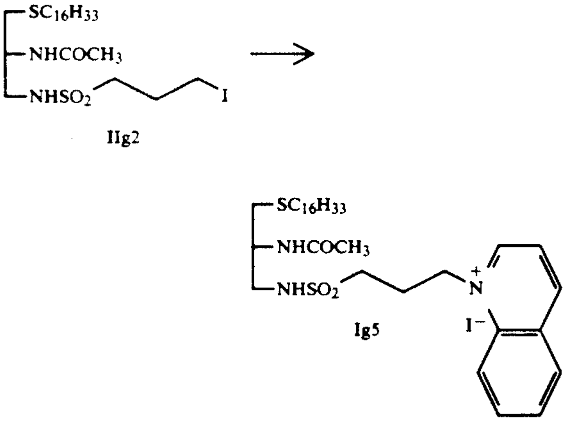

IIg2 Ig5

2-Acetamido-1-hexadecylthio-3-(3-iodopropylsulfonylamino)propane II g2 is allowed to react and worked up by the same procedure as described in Example 25. The summary of the experimental condition and the physical data of the product are listed in Table 10.

EXAMPLE 51

Preparation of 1-hexadecylthio-2-(3-methylureido)-3-(3-quinoliniopropylamino)propane iodide I f4

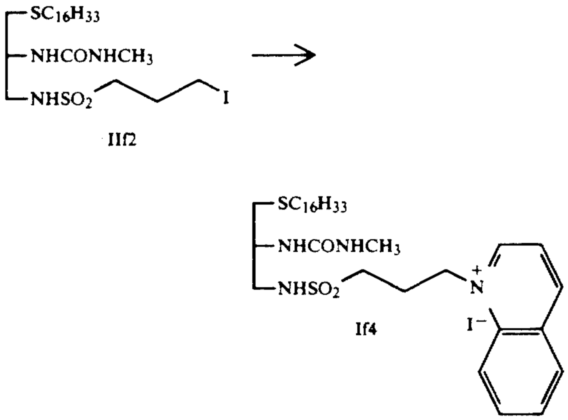

IIf2 If4

1-Hexadecylthio-3-(3-iodopropylsulfonylamino)-2-(3-methylureido)propane II f2 is allowed to react and worked up by the same procedure as described in Example 25. The summary of the experimental condition and the physical data of the product are listed in Table 10.

EXAMPLE 52

Preparation of 3-(N-acetyl-3-quinoliniopropylsulfonylamino)-2-acetamido-1-octadecylcarbamoyloxypropane iodide I g6

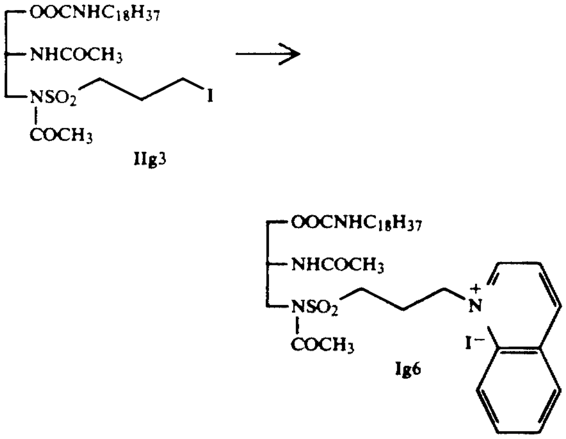

IIg3 Ig6

3-(N-Acetyl-3-iodopropylsulfonylamino)-2-acetamido-1-octadecylcarbamoyloxypropane II g3 is allowed to react and worked up by the same procedure as described in Example 25. The summary of the experimental condition and the physical data of the product are listed in Table 10.

(76) Preparation of 1-tert-butyldimethylsilyloxy-3-triphenylmethoxypropan-2-ol 2h

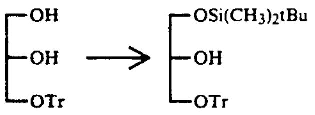

Ih 2h

A solution of 14.2 g (94 mM) of tert-butyldimethylsilyl chloride and 12.8 g (198 mM) of imidazole in 200 ml of dimethylformamide is stirred at room temperature for 30 minutes. To this solution is added a solution of 31.45 g (94 mM) of 3-triphenylmethoxy-1,2-propanediol 1h in 100 ml of dimethylformamide dropwise and the mixture is stirred at room temperature for another 2 hr. The mixture is poured into ice-water and the product is isolated by dichloromethane extraction. The dichloromethane layer is washed with water (twice) and saturated aqueous sodium chloride, dried over anhydrous magnesium sulfate and evaporated. The residue is purified by column silica gel chromatography using toluene:ethyl acetate (9:1) mixture as an eluent and 40.7 g (90% yield) of the title compound 2h is obtained.

NMR: δ ppm($CDCl_3$) 0.02&0.03(s, each 3H), 0.84(s, 9H), 2.46(d, J=5 Hz, 1H), 3.14(ABX, J=9.2&5.84 Hz, 1H), 3.22 (ABX, J=9.2&5.76 Hz, 1H), 3.67(ABX, J=9.40&4.91 Hz, 1H), 3.70(ABX, J=9.40&3.09 Hz, 1H), 3.75-3.9(m, 1H), 71.-7.5(m, 15H).

(77) Preparation of 1-tert-butyldimethylsilyloxy-2-(5-methyl-2H-tetrazol-2-yl)-3-triphenylmethoxypropane 3h and 1-tert-butyldimethylsilyloxy-2-(5-methyl-1H-tetrazol-1-yl)-3-triphenylmethoxypropane 3i

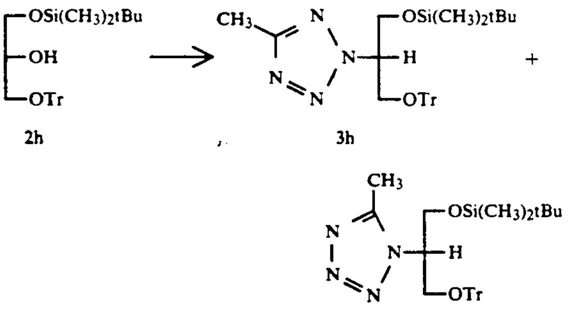

2h , 3h +

3i

To a stirred solution of 1.0 g (2.23 mM) of 1-tert-butyldimethylsilyloxy-3-triphenylmethoxypropan-2-ol 2h, 877 mg (3.35 mM) of triphenylphosphine, and 0.53 ml (3.35 mM) of diethyl azodicarboxylate in 30 ml of tetrahydrofuran at 0° C., is added 281 mg (3.35 mM) of 5-methyltetrazole dropwise and the mixture is stirred at room temperature for 15 hr. The product is isolated by dichloromethane extraction. The dichloromethane layer is washed with saturated aqueous sodium bicarbonate, dried and evaporated. The residue is separated by column silica gel chromatography using n-hexane:toluene (1:1) and toluene:ethyl acetate (9:1) mixture as an eluent and 0.74 g (64% yield) of the title compounds 3h and 0.36 g (31% yield) of 3i are obtained.

Compound 3h: Oil,

NMR: δ ppm($CDCl_3$)−0.10(s, 3H), −0.08 (s, 3H), 0.74(s, 9H), 2.54(s, 3H), 3.57 (ABX, J=9.8&4.6 Hz, 1H), 3.63(ABX, J=9.8&7.6 Hz, 1H), 4.0-4.15(m, 2H), 4.95-5.15(m, 1H), 7.1-7.35(m, 15H).

Compound 3i: Oil,

NMR: δ ppm($CDCl_3$)−0.16(s, 3H), −0.09 (s, 3H), 0.73(s, 9H), 2.56(s, 3H), 3.59 (ABX, J=9.8&5.6 Hz, 1H), 3.67(ABX, J=9.8&9.4 Hz, 1H), 3.91(ABX, J=10.4&9.9 Hz, 1H), 3.97(ABX, J=10.4&5.9 Hz, 1H), 4.35-4.5(m, 1H), 7.15-7.4 (m, 15H).

(78) Preparation of 2-(5-methyl-2H-tetrazol-2-yl)-3-triphenylmethoxypropanol 4h

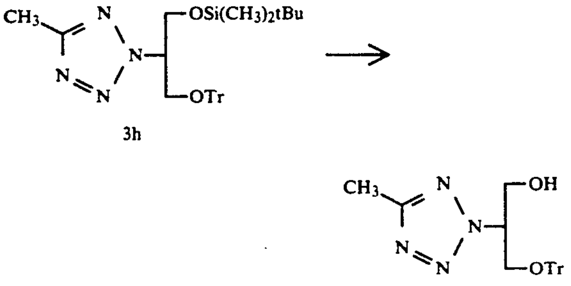

3h

4h

To a solution of 17.2 g (33.4 mM) of 1-tert-butyldimethylsilyloxy-2-(5-methyl-2H-tetrazol-2-yl)-3-triphenylmethoxypropane 3h in 300 ml of tetrahydrofuran is added a solution of 36.8 ml (36.8 mM) of 1M tetra-b-butylammonium fluoride in tetrahydrofuran and the mixture is stirred at room temperature for 10 minutes. The product is isolated by dichloromethane extraction. The dichloromethane layer is washed with water and saturated aqueous sodium chloride, dried over anhydrous magnesium sulfate and evaporated. The residue is purified by column silica gel chromatography using toluene:ethyl acetate (9:1) mixture as an eluent and 12.8 g (96% yield) of the title compound 4h is obtained. mp. 126°-127° C. (Recryastallized from dichloromethane-methanol)

NMR: δ ppm($CDCl_3$)2.49(s, 3H), 2.94 (t, J=6.5 Hz, 1H), 3.63.75(m, 2H), 3.954.3(m, 2H), 4.95.1(m, 1H), 7.157.45(m, 15H).

(79) Preparation of 2-(5-methyl-1H-tetrazol-1-yl)-3-triphenylmethoxypropanol 4i

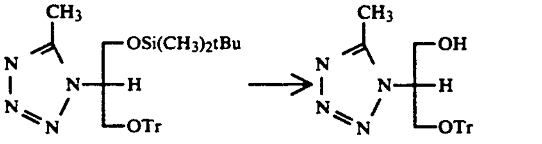

3i 4i

A solution of 5.92 g (12 mM) of 1-1-tert-butyldimethylsilyloxy-2-(5-methyl-1H-tetrazol-1-yl)-3-triphenyl methoxypropane 3i in 100 ml of tetrahydrofuran is allowed to react with 12.7 ml (12.7 mM) of tetra-n-butylammonium fluoride in 100 ml of tetrahydrofuran and the resulting mixture is worked up by the same procedure as described in (78) to give 4.17 g of the titled compound 4i. (Yield 91%).

NMR: δ ppm($CDCl_3$) 2.49(s, 3H), 3.5–3.65(m, 3H), 3.9–4.2(m, 3H), 4.35–4.5(m, 1H), 7.1–7.35(m, 15H).

(80) Preparation of 1-hexadecylthio-2-(5-methyl-1H-tetrazol-1-yl)-3-triphenylmethoxypropane 5i

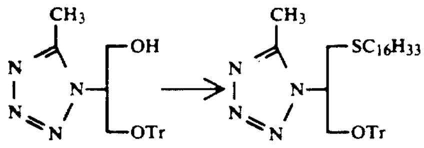

4i 5i

To a stirred solution of 1.86 g (4.6 mM) 2-(5-methyl-1H-tetrazol-1-yl)-3-triphenylmethoxypropanol 4i and 0.71 ml (5.1 mM) of triethylamine in 50 ml of dichloromethane at 0° C., is added 0.38 ml (4.8 mM) of methanesulfonyl chloride dropwise and the mixture is stirred at room temperature for overnight. The product is isolated by dichloromethane extraction. The dichloromethane layer is washed with water (twice) and saturated aqueous sodium chloride, dried over anhydrous magnesium sulfate and evaporated to obtain crude methane sulfonate product. A mixture of 204 mg (5.1 mM) of 60% sodium hydride in oil, 1.75 ml (5.5 mM) of n-hexadecyl mercaptane (98% purity) in 20 ml of benzene is allowed to react at 70° C. for 30 min and to the resulting mixture after cooling is added a solution of the methane sulfonate product obtained above in 20 ml of benzene and 100 mg of dicyclohexyl-18-crown-6 and the mixture is stirred at room temperature for 4 hr. The mixture is poured into ice-water and the product is isolated by ethyl acetate extraction. The ethyl acetate layer is washed with water and saturated aqueous sodium chloride, dried over magnesium sulfate and evaporated. The residue is purified by column silica gel chromatography using toluene:ethyl acetate (9:1) mixture as an eluent and 2.97 g (100% yield) of the title compound 5i is obtained.

NMR: δ ppm($CDCl_3$)0.88(t, J=6 Hz, 3H), 2.21(t, J=7.5 Hz, 2H), 2.56(s, 3H), 2.99(d, J=7.2 Hz, 2H), 3.62(ABX, J=10 &4.9 Hz, 1H), 3.68(ABX, J=10&8.2 Hz, 1H), 4.2–4.4 (m, 1H), 7.1–7.4 (m, 15H).

(81) Preparation of 3-hexadecylthio-2-(5-methyl-1H-tetrazol-1-yl)propanol Vi1

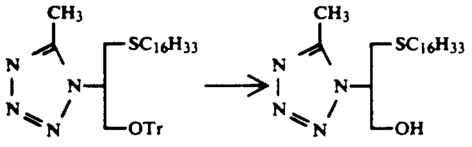

5i Vi1 a mixture of 2.90 g (4.5 mM) of 1-hexadecylthio-2-(5-methyl-1H-tetrazol-1-yl)-3-triphenylmethoxypropane and 170 mg (0.9 mM) of p-toluenesulfonic acid monohydrate in 60 ml of methanoltetrahydrofuran (1:1) mixture is stirred at room temperature for overnight. The mixture was poured into ice-water containing 151 mg (1.8 mM) of sodium bicarbonate and the product is isolated by ethyl acetate extraction. The ethyl acetate layer is washed with saturated aqueous sodium chloride, dried over anhydrous magnesium sulfate and evaporated. The residue is purified by column silica gel chromatography using toluene:ethyl acetate (4:1-1:1) mixture as an eluent and 1.46 g (81% yield) of the title compound V i1 is obtained. mp. 77°–78° C.

NMR: δ ppm($CDCl_3$) 0.88(t, J=7 Hz, 3H), 1.4–1.6(m, 2H), 2.34(t, J=7.4 Hz, 2H), 2.59(s, 3H), 3.03(ABX, J=14.4& 10.1 Hz, 1H), 3.07(ABX, J=14.4& 5.9 Hz, 1H), 4.08(ABX, J=10.8&3.2 Hz, 1H), 4.15(ABX, J=10.8&7.6 Hz, 1H), 4.35–4.55(m, 1H).

(82) Preparation of 2-(5-methyl-1H-tetrazol-1-yl)-3-octadecylcarbamoyloxypropanol V i2

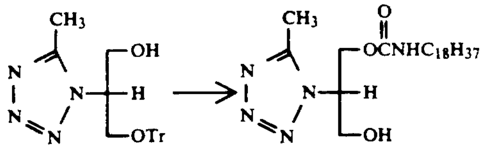

4i Vi2

A mixture of 1.9 g (4.7 mM) of 2-(5-methyl-1H-tetrazol-1-yl)-3-triphenylmethoxypropane-1-ol and 20 ml (5.6 mM) of n-octadecyl isocyanate in 40 ml of pyridine is allowed to react at room temperature of 60 hr. and at 60° C. for 2 hr. The mixture is isolated by dichloromethane extraction. The dichloromethane layer is washed with water and saturated aqueous sodium chloride, dried over anhydrous magnesium sulfate and evaporated. The residue is purified by column silica gel chromatography using toluene:ethyl acetate (9:1–2:1) mixture as an eluent to obtain 1.84 g of crude 1-n-octadecylcarbamate derivative. A mixture of 1.84 g of the crude 1-n-octadecylcarbamate derivative obtained above and 150 mg (0.79 mM) of p-toluenesulfonic acid monohydrate in 50 ml of methanol-tetrahydrofuran (1:1) mixture is stirred at room temperature for overnight. The mixture is poured into ice-water containing 132 mg (1.6 mM) of sodium bicarbonate and the product is isolated by dichloromethane extraction. The dichloromethane layer is washed with saturated aqueous sodium chloride, dried over magnesium sulfate and evaporated. The residue is purified by column silica gel chromatography using toluene-ethyl acetate (2:1–1:1) mixture and ethyl acetate as an eluent and 1.05 g (49% from 4i) of the title compound V i2 is obtained. mp. 80°–83° C.

NMR:δ ppm($CDCl_3$) 0.88(t, J=6.4 Hz, 3H), 1.4–1.6(m, 2H), 2.54(s, 3H), 3.13 (quartet, J=6.4 Hz, 2H), 4.0–4.25(m, 2H), 4.38(ABX, J=11.8&8.3 Hz, 1H), 4.56(ABX, J=11.8& 4.5 Hz, 1H), 4.65–4.8(m, 1H), 5.01(t, J=5.7 Hz, 1H).

(83) Preparation of 1-hexadecylthio-2-(5-methyl-2H-tetrazol-2yl)-3-triphenylmethoxypropane 5h

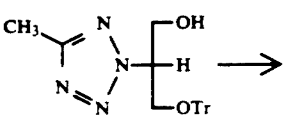

4h

-continued

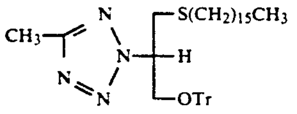

5h

Using 2.5 ml (18 mM) of triethylamine and 1.3 ml (17 mM) of methanesulfonyl chloride in 150 ml of dichloromethane, 6.50 g (16 mM) of 2-(5-methyl-2H-tetrazol-2-yl)-3-triphenylmethoxypropanol 4h is converted to methanesulfonate derivative by the same procedure as described in example 80. Using 0.71 g (18 mM) of 60% sodium hydride in oil, 4.70 g (18 mM) of n-hexadecyl mercaptane (98% purity), and the crude methane sulfonate derivative obtained above in 150 ml of benzene is converted to the title compound 5h by the same procedure as described in (80). The product is used for the next reaction without further purification.

NMR:δ ppm($CDCl_3$)0.88(t, J=7 Hz, 3H), 2.34(t, J=7.5 Hz, 2H), 2.55(s, 3H), 3.05(d, J=7.2 Hz, 2H), 3.60(ABX, J=10 &5.0 Hz, 1H), 3.66(ABX, J=10&7.3 Hz, 1H), 4.9-5.1(m, 1H), 7.15-7.5(m, 15H).

(84) Preparation of 3-hexadecylthio-2-(5-methyl-2H-tetrazol-2-yl)propanol V h1

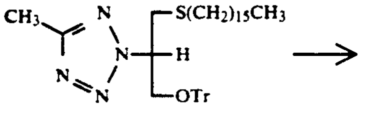

5h

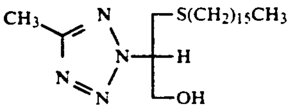

Vh1

Using 10.2 g of crude 1-hexadecylthio-2-(5-methyl-2H-tetrazol-2-yl)-3-triphenylmethoxypropane 5h and 500 mg (2.6 mM) of p-toluene sulfonic acid monohydrate in 200 ml of methanoltetrahydrofurane (1:1) mixture is converted to 3.17 g (49% from the compound 4h) of the title compound V h1 by the same procedure as described in (81).

NMR δ ppm($CDCl_3$)0.88(t, J=7 Hz, 3H), 1.45-1.65(m, 2H), 2.48(t, J=7.4 Hz, 2H), 2.52(s, 3H), 3.08(ABX, J=14.6&7.6 Hz, 1H), 3.12(ABX, J=14.6&7.4 Hz, 1H), 4.16(ABX, J=12.4&4.3 Hz, 1H), 4.19 (ABX, J=12.4&7.7 Hz, 1H), 4.9-5.1 (m, 1H).

(85) Preparation of 2-(5-methyl-2H-tetrazol-2-yl)-3-octadecylcarbamoyloxypropanol V h2

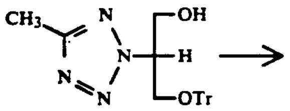

4h

-continued

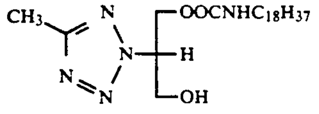

Vh2

Using 5.71 g (14 mM) of 2-(5-methyl-2H-tetrazol-2-yl)-3-triphenylmethoxypropanol 4h and 5.9 ml (17 mM) of n-octadecyl isocyanate in 120 ml of pyridine is converted to the crude carbamate derivative by the same procedure as described in (82). Using 5.74 g of the crude carbamate derivative obtained above and 400 mg (2.1 mM) of p-toluenesulfonic acid monohydrate in 150 ml of methanol-tetrahydrofuran (1:1) mixture is converted to 3.39 g (52% from the compound 4h) of the title compound V h2 by the same procedure as described in (82). mp. 76°-77° C.

NMR:δ ppm($CDCl_3$)0.88(t, J=7 Hz, 3H), 1.35-1.55(m, 2H), 2.54(s, 3H), 3.14 (quartet, J=6.5 Hz, 2H), 4.14(d, J=5.8 Hz, 2H), 4.55-4.7(m, 2H), 4.8-4.95(m, 1H), 5.0-5.2(m, 1H).

(86) Preparation of 3-hexadecylthio-2-(5-methyl-1H-tetrazol-1-yl)propylamine IV i1

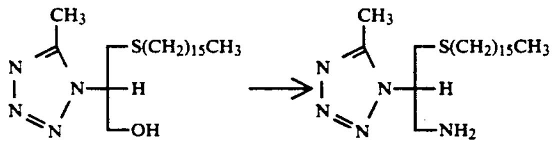

Vi1 IVi1

3-Hexadecylthio-2-(5-methyl-1H -tetrazol-1-yl)propanol V i1 is allowed to react and worked up by the same procedure as described in (3). The summary of the experimental condition and the physical data of the product are listed in Tables 5 and 6.

The prepared phthalimide is used for the next reaction without further purification.

(87) Preparation of 3-(3-chloropropylsulfonylamino)-1-hexadecylthio-2-(5-methyl-1H-tetrazol-1-yl)propane III i1

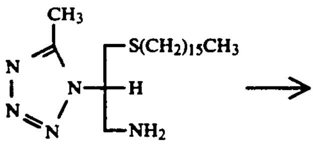

IVi1

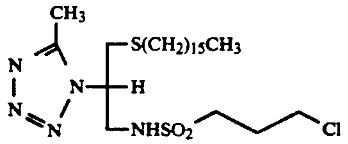

IIIi1

3-Hexadecylthio-2-(5-methyl-1H -tetrazol-1-yl)propylamine IV i1 is allowed to react and worked up by the same procedure as described in (4). m.p. 62°-62.5° C. The summary of the experimental condition and the physical data of the product are listed in Table 7.

The yield is calculated from the 3-hydroxy compound 5i.

(88) Preparation of 1-hexadecylthio-3-(3-iodopropylsulfonylamino)-2-(5-methyl-1H-tetrazol-1yl)propane II i1

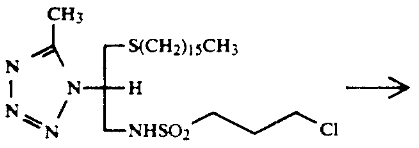

IIIi1

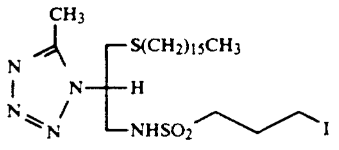

IIi1

3-(3-Chloropropysulfonylamino)-1-hexadecylthio-2-(5-methyl-1H-tetrazol-1-yl)propane III i1 is allowed to react and worked up by the same procedure as described in (5). m.p. 63.5°-65.5° C. The summary of the experimental condition and the physical data of the product are listed in Table 8.

EXAMPLE 53

Preparation of 1-n-hexadecylthio-2-(5-methyl-1H-tetrazol-1-yl)-3-(3-trimethylammoniopropylsulfonylamino)propane iodide I i1

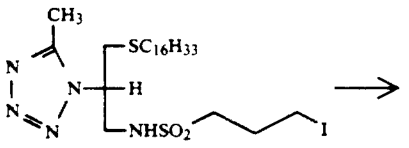

IIi1

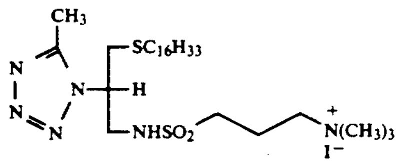

Ii1

1-Hexadecylthio-3-(3-iodopropylsulfonylamino)-2-(5-methyl-1H-tetrazol-1-yl)propane II i1 is allowed to react and worked up by the same procedure as described in Example 8. The summary of the experimental condition and the physical data of the product are listed in Table 9.

(89) Preparation of 2-(5-methyl-1H-tetrazol-1-yl)-3-octadecylcarbamoyloxypropylamine IV i2

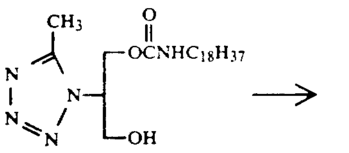

Vi2

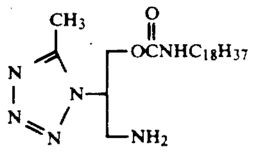

IVi2

To a stirred solution of 1.02 g (2.25 mM) of 2-(5-methyl-1H-tetrazol-1-yl)-3-octadecylcarbamoyloxypropanol V i2, 885 mg (3.38 mM) of triphenylphosphine, and 1.9 ml (3.38 mM) of 1.8 mM benzene solution of hydrazoic acid in 50 ml of tetrahydrofurane at −50° C. is added 0.53 ml (3.38 mM) of diethyl azodicarboxylate dropwise and the mixture is raised to room temperature during 2 hr. Subsequently, 150 mg of 10% palladium carbon is added to the mixture which is stirred under hydrogen gas for 30 minutes. After 10% palladium carbon filtered off, the solvent is evaporated. The residue obtained is purified by column silica gel chromatography using ethyl acetate-chloroform/methanol (9/1) mixture as an eluent and 0.82 g (81% yield) of the title compound is obtained.

NMR: δ ppm ($CDCl_3$) 0.88 (t, J=7 Hz, 3H), 2.52 (s, 3H), 3.13 (quartet, J=6.6 Hz, 2H), 3.15-3.45 (m, 2H), 4.23 (ABX, J=12.6 & 9.8 Hz, 1H), 4.52 (ABX, J=12.6 & 4.2 Hz, 1H), 4.5-4.65 (m, 1H), 5.07 (t, J=6 Hz, 1H).

(90) Preparation of 3-(3-chloropropylsulfonylamino)-2-(5-methyl-1H-tetrazol-1-yl)-1-octadecylcarbamoyloxypropane III i2

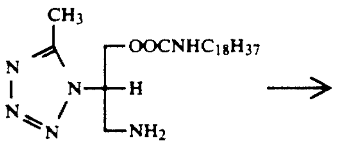

IVi2

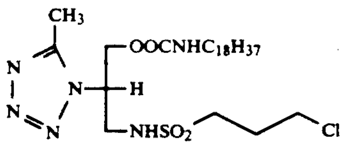

IIIi2

2-(5-Methyl-1H-tetrazol-1-yl)-3-octadecylcarbamoyloxypropylamine IV i2 is allowed to react and worked up by the same procedure as described in (4). m.p. 74°-77° C. The summary of the experimental condition and the physical data of the product are listed in Table 7.

(91) Preparation of 3-(3-iodopropylsulfonylamino)-2-(5-methyl-1H-tetrazol-1-yl)-1-octadecylcarbamoyloxypropane II i2

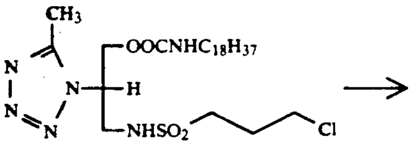

IIIi2

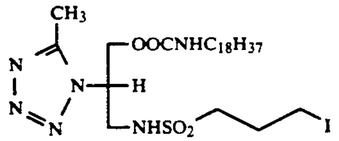

IIi2

3-(3-Iodopropylsulfonylamino)-2-(5-methyl-1H-tetrazol-1-yl)-1-octadecylcarbamoyloxypropane III i2 is allowed to react and worked up by the same procedure as described in (5). m.p. 82.5°-83.5° C. The summary of the experimental condition and the physical data of the product are listed in Table 8.

EXAMPLE 54

Preparation of 2-(5-methyl-1H-tetrazol-1-yl)-1-octadecylcarbamoyloxy-3-(3-quinoliniopropylsulfonylamino)propane iodide I i3

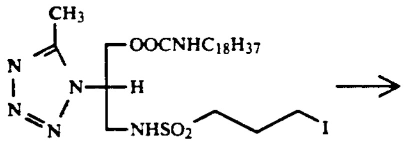

IIi2

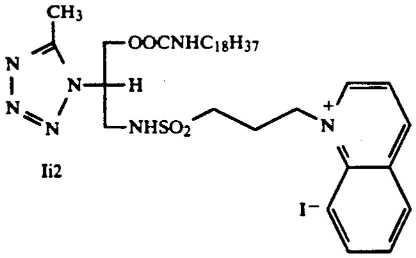

Ii2

3-(3-Iodopropylsulfonylamino)-2-(5-methyl-1H-tetrazol-1-yl)-1-octadecylcarbamoyloxypropane II i2 is allowed to react and worked up by the same procedure as described in Example 25. The summary of the experimental condition and the physical data of the product are listed in Table 10.

(92) Preparation of 3-hexadecylthio-2-(5-methyl-2H-tetrazol-2-yl)propylamine IV h1

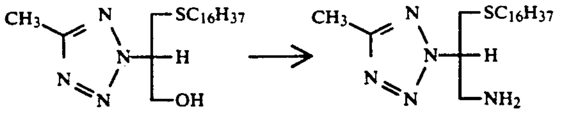

Vh1 IVh1

3-hexadecylthio-2(5-methyl-2H-tetrazol-2-yl)propanol V h1 is allowed to react and worked up by the same procedure as described in (3). The phthalimide compound: m.p. 82°-83° C. The summary of the experimental condition and the physical data of the product are listed in Tables 5 and 6.

(93) Preparation of 3-(3-chloropropylsulfonylamino)-1-hexadecylthio-2-(5-methyl-2H-tetrazol-2-yl)propane III h1

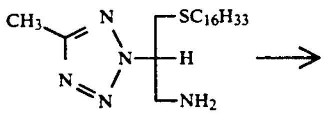

IVh1

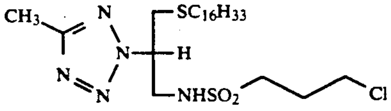

IIIh1

3-Hexadecylthio-2-(5-methyl-2H-tetrazol-2-yl)propylamine IV h1 is allowed to react and worked up by the same procedure as described in (4). The summary of the experimental condition and the physical data of the product are listed in Table 7.

(94) Preparation of 1-hexadecylthio-3-(3-iodopropylsulfonylamino)-2-(5-methyl-2H-tetrazol-2-yl)propane II h1

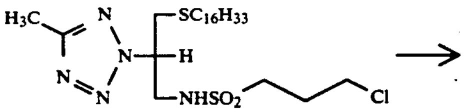

IIIh1

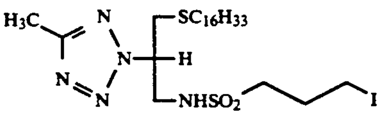

IIh1

3-(3-Chloropropylsulfonylamino)-1-hexadecylthio-2-(5-methyl-2H-tetrazol-2-yl)propane III h1 is allowed to react and worked up by the same procedure as described in (5). m.p. 50°-51° C. The summary of the experimental condition and the physical data of the product are listed in Table 8.

EXAMPLE 55

Preparation of 1-hexadecylthio-2-(5-methyl-2H-tetrazol-2-yl)-3-(3-trimethylammoniopropylsulfonylamino)propane iodide I h1

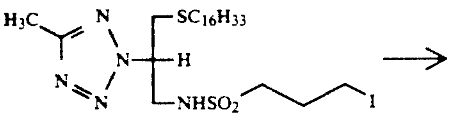

IIh1

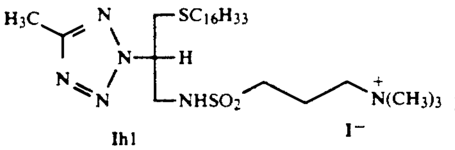

Ih1

1-Hexadecylthio-3-(3-iodopropylsulfonylamino)-2-(5-methyl-2H-tetrazol-2-yl)propane II h1 is allowed to react and worked up by the same procedure as described in Example 8.

The summary of the experimental condition and the physical data of the product are listed in Table 9.

(95) Preparation of 2-(5-methyl-2H-tetrazol-2-yl)-3-octadecylcarbamoyloxypropylamine VI h2

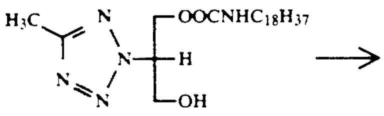

Vh2

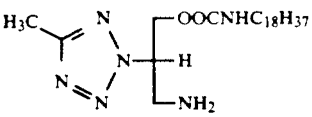

IVh2

Using 2.57 g (5.7 mM) of 2-(5-methyl-2H-tetrazoyl-2-yl)-3-octadecylcarbamoyloxypropanol V h2, 2.23 g (8.6 mM) of triphenylphosphine, 4.7 ml (8.6 mM) of 1.8 mM benzene solution of hydrazoic acid, and 1.44 g (8.6 mM) of diethyl azodicarboxylate in tetrahydrofurane is converted to azido derivative by the same procedure as described in (89). Using the azido derivative obtained above and 350 mg of 10% palladium carbon is converted to the title compound by the same procedure as described in (89). The crude product containing a trace of impurity can be purified at the next step.

NMR: δ ppm ($CDCl_3$) 0.88 (t, J=6.5 Hz, 3H), 1.4–1.65 (m, 2H), 2.55 (s, 3H), 3.12 (quartet, J=6.6 Hz, 2H), 3.25-3.35 (m, 2H), 4.47 (ABX, J=11.6 & 8.0 Hz, 1H), 4.59 (ABX, J=11.6 & 4.1 Hz, 1H), 4.8–4.95 (m, 1H), 4.95-5.1 (m, 1H).

(96) Preparation of 3-(3-chloropropylsulfonylamino)-2-(5-methyl-2H-tetrazol-2-yl)-1-octadecylcarbamoyloxypropane III h2

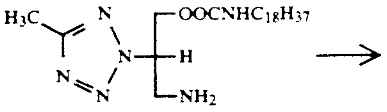

IVh2

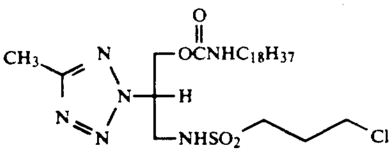

IIIh2

2-(5-Methyl-2H-tetrazol-2-yl)-1-octadecylcarbamoyloxypropylamine IV h2 is allowed to react and worked up by the same procedure as described in (4). m.p. 70°-70.5° C. The summary of the experimental condition and the physical data of the product are listed in Table 7.

The yield is calculated from the hydroxy compound V h2.

(97) Preparation of 3-(3-iodopropylsulfonylamino)-2-(5-methyl-2H-tetrazol-2-yl)-1-octadecylcarbamoyloxypropane II h2

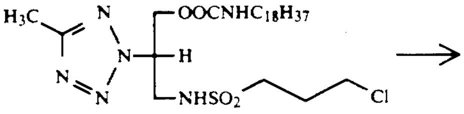

IIIh3

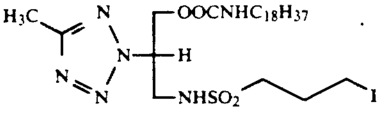

IIh2

3-(3-Chloropropylsulfonylamino)-2-(5-methyl-2H-tetrazol-2-yl)-1-octadecylcarbamoyloxypropane III h3 is allowed to react and worked up by the same procedure as described in (5). m.p. 53.5°- 54° C. The summary of the experimental condition and the physical data of the product are listed in Table 8.

EXAMPLE 56

Preparation of 2-(5-methyl-2H-tetrazol-2-yl)-1-octadecylcarbamoyloxy-3-(3-quinoliniopropylsulfonylamino)propane iodide I h3

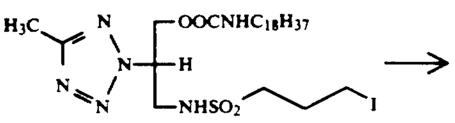

IIh2

-continued

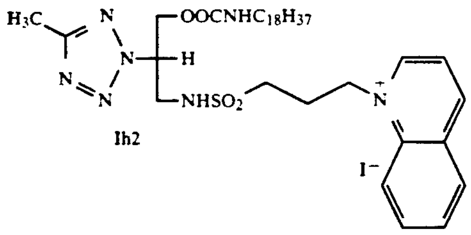

Ih2

3-(3-Iodopropylsulfonylamino)-2-(5-methyl-2H-tetrazol-2-yl)-1-octadecylcarbamoyloxypropane II h2 is allowed to react and worked up by the same procedure as described in Example 25. The summary of the experimental condition and the physical data of the product are listed in Table 10.

(98) Preparation of 1-tert-butyldimethylsilyloxy-2-(3-isoxazolyloxy)-3-triphenylmethoxypropane 3j

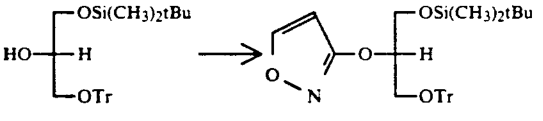

2h 3j

A mixture of 6.72 g (15 mM) of 1-tert-butyldimethylsilyloxy-3-triphenylmethoxypropane-2-ol 2h, 1.53 g (18 mM) of 3-hydroxyisoxazole, 4.71 g (18 mM) of triphenylphosphine, and 3.10 g of diethyl azodicarboxylate in 100 ml of tetrahydrofuran is allowed to react by the same procedure as described in (77) to give 7.24 g of the titled compound 3j (94% yield).

NMR: δ ppm ($CDCl_3$) 0 & 0.01 (s, each 3H), 0.82(s, 9H), 3.36(ABX, J=10.2 & 5.31 Hz, 1H), 3.47(ABX, J=10.2 & 4.09, 1H), 3.96(d, J=5.2 Hz, 2H), 4.85-5.0 (m, 1H), 6.01(d, J=1.6 Hz, 1H), 7.15-7.6(m, 15H), 8.13(d, J=1.6 Hz, 1H).

(99) Preparation of 2-(3-isoxazolyloxy)-3-triphenylmethoxypropanol 4j

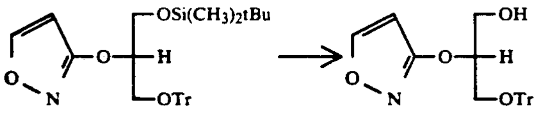

3j 4j

A mixture of 7.24 g (1.4 mM) of 1-tert-butyldimethylsilyloxy-2-(3-isoxazolyloxy)-3-triphenylmethoxypropane 3j, and 15.4 ml (15 mM) of 1M tetra-n-butylammonium fluoride in tetrahydrofuran in 100 ml of tetrahydrofuran is allowed to react by the same procedure as described in (78) to give 5.37 g of the titled compound 4j (95% yield).

NMR: δ ppm ($CDCl_3$) 2.31(t, J=6 Hz, 1H), 3.40(ABX, J=10.2 & 4.89 Hz, 1H), 3.50 (ABX, J=10.2 & 4.51 Hz, 1H), 3.94 (quartet, J=4.6 Hz, 1H), 3.96(quartet, J=4.6 Hz, 1H), 4.85-4.95(m, 1H), 6.01 (d, J=1.8 Hz, 1H), 7.15-7.55(m, 15H), 8.12(d, J=1.81 Hz, 1H).

(100) Preparation of 1-hexadecylthio-2-(3-isoxazolyloxy)-3-triphenylmethoxypropane 5j

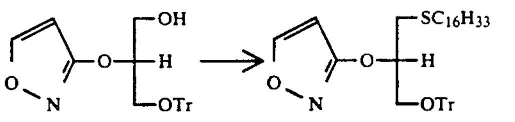

4j 5j

A mixture of 0.17 g (0.42 mM) of 2-(3-isoxazolyloxy)-3-triphenylmethoxypropanol 4j, 65 μl (0.46 mM) of triethylamine, and 34 μl (0.44 mM) of methanesulfonyl chloride in 4 ml is allowed to react by the same procedure as described in (80) to give the methanesulfonate which is then allowed to react with 18 mg (0.46 mM) of 60% suspension of sodium hydride in mineral oil and 0.12 g (0.46 mM), of n-hexadecyl mercarptan (purity 98%) in 6 ml of benzene by the same procedure as described in (80) to give 0.19 g of the titled compound 5j (70% yield).

m.p. 41°-44° C.

NMR: δ ppm ($CDCl_3$) 0.88(t, J=7 Hz, 3H), 2.48(t, J=7.3 Hz, 2H), 2.96(d, J=7.8 Hz, 2H), 3.38(ABX, J=10.2 & 4.78 Hz, 1H), 3.52(ABX, J=10.2 & 3.98 Hz, 1H), 4.9-5.05(m, 1H), 6.00 (d, J=1.8 Hz, 1H), 7.15-7.5(m, 15H), 8.11(d, J=1.8 Hz, 1H).

(101) Preparation of 3-hexadecylthio-2-(3-isoxazolyloxy)propanol V j1

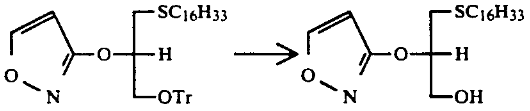

5j Vj1

A mixture of 7.30 g (1.1 mM) of 1-hexadecylthio-2-(3-isoxazolyloxy)-3-triphenylmethoxypropane 5j and 433 mg (2.3 mM) of p-toluenesulfonic acid monohydrate in 150 ml of methanol-tetrahydrofuran (1:1) mixture by the same procedure as described in (81) to give 4.25 g of the titled compound V j1 (94% yield).

NMR: δ ppm($CDCl_3$)0.88(t, J=6.2 Hz, 3H), 1.45-1.7(m, 2H), 2.5 (broad, 1H), 2.60(t, J=7.4 Hz), 2.87(ABX, J=12.8 & 6.48 Hz, 1H), 2.95 (ABX, J=12.8 & 3.52 Hz, 1H), 3.92(ABX, J=13.0 & 4.8 Hz, 1H), 4.01 (ABX, J=13.0 & 3.2 Hz, 1H), 4.8-4.9(m, 1H), 5.99(d, J=1.8 Hz, 1H), 8.13(d, J=1.8 Hz, 1H).

(102) Preparation of 3-hexadecylthio-2-(3-isoxazolyloxy)propylamine IV j1

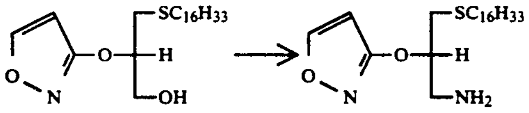

Vj1 Nj1

3-Hexadecylthio-2-(3-isoxazolyloxy)propanol V j1 is allowed to react and worked up by the same procedure as described in (3). The phthalimide compound: m.p. 73°-74° C. The summary of the experimental condition and the physical data of the product are listed in Tables 5 and 6.

(103) Preparation of 3-(3-chloropropylsulfonylamino-1-hexadecylthio-2-(3-isoxazolyloxy)propane III j1

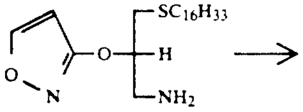

Nj1

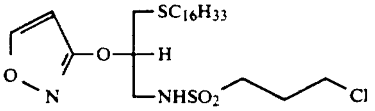

IIIj1

3-Hexadecylthio-2-(3-isoxazolyloxy)propylamine IV j1 is allowed to react and worked up by the same procedure as described in (4). The summary of the experimental condition and the physical data of the product are listed in Table 7.

(104) Preparation of 1-hexadecylthio-3-(3-iodopropylsulfonylamino)-2-(3-isoxazolyloxy)propane II j1

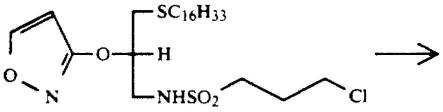

IIIj1

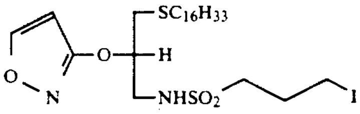

IIj1

3-(3-Chloropropylsulfonylamino)-1-hexadecylthio-2-(3-isoxazolyloxy)propane III j1 is allowed to react and worked up by the same procedure as described in (5). The summary of the experimental condition and the physical data of the product are listed in Table 8.

EXAMPLE 57

Preparation of 1-hexadecylthio-2-(3-isoxazolyloxy)-3-(3-trimethylammoniopropylsulfonylamino)propane iodide I j1

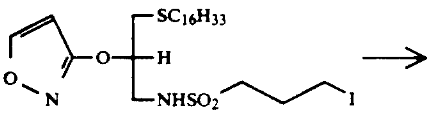

IIj1

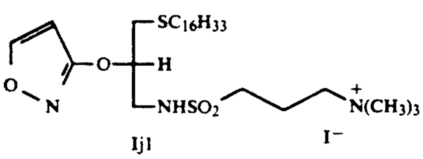

Ij1

1-Hexadecylthio-3-(3-iodopropylsulfonylamino)-2-(3-isoxazolyloxy)propane II j1 is allowed to react and worked up by the same.procedure as described in Example 8. The summary of the experimental condition and the physical data of the product are listed in Table 9.

(105) Preparation of 3-(3-chloropropylsulfonylamino)-2-(3-isoxazolyloxy)-1-octadecylcarbamoyloxypropane III j2

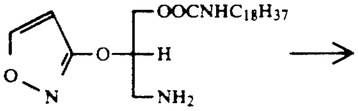

IVj2

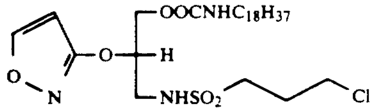

IIIj2

2-(3-Isoxazolyloxy)-1-octadecylcarbamoyloxypropylamine IV j2 is allowed to react and worked up by the same procedure as described in (4). m.p. 63.5°–65° C. The summary of the experimental condition and the physical data of the product are listed in Table 7.

(106) Preparation of 3-(3-iodopropylsulfonylamino)-2-(3-isoxazolyloxy)-1-octadecylcarbamoyloxypropane II j2

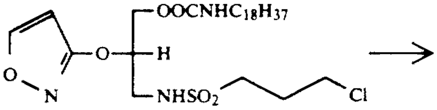

IIIj2

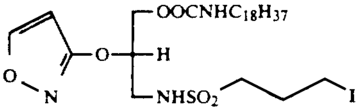

IIj2

3-(3-Chloropropylsulfonylamino)-2-(3-isoxazolyloxy)-1-octadecylcarbamoyloxypropane III j2 is allowed to react and worked up by the same procedure as described in (5). m.p. 69°–71.5° C. The summary of the experimental condition and the physical data of the product are listed in Table 8.

EXAMPLE 58

Preparation of 2-(3-isoxazolyloxy)-1-octadecylcarbamoyloxy-3-(3-trimethylammoniopropylsulfonylamino)propane idodide I j2

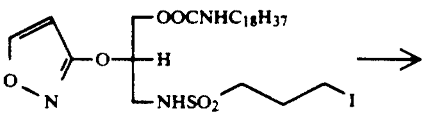

IIj2

-continued

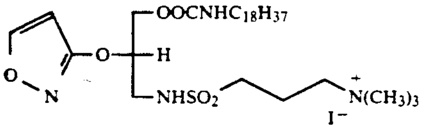

Ij2

3-(3-Iodopropylsulfonylamino)-2-(3-isoxazolyloxy)-1-octadecylcarbamoyloxypropane II j2 is allowed to react and worked up by the same procedure as described in Example 8. The summary of the experimental condition and the physical data of the product are listed in Table 9.

EXAMPLE 59

Preparation of 2-(3-isoxazolyloxy)-1-octadecylcarbamoyloxy-3-(3-quinoliniopropylsulfonylamino)propane iodide I j3

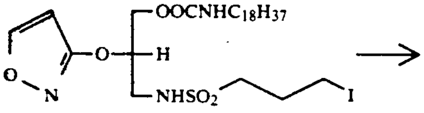

IIj3

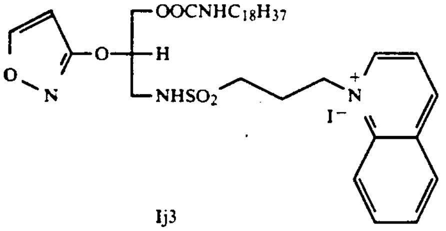

Ij3

3-(3-Iodopropylsulfonylamino)-2-(3-isoxazolyloxy)-1-octadecylcarbamoyloxypropane II j3 is allowed to react and worked up by the same procedure as described in Example 25. The summary of the experimental condition and the physical data of the product are listed in Table 10.

(107) Preparation of 3-hexadecyloxy-2-methoxymethylpropylamine IV k1

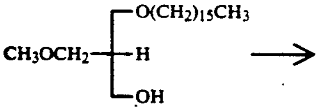

Vk1

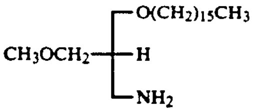

IVk1

3-Hexadecyloxy-2-methoxymethylpropanol V k1 is allowed to react and worked up by the same procedure as described in (3). The phthalimide compound: m.p. 49°-51° C. The summary of the experimental condition and the physical data of the product are listed in Tables 5 and 6.

(108) Preparation of 3-(3-chloropropylsulfonylamino)-1-hexadecyloxy-2-methoxymethylpropane III k1

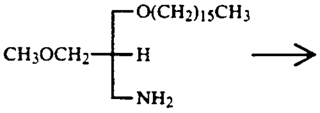

IVk1

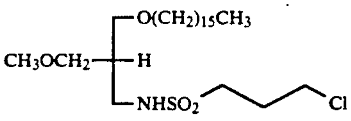

IIIk1

3-Hexadecyloxy-2-methoxymethylpropylamine IV k1 is allowed to react and worked up by the same procedure as described in (4). m.p. 44°-46.5° C. The summary of the experimental condition and the physical data of the product are listed in Table 7.

(109) Preparation of 1-hexadecyloxy-3-(3-iodopropylsulfonylamino-2-methoxymethylpropane II k1

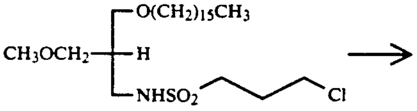

IIIk1

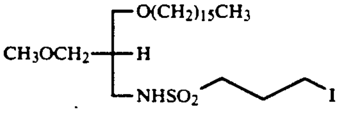

IIk1

3-(3-Chloropropylsulfonylamino)-1-hexadecyloxy-2-methoxymethylpropane III k1 is allowed to react and worked up by the same procedure as described in (5). m.p. 42.5°-44° C. The summary of the experimental condition and the physical data of the product are listed in Table 8.

(110) Preparation of 3-(N-acetyl-3-iodopropylsulfonylamino)-1-hexadecyloxy-2-methoxymethylpropane II k1

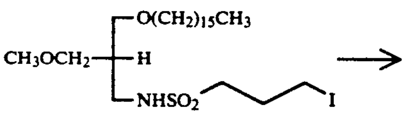

IIk1

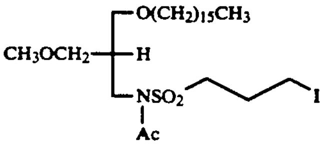

IIk1

To a cooled mixture of 0.76 g (1.3 mM) of 1-hexadecyloxy-3-(3-iodopropylsulfonylamino)-2-methoxymethylpropane II k1 and 0.14 ml (2.0 mM) of acetyl chloride in 10 ml of dichloromethane at 0° C., is added 0.39 ml (2.2 mM) of diisopropylamine and the mixture is stirred at 0° C., for 3 hours. The mixture is poured into ice-water and the product is isolated by dichloromethane extraction. The dichloromethane layer is washed with saturated aqueous sodium chloride, dried over anhydrous magnesium sulfate and evaporated. The residue is purified by column silfica gel chromatography using toluene-ethyl acetate (9:1) mixture and 0.81 g (99% yield) of the titled compound II k1' is obtained.

NMR δ ppm ($CDCl_3$): 0.88 (t, J=6 Hz, 3H), 1.95-2.15 (m, 1H), 2.2-2.45 (m, 2H), 2.38 (s, 3H), 3.29 (t, J=5 Hz, 2H), 3.32 (s, 3H), 3.59 (t, J=8 Hz, 2H), 3.82 (d, J=6 Hz, 2H).

EXAMPLE 60

Preparation of 3-(N-acetyl-3-trimethylammoniopropylsulfonylamino)-1-hexadecyloxy-2-methoxymethylpropane iodide I k1

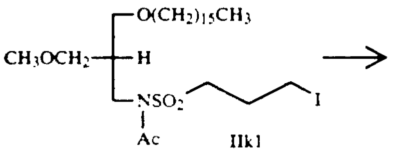

IIk1

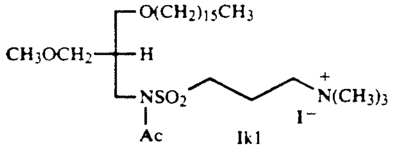

Ik1

3-(N-Acetyl-3-iodopropylsulfonylamino-1-hexadecyloxy-2-methoxymethylpropane II k1' is allowed to react and worked up by the same procedure as described in Example 8. The summary of the experimental condition and the physical data of the product are listed in Table 8.

EXAMPLE 61

Preparation of 1-hexadecyloxy-2-methoxymethyl-3-(3-trimethylammoniopropylsulfonylamino)propane iodide I k2

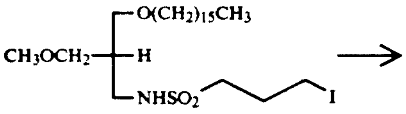

IIk1

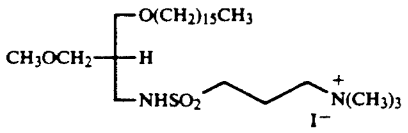

Ik2

1-Hexadecyloxy-3-(3-iodopropylsulfonylamino)-2-methoxymethylpropane II k1 is allowed to react and worked up by the same procedure as described in Example 8. The summary of the experimental condition and the physical data of the product are listed in Table 9.

EXAMPLE 62

Preparation of 1-hexadecyloxy-2-methoxymethyl-3-(3-quinolinio-propylsulfonylamino)propane iodide I k3

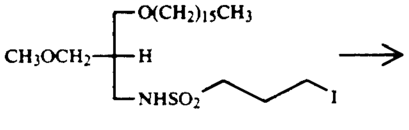

IIk1

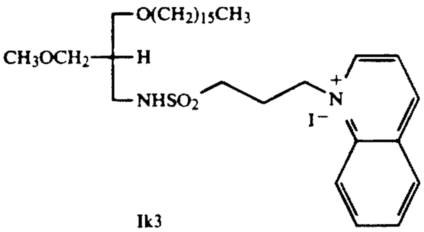

Ik3

1-Hexadecyloxy-3-(3-iodopropylsulfonylamino)-2-methoxymethylpropane II k1 is allowed to react and worked up by the same procedure as described in Example 25. The summary of the experimental condition and the physical data of the product are listed in Table 10.

(111) Preparation of 3-hexadecylthio-2-methoxymethylpropylamine IV k3

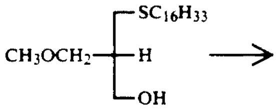

Vk3

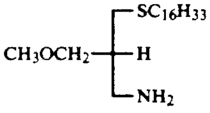

IVk3

3-Hexadecylthio-2-methoxymethylpropanol IV k3 is allowed to react and worked up by the same procedure as described in (4). The phthalimide compound m.p. 45° C. The summary of the experimental condition and the physical data of the product are listed in Tables 5 and 6.

(112) Preparation of 3-(3-chloropropylsulfonylamino)-1-hexadecylthio-2-methoxymethylpropane IV k3

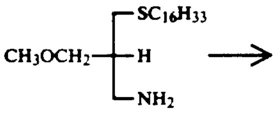

IVk3

-continued

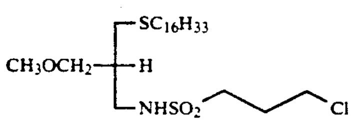

IIIk3

3-Hexadecylthio-2-methoxymethylpropylamine IV k3 is allowed to react and worked up by the same procedure as described in (4). m.p. 41.5°–43° C. The summary of the experimental condition and the physical data of the product are listed in Table 7.

(113) Preparation of 1-hexadecylthio-3-(3-iodopropylsulfonylamino)-2-methoxymethylpropane II k3

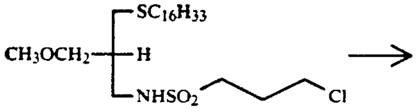

IIIk3

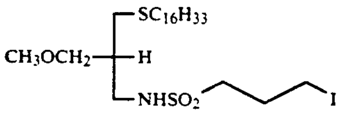

IIk3

3-(3-Chloropropylsulfonylamino)-1-hexadecylthio-2-methoxymethylpropane III k3 is allowed to react and worked up by the same procedure as described in (5). The summary of the experimental condition and the physical data of the product are listed in Table 8.

EXAMPLE 63

Preparation of 1-hexadecylthio-2-methoxymethyl-3-(3-trimethylammoniopropylsulfonylamino)propane iodide I k4

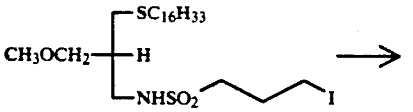

IIk3

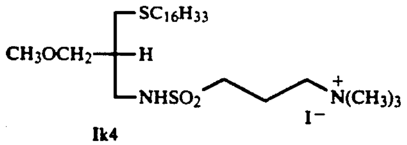

Ik4

1-Hexadecylthio-3-(3-iodopropylsulfonylamino)-2-methoxymethylpropane II k3 is allowed to react and worked up by the same procedure as described in Example 8. The summary of the experimental condition and the physical data of the product are listed in Table 9.

(114) Preparation of 2-methoxymethyl-3-octadecylcarbamoyloxypropylamine IV k2

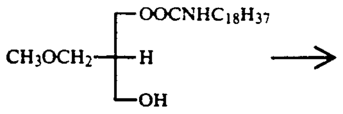

Vk2

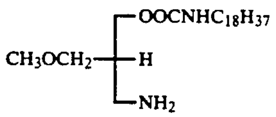

IVk2

2-Methoxymethyl-3-octadecylcarbamoyloxypropanol V k2 is allowed to react and worked up by the same procedure as described in (4). The phthalimide compound: m.p. 84°–85° C. The summary of the experimental condition and the physical data of the product are listed in Table 6.

(115) Preparation of 3-(3-chloropropylsulfonylamino)-2-methoxymethyl-1-octadecylcarbamoyloxypropane III k2

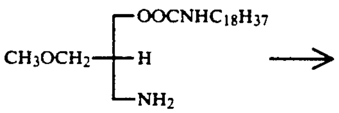

IVk2

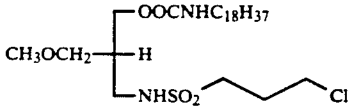

IIIk2

2-Methoxymethyl-3-octadecylcarbamoyloxypropylamine IV k2 is allowed to react and worked up by the same procedure as described in (4). m.p. 72°–73° C. The summary of the experimental condition and the physical data of the product are listed in Table 7.

(116) Preparation of 3-(3-iodopropylsulfonylamino)-2-methoxymethyl-1-octadecylcarbamoyloxypropane II k2

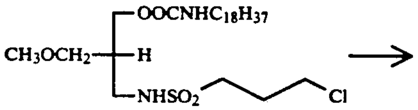

IIIk2

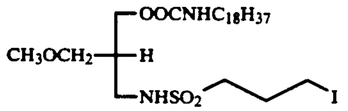

IIk2

3-(3-Chloropropylsulfonylamino)-2-methoxymethyl-1-octadecylcarbamoyl oxypropane III k2 is allowed to react and worked up by the same procedure as described in (5). m.p. 69°-70° C. The summary of the experimental condition and the physical data of the product are listed in Table 8.

(117) Preparation of 3-(N-acetyl-3-iodopropylsulfonylamino)-2-methoxymethyl-1-octadecylcarbamoyloxypropane II k2'

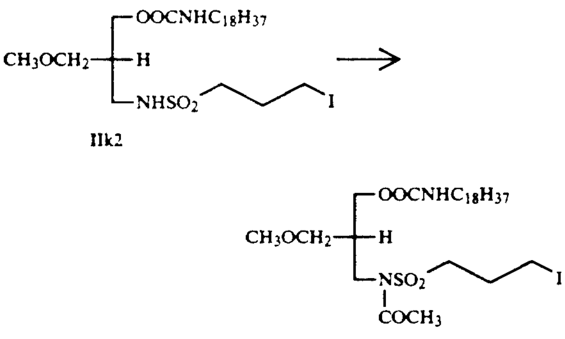

IIk2

IIk2'

A mixture of 0.72 g (1.1 mM) of 3-(3-iodopropylsulfonylamino)-2-methoxymethyl-1-octadecylcarbamoyloxypropane II k2, 88 μl (1.2 mM) of acetyl chloride and 0.25 ml (1.4 mM) of N,N-diisopropylethylamine is allowed to react by the same procedure as described in (110) and 0.65 g (85% yield) of the title compound II k2' is obtained. m.p. 71°-72° C.

NMR: δ ppm ($CDCl_3$) 0.88 (t, J=6 Hz, 3H), 1.4-1.6 (m, 2H), 2.25-2.5 (m, 3H), 2.40(s, 3H), 3.15 (q, J=6 Hz, 2H), 3.30 (t, J=7 Hz, 3H), 3.32 (s, 3H), 3.35-3.5 (m, 2H), 3.56 (t, J=8 Hz, 2H), 3.84 (d, J=7 Hz, 2H), 4-4.2 (m, 2H), 4.79 (t, J=6 Hz, 1H).

EXAMPLE 64

Preparation of 2-methoxymethyl-1-octadecylcarbamoyloxy-3-(3-quinoliniopropylsulfonylamino)propane iodide I k5

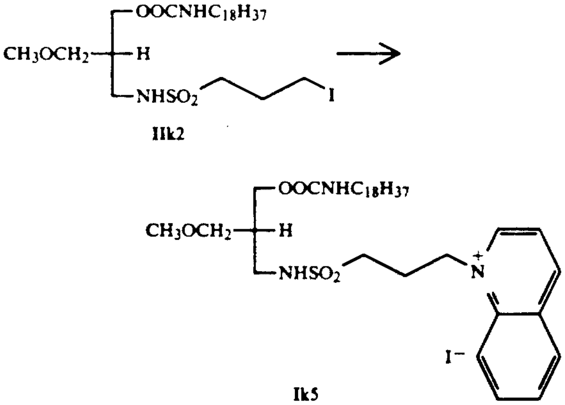

IIk2

Ik5

3-(3-Iodopropylsulfonylamino)-2-methoxymethyl-1-octadecylcarbamoyloxypropane II k2 is allowed to react and worked up by the same procedure as described in Example 25. The summary of the experimental condition and the physical data of the product are listed in Table 10.

EXAMPLE 65

Preparation of 3-(N-acetyl-3-quinoliniopropylsulfonylamino)-2-methoxymethyl-1-octadecylcarbamoyloxypropane iodide I k6

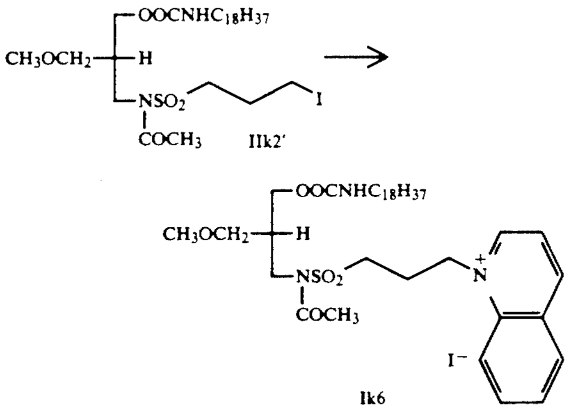

IIk2'

Ik6

3-(N-Acetyl-3-iodopropylsulfonylamino)-2-methoxymethyl-1-octadecylcarbamoyloxypropane II k2' is allowed to react and worked up by the same procedure as described in Example 25. The summary of the experimental condition and the physical data of the product are listed in Table 10.

(118) Preparation of 5-bromomethyl-2-phenyl-1,3-dioxane m2

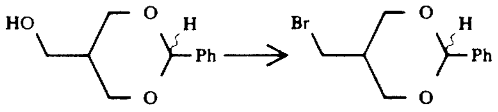

m1 m2

To a vigorously stirred solution of 19.4 g (0.1M) of 5-hydroxymethyl-2-phenyl-1,3-dioxane m1 and 33.1 g (0.1M) of tetrabromomethane in 60 ml of anhydrous benzene at 70° C., is added 26.2 g (0.1M) of triphenylphosphine in 45 minutes. After stirring at 70° C. for an another 30 minutes, the solvent is evaporated. To the residue is added 200 ml of ether and ether insoluble triphenylphosphine oxide is removed by filtration. After repeating this procedure twice, the solvent of the filtrated is evaporated. Distillation of the residual product gives 19.391 g (75.4% yield) of the titled compound m2. B.P. 145°~158° C. (1 mmHg).

(119) Preparation of 5-(2-hydroxypropan-1-yl)-2-phenyl-1,3-dioxane m3

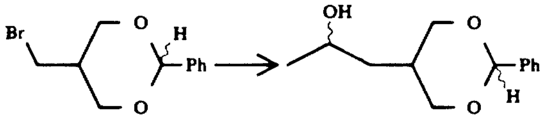

m2 m3

To a solution of 19.39 g (75.4 mM) of 5-bromomethyl-2-phenyl-1,3-dioxane m2 in 200 ml of tetrahydrofuran is added 1.923 g (79.17 mM) of magnesium and the mixture is allowed to react for 7 hours under ultrasonic bibration. The mixture is cooled to −70° C. and 21.27 ml (377 mM) of acetaldehyde is added and then the mixture is stirred at 0° C. for 15 hours. The mixture is poured into an ice-cooled saturated aqueous ammonium chloride solution and the product is isolated by ethyl acetate extraction. The ethyl acetate layer is washed with saturated aqueous sodium chloride, dried over anhydrous magnesium sulfate and evaporated. By eliminating the polar impurity by passing short column of silica gel, 11.353 g of the crude titled compound m3 is obtained which is used to the next reaction without further purification.

IR: ν max ($CHCl_3$) 3620∼3150 $cm^{-1}$ (broad)

(120) Preparation of 5-(2-benzoyloxypropan-1-yl)-2-phenyl-1,3-dioxane m4

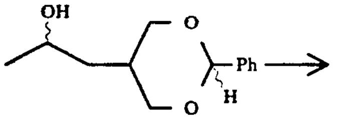

m3

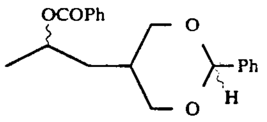

m4

To a solution of 10.829 g of crude 5-(2-hydroxypropan-1-yl)-2-phenyl-1,3-dioxane m3 in 200 ml of dichloromethane at 0° C., is added 11.3 ml (97.4 mM) of benzoyl chloride and 20.5 ml (146.1 mM) of triethylamine and 100 mg of 4-dimethylaminopyridine. After stirring at room temperature for 15 hours, the mixture is poured into 2N aqueous hydrochloric acid and the product is isolated by dichloromethane extraction. The dichloromethane layer is washed with saturated aqueous sodium bicarbonate and saturated aqueous sodium chloride, dried over anhydrous magnesium sulfate and evaporated. By eliminating the polar by-product by passing a short column of silica gel using n-hexane-ethyl acetate (4:1) mixture, as an eluent 17.125 g of the crude product of the titled compound m4 is obtained.

IR: ν max ($CHCl_3$) 1715 $cm^{-1}$ (121) Preparation of 2-(2-benzoyloxypropan-1-yl)-3-hydroxypropyl benzoate m5

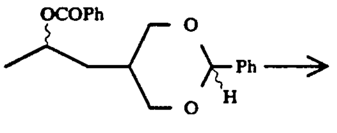

m4

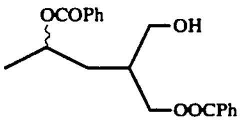

m5

To a stirred and ice cooled suspension of 9.344 g (52.5 mM) of N-bromosuccinimide in 250 ml of water are added a drop of conc. hydrobromic acid and 17.125 g of the crude 5-(2-benzoyloxypropan-1-yl)-2-phenyl-1,3-dioxane m4 obtained in the previous reaction dropwise. After standing at 0° C. for another 1 hour, 22 g (260 mM) of sodium bicarbonate is added to the reaction mixture and the product is isolated by ethyl acetate extraction. The ethyl acetate layer is washed with saturated aqueous sodium chloride, dried over anhydrous magnesium sulfate and evaporated. Purification of the product by column silica gel chromatography using n-hexane-ethyl acetate (1:1) as an eluent gives 7.401 g (29.7% yield from the compound m2) of the titled compound m5 as an oily product.

IR: ν max ($CHCl_3$) 3600∼3250 (broad), 1700 $cm^{-1}$.

NMR: δ ppm ($CDCl_3$) 1.40 (d, J=2.6 Hz, 1.5H), 1.43 (d, J=2.6 Hz, 1.5H), 1.67–1.99 (m, 2H), 2.01–2.24 (m, 1H), 2.51–1.52 (br.1H), 3.57–3.82 (m, 2H), 4.32–4.60 (m, 2H), 5.26–5.47 (m, 1H), 7.37–7.67 (m, 6H), 7.93–8.13 (m, 4H).

(122) Preparation of 2-(2-benzoyloxypropan-1-yl)-3-octadecylcarbamoyloxypropyl benzoate m6

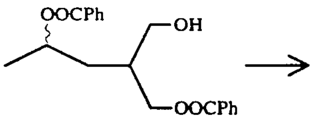

m5

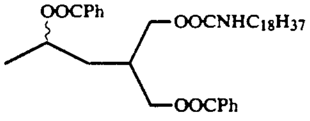

m6

A mixture of 3.70 g (11.2 mM) of 2-(2-benzoyloxypropan-1-yl)-3-hydroxypropyl benzoate m5 and 4.964 g (16.8 mM) of octadecyl isocyanate in 74 ml of pyridine is heated at 70° C. for 15 hours and the solvent is evaporated. To the residue with cooling, is added 2N aqueous hydrochloric acid and the product is isolated by ethyl acetate extraction. The ethyl acetate layer is washed with saturated aqueous sodium bicarbonate and saturated aqueous sodium chloride, dried over anhydrous magnesium sulfate and evaporated. Purification of the product by column silica gel chromatography using n-hexane-ethyl acetate (1:1) as an eluent gives 6.28 g (87.8% yield) of the titled compound m6.

IR: νmax ($CHCl_3$) 3440, 1705 $cm^{-1}$.

NMR: δ ppm ($CDCl_3$) 0.88 (t, J=6.4 Hz, 3H), 1.10–1.35 (m, 30H), 1.36–1.55 (m, 5H), 1.68–2.07 (m, 2H), 2.22–2.45 (m, 1H), 2.97–3.21 (m, 2H), 4.10–4.27 (m, 2H), 4.27–4.45 (m, 2H), 4.62–4.83 (br., 1H), 5.28–5.50 (m, 1H), 7.38–7.64 (m, 6H), 7.97–8.13 (m, 4H).

(123) Preparation of 2-(2-benzoyloxypropan-1-yl)-3-methanesulfonyloxypropyl benzoate m11'

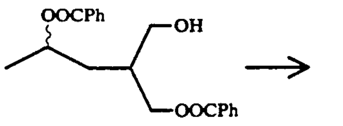

m5

-continued

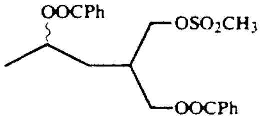

m11'

To an ice cooled solution of 1.85 g (5.60 mM) of 2-(2-benzoyloxypropan-1-yl)-3-hydroxy-propyl benzoate m5 in 40 ml of dichloromethane are added 0.607 ml (7.84 mM) of methanesulfonyl chloride and 1.34 ml (9.52 mM) of triethylamine. After stirring at 0° C. for 30 minutes, the mixture is poured into an ice cooled 2N aqueous hydrochloric acid and the product is isolated by dichloromethane extraction. The dichloromethane layer is washed with saturated aqueous sodium bicarbonate and saturated aqueous sodium chloride, dried over anhydrous magnesium sulfate. Evaporation of the solvent gives the crude product of the titled compound m11'.

NMR: δ ppm ($CDCl_3$) 1.43 (d, J=6.2 Hz, 3H), 1.74-2.08 (m, 2H), 2.27-2.53 (m, 1H), 3.01 (s, 3H), 4.25-4.54 (m, 4H), 5.27-5.47 (m, 1H), 7.37-7.65 (m, 6H), 7.95-8.11 (m, 4H).

(124) Preparation of 2-(2-benzoyloxypropan-1-yl)-3-hexadecylthiopropyl benzoate m11

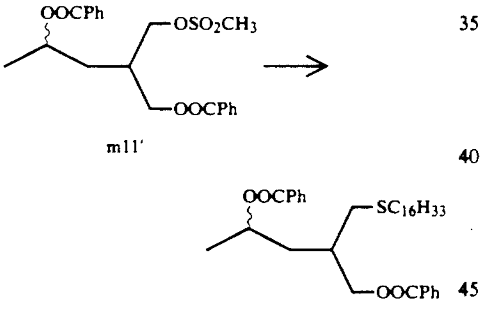

m11' → m11

A mixture of 3.858 g (14.92 mM) of n-hexadecyl mercaptane and 554 mg (13.86 mM) of 60% sodium hydride in oil in 100 ml of benzene is heated at 50° C. for 1 hour and a solution of the crude 2-(2-benzoyloxypropan-1-yl)-3-methanesulfonyloxypropyl benzoate m11' in 5 ml of benzene is added. After heating the mixture at 50° C. for another 1 hour, the product is isolated by ethyl acetate extraction. The ethyl acetate layer is washed with saturated aqueous sodium chloride, dried over anhydrous magnesium sulfate and evaporated. Purification of the product by column silica gel chromatography using n-hexane-ethyl acetate (95:5) as an eluent gives 4.416 g (71.1% yield) of the titled compound m11.

NMR: δ ppm ($CDCl_3$) 0.88 (t, J=6.4 Hz, 3H), 1.12-1.38 (m, 26H), 1.40 (d, J=6.2 Hz, 3H), 1.45-1.65 (m, 2H), 1.67-2.31 (m, 3H), 2.49-2.53 (m, 2H), 2.57-2.82 (m, 2H), 4.29-4.55 (m, 2H), 5.26-5.45 (m, 1H), 7.36-7.63 (m, 6H), 7.97-8.11 (m, 4H)

(125) Preparation of 2-(2-benzoyloxypropan-1-yl)-3-octadecylcarbamoyloxypropanol m7

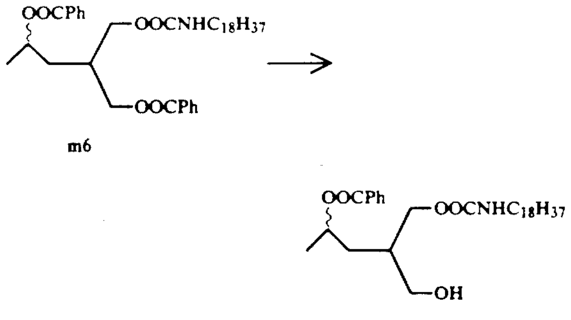

m6 → m7

To an ice cooled solution of 2.879 g (4.51 mM) of 2-(2-benzoyloxypropan-1-yl)-3-octadecylcarbamoyloxypropyl benzoate m6 in 25 ml of methanol and 25 ml of tetrahydrofuran, is added 4.51 ml (9.02 mM) of 2N aqueous sodium hydroxide and the mixture is stirred at 0° C. for 2 hours. The mixture is poured into ice-water and the product is isolated by ethyl acetate extraction. The ethyl acetate layer is washed with saturated aqueous sodium chloride, dried over anhydrous magnesium sulfate and evaporated. Purification of the product by column silica gel chromatography using n-hexane-ethyl acetate (2:1) as an eluent gives 1.72 g (71.4% yield) of the titled compound m7.

NMR: δ ppm ($CDCl_3$) 0.88 (t, J=6.4 Hz, 3H), 1.10-1.39 (m, 30H), 1.37 (d, J=6.2 Hz, 3H), 1.38-1.53 (m, 2H), 1.60-1.81 (m, 2H), 1.85-2.02 (m, 1H), 2.92-3.24 (m, 2H), 3.39-3.70 (m, 2H), 4.05-4.32 (m, 2H), 4.68-4.88 (m, 1H), 5.20-5.40 (m, 1H), 7.35-7.66 (m, 3H), 8.04 (d, J=6.8 Hz, 2H).

(126) Preparation of 2-(2-benzoyloxypropan-1-yl)-3-hexadecylthiopropanol m12

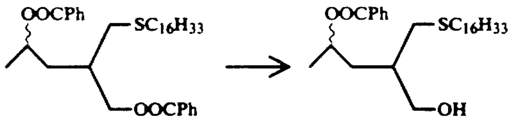

m11 m12

Using 6.89 ml (13.78 mM) of 2N aqueous sodium hydroxide, 4.017 g (6.89 mM) of 2-(2-benzoyloxypropan-1-yl)-3-hexadecylthio-propyl benzoate m11 in 38 ml of methanol and 43 ml of tetrahydrofuran is converted to 2.071 g (62.8% yield) of the titled compound m12 by the same procedure as described in (125).

NMR: δ ppm ($CDCl_3$) 0.88 (t, J=6.4 Hz, 3H), 1.12-1.38 (m, 26H), 1.38 (d, J=6.2 Hz, 3H), 1.45-1.63 (m, 2H), 1.63-2.01 (m, 3H), 2.47 (t, J=7.0 Hz, 2H), 2.51-2.75 (m, 2H), 3.62-3.82 (m, 2H), 5.15-5.42 (m, 1H), 7.39-7.61 (m, 3H), 8.04 (d, J=7.2 Hz, 2H).

(127) Preparation of 2-(2-benzoyloxypropan-1-yl)-3-octadecylcarbamoyloxypropyl methanesulfonate m7a

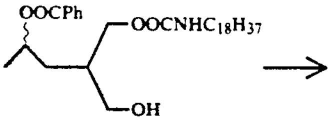

m7

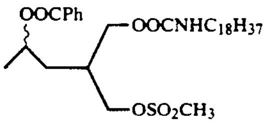

m7a

Using 0.358 ml (4.63 mM) of methanesulfonyl chloride and 0.814 ml (5.79 mM) of triethylamine, 2.059 g (3.86 mM) of 2-(2-benzoyloxypropan-1-yl)-3-octadecylcarbamoyloxypropanol m7 in dichloromethane is converted to the crude titled compound m7a by the same procedure as described in (50).

NMR: δ ppm ($CDCl_3$) 0.88 (t, J=6.4 Hz, 3H), 1.14–1.35 (m, 30H), 1.39 (d, J=6.2 Hz, 3H), 1.36–1.56 (m, 2H), 1.59–2.01 (m, 2H), 2.15–2.37 (m, 1H), 3.02 (s, 3H), 3.05–3.22 (m, 2H), 3.99–4.37 (m, 4H), 4.63–4.84 (m, 1H), 5.20–5.45 (m, 1H), 7.35–7.66 (m, 3H), 8.04 (d, J=6.8 Hz, 2H).

(128) Preparation of 1-azido-2-(2-benzoyloxypropan-1-yl)-3-n-octadecylcarbamoyloxypropane m7b

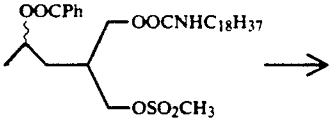

m7a

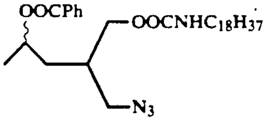

m7b

Using 1.889 g (38.6 mM) of lithium azide, the previously obtained crude 2-(2-benzoyloxypropan-1-yl)-3-octadecylcarbamoyloxypropyl methanesulfonate m7a in 50 ml of dimethylformamide is converted to 1.986 g (92.0% yield) of the titled compound m7b by the same procedure as described in (52).

NMR: δ ppm ($CDCl_3$) 0.88 (t, J=6.4 Hz, 3H), 1.17–1.36 (m, 30H), 1.38 (d, J=6.2 Hz, 3 Hz), 1.39–1.53 (m, 2H), 1.55–1.98 (m, 2H), 1.99–2.17 (m, 1H), 3.02–3.03 (m, 2H), 3.32–3.53 (m, 2H), 3.93–4.22 (m, 2H), 4.60–4.80 (br., 1H), 5.20–5.42 (m, 1H), 7.39–7.64 (m, 3H), 8.04 (d, J=6.8 Hz, 2H).

(129) Preparation of 2-(2-benzoyloxypropan-1-yl)-3-octadecylcarbamoyloxypropylamine m8

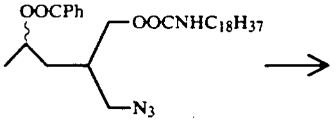

m7b

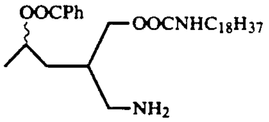

m8

A suspension of 1.617 g (2.89 mM) of 1-azido-2-(2-benzoyloxypropan-1-yl)-3-octadecylcarbamoyloxypropane m7b and 170 mg of 10% palladium on charcoal in 150 ml of methanol is hydrogenated under hydrogen atmosphere for 1 hour. The mixture is filtered and the solvent of the filtrate is evaporated to obtain crude titled compound m8.

NMR: δ ppm ($CDCl_3$) 0.88 (t, J=6.4 Hz, 3H), 1.17–1.36 (m, 30H), 1.37 (d, J=6.2 Hz, 3H), 1.39–1.53 (m, 2H), 1.55–1.96 (m, 5H), 2.59–2.85 (m, 2H), 2.98–3.27 (m, 2H), 4.00–4.27 (m, 2H), 4.65–4.87 (br., 1H), 5.20–5.46 (m, 1H), 7.36–7.65 (m, 3H), 8.04 (d, J=6.8 Hz, 2H).

(130) Preparation of 2-(2-benzoyloxypropan-1-yl)-1-(3-chloropropylsulfonylamino)-3-n-octadecylcarbamoyloxypropane m9

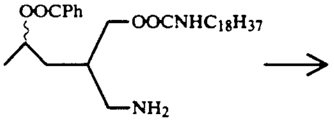

m8

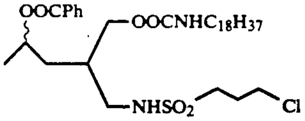

m9

Using 0.33 ml (2.71 mM) of 3-chloropropanesulfonyl chloride and 0.495 ml (3.52 mM) of triethylamine, the previously obtained crude product of 2-(2-benzoyloxypropan-1-yl)-3-octadecylcarbamoyloxypropylamine m8 in 60 ml of dichloromethane is converted to 1.56 g (80.2% yield from the azide m7b) of the titled compound m9 as a wax.

NMR: δ ppm ($CDCl_3$) 0.88 (t, J=6.4 Hz, 3H), 1.17–1.36 (m, 30H), 1.39 (d, J=6.2 Hz, 3H), 1.37–1.53 (m, 2H), 1.57–1.88 (m, 2H), 1.90–2.11 (m, 1H), 2.17–2.36 (m, 2H), 2.92–3.29 (m, 6H), 3.65 (t, J=6.2 Hz, 2H), 3.97–4.35 (m, 2H), 4.70–4.86 (br., 1H), 5.20–5.50 (m, 2H), 7.39–7.64 (m, 3H), 8.04 (d, J=6.8 Hz, 2H).

(131) Preparation of 1-(3-chloropropylsulfonylamino)-2-(2-hydroxypropan-1-yl)-3-octadecylcarbamoyloxypropane m10

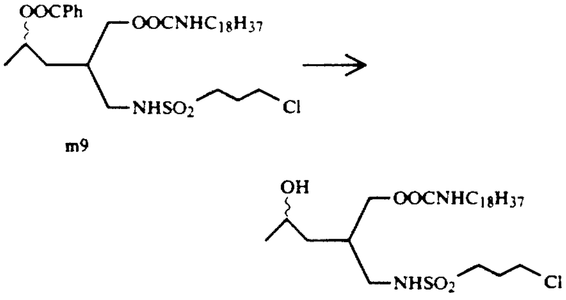

m9 m10

To an ice cooled solution of 941 mg (1.41 mM) of 2-(2-benzoyloxypropan-1-yl)-1-(3-chloropropylsulfonylamino-3-octadecylcarbamoyloxypropane m9 in 50 ml of methanol is added 0.539 ml (2.80 mM) of 5.18 M/L sodium methoxide in methanol. After stirring at room temperature for 15 hours, the solvent is evaporated. The product is isolated by ethyl acetate extraction. The ethyl acetate layer is washed with saturated aqueous sodium chloride, dried over anhydrous magnesium sulfate and evaporated. Purification of the product by column silica gel chromatography using n-hexane-ethyl acetate (1:2) mixture as an eluent gives 491 mg (61.7% yield) of the titled compound m10.

NMR: δ ppm ($CDCl_3$) 0.88(t, J=6.4 Hz, 3H), 1.12-1.36(m, 33H), 1.36-1.60(m, 4H), 1.80-2.20(m, 2H), 2.18-2.37(m, 2H), 2.99-3.27(m, 6H), 3.68(t, J=6.2 Hz, 2H), 3.83-4.27(m, 3H), 4.67-4.96 (br., 1H), 5.27-5.85(br., 1H).

(132) Preparation of 1-(3-chloropropylsulfonylamino)-3-octadecylcarbamoyloxy-2-(2-oxopropan-1-yl)propane III ml

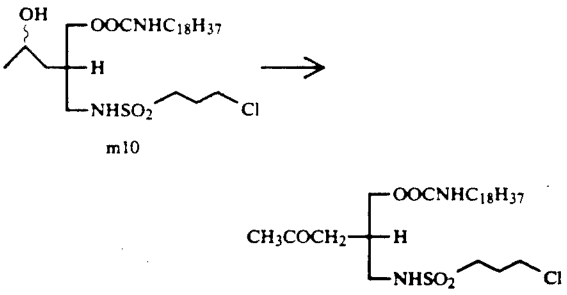

m10

III ml

To a cooled solution of 0.0645 ml (0.75 mM) of oxalyl chloride in 50 ml of dichloromethane at −78° C., is added 0.106 ml (1.5 mM) of dimethylsulfoxide dropwise and the mixture is stirred for another 5 minutes. To this mixture is added a solution of 285 mg (0.5 mM) of 1-(3-chloropropylsulfonylamino)-2-(2-hydroxypropan-1-yl)-3-octadecylcarbamoyloxypropane m10 in 2 ml of dichloromethane at −70° C. with vigorous stirring. The mixture is allowed to react at −70° C. for 15 minutes and 0.836 ml (6 mM) of triethylamine is added. After allowing the temperature of the reaction mixture to rise to room temperature, the product is isolated with dichloromethane extraction. The dichloromethane layer is washed with 2N aqueous hydrochloric acid, water and saturated aqueous sodium bicarbonate, dried over anhydrous magnesium sulfate and evaporated to obtain crude product of the titled compound III ml.

NMR: δ ppm ($CDCl_3$) 0.88(t, J=6.4 Hz, 3H), 1.14-1.41(m, 30H), 1.37-1.61(m, 2H), 2.12-2.77(m, 5H), 2.18(s, 3H), 2.97-3.28(m, 6H), 3.68(t, J=6.2 Hz, 2H), 3.86-4.25(m, 2H), 4.65-4.86(br, 1H), 5.26-5.42(br., 1H).

(133) Preparation of 1-(3-iodopropylsulfonylamino)-3-octadecylcarbamoyloxy-2-(2-oxopropan-1-yl)propane II ml

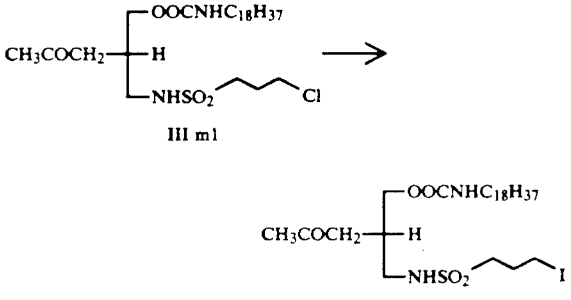

III ml

II ml 1-(3-Chloropropylsulfonylamino)-3-octadecylcarbamoyloxy-2-(2-oxopropan-1-yl)propane III ml is allowed to react by the same procedure as described in (5). The summary of the experimental condition and the physical data of the product are listed in Table 8.

As a starting material the crude product prepared in (132) is used without further purification. The yield calculated from the compound m10 is 66%.

EXAMPLE 66

Preparation of 3-n-octadecylcarbamoyloxy-2-(2-oxopropan-1-yl)-1-(3-quinoliniopropylsulfonylamino)propane iodide I ml

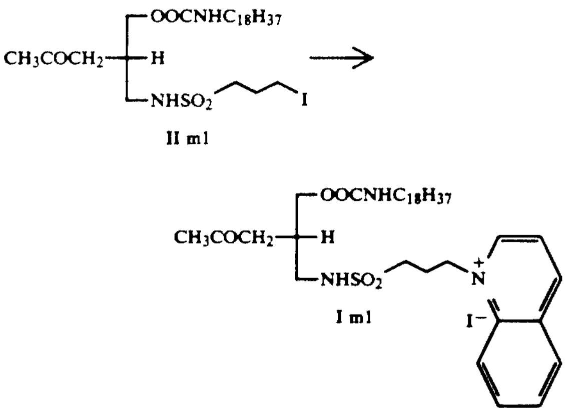

II ml

I ml 1-(3-iodopropylsulfonylamino)-3-octadecylcarbamoyloxy-2-(2-oxopropan-1-yl)propane II ml is allowed to react by the same procedure as described in Example 25. The summary of the experimental condition and the physical data of the product are listed in Table 10.

(134) Preparation of
5-hexadecyloxymethyl-2-phenyl-1,3-dioxane n2

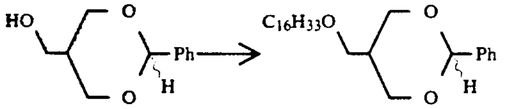

n1 n2

A suspension of 7.769 g (40 mM) of 5-hydroxymethyl-2-phenyl-1,3-dioxane n1 and 2.08 g (52 mM) of 60% sodium hydride in oil in 150 ml of anhydrous benzene is heated at 50° C. for 1 hour then a solution of 17.28 g (54 mM) of n-hexadecyl methanesulfonate in 50 ml of anhydrous benzene is added. The reaction mixture is heated under refluxing for 7 hours. The product is isolated by ethyl acetate extraction. The ethyl acetate layer is washed with saturated aqueous sodium chloride, dried over anhydrous magnesium sulfate and evaporated. Crystallization of the residue from n-pentane-methanol affords 16.203 g (97% yield) of the titled compound n2.

(135) Preparation of
2-bromomethyl-3-hexadecyloxypropanol benzoate n3

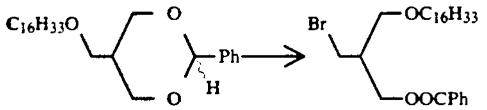

n2 n3

A mixture of 14.703 g (35.2 mM) of 5-n-hexadecyloxymethyl-2-phenyl-1,3-dioxane n2, 6.90 g (38.4 mM) of N-bromosuccinimide and 700 mg of barium carbonate in 200 ml of dichloromethane is heated under refluxing for 1 hour. After cooling, the mixture is poured into an ice cooled saturated aqueous sodium bicarbonate and the product is isolated by dichloromethane extraction. The dichloromethane layer is washed with 10% aqueous sodium thiosulfate and saturated aqueous sodium chloride, dried over anhydrous magnesium sulfate and evaporated. Purification of the residue by column silica gel chromatography using n-hexane-ethyl acetate (9:1) mixture as an eluent affords 13.843 g (79.3% yield) of the titled compound n3.

(136) Preparation of
2-cyanomethyl-3-hexadecyloxypropyl benzoate n3'

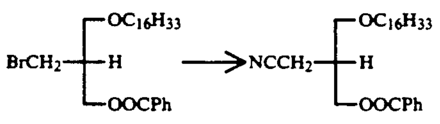

n3 n3'

A mixture of 13.845 g (27.9 mM) of 2-bromomethyl-3-n-hexadecyloxypropyl benzoate n3 and 1.439 g (27.9 mM) of sodium cyanide (95% purity) in 150 ml of dimethylsulfoxide is heated at 90° C. for 1 hour. The product is isolated by ethyl acetate extraction. The ethyl acetate layer is washed with water (four times) and saturated aqueous sodium chloride, dried over anhydrous magnesium sulfate and evaporated to obtain 12.42 g of the crude product of the titled compound n3'.

NMR: δ ppm ($CDCl_3$) 0.88(t, J=6.4 Hz, 3H), 1.15-1.43(m, 26H), 1.45-1.70(m, 2H), 2.39-2.67(m, 3H), 3.45(t, J=4.8 Hz, 2H), 3.50-3.67(m, 2H), 4.26-4.52(m, 2H), 7.40-7.65(m, 3H), 8.05(dd, J=6.4 & 1.6 Hz, 2H).

(137) Preparation of
2-cyanomethyl-3-hexadecyloxypropanol V n1

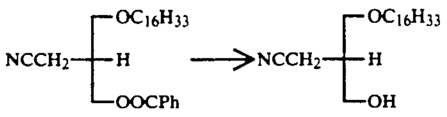

n3' Vn1

A mixture of 12.42 g of 2-cyanomethyl-3-hexadecyloxypropyl benzoate n3' and 15.5 ml (31.0 mM) of 2N aqueous sodium hydroxide in 60 ml of methanol and 100 ml of tetrahydrofuran is stirred at room temperature for 1 hour and solvents are evaporated. The product is isolated by ethyl acetate extraction. The ethyl acetate layer is washed with water, dried over anhydrous magnesium sulfate and evaporated. Purification by column silica gel chromatography using n-hexane-ethyl acetate (4:1) affords 6.430 g (67.8% yield) of the titled compound Vn1.

NMR: δ ppm ($CDCl_3$) 0.88(t, J=6.4 Hz, 3H), 1.15-1.43(m, 26H), 1.45-1.70(m, 2H), 1.96-2.27(m, 2H), 2.45-2.69(m, 2H), 3.45(t, J=6.6 Hz, 2H), 3.59(d, J=4.8 Hz, 2H), 3.67-3.88(m, 2H).

(138) Preparation of
2-cyanomethyl-3-hexadecyloxypropyl
methanesulfonate Vn1a

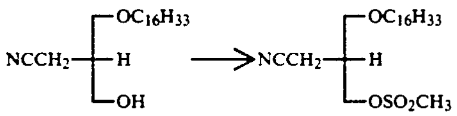

Vn1 Vn1a

Using 1.08 ml (14 mM) of methanesulfonyl chloride and 2.39 ml (17 mM) of triethylamine, 3.40 g (10 mM) of 2-cyamomethyl-3-n-hexadecyloxypropanol Vn1 in 60 ml of dichloromethane is converted by the same procedure as described in (50) and the crude product of the titled compound Vn1a is obtained.

NMR: δ ppm ($CDCl_3$) 0.88(t, J=6.4 Hz, 3H), 1.15-1.43(m, 26H), 1.45-1.64(m, 2H), 2.33-2.57(m, 1H), 2.50-2.62(m, 2H), 3.06(s, 3H), 3.43(t, J=6.6 Hz, 2H), 3.43-3.59(m, 2H), 4.19-4.42(m, 2H).

(139) Preparation of
1-azido-2-cyanomethyl-3-hexadecyloxypropane Vn1b

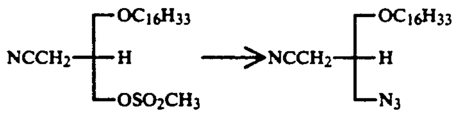

Vn1a Vn1b

Using 4.9 g (100 mM) of lithium azide, crude product of 2-cyanomethyl-3-hexadecyloxypropyl methanesulfonate Vn1a obtained in the previous reaction in 30 ml of dimethylformamide is converted by the same procedure as described in the (52) and 3.504 g (96.1% yield) of the titled compound V n1a is obtained.

NMR: δ ppm ($CDCl_3$) 0.88(t, J=6.4 Hz, 3H), 1.15-1.43(m, 26H), 1.45-1.64(m, 2H), 2.10-2.30(m, 1H), 2.50(d, J=6.8 Hz, 2H), 3.37-3.59(m, 6H).

(140) Preparation of 2-cyanomethyl-3-hexadecyloxypropylamine IV n1

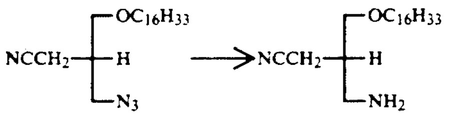

Vnlb IVnl

A suspension of 3.00 g (23 mM) of 1-azido-2-cyanomethyl-3-hexadecyloxypropane V nlb and 300 mg of 10% palladium on charcoal in 100 ml of methanol is hydrogenated as described in (129) and the crude product of the titled compound IV n1 is obtained.

NMR: δ ppm ($CDCl_3$) 0.88(t, J=6.4 Hz, 3H), 1.15-1.43(m, 28H), 1.45-1.64(m, 2H), 1.88-2.11(m, 1H), 2.53(d, J=6.4 Hz, 2H), 2.70-2.93(m, 2H), 3.31-3.50 (m, 4H).

(141) Preparation of 1-(3-chloropropylsulfonylamino)-2-cyanomethyl-3-hexadecyloxypropane III n1

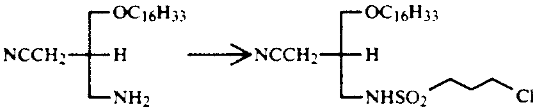

IVn1 IIIn1

The crude 2-cyanomethyl-3-hexadecyloxypropylamine IV n1 prepared above is allowed to react by the same procedure as described in (4). The summary of the experimental condition and the physical data of the product are listed in Table 7.

(142) Preparation of 2-cyanomethyl-3-hexadecyloxy-1-(3-iodopropylsulfonylamino)propane II n1

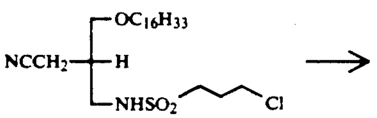

IIIn1

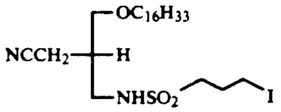

IIn1

1-(3-Chloropropylsulfonylamino)-2-cyanomethyl-3-hexadecyloxypropane III n1 is allowed to react by the same procedure as described in (5). The summary of the experimental condition and the physical data of the product are listed in Table 8.

EXAMPLE 67

Preparation of 2-cyanomethyl-3-hexadecyloxy-1-(3-trimethylammoniopropylsulfonylamino)propane iodide I n1

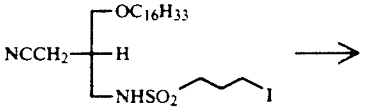

IIn1

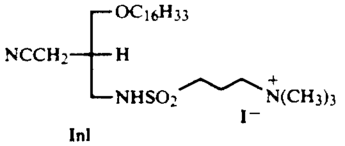

In1

2-Cyanomethyl-3-hexadecyloxy-1-(3-iodopropylsulfonylamino)propane II n1 is allowed to react by the same procedure as described in Example 8. The summary of the experimental condition and the physical data of the product are listed in Table 9.

EXAMPLE 68

Preparation of 2-cyanomethyl-3-hexadecyloxy-1-(3-quinoliniopropylsulfonylamino)propane iodide I n2

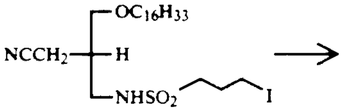

II n1

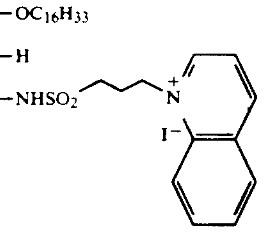

I n2

2-Cyanomethyl-3-hexadecyloxy-1-(3-iodopropylsulfonylamino)-propane II n1 is allowed to react by the same procedure as described, in Example 25. The summary of the experimental condition and the physical data of the product are listed in Table 10.

(143) Preparation of 5-octadecylcarbamoyloxy-2-phenyl-1,3-dioxane n4

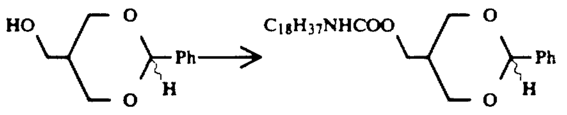

n1 n4

A solution of 7.769 g (40 mM) of 5-hydroxymethyl-2-phenyl-1,3-dioxane n1, 21.991 ml (64 mM) of octadecyl isocyanate and 100 mg of 4-dimethyaminopyridine in 100 ml of pyridine is allowed to react by the same procedure as described in (122) and crystallization of the product from ethanol affords 15.861 g (81.0% yield) of the titled compound n4.

IR: νmax ($CHCl_3$) 3440, 1705 $cm^{-1}$.

(144) Preparation of 2-bromemethyl-3-octadecylcarbamoyloxypropyl benzoate n5

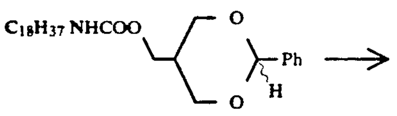

n4

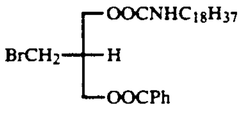

n5

A mixture of 2.55 g (5.22 mM) of 5-n-octadecylcarbamoyloxy-2-phenyl-1, 3-dioxane n4, 938 mg (5.22 mM) of N-bromosuccinimide and 100 mg of barium carbonate in 50 ml of dichloromethane is allowed to react by the same procedure as described in (135) and 1.86 g (62.6% yield) of the titled compound n5 is obtained.

NMR: δ ppm ($CDCl_3$) 0.88(t, J=6.4 Hz, 3H), 1.17-1.41(m, 30H), 1.36-1.57(m, 2H), 2.46-2.68(m, 1H), 3.16(q, J=6.2 Hz, 2H), 3.57(d, J=5.6 Hz, 2H), 4.26(d, J=6.4 Hz, 2H), 4.44(d, J=6.0 Hz, 2H), 4.59-4.77(br.1H), 7.40-7.60(m, 3H), 8.03(d, J=7.0 Hz, 2H)

(145) Preparation of 2-cyanomethyl-3-octadecylcarbamoyloxypropyl benzoate n5'

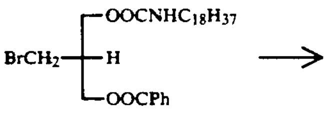

n5

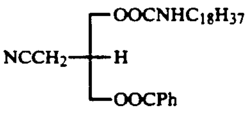

n5'

A mixture of 1.76 g (3.10 mM) of 2-bromomethyl-3-n-octadecylcarbamoyloxypropyl benzoate, 185 mg (3.26 mM) of 95% sodium cyanide in 30 ml of dimethylsulfoxide is allowed to react by the same procedure as described in the (136) and 1.49 g (95.5% yield) of the titled compound n5' is obtained.

NMR: δ ppm ($CDCl_3$) 0.88(t, J=6.4 Hz, 3H), 1.17-1.41(m, 30H), 1.36-1.57(m, 2H), 2.61(s, 3H), 3.17(q, J=6.2 Hz, 2H), 4.16-4.53(m, 4H), 4.65-4.81(m, 1H), 7.41-7.67(m, 3H), 8.05(d, J=7.0 Hz, 2H).

(146) Preparation of 2-cyanomethyl-3-octadecylcarbamoyloxypropanol V n2

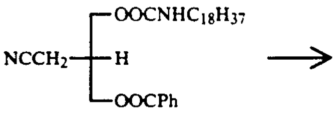

n5'

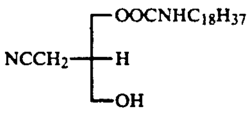

V n2

A mixture of 1.49 g (2.96 mM) of 2-cyanomethyl-3-n-octadecylcarbamoyloxypropyl benzoate n5', 1.66 ml (3.32 mM) of 2N aqueous sodium hydroxide in 15 ml of methanol and 15 ml of tetrahydrofuran is allowed to react by the same procedure as described in (137) and 966 mg (76.8% yield) of the titled compound V n2 is obtained.

NMR: δppm ($CDCl_3$) 0.88 (t, J=6.4 Hz, 3H), 1.17-1.40 (m, 30H), 1.37-1.57 (m, 2H), 2.11-2.32 (m, 1H), 2.47 (d, J=7.2 Hz, 2H), 2.56-2.77 (br, 1H), 3.18 (q, J=6.4 Hz, 2H), 3.65 (d, J=4.8 Hz, 2H), 4.22 (d, J=5.4 Hz, 2H), 4.70-4.87 (br., 1H)

(147) Preparation of 2-cyanomethyl-3-octadecylcarbamoyloxypropyl methanesulfonate V n2a

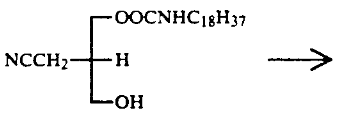

V n2

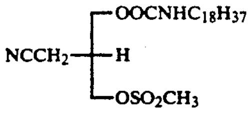

V n2a

A mixture of 940 mg (2.29 mM) of 2-cyanomethyl-3-octadecylcarbamoyloxypropanol V n2, 0.231 ml (2.98 mM) of methanesulfonyl chloride and 0.483 ml (3.44 mM) of triethylamine in 10 ml of dichloromethane is allowed to react by the same procedure as described in (52) and crude product of the titled compound V n2a is obtained.

NMR: δppm ($CDCl_3$) 0.88 (t, J=6.4 Hz, 3H), 1.16-1.38 (m, 30H), 1.40-1.58 (m, 1H), 2.45-2.63 (m, 3H), 3.80 (s, 3H), 3.16 (q, J=6.4 Hz, 2H), 4.09-4.45 (m, 4H), 4.73-4.87 (br., 1H).

(148) Preparation of 1-azido-2-cyanomethyl-3-octadecylcarbamoyloxypropane V n2b

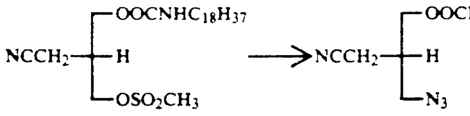

Vn2a Vn2b

A mixture of the previously obtained crude 2-cyanomethyl-3-n-octadecylcarbamoyloxypropyl methanesulfonate V n2a, 1.121 g (22.9 mM) of lithium azide in 15 ml of dimethylformamide is allowed to react by the same procedure as described in (53) and 854 mg (85.6% yield) of titled compound V n2b is obtained.

NMR: δppm ($CDCl_3$) 0.88 (t, J=6.4 Hz, 3H), 1.16–1.40 (m, 30H), 1.40–1.58 (m, 2H), 2.20–2.40 (m, 1H), 2.51 (d, J=6.6 Hz, 2H), 3.18 (q, J=6.4 Hz, 2H), 3.40–3.66 (m, 2H), 4.00–4.23 (m, 2H), 4.60–4.84 (br., 1H). (149) Preparation of 2-cyanomethyl-3-octadecylcarbamoyloxypropylamine IV n2

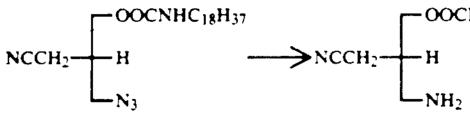

Vn2b IVn2

A mixture of 1-azido-2-cyanomethyl-3-octadecylcarbamoyloxypropane V n2b, 80 mg of 10% palladium on charcoal in 40 ml of methanol is hydrogenated by the same procedure as described in (129) and crude product of the titled compound IV n2 is obtained.

NMR: δppm ($CDCl_3$) 0.88 (t, J=6.4 Hz, 3H), 1.16–1.40 (m, 30H), 1.40–1.58 (m, 2H), 1.96–2.97 (m, 7H), 3.00–3.29 (m, 2H), 3.96–4.27 (m, 2H), 4.60–4.90 (br., 1H).

(150) Preparation of 1-(3-chloropropylsulfonylamino)-2-cyanomethyl-3-octadecylcarbamoyloxypropane III n2

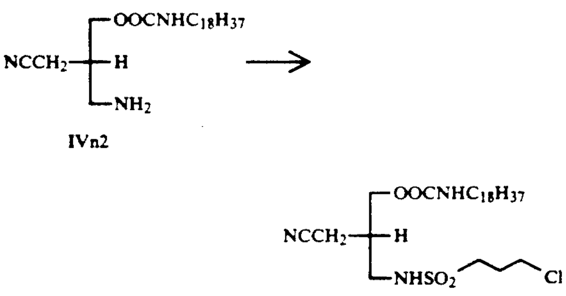

IVn2

IIIn2

The crude 2-cyanomethyl-3-n-octadecylcarbamoyloxypropylamine IV n2 which was prepared above is allowed to react by the same procedure as described in (4). The summary of the experimental condition and the physical data of the product are listed in Table 7.

(151) Preparation of 2-cyanomethyl-3-octadecylcarbamoyloxy-1-(3-iodopropylsulfonylamino)propane II n2

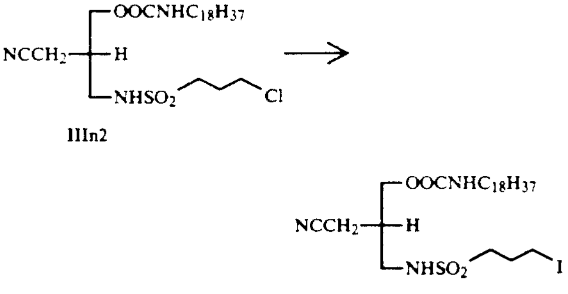

IIIn2

IIn2

1-(3-Chloropropylsulfonylamino)-2-cyanomethyl-3-octadecylcarbamoyloxypropane III n2 is allowed to react by the same procedure as described in (5). The summary of the experimental condition and the physical data of the product are listed in Table 8.

EXAMPLE 69

Preparation of 2-cyanomethyl-3-octadecylcarbamoyloxy-1-(3-quinoliniopropylsulfonylamino)propane I n3

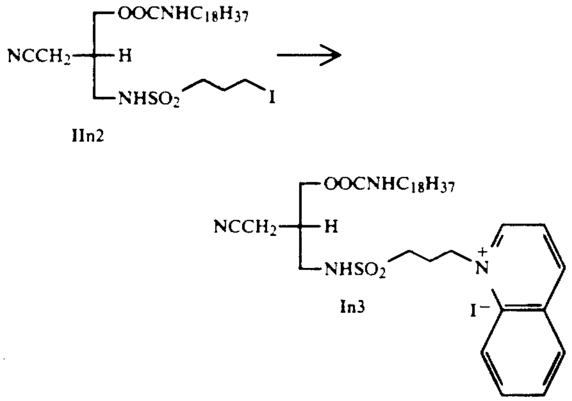

IIn2

In3

2-Cyanomethyl-3-octadecylcarbamoyloxy-1-(3-iodopropylsulfonylamino)propane II n2 is allowed to react by the same procedure as described in Example 25. The summary of the experimental condition and the physical data of the product are listed in Table 10.

(152) Preparation of 2-(2-benzoyloxypropan-1-yl)-3-hexadecylthiopropanol methanesulfonate m12a

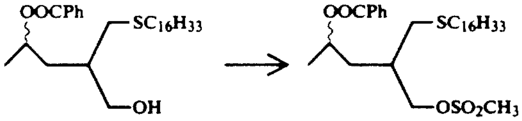

m12 m12a

A mixture of 1.268 g (2.65 mM) of 2-(2-benzoyloxypropan-1-yl)-3-n-hexadecylthiopropanol m12, 0.270 ml (3.45 mM) of methanesulfonyl chloride and 0.56 ml (3.98 mM) of triethylamine in 30 ml of dichloromethane is allowed to react by the same procedure as described in (52) and the crude product of the titled compound m12a is obtained.

NMR: δppm ($CDCl_3$) 0.88 (t, J=6.4 Hz, 3H), 1.15-1.37 (m, 26H), 1.39 (d, J=6.4 Hz, 3 Hz), 1.41-1.62 (m, 2H), 1.68-1.86 (m, 1H), 1.88-2.21 (m, 2H), 3.02 (s, 3H), 4.24-4.43 (m, 2H), 5.19-5.42 (m, 1H), 7.38-7.63 (m, 3H), 8.03 (d, J=7.2 Hz, 2H).

(153) Preparation of 1-azido-2-(2-benzoyloxypropan-1-yl)-3-hexadecylthiopropane m12b

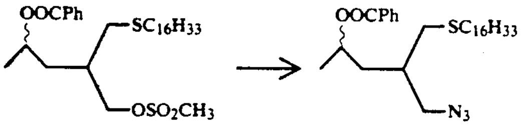

m12a m12b

A mixture of the previously obtained 2-(2-benzoyloxypropan-1-yl)-3-n-hexadecylthiopropyl methanesulfonate m12a and 1.297 g (26.5 mM) of lithium azide in 50 ml of dimethylformamide is allowed to react by the same procedure as described in (53) and 1.291 g (96.6% yield) of the titled compound m12b is obtained.

NMR: δppm ($CDCl_3$) 0.88 (t, J=6.4 Hz, 3H), 1.16~1.37 (m, 26H), 1.38 (d, J=6.0 Hz, 3H), 1.44-1.62 (m, 2H), 1.63-1.78 (m, 1H), 1.80-2.03 (m, 2H), 2.38-2.50 (m, 2H), 2.49-2.72 (m, 2H), 3.41-3.62 (m, 2H), 5.17-5.37 (m, 1H), 7.39-7.62 (m, 3H), 8.03 (d, J=7.2 Hz, 2H).

(154) Preparation of 2-(2-benzoyloxypropan-1-yl)-3-hexadecylthiopropylamine m13

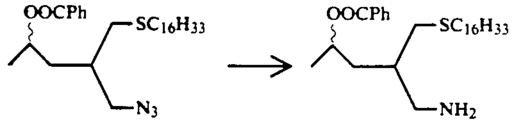

m12b m13

A mixture is 1.291 g (2.56 mM) of 1-azido-2-(2-benzoyloxypropan-1-yl)-3-n-hexadecylthiopropane m12b, 130 mg of 10% palladium on charcoal in 130 ml of methanol is hydrogenated by the same procedure as described in (129) and crude product of the titled compound m13 is obtained.

NMR: δppm ($CDCl_3$) 0.88 (t, J=6.4 Hz, 3H), 1.12-2.00 (m, 36H), 2.34-2.91 (m, 6H), 5.19-5.38 (m, 1H), 7.39-7.62 (m, 3H), 8.03 (d, J=7.2 Hz, 2H).

(155) Preparation of 2-(2-benzoyloxypropan-1-yl)-1-(3-chloropropylsulfonylamino)-3-hexadecylthiopropane m14

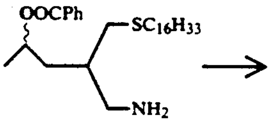

m13

-continued

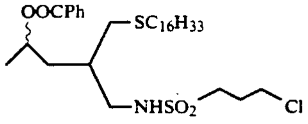

m14

A solution of the previously obtained crude 2-(benzoyloxypropan-1-yl)-3-n-hexadecylthiopropylamine m13, 0.54 ml (3.84 mM) of triethylamine and 0.37 ml (3.07 mM) of 3-chloropropanesulfonyl chloride in 30 ml of dichloromethane is allowed to react by the same procedure as described in (4) and 1.295 g (81.6% yield) of the titled compound m14 is obtained.

NMR: δppm ($CDCl_3$) 0.88 (t, J=6.4 Hz, 3H), 1.14-1.45 (m, 29H), 1.41-1.61 (m, 2H), 1.63-1.81 (m, 1H), 1.82-2.01 (m, 2H), 2.15-2.37 (m, 2H), 2.37-2.77 (m, 4H), 3.09-3.34 (m, 4H), 3.65 (t, J=6.4 Hz, 2H), 4.65-5.08 (br., 1H), 5.10-5.46 (m, 1H), 7.39-7.62 (m, 3H), 8.03 (d, J=7.2 Hz, 2H).

(156) Preparation of 1-(3-chloropropylsulfonylamino)-3-hexadecylthio-2-(2-hydroxypropan-1-yl)propane m15

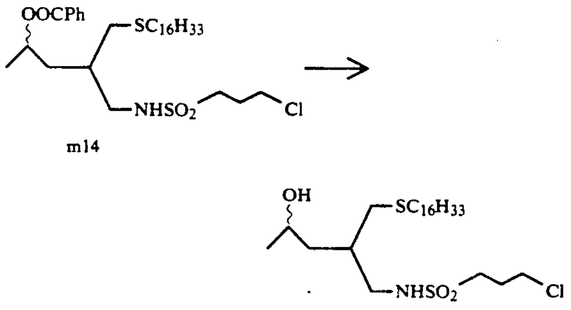

m14 m15

A mixture of 1.24 g (2.0 mM) of 2-(benzoyloxypropan-1-yl)-1-(3-chloropropylsulfonylamino)-3-n-hexadecylthiopropane m14 and 0.77 ml (2 mM) of 5.18 M/L sodium methoxide in methanol solution in 50 ml of methanol is allowed to react by the same procedure as described in (131) and 562 mg (54.5% yield) of the titled compound m15 is obtained.

NMR: δppm ($CDCl_3$) 0.88 (t, J=6.4 Hz, 3H), 1.17-1.42 (m, 29H), 1.43-1.77 (m, 5H), 1.91-2.18 (m, 1H), 2.20-2.37 (m, 2H), 2.42-2.65 (m, 4H), 3.02-3.38 (m, 4H), 3.69 (t, J=6.0 Hz, 2H), 3.80-4.13 (m, 1H), 5.10-5.45 (broad, 1H).

(157) Preparation of 1-(3-chloropropylsulfonylamino)-3-hexadecylthio-2-(2-oxopropan-1-yl)propane III m2

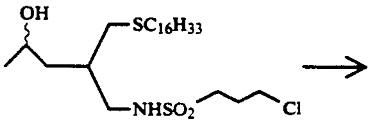

m15

-continued

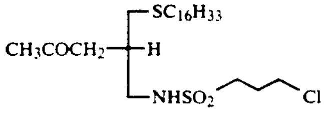

III m2

To a cooled solution of 0.19 ml (1.33 mM) of trifluoroacetic anhydride in 20 ml of dichloromethane at −78° C. is added 0.19 ml (2.66 mM) of dimethylsulfoxide and the mixture is stirred at −78° C. for 5 minutes. To the reaction mixture is added a solution of 428 mg (0.83 mM) of 1-(3-chloropropylsulfonylamino)-2-(2-hydroxypropan-1-yl)-3-n-hexadecylthiopropane ml5 in 2 ml of dichloromethane with stirring and the mixture is stirred at −70° C. for an additional 15 minutes. 3.50 ml (24.9 mM) of triethylamine is added and the mixture is allowed to react by the same procedure as described in (132) and 213 mg (41.6% yield) of the titled compound III m2 is obtained.

NMR: δppm ($CDCl_3$) 0.88 (t, J=6.4Hz, 1H), 1.10–1.43 (m, 26H), 1.46–1.66 (m, 2H), 2.22–2.44 (m, 3H), 2.44–2.59 (m, 4H), 2.65 (d, J=6.0 Hz, 2H), 3.09–3.29 (m, 4H), 3.68 (t, J=6.4 Hz, 2H), 4.80 (t, J=6.4 Hz, 1H).

(158) Preparation of 3-n-hexadecylthio-1-(3-iodopropylsulfonylamino)-2-(2-oxopropan-1-yl)propane II m2

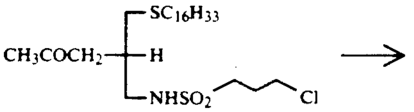

III m2

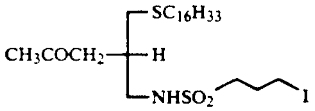

II m2

1-(3-Chloropropylsulfonylamino)-3-hexadecylthio-2-(2-oxopropan-1-yl)propane III m2 is allowed to react by the same procedure as described in (5). The summary of the experimental condition and the physical data of the product are listed in Table 8.

EXAMPLE 70

Preparation of 3-hexadecylthio-2-(2-oxopropan-1-yl)-1-(3-trimethylammoniopropylsulfonylamino)propane iodide I m2

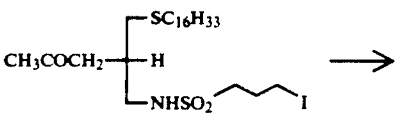

II m2

-continued

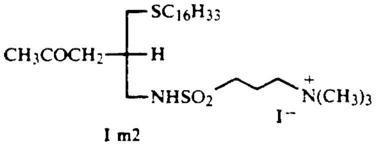

I m2

3-n-Hexadecylthio-1-(3-iodopropylsulfonylamino)-2-(2-oxopropan-1-yl)propane II m2 is allowed to react by the same procedure as described in Example 8. The summary of the experimental condition and the physical data of the product are listed in Table 9.

EXAMPLE 71

Preparation of 1-hexadecylthio-2-(3-methyl-2H-1,2,4-triazoli-2-yl)-3-(3-trimethylammoniopropylsulfonylamino)propane iodide I o1

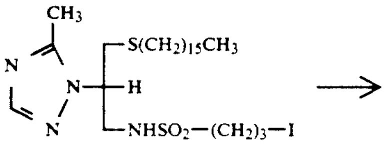

II o1

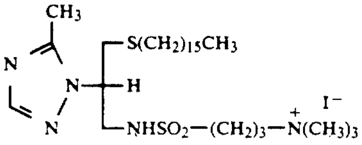

I o1

1-Hexadecylthio-3-(3-iodopropylsulfonylamino)-2-(3-methyl-2H-1,2,4-triazol-2-yl)propane II o2 is allowed to react and worked up by the same procedure as described in Example 8. The summary of the experimental condition and the physical data of the product are listed in Table 9.

The said starting material is prepared by the same procedure as described in (77), (79), (80), (81), (3), (4), and (5) using 3-methyl-2H-1,2,4-triazole instead of 5-methyltetrazole in (77).

EXAMPLE 72

Preparation of 2-(3-methyl-2H-1,2,4-triazol-2-yl)-1-octadecyl-carbamoyloxy-3-(3-quinoliniopropylsulfonylamino)propane iodide I o2

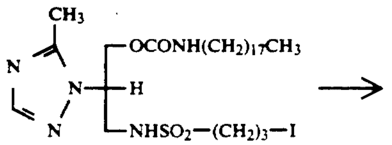

II o2

-continued

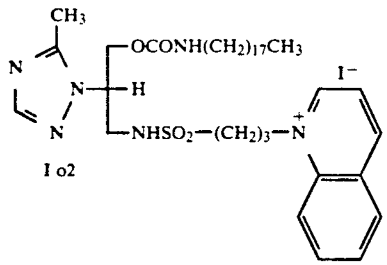

I o2

3-(3-Iodopropylsulfonylamino)-2-(3-methyl-2H-1,2,4-triazol-2-yl)-1-octadecylcarbamoyloxypropane II o2 is allowed to react and worked up by the same procedure as described in Example 25. The summary of the experimental condition and the physical data of the product are listed in Table 10.

The said starting material is prepared by the same procedure as described in (77), (79), (80), (82), (3), (4), and (5) using 3-methyl-2H-1,2,4-triazole instead of 5-methyltetrazole in (77).

EXAMPLE 73

Preparation of 2-(3-methyl-1H-1,2,4-triazol-1-yl)-1-octadecyl-carbamoyloxy-3-(3-quinoliniopropylsulfonylamino)propane iodide I o3

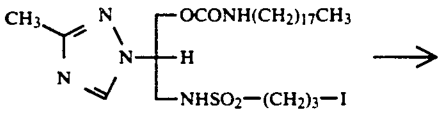

II o3

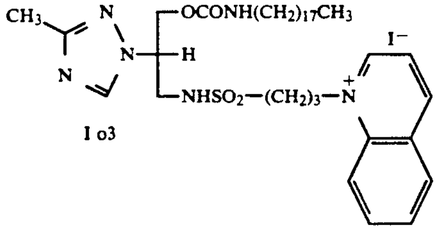

I o3

3-(3-Iodopropylsulfonylamino)-2-(3-methyl-1H-1,2,4-triazol-1-yl)-1-octadecylcarbamoyloxypropane II o3 is allowed to react and worked up by the same procedure as described in Example 25. The summary of the experimental condition and the physical data of the product are listed in Table 10.

The said starting material is prepared by the same procedure as described in (77), (79), (80), (82), (3), (4), and (5) using 3-methyl-2H-1,2,4-triazole instead of 3-methyltetrazole in (77).

TABLE 5

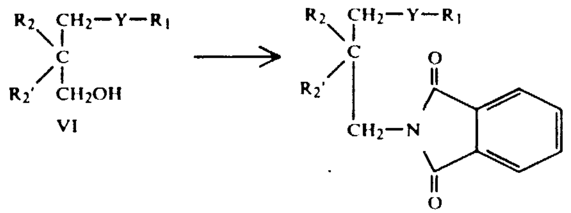

| (Ref. Ex. No.) | $R_1$ | $R_2$ | $R_2'$ | Y | S.M. [g] ([mM]) | Imide [g] ([mM]) | $PPh_3$ [g] ([mM]) | DEAD [ml] ([mM]) | THF [ml] | Yield [g] (%) | | NMR δ ppm |
|---|---|---|---|---|---|---|---|---|---|---|---|---|
| (23) | $-C_{16}H_{33}$ | $-O-(CH_2)_3-$ | | S | 2.26 (6.05) | .34 (9.08) | 2.38 (9.08) | 1.43 (9.08) | 60 | 2.66 (88) | ($CDCl_3$) | 0.88(t, 3H), 1.25(s, 26H), 1.45-1.65(m, 2H), 1.90-2.10(m, 4H), 2.59(t, 2H, J=7.2Hz), 2.71, 2.84(ABq, 2H, J=13.3Hz), 3.83(s, 2H), 3.80-4.00(m, 2H), 7.68-7.80(m, 2H), 7.80-7.92 (m, 2H). |
| (26) | $-CONHC_{18}H_{37}$ | $-O-(CH_2)_3-$ | | O | 1.71 (4) | 0.907 (6.16) | 1.61 (6.16) | 0.972 (6.16) | 30 | 2.08 (94) | ($CDCl_3$) | 0.88(t, 3H), 1.25(s, 30H), 1.40-1.60(m, 2H), 1.75-2.10(m, 4H), 3.16(q, 2H, J=6.4Hz), 3.84 (s, 2H), 3.80-4.00(m, 2H), 4.03(s, 2H), 4.70-4.85(br, 1H), 7.70-7.80(m, 2H), 7.80-7.90 (m, 2H). |
| (30) | $-C_{16}H_{33}$ | $-OOCNHCH_3$ | H | S | 1.362 (3.5) | 1.029 (7.0) | 1.834 (7.0) | 1.218 (7.7) | 55 | 1.9 | ($CDCl_3$) | 0.80-1.80(m, 31H), 2.50-2.80(m, 4H), 2.68 (d, J=5Hz, 3H), 4.00(m, 2H), 4.65(br, 1H), 5.15(m, 1H), 7.65-7.95(m, 4H). |
| (35) | $-CONHC_{18}H_{37}$ | $-OOCNHCH_3$ | H | O | 2.0 (4.5) | 1.32 (9.0) | 2.36 (9.0) | 1.57 (9.0) | 45 | 2.54 | ($CDCl_3$) | 0.86(t, J=6Hz, 3H), 1.26(br.s, 32H), 2.68(d, J=6Hz, 3H), 3.20(m, 2H), 3.80(m, 2H), 4.22 (d, J=6Hz, 2H), 4.80(m, 2H), 5.35(m, 1H), 7.65-8.05(m, 4H). |
| (43) | $-CONHC_{18}H_{37}$ | $-NHCOOCH_3$ | H | O | 0.224 (0.504) | 0.100 (0.680) | 0.176 (0.671) | 0.117 (0.672) | 4 | 0.237 (82) | ($CDCl_3$) | 0.87(3H, t, J=4Hz), 1.27(30H, s), 1.50(2H, (br.s), 3.18(2H, m), 3.56(3H, s), 3.87(2H, d, J=7Hz), 4.19(2H, m), 4.26(1H, m), 4.78 (1H, m), 5.26(1H, m), 7.7-7.8(2H, m), 7.8-7.95(2H, m). |
| (44) | $-CONHC_{18}H_{37}$ | $-NHCOOtBu$ | H | O | 0.109 (0.224) | 0.040 (0.272) | 0.071 (0.271) | 0.047 (0.263) | 6 | 0.134 (97.2) | ($CDCl_3$) | 0.89(3H, t, J=5Hz), 1.26(30H, s), 1.51(2H, m), 3.18(2H, m), 3.7-4.0(2H), 4.1-4.3(3H), 4.79(1H, t, J=5Hz), 5.01(1H, d, J=5Hz), 7.7-7.9(4H, m). |
| (86) | $-C_{16}H_{33}$ | 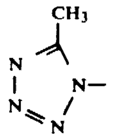 | H | S | 1.13 (2.8) | 1.25 (8.4) | 1.12 (4.2) | 0.74 (4.2) | 50 | — | ($CDCl_3$) | 0.88(t, J=7Hz, 3H), 1.35-1.55(m, 2H), 2.27 (t, J=7Hz, 2H), 2.56(s, 3H), 3.16(ABX, J=13.8 & 1.6Hz, 1H), 3.19(ABX, J=13.8 & 11.4Hz, 1H), 4.24(d, J=7Hz, 2H), 4.8-5.0(m, 1H), 8.7-8.95 (m, 4H). |

TABLE 5-continued

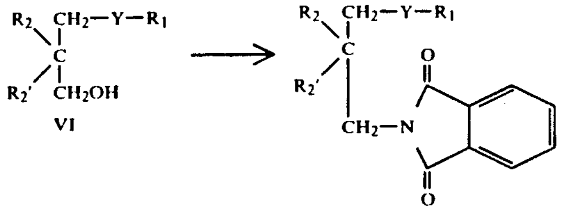

VI

| (Ref. Ex. No.) | R1 | R2 | R2' | Y | S.M. [g] ([mM]) | Imide [g] ([mM]) | PPh3 [g] ([mM]) | DEAD [ml] ([mM]) | THF [ml] | Yield [g] (%) | | NMR δ ppm |
|---|---|---|---|---|---|---|---|---|---|---|---|---|
| (92) | $-C_{16}H_{33}$ | 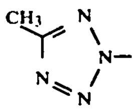 | H | S | 2.65 (6.6) | 2.93 (19.8) | 2.62 (9.9) | 1.77 (9.9) | 100 | 2.61 (74) | ($CDCl_3$) | 0.88(t, J=7Hz, 3H), 1.45-1.65(m, 2H), 2.50 (t, J=7Hz, 2H), 2.53(s, 3H), 3.18(ABX, J=14.2 & 6.3Hz, 1H), 3.26(ABX, J=14.2 & 8.7Hz, 1H), 4.21(ABX, J=14.9 & 9.0Hz, 1H), 4.26(ABX, J=14 & 3.6Hz, 1H), 5.2-5.4(m, 1H), 7.7-7.9(m, 4H). |
| (102) | $-C_{16}H_{33}$ | 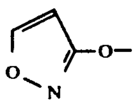 | H | S | 2.25 (5.6) | 1.24 (8.4) | 2.22 (8.4) | 1.44 (8.4) | 60 | 2.98 quant. | ($CDCl_3$) | 0.88(t, J=7Hz, 3H), 1.5-1.7(m, 2H), 2.63(t, J=7.4Hz, 2H), 2.86(ABX, J=14.4 & 6.74Hz, 1H), 2.96(ABX, J=14.4 & 5.66Hz, 1H), 4.13(ABX, J=14.4 & 7.26Hz, 1H), 4.19(ABX, J=14.4 & 3.54Hz, 1H), 5.1-5.25( m, 1H), 5.93(d, J=1.8Hz, 1H), 7.65-7.8(m, 2H), 7.8-7.95(m, 2H), 8.05(d, J=1.8Hz, 1H). |
| (107) | $-C_{16}H_{33}$ | $CH_3OCH_2-$ | H | O | 7.77 (22.5) | 6.63 (45) | 11.8 (45) | 7.84 (45) | 200 | 10.64 quant. | ($CDCl_3$) | 0.88(t, J=6Hz, 3H), 2.4(septet, J=5Hz, 1H), 3.25-3.55(m, 6H), 3.27(s, 3H), 3.78(d, J=7Hz, 2H), 7.65-7.8(m, 2H), 7.8-7.95(m, 2H). |
| (111) | $-C_{16}H_{33}$ | $CH_3OCH_2-$ | H | S | 3.6 (10) | 2.21 (15) | 3.93 (15) | 2.36 (15) | 50 | 3.60 (74) | ($CDCl_3$) | 0.88(t, 3H), 1.25(s, 26H), 1.40-1.65(m, 2H), 2.22-2.42(m, 1H), 2.42-2.72(m, 4H), 3.29(s, 3H), 3.36-3.52(m, 2H), 3.80(d, 2H, J=7.0Hz), 7.68-7.80(m, 2H), 7.80-7.95(m, 2H). |
| (114) | $-CONHC_{18}H_{37}$ | $CH_3OCH_2-$ | H | O | 6.0 (14) | 4.25 (29) | 7.57 (29) | 4.98 (29) | 200 | 6.51 (83) | ($CDCl_3$) | 0.88(t, J=6Hz, 3H), 1.4-1.6(m, 2H), 2.35-2.6 (m, 1H), 3.12(q, J=7Hz, 2H), 3.28(s, 3H), 3.41 (d, J=5.6Hz, 2H), 3.79(d, J=7Hz, 2H), 4.12(d, J=5Hz, 2H), 4.67(broad, 1H), 7.2-7.8(m, 2H), 7.8-7.95(m, 2H). |

S.M.: starting material, Imide: phthalimide, Ph: phenyl, DEAD: diethyl azocarboxylate, THF: tetrahydrofuran, tBu: tert-butyl.

TABLE 6

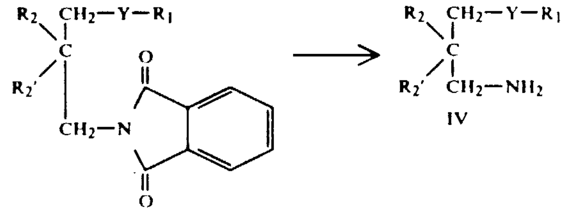

| (Ref. Ex. No.) | $R_1$ | $R_2$ | $R_2'$ | Y | S.M. [g] ([mM]) | $NH_2NH_2 \cdot H_2O$ [g] ([mM]) | $CH_3OH$ [ml] | Yield [g] (%) | | NMR δ ppm |
|---|---|---|---|---|---|---|---|---|---|---|
| (23) | $-C_{16}H_{33}$ | $-O-(CH_2)_3-$ | | S | 1.58 (3.17) | 0.19 (3.8) | 30 | 1.054 (89) | ($CDCl_3$) | 0.88(t, 3H), 1.26(s, 26H), 1.48-1.70(m, 2H), 1.70-2.10 (m, 4H), 2.56(t, 2H, J=7.4Hz), 2.64-2.86(m, 4H), 3.76-3.98 (m, 2H). |
| (26) | $-CONHC_{18}H_{37}$ | $-O-(CH_2)_3-$ | | O | 2.08 (3.74) | 0.281 (5.61) | 50 | 1.52 (95) | ($CDCl_3$) | 0.88(t, 3H), 1.26(s, 30H), 1.40-1.60(m, 2H), 1.72(s, 2H), 1.70-1.85(m, 2H), 1.85-2.05(m, 2H), 2.70, 2.78(ABq, 2H, J=13.3Hz), 3.16(q, 2H, J=6.6Hz), 3.87(t, 2H, J=6.4Hz), 4.04(s, 2H), 4.75-4.92(br. 1H). |
| (30) | $-C_{16}H_{33}$ | $-OOCNHCH_3$ | H | S | 1.6 | 0.34 (6.6) | 60 | 0.929 | ($CDCl_3$) | 0.75-1.75(m, 33H), 2.46-3.03(m, 9H), 4.80(m, 2H). |
| (35) | $-CONHC_{18}H_{37}$ | $-OOCNHCH_3$ | H | O | 2.54 (4.42) | 0.336 (6.64) | 25 | 1.208 | ($CDCl_3$) | 0.86(t, J=6Hz, 3H), 1.26(br.s, 32H), 2.80(d, J=6Hz, 3H), 2.92(m, 2H), 3.16(m, 2H), 4.22(d, J=6Hz, 2H), 4.86(m, 3H). |
| (43) | $-CONHC_{18}H_{37}$ | $-NHCOOCH_3$ | H | O | 1.47 (2.56) | 1.0 (20) | 30 | 0.872 (76.7) | ($CDCl_3$) | 0.89(3H, t, J=5Hz), 1.27(30H, s), 1.49(4H), 2.80(2H, s), 3.18(2H, m), 3.69(3H, s), 3.79(1H, s), 4.17(2H, s), 4.76 (1H, s), 5.25(1H, s). |
| (44) | $-CONHC_{18}H_{37}$ | $-NHCOOtBu$ | H | O | 0.840 (1.36) | 2 (40) | 20 | 0.540 (64.4) | ($CDCl_3$) | 0.88(3H, t, J=6Hz), 1.26(30H, s), 1.45(11H), 1.87(2H, s), 2.81(2H, br.s), 3.16(2H, m), 3.79(1H, br.s), 4.15(2H, m), 4.83(1H, t, J=4Hz), 5.79(1H, d, J=4Hz). |
| (86) | $-C_{16}H_{33}$ | 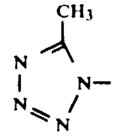 | H | S | — | 0.35 (7.0) | 70 | 1.47 | ($CDCl_3$) | 0.89(t, J=6Hz, 3H), 1.4-1.65(m, 2H), 2.31(t, J=7.3Hz, 2H), 2.64(s, 3H), 2.93(ABX, J=14 & 11Hz, 1H), 3.02(ABX, J=14 & 5.4Hz, 1H), 3.2-3.45(m, 2H), 4.25-4.45(m, 1H). |
| (92) | $-C_{16}H_{33}$ | 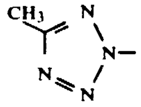 | H | S | 2.61 (4.9) | 0.49 (9.8) | 100 | 1.63 (83) | ($CDCl_3$) | 0.88(t, J=7Hz, 3H), 2.46(t, J=7Hz, 2H), 2.56(s, 3H), 3.07 (d, J=7Hz, 2H), 3.34(d, J=6.2Hz, 2H), 4.8-4.95(m, 1H). |
| (102) | $-C_{16}H_{33}$ | 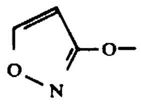 | H | S | 2.94 (5.6) | 0.56 (11.1) | 100 | 1.36 (62) | ($CDCl_3$) | 0.88(t, J=7Hz, 3H), 1.45-1.7(m, 2H), 2.55-2.7(m, 2H), 2.81 (ABX, J=13.8 & 7.8Hz, 1H), 2.94(ABX, J=13.8 & 4.8Hz, 1H), 3.16(sextet, J=16 & 5Hz, 2H), 4.7-4.9(m, 1H), 5.98(d, J=1.8Hz, 1H), 8.14(d, J=1.8Hz, 1H). |
| (107) | $-C_{16}H_{33}$ | $CH_3OCH_2-$ | H | O | 10.64 | 1.44 | 300 | 7.62 | ($CDCl_3$) | 0.85(t, J=6Hz, 3H), 1.40(broad-s, 2H), 1.4-1.6(m, 2H), 1.89 |

TABLE 6-continued
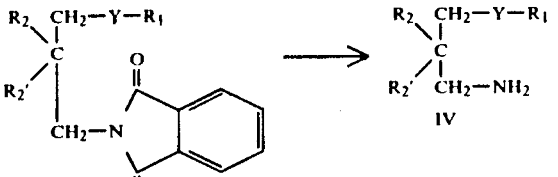
IV
| (Ref. Ex. No.) | $R_1$ | $R_2$ | $R_2'$ | Y | S.M. [g] ([mM]) | $NH_2NH_2 \cdot H_2O$ [g] ([mM]) | $CH_3OH$ [ml] | Yield [g] (%) | | NMR δ ppm |
|---|---|---|---|---|---|---|---|---|---|---|
| | | | | | (22.5) | (45) | | (99) | | (septet, J = 6Hz, 1H), 2.75(d, J = 6.2Hz, 12H), 3.30(s, 3H), 3.3-3.55(m, 6H). |
| (111) | $-C_{16}H_{33}$ | $CH_3OCH_2-$ | H | S | 3.43 (7) | 0.39 (7.7) | 100 | 2.60 (quant.) | ($CDCl_3$) | 0.88(t, 3H), 1.26(s, 26H), 1.6(m, 2H), 2.5-3.0(m, 6H), 3.33(m, 1H), 3.43(s, 3H). |
| (114) | $-CONHC_{18}H_{37}$ | $CH_3OCH_2-$ | H | O | 6.51 (12) | 1.24 (24) | 120 | 4.63 (94) | ($CDCl_3$) | 0.88(t, J = 6Hz, 3H), 1.4-1.6(m, 2H), 1.95-2.15(m, 1H), 2.18 (s, 2H), 2.80(d, J = 6Hz, 2H), 3.16(q, J = 6Hz, 2H), 3.34(s, 3H), 3.35-3.55(m, 2H), 4.0-4.3(m, 2H), 4.89(broad-s, 1H). |

TABLE 7

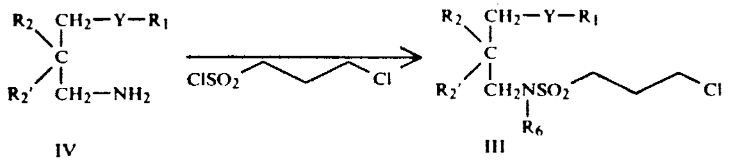

IV III

| (Ref. Ex. No.) | $R_1$ | $R_2$ | $R_2'$ | $R_6$ | Y | S.M. [g] ([mM]) | $NEt_3$ [ml] ([mM]) | Chloride [g] ([mM]) | $CH_2Cl_2$ [ml] | Yield [g] (%) | | NMR δ ppm |
|---|---|---|---|---|---|---|---|---|---|---|---|---|
| (24) | $-C_{16}H_{33}$ | $-O-(CH_2)_3-$ | | H | S | 1.0 (2.7) | 0.488 (3.51) | 0.526 (2.97) | 20 | 1.194 (86) | ($CDCl_3$) | 0.88(t, 3H), 1.26(s, 26H), 1.45-1.67(m, 2H), 1.80-2.08(m, 4H), 2.22-2.38(m, 2H), 2.57(t, 2H, J=7.3Hz), 2.69, 2.72(ABq, 2H, J=12.5Hz), 3.14-3.38 (m, 4H), 3.69(t, 2H, J=6.2Hz), 3.82-3.94(m, 2H), 4.65(t, 1H, J=6.4Hz). |
| (27) | $-CONHC_{18}H_{37}$ | $-O-(CH_2)_3-$ | | H | O | 1.513 (3.55) | 0.593 (4.26) | 0.69 (3.90) | 20 | 1.693 (84) | ($CDCl_3$) | 0.88(t, 3H), 1.26(s, 30H), 1.40-1.60(m, 2H), 1.70-2.10(m, 4H), 2.20-2.38(m, 2H), 3.08-3.28(m, 6H), 3.68(t, 2H, J=6.2Hz), 3.80-4.16(m, 4H), 4.78-4.90 (br, 1H), 5.14(t, 1H, J=6.5Hz). |
| (31) | $-C_{16}H_{33}$ | $-OOCNHCH_3$ | H | H | S | 1.161 (3.0) | 0.501 (3.6) | 0.636 (3.6) | 40 | 1.459 (92) | ($CDCl_3$) | 0.80-1.80(m, 31H), 2.15-2.80(m, 6H), 2.81(d, J=5Hz, 3H), 3.15-3.35(m, 2H), 3.35-3.55(m, 2H), 3.68(t, J=6Hz, 2H), 4.75-5.20(br.m, 3H). |
| (36) | $-CONHC_{18}H_{37}$ | $-OOCNHCH_3$ | H | H | O | 1.10 (2.48) | 0.301 (2.98) | 0.527 (2.98) | 110 | 1.225 (85) | ($CDCl_3$) | 0.84(t, J=6Hz, 3H), 1.24(br.s, 32H), 2.24(m, 2H), 2.74(d, J=6Hz, 3H), 2.95-3.50(m, 6H), 3.65(t, J=6Hz, 2H), 4.20(d, J=6Hz, 2H), 4.50(br.s, 1H), 4.95(m, 3H). |
| (56) | $-CONHC_{18}H_{37}$ | $-NHCOOCH_3$ | H | H | O | 0.836 (1.88) | 1 (7.17) | 0.750 (4.24) | 22 | 0.745 (67.6) | ($CDCl_3$) | 0.88(3H, t, J=5Hz), 1.27(30H, s), 1.50(2H, m), 2.27 (2H, m), 3.1-3.4(6H), 3.70(3H, s), 3.6-3.8(2H, m), 3.95(1H, m), 4.19(2H, d, J=5Hz), 4.86(1H, t, J=5Hz), 5.45(1H, t, J=5Hz). |
| (57) | $-CONHC_{18}H_{37}$ | $-NHCOOtBu$ | H | H | O | 0.501 (1.03) | 1.5 (21) | 0.365 (2.06) | 13 | 0.500 (77.4) | ($CDCl_3$) | 0.89(3H, t, J=5Hz), 1.26(30H, s), 1.45(9H, s), 1.50(2H, m), 2.29(2H, m), 3.20(6H), 3.69(2H, t, J=6Hz), 3.88(1H, br.s), 4.17(2H, d, J=5Hz), 4.80 (1H, t, J=4Hz), 5.14(1H, br.s), 5.43(1H, br.s). |
| (58) | $-C_{16}H_{33}$ | $-NHCOOCH_3$ | H | H | S | 3.470 (8.928) | 1.5 (10.9) | 1.77 g (10) | 45 | 4.603 (97.4) | ($CDCl_3$) | 0.88(3H, t, J=6.5Hz), 1.26(26H, s), 1.58(2H, m), 2.29(2H, m), 2.54(2H, t, J=7.3Hz), 2.65(1H, dd, J=7.2, 13.2Hz), 2.76(1H, dd, J=6.0, 13.2Hz), 3.18-3.46(4H), 3.69(2H, t, J=6.2Hz), 3.69(3H, s), 3.88 (1H, m), 4.97(1H, t, J=6.5Hz), 5.25(1H, d, J=7.3Hz). |
| (59) | $-C_{16}H_{33}$ | $-NHCOOtBu$ | H | H | S | 3.69 (8.567) | 1.5 (10.9) | 1.77 (10) | 50 | 4.74 (96.8) | ($CDCl_3$) | 0.88(3H, t, J=6.5Hz), 1.26(26H, s), 1.46(9H, s), 1.58(2H, m), 2.29(2H, m), 2.54(2H, t, J=7.2Hz), 2.65(1H, dd, J=6.3, 13.7Hz), 2.74(1H, dd, J=5.9, 13.7Hz), 3.18-3.45(4H), 3.69(2H, t, J=6.2Hz), 3.84(1H, m), 4.90-5.10(2H). |
| (87) | $-C_{16}H_{33}$ | 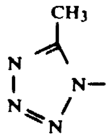 | H | H | S | 1.47 | 0.67 (4.8) | 0.73 (4.1) | 20 | 1.34 (70) | ($CDCl_3$) | 0.88(t, J=6Hz, 3H), 1.4-1.6(m, 2H), 2.15-2.3(m, 2H), 2.35(t, J=7Hz, 2H), 2.63(s, 3H), 2.99(ABX, J=14 & 9.7Hz, 1H), 3.07(ABX, J=14 & 4.9Hz, 1H). |

TABLE 7-continued

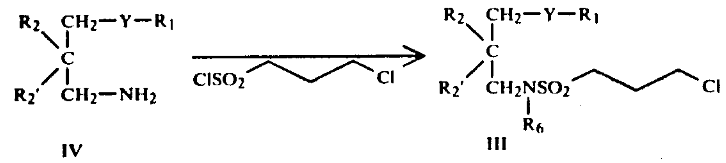

IV III

| (Ref. Ex. No.) | $R_1$ | $R_2$ | $R_2'$ | $R_6$ | Y | S.M. [g] ([mM]) | $NEt_3$ [ml] ([mM]) | Chloride [g] ([mM]) | $CH_2Cl_2$ [ml] | Yield [g] (%) | NMR δ ppm |
|---|---|---|---|---|---|---|---|---|---|---|---|
| (90) | $-CONHC_{18}H_{37}$ | 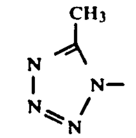 | H | H | O | 0.82 (1.8) | 0.33 (2.3) | 0.35 (2.0) | 15 | 0.86 (80) | ($CDCl_3$) 0.88(t, J=6.5Hz, 3H), 1.4-1.6(m, 2H), 2.15-2.35 (m, 2H), 2.57(s, 3H), 3.12(quartet, J=6.8Hz, 2H), 3.23(t, J=7Hz, 2H), 3.67(t, J=6.2Hz, 2H), 3.74(t, J=7Hz, 2H), 4.35(ABX, J=11.8 &7.5Hz, 1H), 4.50 (ABX, J=11.8 4.5Hz, 1H), 4.75-5.0(m, 1H), 5.01 (t, J=6Hz, 1H), 6.22(t, J=7Hz, 1H). |
| (93) | $-C_{16}H_{33}$ | 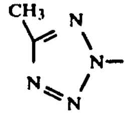 | H | H | S | 1.62 (4.1) | 0.74 (5.3) | 0.80 (4.5) | 20 | 2.20 quant. | ($CDCl_3$) 0.88(t, J=7Hz, 3H), 1.45-1.65(m, 2H), 2.15-2.3 (m, 2H), 2.47(t, J=7.5Hz, 2H), 2.55(s, 3H), 3.05-3.15(m, 2H), 3.15-3.25(m, 2H), 3.66(t, J=6Hz, 2H), 3.8-3.95(m, 2H), 5.0-5.15(m, 1H). |
| (96) | $-CONHC_{18}H_{37}$ | 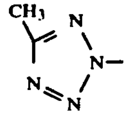 | H | H | O | 2.19 (4.8) | 0.88 (6.2) | 0.95 (5.3) | 30 | 2.35 (63) | ($CDCl_3$) 0.88(t, J=7Hz, 3H), 2.15-2.35(m, 2H), 2.55(s, 3H), 3.05-3.25(m, 4H), 3.66(t, J=6Hz, 2H), 3.7-3.9(m, 2H), 4.56(d, J=5.6Hz, 2H), 4.92(t, J=6Hz, H), 5.1-5.3(m, 1H), 5.64(t, J=6Hz, 1H). |
| (103) | $-C_{16}H_{33}$ | 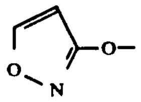 | H | H | S | 1.36 (3.4) | 0.62 (4.4) | 0.67 (3.8) | 15 | 1.81 (98) | ($CDCl_3$) 0.88(t, J=6Hz, 3H), 1.5-1.7(m, 2H), 2.2-2.35(m, 2H), 2.59(t, J=7Hz, 2H), 2.82(ABX, J=14 7.8Hz, 1H), 2.98(ABX, J=14 4.6Hz, 1H), 3.23(t, J=7.5Hz, 2H), 3.4-3.8(m, 2H), 3.66(t, J=6.2Hz, 2H), 4.8-4.95(m, 1H), 5.00(t, J=6.4Hz 1H), 6.00 (d, J=1.7Hz, 1H), 8.16(d, J=1.7Hz, 1H). |
| (105) | $-CONHC_{18}H_{37}$ | 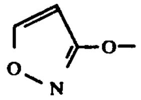 | H | H | O | 3.23 (7.1) | 1.3 (9.3) | 1.38 (7.8) | 30 | 4.05 (96) | ($CDCl_3$) 0.88(t, J=6Hz, 3H), 1.4-1.6(m, 2H), 2.2-2.35(m, 2H), 3.05-3.3(m, 2H), 3.4-3.6(m, 2H), 3.64(t, J=6.2Hz, 2H), 4.40(d, J=4.4Hz, 2H), 4.8-5.0(m, 2H), 5.36(t, J=7Hz, 1H), 6.02(d, J=1.7Hz, 1H), 8.18 (d, J=1.7Hz, 1H). |
| (108) | $-C_{16}H_{33}$ | $CH_3OCH_2-$ | H | H | O | 2.0 (5.8) | 1.06 (7.6) | 1.14 (6.4) | 20 | 2.63 (93) | ($CDCl_3$) 0.88(t, J=6Hz, 3H), 1.35-1.65(m, 2H), 2.05-2.3 (m, 1H), 2.15-2.45(m, 2H), 3.34(s, 3H), 3.69(t, J=6.5Hz, 2H), 5.26(t, J=6Hz, 1H). |
| (112) | $-C_{16}H_{33}$ | $CH_3OCH_2-$ | H | H | S | 1.44 (4) | 0.67 (4.8) | 0.78 (4.4) | 20 | 1.374 (69) | ($CDCl_3$) 0.88(t, 3H), 1.26(s, 26H), 1.50-1.65(m, 2H), 1.96-2.16(m, 1H), 2.22-2.36(m, 2H), 2.44-2.66 (m, 4H), 3.15-3.32(m, 4H), 3.35(s, 3H), 3.38-3.60 (m, 2H), 3.69(t, 2H, J=6.2Hz), 5.06(t, 1H, J=5.8Hz). |

TABLE 7-continued
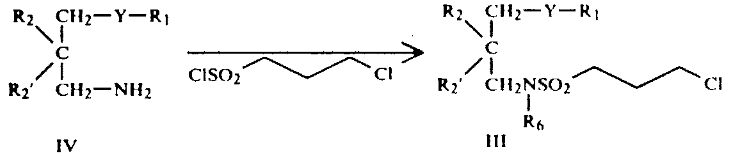
IV III
| (Ref. Ex. No.) | $R_1$ | $R_2$ | $R_2'$ | $R_6$ | Y | S.M. [g] ([mM]) | $NEt_3$ [ml] ([mM]) | Chloride [g] ([mM]) | $CH_2Cl_2$ [ml] | Yield [g] (%) | | NMR δ ppm |
|---|---|---|---|---|---|---|---|---|---|---|---|---|
| (115) | $-CONHC_{18}H_{37}$ | $CH_3OCH_2-$ | H | H | O | 2.0 (4.8) | 0.88 (6.3) | 0.95 (5.3) | 60 | 2.52 (94) | $(CDCl_3)$ | 0.88(t, J=6Hz, 3H), 1.4-1.6(m, 2H), 2.1-2.4(m, 3H), 3.0-3.3(m, 6H), 3.34(s, 3H), 3.35-3.55(m, 2H), 3.69(t, J=6.2Hz, 2H), 4.06(ABX, J=14 & 7.3Hz, 1H), 4.18(ABX, J=14 & 6.7Hz, 1H), 4.81(t, J=6Hz, 1H), 5.36(t, J=7Hz, 1H). |
| (141) | $-C_{16}H_{33}$ | $NCCH_2-$ | H | H | O | — | 1.51 (10.76) | 1.456 (8.28) | 30 | 3.233 (87.8) | $(CDCl_3)$ | 0.88(t, J=6.4Hz, 3H), 1.15-1.43(m, 26H), 1.46-1.67(m, 2H), 2.17-2.37(m, 3H), 2.45-2.69(m, 2H), 3.13-3.36(m, 4H), 3.45(t, J=6.6Hz, 2H), 3.48-3.63 (m, 2H), 3.69(t, J=6.4Hz, 2H), 4.92(t, J=6.3Hz, 1H). |
| (150) | $-CONHC_{18}H_{37}$ | $NCCH_2-$ | H | H | O | — | 0.36 (2.58) | 0.335 (1.89) | 10 | 0.965 (95.6) | $(CDCl_3)$ | 0.88(t, J=6.4Hz, 3H), 1.16-1.38(m, 30H), 1.40-1.58(m, 2H), 2.20-2.40(m, 3H), 2.50(d, J=6.8Hz, 2H), 3.01-3.33(m, 6H), 3.69(t, J=6.2Hz, 2H), 4.32 (dd, J=9.2 & 3.3Hz, 1H), 4.15(dd, J=9.2 & 4.2Hz, 1H), 4.84(t, J=4.4Hz, 1H), 5.44(t, J=5.4Hz, 1H). |

TABLE 8

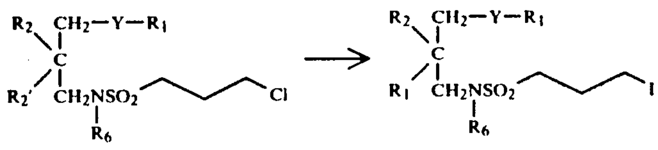

III → II

| (Ref. Ex. No.) | $R_1$ | $R_2$ | $R_2'$ | $R_6$ | Y | S.M. [g] ([mM]) | NaI [mg] ([mM]) | MEK [ml] | Yield [g] (%) | NMR δ ppm |
|---|---|---|---|---|---|---|---|---|---|---|
| (25) | $-C_{16}H_{33}$ | $-O-(CH_2)_3-$ | | H | S | 1.0 (1.95) | 1100 (7.33) | 20 | 1.063 (90) | ($CDCl_3$) 0.88(t, 3H), 1.26(s, 26H), 1.45-1.70(m, 2H), 1.85-2.10(m, 4H), 2.25-2.42(m, 2H), 2.58(t, 2H, J=7.3Hz), 2.69, 2.72 (ABq, 2H, J=12.9Hz), 3.14-3.26(m, 4H), 3.30(t, 2H, J=6.7Hz), 3.82-3.96(m, 2H), 4.67(t, 1H, J=6.3Hz). |
| (28) | $-CONHC_{18}H_{37}$ | $-O-(CH_2)_3-$ | | H | O | 1.50 (2.64) | 1500 (10) | 30 | 1.325 (76) | ($CDCl_3$) 0.88(t, 3H), 1.26(s, 30H), 1.40-1.60(m, 2H), 1.70-2.10(m, 4H), 2.25-2.40(m, 2H), 3.10-3.24(m, 6H), 3.30(t, 2H, J=6.6Hz), 3.84-4.14(m, 4H), 4.78-4.92(br, 1H), 5.14(t, 1H, J=6.4Hz). |
| (32) | $-C_{16}H_{33}$ | $-OOCNHCH_3$ | H | H | S | 0.528 (1.0) | 450 (3.0) | 10 | 0.593 (96) | ($CDCl_3$) 0.75-1.75(m, 31H), 2.13-2.80(m, 6H), 2.80(d, J=5Hz, 3H), 3.05-3.55(m, 6H), 4.75-5.23(br.m, 3H). |
| (37) | $-CONHC_{18}H_{37}$ | $-OOCNHCH_3$ | H | H | O | 1.22 (2.09) | 626 (4.18) | 60 | 1.151 (82) | ($CDCl_3$) 0.90(t, J=6Hz, 3H), 1.26(br.s, 32H), 2.30(m, 2H), 2.80 (d, J=6Hz, 3H), 3.00-3.45(m, 8H), 4.22(d, J=6Hz, 2H), 4.96 (m, 3H), 5.52(m, 1H). |
| (67) | $-CONHC_{18}H_{37}$ | $-NHCOOCH_3$ | H | H | O | 0.340 (0.582) | 170 (1.13) | 5 | 0.375 (95.4) | ($CDCl_3$) 0.90(3H, t, J=4Hz), 1.28(30H, s), 1.51(2H, m), 2.34(2H, m), 3.1-3.4(8H), 3.71(3H, s), 3.97(1H, m), 4.19(2H, s), 4.85 (1H, s), 5.43(1H, s). |
| (68) | $-CONHC_{18}H_{37}$ | $-NHCOOtBu$ | H | H | O | 0.402 (0.642) | 180 (1.20) | 5 | 0.409 (88.8) | ($CDCl_3$) 0.88(3H, t, J=6Hz), 1.26(30H, s), 1.45(11H), 2.32(2H, m), 3.1-3.3(6H), 3.31(2H, t, J=7Hz), 3.89(1H, br.s), 4.17(2H, br.s), 4.82(1H, br.s), 5.15(1H, br.s), 5.44(1H, br.s). |
| (69) | $-CONHC_{18}H_{37}$ | $-NHCOCH_3$ | H | H | O | 0.427 (0.751) | 180 (1.20) | 5 | 0.457 (92.2) | ($CDCl_3$) 0.88(3H, t, J=6Hz), 1.26(30H, s), 1.50(2H, m), 2.02(3H, s), 2.31(2H, m), 3.1-3.3(4H), 3.15(2H, t, J=7Hz), 3.30(2H, t, J=7Hz), 4.17(3H), 4.93(1H, t, J=5Hz), 5.74(1H, t, J=5Hz), 6.49(1H, s). |
| (70) | $-CONHC_{18}H_{37}$ | $-NHCONHCH_3$ | H | H | O | 0.460 (0.789) | 180 (1.20) | 5 | 0.508 (95.5) | ($CDCl_3$) 0.88(3H, t, J=6Hz), 1.26(30H, s), 1.50(2H, m), 1.69(1H, br. s), 2.31(2H, m), 2.77(3H, s), 3.1-3.3(4H), 3.14(2H, t, J=7Hz), 3.30(2H, t, J=7Hz), 4.05(1H, m), 4.14(2H, d, J=4Hz), 5.01(1H, t, J=5Hz), 5.45(1H, s), 6.06(1H, s). |
| (71) | $-C_{16}H_{33}$ | $-NHCOOCH_3$ | H | H | S | 4.500 (8.503) | 2548 (16.999) | 50 | 4.771 (90.4) | ($CDCl_3$) 0.88(3H, t, J=6.5Hz), 1.26(26H, s), 1.58(2H, m), 2.32(2H, m), 2.54(2H, t, J=7.3Hz), 2.66(1H, dd, J=6.8, 13.5Hz), 2.77 (1H, dd, J=6.1, 13.5Hz), 3.12-3.47(6H), 3.70(3H, s), 3.58 (1H, m), 4.95(1H, t, J=6.0Hz), 5.25(1H, d, J=7.5Hz). |
| (72) | $-C_{16}H_{33}$ | $-NHCOOtBu$ | H | H | S | 1.518 (2.657) | 800 (5.337) | 15 | 1.671 (94.9) | ($CDCl_3$) 0.88(3H, t, J=6.4Hz), 1.26(26H, s), 1.46(9H, s), 1.58(2H, m), 2.32(2H, m), 2.54(2H, t, J=7.0Hz), 2.70(2H, m), 3.12-3.45(4H), 3.30(2H, t, J=6.6Hz), 3.83(1H, m), 4.9-5.1(2H). |
| (73) | $-C_{16}H_{33}$ | $-NHCOCH_3$ | H | H | S | 0.914 (1.781) | 550 (3.669) | 12 | 1.002 (93.0) | ($CDCl_3$) 0.88(3H, t, J=6.5Hz), 1.26(26H, s), 1.58(2H, m), 2.03(3H, s), 2.31(2H, m), 2.54(2H, t, J=7.3Hz), 2.65(1H, dd, J=7.1, 13.3Hz), 2.77(1H, dd, J=5.9, 13.3Hz), 3.12-3.37(4H), 3.30 (2H, t, J=6.6Hz), 4.12(1H, m), 5.24(1H, t, J=6.2Hz), 6.24 (1H, d, J=7.5Hz). |
| (74) | $-C_{16}H_{33}$ | $-NHCONHCH_3$ | H | H | S | 1.039 | 600 | 17 | 1.156 | ($CDCl_3$) 0.88(3H, t, J=6.5Hz), 1.26(26H, s), 1.58(2H, m), 1.70(1H, |

TABLE 8-continued

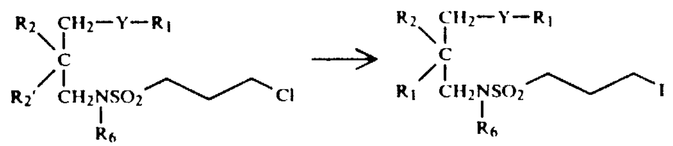

III → II

| (Ref. Ex. No.) | $R_1$ | $R_2$ | $R_2'$ | $R_6$ | Y | S.M. [g] ([mM]) | NaI [mg] ([mM]) | MEK [ml] | Yield [g] (%) | | NMR δ ppm |
|---|---|---|---|---|---|---|---|---|---|---|---|
| | | | | | | (1.967) | (4.003) | | (94.8) | | br.s), 2.31(2H, m), 2.54(2H, t, J=7.2Hz), 2.66(1H, dd, J=6.8, 13.5Hz), 2.75(1H, dd, J=6.1, 13.5Hz), 2.78(3H, s), 3.12-3.44(4H), 3.30(2H, t, J=6.6Hz), 4.00(1H, br.s), 5.09 (1H, br.s), 5.75(1H, br.s). |
| (75) | $-CONHC_{18}H_{37}$ | $-NHCOCH_3$ | H | Ac | O | 0.335 (0.549) | 180 (1.20) | 5 | 0.351 (91.1) | ($CDCl_3$) | 0.88(3H, t, J=6Hz), 1.26(30H, s), 1.50(2H, m), 1.99(3H, s), 2.35(2H, m), 2.47(3H, s), 3.18(2H, m), 3.30(2H, t, J=7Hz), 3.53(2H, t, J=7Hz), 3.90(2H, m), 4.15(2H, m), 4.48(1H, m), 4.81(1H, t, J=6Hz), 6.09(1H, d, J=6Hz). |
| (88) | $-C_{18}H_{37}$ | 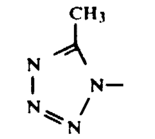 | H | H | S | 1.29 (2.4) | 540 (3.6) | 20 | 1.33 (88) | ($CDCl_3$) | 0.88(t, J=6.5Hz, 3H), 1.4-1.6(m, 2H), 2.2-1.4(m, 4H), 2.61 (s, 3H), 2.95-3.1(m, 2H), 3.1-3.3(m, 2H), 3.28(t, J=6.6Hz, 2H), 3.6-3.85(m, 2H), 4.55-4.7(m, 1H), 4.6-4.75(m, 1H), 3.15-3.3(m, 2H), 3.55-3.8(m, 4H), 4.6-4.75(m, 1H). |
| (91) | $-CONHC_{18}H_{37}$ | 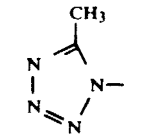 | H | H | O | 0.83 (1.4) | 475 (3.2) | 10 | 0.905 (94) | ($CDCl_3$) | 0.88(t, J=5Hz, 3H), 1.4-1.6(m, 2H), 2.15-2.35(m, 2H), 2.58(s, 3H), 3.05-3.25(m, 4H), 3.29(t, J=7Hz, 3H), 3.74 (t, J=6Hz, 2H), 4.35(ABX, J=11.0 & 7.7Hz, 1H), 4.51(ABX, J=11.0 & 5.3Hz, 1H), 4.75-4.95(m, 1H), 5.02(t, J=6Hz, 1H), 6.26(t, J=6Hz, 1H). |
| (94) | $-C_{16}H_{33}$ | 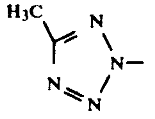 | H | H | S | 2.2 (4.1) | 920 (6.2) | 30 | 2.27 (88) | ($CDCl_3$) | 0.88(t, J=7Hz, 3H), 1.45-1.55(m, 2H), 2.15-2.3(m, 2H), 2.45(t, J=7Hz, 2H), 2.56(s, 3H), 3.07(d, J=6.5Hz, 2H), 3.09(t, J=7Hz, 2H), 3.27(t, J=6.7Hz, 2H), 4.7-4.9(m, 2H), 5.0-5.15(m, 1H). |
| (97) | $-CONHC_{18}H_{37}$ | 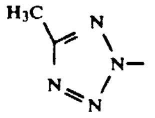 | H | H | O | 2.29 (3.9) | 1170 (7.8) | 30 | 2.42 (92) | ($CDCl_3$) | 0.88(t, J=7Hz, 3H), 2.26(quintet, J=6Hz, 2H), 2.56(s, 3H), 3.05-3.20(m, 4H), 3.27(t, J=6.7Hz, 2H), 3.73(ABX, J=15.4 & 5.7Hz, 1H), 3.85(ABX, J=15.4 & 7.3Hz, 1H), 4.56(d, J=5.4Hz, 2H), 4.91(t, J=6Hz, 1H), 5.1-5.3(m, 1H), 5.6(t, J=6Hz, 1H). |

TABLE 8-continued

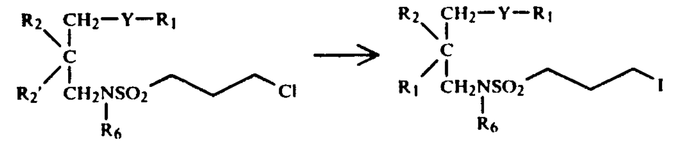

III → II

| (Ref. Ex. No.) | $R_1$ | $R_2$ | $R_2'$ | $R_6$ | Y | S.M. [g] ([mM]) | NaI [mg] ([mM]) | MEK [ml] | Yield [g] (%) | NMR δ ppm |
|---|---|---|---|---|---|---|---|---|---|---|
| (104) | $-C_{16}H_{33}$ | 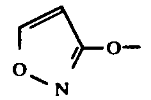 | H | H | S | 1.76 (3.3) | 833 (5.6) | 25 | 1.78 (86) | ($CDCl_3$) 0.88(t, J=7Hz, 3H), 1.5-1.7(m, 2H), 2.2-2.4(m, 2H), 2.59 (t, J=7Hz, 2H), 2.82(ABX, J=13.6 & 7.8Hz, 1H), 2.98(ABX, J=13.6 & 4.2Hz, 1H), 3.18(t, J=7.5Hz, 2H), 3.28(t, J=6.7Hz, 2H), 3.4-3.8(m, 2H), 4.8-5.0(m, 1H), 5.09(t, J=6Hz, 1H), 6.01(d, J=1.8Hz, 1H), 8.16(d, J=1.8Hz, 1H). |
| (107) | $-CONHC_{18}H_{37}$ | 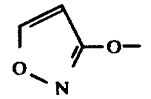 | H | H | O | 4.05 (6.8) | 1740 (11.6) | 50 | 3.96 (85) | ($CDCl_3$) 0.88(t, J=6Hz, 3H), 1.4-1.6(m, 2H), 2.2-2.4(m, 2H), 3.05-3.3(m, 4H), 3.28(t, J=6.6Hz, 2H), 3.4-3.6(m, 2H), 4.40 (d, J=5Hz, 2H), 4.85-5.0(m, 2H), 5.40(t, J=7Hz, 1H), 6.06 (d, J=1.8Hz, 1H), 8.18(d, J=1.8Hz, 1H). |
| (109) | $-C_{16}H_{33}$ | $CH_3OCH_2-$ | H | H | O | 2.63 (5.4) | 1380 (9.2) | 30 | 3.09 (99) | ($CDCl_3$) 0.88(t, J=6Hz, 3H), 2.2-2.4(m, 1H), 2.05-2.25(m, 2H), 3.12 (t, J=7Hz, 2H), 3.34(s, 3H), 5.27(t, J=6Hz, 1H). |
| (113) | $-C_{16}H_{33}$ | $CH_3OCH_2-$ | H | H | S | 1.37 (2.75) | 3000 (20) | 70 | 1.06 (65) | ($CDCl_3$) 0.88(t, 3H), 1.26(s, 26H), 1.48-1.65(m, 2H), 1.98-2.16(m, 1H), 2.24-2.40(m, 2H), 2.45-2.60(m, 4H), 3.10-3.34(m, 4H), 3.31(t, 2H, J=6.7Hz), 3.35(s, 3H), 3.40-3.60(m, 2H), 5.10 (t, 1H, J=6.5Hz). |
| (116) | $-CONHC_{18}H_{37}$ | $CH_3OCH_2-$ | H | H | O | 2.52 (4.6) | 1160 (7.7) | 30 | 2.41 (82) | ($CDCl_3$) 0.88(s, 3H), 1.4-1.6(m, 2H), 2.1-2.4(m, 3H), 3.05-3.3(m, 4H), 3.31(t, J=7Hz, 2H), 3.35-3.55(m, 2H), 3.35(s, 3H), 4.06(ABX, J=12 & 6.8Hz, 1H), 4.18(ABX, J=12 & 5.2Hz, 1H), 4.86(t, J=6Hz, 1H), 5.40(t, J=6Hz, 1H). |
| (133) | $-CONHC_{18}H_{37}$ | $CH_3COCH_2-$ | H | H | O | — | 750 (5) | 10 | 0.218 | ($CDCl_3$) 0.88(t, J=6.4Hz, 3H), 1.18-1.38(m, 30H), 1.40-1.57(m, 2H), 2.19(s, 3H), 2.20-2.77(m, 5H), 3.03-3.24(m, 6H), 3.29(t, J=6.4Hz, 2H), 3.95-4.20(m, 2H), 4.67-4.82(br., 1H), 5.22-5.36(br., 1H). |
| (142) | $-C_{16}H_{33}$ | $NOCH_2-$ | H | H | O | 0.447 (1.0) | 1490 (10.0) | 20 | 0.493 (86.4) | ($CDCl_3$) 0.88(t, J=6.4Hz, 3H), 1.15-1.43(m, 26H), 1.46-1.67(m, 2H), 2.17-2.40(m, 3H), 2.44-2.68(m, 2H), 3.08-3.12(m, 2H), 3.23-3.37(m, 4H), 3.45(t, J=6.6Hz, 2H), 3.49-3.63(m, 2H), 4.96 (t, J=6.3Hz, 1H). |
| (151) | $-CONHC_{18}H_{37}$ | $NOCH_2-$ | H | H | O | 0.6 (1.09) | 1633 (10.9) | 30 | 0.622 (88.9) | ($CDCl_3$) 0.88(t, J=6.4Hz, 3H), 1.18-1.40(m, 30H), 1.40-1.58(m, 2H), 2.20-2.44(m, 3H), 2.50(d, J=6.6Hz, 2H), 3.04-3.29(m, 6H), 3.30(t, J=6.4Hz, 2H), 4.15(dd, J=9.2 & 4.2Hz, 1H), 4.32(dd, J=9.2 & 3.3Hz, 1H), 4.84(t, J=4.4Hz, 1H), 5.44(t, J=5.4Hz, 1H). |
| (158) | $-C_{16}H_{33}$ | $CH_3COCH_2-$ | H | H | S | 0.213 (0.42) | 630 (4.2) | 20 | 0.186 (73.8) | ($CDCl_3$) 0.88(t, J=6.4Hz, 3H), 1.13-1.47(m, 26H), 1.47-1.67(m, 2H), 2.19(s, 3H), 2.23-2.44(m, 3H), 2.44-2.60(m, 4H), 2.65(d, J=6.0Hz, 2H), 3.07-3.27(m, 4H), 3.30(t, J=6.4Hz, 2H), 4.69 (t, J=6.4Hz, 1H). |

MEK: methyl ethyl ketone

TABLE 9

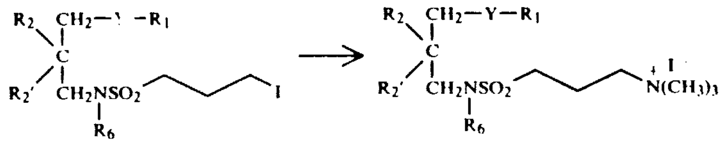

II → I

| Ex. No. | R1 | R2 | R2' | R6 | Y | S.M. [mg] ([mM]) | 4.2M/L-toluene [ml] | Yield [mg] (%) | | NMR δ ppm | IRνmax [cm⁻¹] | m.p. [°C.] |
|---|---|---|---|---|---|---|---|---|---|---|---|---|
| 29 | $-C_{16}H_{33}$ | $-O-(CH_2)_3-$ | | H | S | 500 (0.828) | 15 | 510 (93) | ($CDCl_3$) | 0.88(t, 3H), 1.26(s, 26H), 1.45-1.65(m, 2H), 1.90-2.10(m, 4H), 2.30-2.52(m, 2H), 2.58(t, 2H, J=7.3Hz), 2.72, 2.84(ABq, 2H, J=13.2Hz), 3.20-3.54(m, 6H), 3.43(s, 9H), 3.68-4.00(m, 2H), 5.99(t, 1H, J=6.4Hz). | ($CHCl_3$) 3380, 2910, 2840, 1465, 1320, 1210, 1140, 1030 | 79～84 |
| 32 | $-C_{16}H_{33}$ | $-OOCNHCH_3$ | H | H | S | 340 (0.548) | 7 | 330 (89) | ($CDCl_3$) | 0.75-1.75(m, 31H), 2.30-3.00(m, 9H), 3.39 (br.s, 13H), 3.80(m, 2H), 4.88(m, 1H), 5.70 (m, 1H), 6.50(m, 1H). | ($CHCl_3$) 3400, 1720, 1330, 1150 | 95～96 |
| 34 | $-CONHC_{18}H_{37}$ | $-OOCNHCH_3$ | H | H | O | 338 (0.5) | 10 | 220 (60) | ($CDCl_3-CD_3OD$) | 0.85(t, J=6Hz, 3H), 1.24(br.s, 32H), 2.72(s, 3H), 2.85-3.25(m, 11H), 3.34 (s, 9H), 3.55-3.85(m, 2H), 4.16(d, J=6Hz, 2H), 4.94(m, 1H). | (Nujol) 3320, 1695, 1540, 1380, 1260, 1140 | 91～93 |
| 35 | $-CONHC_{18}H_{37}$ | $-NHCOOCH_3$ | H | H | O | 561 (0.830) | 7 | 323 (52.9) | ($CDCl_3$) | 0.87(3H, t, J=5Hz), 1.25(30H, s), 1.50(2H, m), 2.43(2H, br.s), 3.12(2H, m), 3.35(2H, m), 3.39(9H, s), 3.66(3H, s), 3.87(2H, m), 4.05(1H, m), 4.16(2H, br.s), 5.42(1H, br.s), 5.92(1H, br.s), 6.35(1H, br.s). | (Nujol) 3320, 1705, 1144 | 57～58 |
| 36 | $-CONHC_{18}H_{37}$ | $-NHCOOtBu$ | H | H | O | 167 (0.233) | 10 | 93 (50.1) | ($CDCl_3$) | 0.88(3H, t, J=6Hz), 1.26(30H, s), 1.44 (11H), 2.43(2H, br.s), 3.12(2H, m), 3.30 (4H), 3.39(9H, s), 3.90(3H), 4.17(2H, br. s), 5.43(2H, br.s), 6.52(1H, br.s). | (Nujol) 3360, 1691, 1323, 1311, 1145 | 80～81 |
| 37 | $-CONHC_{18}H_{37}$ | $-NHCOCH_3$ | H | H | O | 212 (0.321) | 10 | 217 (93.9) | ($CD_3OD$) | 0.90(3H, t, J=6Hz), 1.28(30H, s), 1.48(2H, m), 1.97(3H, s), 2.28(2H, m), 3.08(2H, t, J=6Hz), 3.18(9H, s), 3.1-3.4(4H), 3.52 (2H, m), 4.0-4.2(3H). | (Nujol) 3330, 3270, 1690, 1646, 1294, 1270, 1142 | 94～97 |
| 38 | $-CONHC_{18}H_{37}$ | $-NHCONHCH_3$ | H | H | O | 242 (0.359) | 10 | 192 (72.9) | ($CDCl_3$) | 0.88(3H, t, J=5Hz), 1.25(30H, s), 1.48(2H, m), 2.32(2H, br.s), 2.71(3H, d, J=3Hz), 3.09(2H, m), 3.2-3.5(2H), 3.36(9H, s), 3.80(2H, br.s), 4.10(3H), 5.75(1H, s), 5.85(1H, s), 6.03(1H, s), 6.71(1H, s). | (Nujol) 3320, 1703, 1647, 1310, 1144 | 75～80 |
| 39 | $-C_{16}H_{33}$ | $-NHCOOCH_3$ | H | H | S | 621 (1) | 10 | 446 (65.6) | ($CDCl_3$) | 0.89(3H, d, J=6.5Hz), 1.26(26H, s), 1.57 (2H, m), 2.42(2H, m), 2.55(2H, t, J=7.3Hz), 2.75(2H, d, J=6.1Hz), 3.24-3.45(4H), 3.41 (9H, s), 3.69(3H, s), 3.86(3H, m), 5.89 (1H, d, J=7.4Hz), 6.60(1H, t, J=6.2Hz). | (KBr) 3380, 3310, 3150, 1702, 1322, 1142 | 68～72 |
| 40 | $-C_{16}H_{33}$ | $-NHCOOtBu$ | H | H | S | 663 (1) | 5 | 555 (76.9) | ($CDCl_3$) | 0.88(3H, t, J=6.5Hz), 1.26(26H, s), 1.45 (9H, s), 1.57(2H, m), 2.43(2H, m), 2.55 (2H, t, J=7.3Hz), 2.74(2H, d, J=6.2Hz), 3.23-3.50(4H), 3.40(9H, s), 3.87(3H, m), 5.37 (1H, d, J=6.5Hz), 6.46(1H, t, J=5.8Hz). | (KBr) 3320, 1676, 1323, 1145 | 60～67 |

TABLE 9-continued

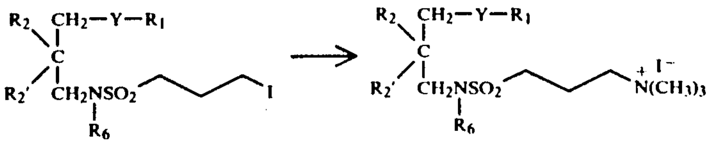

II → I

| Ex. No. | R1 | R2 | R2' | R6 | Y | S.M. [mg] ([mM]) | 4.2M/L-toluene [ml] | Yield [mg] (%) | | NMR δ ppm | IRνmax [cm⁻¹] | m.p. [°C.] |
|---|---|---|---|---|---|---|---|---|---|---|---|---|
| 41 | $-C_{16}H_{33}$ | $-NHCOCH_3$ | H | H | S | 478 (0.791) | 5 | 462 (88.0) | ($CDCl_3+CD_3OD$) | 0.88(3H, t, J=6.3Hz), 1.26(26H, s), 1.57(2H, m), 2.06(3H, s), 2.37(2H, m), 2.54(2H, t, J=7.3Hz), 2.68(2H, d, J=6.7Hz), 3.18-3.50(4H), 3.29(9H, s), 3.75(2H, m), 4.14(1H, m). | (KBr) 3360, 3285, 3190, 1673, 1631, 1325, 1142 | 103~106 |
| 42 | $-C_{16}H_{33}$ | $-NHCONHCH_3$ | H | H | S | 546 (0.881) | 5 | 555 (92.8) | ($CDCl_3+CD_3OD$) | 0.88(3H, t, J=6.5Hz), 1.26(26H, s), 1.57(2H, m), 2.22-2.46(2H), 2.55(2H, t, J=7.2Hz), 2.62(1H, dd, J=6.6, 13.0Hz), 2.70 (1H, dd, J=5.2, 13.2Hz), 2.73(3H, s), 3.12-3.30(3H), 3.27(9H, s), 3.43(1H, dd, J=3.3, 13.1Hz), 3.76(2H, m), 3.99(1H, m). | (KBr) 3315, 3165, 1652, 1319, 1140 | 111~115 |
| 43 | $-CONHC_{18}H_{37}$ | $-NHCOCH_3$ | H | Ac | O | 132 (0.188) | 10 | 106 (72) | ($CDCl_3$) | 0.88(3H, t, J=6Hz), 1.26(30H, s), 1.50(2H, m), 2.02(3H, s), 2.46(2H, br.s), 2.50(3H, s), 3.12(2H, m), 3.35(2H, m), 3.41(9H, s), 3.7-4.05(4H), 4.14(2H, m), 4.48(1H, m), 5.56(1H, t, J=5Hz), 6.91(1H, t, J=5Hz). | (Nujol) 3330, 1690, 1658, 1270, 1152 | 90~93 |
| 53 | $-C_{16}H_{33}$ | 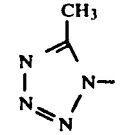 | H | H | S | 600 (0.95) | 13 | 590 (90) | ($CDCl_3$) | 0.88(t, J=6Hz, 3H), 1.4-1.6(m, 2H), 2.1-2.35(m, 2H), 2.41(t, J=7Hz, 2H), 2.72(s, 3H), 3.0-3.4(m, 4H), 3.30(s, 9H), 3.5-3.9 (m, 4H), 4.75-4.95(m, 1H), 6.9-7.15 (m, 1H). | 1340 | 104~107.5 |
| 55 | $-C_{16}H_{33}$ | 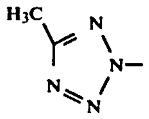 | H | H | S | 700 (1.1) | 13 | 650 (85) | ($CDCl_3$) | 0.88(t, J=7Hz, 3H), 1.4-1.6(m, 2H), 2.2-2.4 (broad, 2H), 2.40(t, J=7Hz, 2H), 2.55(s, 3H), 3.0-3.3(m, 4H), 3.35(s, 9H), 3.6-3.9 (m, 4H), 5.1-5.25(m, 1H), 6.75-6.9(m, 1H). | 1340 | Amorphous powder |
| 57 | $-C_{16}H_{33}$ | 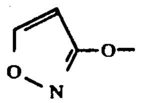 | H | H | S | 700 (1.1) | 15 | 670 (87) | ($CDCl_3$) | 0.88(t, J=7Hz, 3H), 1.45-1.65(m, 2H), 2.25-2.7(m, 2H), 2.58(t, J=7Hz, 2H), 2.92(d, J=5Hz, 2H), 3.2-3.45(m, 2H), 3.35(s, 9H), 3.5-3.9(m, 4H), 4.95-5.05(m, 1H), 6.18(d, J=1.8Hz, 1H), 6.55-6.75(m, 1H), 8.24(d, J=1.8Hz, 1H). | 1336 | Amorphous powder |

TABLE 9-continued

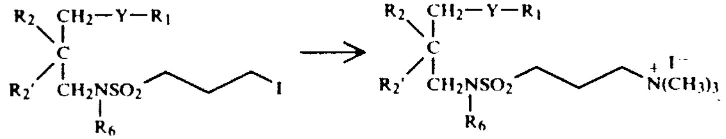

II → I

| Ex. No. | $R_1$ | $R_2$ | $R_2'$ | $R_6$ | Y | S.M. [mg] ([mM]) | 4.2M/L-toluene [ml] | Yield [mg] (%) | | NMR δ ppm | IRνmax [$cm^{-1}$] | m.p. [°C.] |
|---|---|---|---|---|---|---|---|---|---|---|---|---|
| 58 | $-CONHC_{18}H_{37}$ | 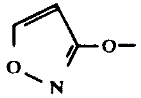 | H | H | O | 700 (1.0) | 30 | 710 (93) | ($CDCl_3$) | 0.88(t, J=6Hz, 3H), 1.35-1.55(m, 2H), 2.2-2.5(m, 2H), 2.95-3.2(m, 2H), 3.2-3.45(m, 2H), 3.35(s, 9H), 3.4-3.65(m, 2H), 3.55-3.9(m, 2H), 4.2-4.45(m, 2H), 4.9-5.05(m, 1H), 5.35-5.55(m, 1H), 6.17(s, 1H), 6.7-6.9(m, 1H), 8.28(s, 1H). | 1719, 1336 | 90~99 |
| 60 | $-C_{16}H_{33}$ | $CH_3OCH_2-$ | H | Ac | O | 810 (1.3) | 19 | 800 (90) | ($CDCl_3$) | 0.88(t, J=6Hz, 3H), 1.4-1.6(m, 2H), 2.2-2.4 (m, 1H), 2.35-2.6(m, 2H), 2.40(s, 3H), 3.47 (s, 3H), 3.73(t, J=7Hz, 2H), 3.86(d, J=7Hz, 2H), 3.9-4.05(m, 2H). | 1698 | Amorphous powder |
| 61 | $-C_{16}H_{33}$ | $CH_3OCH_2-$ | H | H | O | 1000 (1.7) | 25 | 950 (86) | ($CDCl_3$) | 0.88(t, J=6Hz, 3H), 1.4-1.6(m, 2H), 2.05-2.25(m, 2H), 2.25-2.5(m, 2H), 3.44(s, 3H), 3.8-4.0(m, 2H), 6.02(t, J=6Hz, 1H). | 1330 | 79~80 |
| 63 | $-C_{16}H_{33}$ | $CH_3OCH_2-$ | H | H | S | 874 (1.48) | 10 | 468 (49) | ($CDCl_3$) | 0.88(t, 3H), 1.26(s, 26H), 1.45-1.65(m, 2H), 1.98-2.20(m, 1H), 2.28-2.52(m, 2H), 2.51(t, 2H, J=7.3Hz), 2.62(d, 2H, J=7.0Hz), 3.10-3.50(m, 4H), 3.36(s, 3H), 3.43(s, 9H), 3.52(d, 2H, J=5.2Hz), 3.76-3.94(m, 2H), 6.20(t, 1H, J=6.0Hz). | 3400, 2930, 2855, 1475, 1330, 1200, 1150 | 65~70 |
| 67 | $-C_{16}H_{33}$ | $NOCH_2-$ | H | H | O | 300 (0.53) | 5.0 | 328 (98.1) | ($CDCl_3$) | 0.88(t, J=6.4Hz, 3H), 1.15-1.43(m, 26H), 1.45-1.60(m, 2H), 2.27-2.57(m, 3H), 2.68 (d, J=6.4Hz, 2H), 3.08-3.63(m, 8H), 3.39(s, 9H), 3.76-3.97(m, 2H), 6.63(t, J=6.3Hz, 1H). | 2230, 1320, 1140 | — |
| 70 | $-C_{16}H_{33}$ | $CH_3COCH_2-$ | H | H | S | 160 | 3.0 | 175 (98.0) | ($CDCl_3$) | 0.88(t, J=6.4Hz, 3H), 1.13-1.45(m, 26H), 1.45-1.64(m, 2H), 2.21(s, 3H), 2.29-2.80 (m, 9H), 3.04-3.37(m, 4H), 3.41(s, 9H), 3.78-3.95(m, 2H), 6.42(t, J=6.4Hz, 1H). | 1700, 1320, 1140 | — |
| 71 | $-C_{16}H_{33}$ | 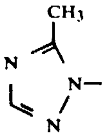 | H | H | S | 600 (0.96) | 13 | 490 (82) | ($CDCl_3$) | 0.88(t, J=6.4Hz, 3H), 1.35-1.6(m, 2H), 2.05-2.3(m, 2H), 2.30(t, J=7.4Hz, 2H), 2.62(s, 3H), 2.9-3.25(m, 4H), 3.30(s, 9H), 3.5-3.85(m, 4H), 4.55-4.75(m, 1H), 7.0-7.2(m, 1H), 7.89(s, 1H). | 1327 | Amorphous powder |

TABLE 10

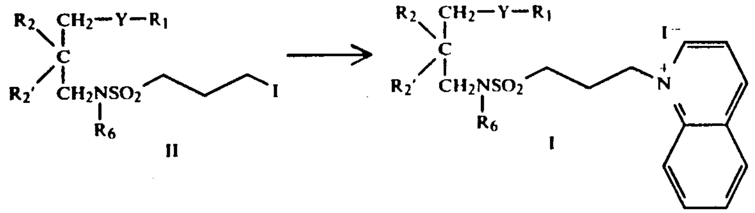

II → I

| Ex. No. | $R_1$ | $R_2$ | $R_2'$ | $R_6$ | Y | S.M. [mg] ([mM]) | Quinoline [ml] | Yield [mg] (%) | NMR δ ppm | IRνmax [$cm^{-1}$] | m.p. [°C.] |
|---|---|---|---|---|---|---|---|---|---|---|---|
| 30 | $-CONHC_{18}H_{37}$ | $-O-(CH_2)_3-$ | | H | O | 500 (0.76) | 0.95 | 150 (25) | ($CDCl_3$) 0.88(t, 3H), 1.25(s, 30H), 1.40-1.60(m, 2H), 1.68-2.00(m, 4H), 2.60-2.82(m, 2H), 3.11(q, 2H, J=6.6Hz), 3.18-3.40(m, 2H), 3.50-3.70(m, 2H), 3.70-3.94(m, 2H), 3.99(s, 2H), 5.48(t, 1H, J=5.7Hz), 5.54-5.72(m, 2H), 5.91(t, 1H, J=6.5Hz), 7.98(t, 1H, J=7.5Hz), 8.15-8.37(m, 3H), 8.70(d, 1H, J=9.2Hz), 9.25(d, 1H, J=8.2Hz), 10.34(d, 1H, J=5.0Hz). | ($CHCl_3$) 3400, 2930, 2850, 1710, 1460, 1430, 1325, 1230, 1140, 1040 | 57~62 |
| 31 | $-C_{16}H_{33}$ | $-OOCNHCH_3$ | H | H | S | 376 (0.6) | 1.5 | 295 (66) | ($CDCl_3$) 0.75-1.75(m, 31H), 2.35-2.90(m, 9H), 3.30-3.70 (m, 4H), 4.85(m, 1H), 5.65(m, 3H), 6.32(m, 1H), 7.85-9.13(m, 6H), 10.15(d, J=6Hz, 1H). | ($CHCl_3$) 3450, 3300, 1715, 1630, 1600, 1320, 1140 | 49~54 |
| 33 | $-CONHC_{18}H_{37}$ | $-OOCNHCH_3$ | H | H | O | 338 (0.5) | 3 | 255 (63) | ($CDCl_3$—$CD_3OD$) 0.90(t, J=6Hz, 3H), 1.30(br.s, 32H), 2.76 (s, 3H), 2.95-3.60(m, 11H), 4.20(m, 2H), 4.96 (m, 1H), 5.48(m, 2H), 7.90-8.40(m, 4H), 8.65 (d, J=9Hz, 1H), 9.05(d, J=8Hz, 1H), 10.02(d, J=5Hz, 1H). | (Nujol) 3360, 1690, 1390, 1260, 1160 | 137~139 (dec.) |
| 44 | $-CONHC_{18}H_{37}$ | $-NHCOOCH_3$ | H | H | O | 361 (0.534) | 3 | 301 (70.0) | ($CDCl_3$) 0.88(3H, t, J=5Hz), 1.25(30H, s), 1.50(2H, m), 2.72(2H, br.s), 3.12(2H, m), 3.35(2H, br.s), 3.59(5H, s), 4.00(1H, br.s), 4.15(2H, br.s), 5.45(1H, br.s), 5.55(2H, br.s), 5.86(1H, br. s), 6.25(1H, br.s), 8.00(1H, t, J=8Hz), 8.20 (1H, m), 8.29(2H, m), 8.69(1H, d, J=8Hz), 9.01 (1H, d, J=8Hz), 10.19(1H, s). | (Nujol) 3320, 1702, 1143 | 70~74 |
| 45 | $-CONHC_{18}H_{37}$ | $-NHCOOtBu$ | H | H | O | 206 (0.287) | 2 | 168 (69.1) | ($CDCl_3$) 0.88(3H, t, J=6Hz), 1.25(30H, s), 1.39(9H, s), 1.50(2H, m), 2.74(2H, m), 3.13(2H, m), 3.32 (2H, t, J=7Hz), 3.58(2H, t, J=7Hz), 3.94(1H, m), 4.15(2H, s), 5.45(1H, s), 5.59(1H, t, J=8Hz), 6.19(1H, s), 7.99(1H, t, J=9Hz), 8.17(1H, dd, J=5, 10Hz), 8.23(2H, d, J=8Hz), 8.65(1H, d, J=5Hz), 8.97(1H, d, J=5Hz), 10.33(1H, d, J=5Hz). | (Nujol) 3360, 1693, 1323, 1148 | 78~82 |
| 46 | $-CONHC_{18}H_{37}$ | $-NHCOCH_3$ | H | H | O | 215 (0.326) | 2 | 211 (82.1) | ($CDCl_3$) 0.88(3H, t, J=6Hz), 1.25(30H, s), 1.48(2H, m), 2.01(3H, s), 2.68(2H, m), 3.10(2H, m), 3.33 (2H, m), 3.56(2H, m), 4.12(2H, m), 4.28(1H, m), 5.54(2H, m), 6.56(1H, m), 7.19(1H, d, J=7Hz), 7.99(1H, t, J=7Hz), 8.17(1H, dd, J=7, 6Hz), 8.25-8.4(2H), 8.70(1H, d, J=9Hz), 8.99(1H, d, J=5Hz), 10.13(1H, d, J=6Hz). | (Nujol) 3335, 1692, 1660, 1310, 1272, 1142 | 77~82 |

TABLE 10-continued

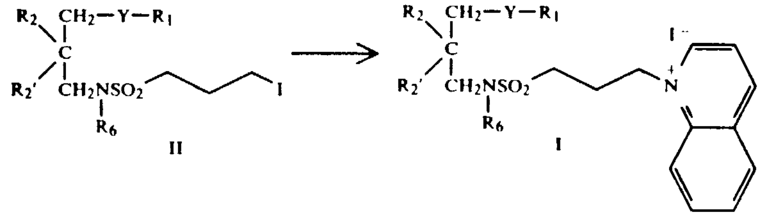

II → I

| Ex. No. | $R_1$ | $R_2$ | $R_2'$ | $R_6$ | Y | S.M. [mg] ([mM]) | Quinoline [ml] | Yield [mg] (%) | NMR δ ppm | IR νmax [$cm^{-1}$] | m.p. [°C.] |
|---|---|---|---|---|---|---|---|---|---|---|---|
| 47 | $-CONHC_{18}H_{37}$ | $-NHCONHCH_3$ | H | H | O | 242 (0.359) | 2 | 230 (79.8) | ($CDCl_3$) 0.88(3H, t, J=5Hz), 1.25(30H, s), 1.48(2H, m), 2.61(3H, d, J=4Hz), 2.65(2H, m), 3.08(2H, m), 3.28(2H, m), 3.54(2H, m), 4.11(3H), 5.4-5.7 (3H), 6.18(1H, d, J=7Hz), 6.30(1H, br.s), 8.01 (1H, t, J=7Hz), 8.16(1H, dd, J=7, 5Hz), 8.25-8.45 (2H), 8.68(1H, d, J=7Hz), 8.99(1H, d, J=7Hz), 10.06(1H, d, J=5Hz). | (Nujol) 3220, 1694, 1634, 1257, 1144 | 83~86 |
| 48 | $-C_{16}H_{33}$ | $-NHCOOCH_3$ | H | H | S | 627 (1.01) | 3 | 556 (73.7) | ($CDCl_3$) 0.87(3H, t, J=6.5Hz), 1.25(26H, s), 1.54(2H, m), 2.52(2H, t, J=7.3Hz), 2.73(4H, d, J=6.7Hz), 3.40(2H, t, J=5.8Hz), 3.50-3.69(2H), 3.60(3H, s), 3.88(1H, m), 5.56(2H, m), 5.86(1H, d, J=8.0Hz), 6.37(1H, t, J=6.3Hz), 7.98(1H, dd, J=7.1, 8.0Hz), 8.19(1H, d, J=5.9, 8.4Hz), 8.12-8.38(2H), 8.68(1H, d, J=8.9Hz), 8.99(1H, d, J=8.4Hz), 10.23(1H, dd, J=1.5, 5.9Hz). | (KBr) 3380, 3300, 3065, 1700, 1625, 1319, 1137 | — |
| 49 | $-C_{16}H_{33}$ | $-NHCOOtBu$ | H | H | S | 663 (1) | 4 | 490 (61.9) | ($CDCl_3$) 0.88(3H, t, J=6.4Hz), 1.25(26H, s), 1.40(9H, s), 1.58(2H, m), 2.53(2H, t, J=7.3Hz), 2.73 (4H, m), 3.38(2H, m), 3.57(2H, m), 3.85(1H, br, s), 5.34(1H, d, J=8.0Hz), 5.58(2H, m), 6.21 (1H, t, J=6.0Hz), 7.99(1H, t, J=7.5Hz), 8.13-8.36 (3H), 8.65(1H, d, J=9.0Hz), 8.98(1H, d, J=8.4Hz), 10.31(1H, d, J=5.2Hz). | (KBr) 3360, 3280, 3095, 1700, 1319, 1138 | — |
| 50 | $-C_{16}H_{33}$ | $-NHCOCH_3$ | H | H | S | 478 (0.791) | 2.5 | 326 (56.2) | ($CDCl_3$) 0.88(3H, t, J=6.4Hz), 1.25(26H, s), 1.54(2H, m), 2.03(3H, s), 2.51(2H, t, J=7.3Hz), 2.59-2.81(4H), 3.40(2H, m), 3.55(2H, t, J=6.3Hz), 4.18(1H, m), 5.53(2H, m), 6.48(1H, t, J=6.0Hz), 6.99(1H, d, J=8.4Hz), 8.00(1H, dd, J=6.6, 7.3Hz), 8.19(1H, dd, J=5.9, 8.4Hz), 8.24-8.38 (2H), 8.67(1H, d, J=8.7Hz), 8.98(1H, d, J=8.4Hz), 10.15(1H, dd, J=1.2, 5.9Hz). | (KBr) 3280, 3075, 1648, 1311, 1139. | — |
| 51 | $-C_{16}H_{33}$ | $-NHCONHCH_3$ | H | H | S | 551 (0.889) | 3 | 413 (62.0) | ($CDCl_3$) 0.88(3H, t, J=6.4Hz), 1.25(26H, s), 1.53(2H, m), 2.45-2.80(4H), 2.52(2H, t, J=7.2Hz), 2.64 (3H, d, J=4.5Hz), 3.15-3.59(4H), 4.04(1H, br. s), 5.49(3H, m), 6.01(1H, d, J=8.0Hz), 6.27 (1H, t, J=5.7Hz), 8.01(1H, t, J=7.5Hz), 8.13-8.40 (3H), 8.66(1H, d, J=8.7Hz), 8.98(1H, d, J=8.4Hz), 10.09(1H, d, J=5.8Hz). | (KBr) 3310, 3100, 1641, 1317, 1138. | — |
| 52 | $-CONHC_{18}H_{37}$ | $-NHCOOH_3$ | H | Ac | O | 132 | 2 | 102 | ($CDCl_3$) 0.88(3H, t, J=6Hz), 1.25(30H, s), 1.50(2H, m), | (Nujol) | 83~85 |

TABLE 10-continued

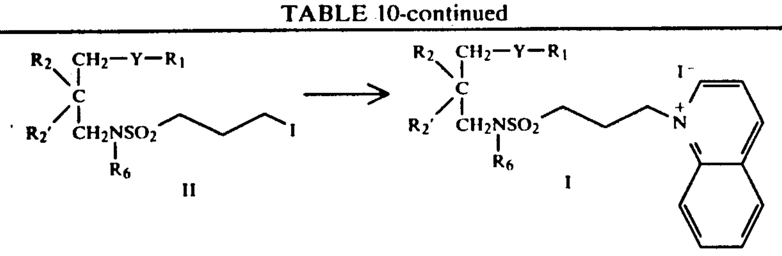

II → I

| Ex. No. | $R_1$ | $R_2$ | $R_2'$ | $R_6$ | Y | S.M. [mg] ([mM]) | Quinoline [ml] | Yield [mg] (%) | NMR δ ppm | IRνmax [$cm^{-1}$] | m.p. [°C.] |
|---|---|---|---|---|---|---|---|---|---|---|---|
| | | | | | | (0.188) | | (65.3) | 2.04(3H, s), 2.48(3H, s), 2.79(2H, m), 3.13 (2H, m), 3.8-4.3(8H), 4.45(1H, m), 5.47(1H, br.s), 5.68(1H, t, J=7Hz), 6.81(1H, d, J=7Hz), 8.03(1H, t, J=7Hz), 8.16(1H, dd, J=5, 7Hz), 8.30 (2H, d, J=7Hz), 8.68(1H, d, J=7Hz), 9.00(1H, dd, J=7Hz), 10.33(1H, d, J=5Hz). | 3330, 1690, 1659, 1150 | |
| 54 | $-CONHC_{18}H_{37}$ | 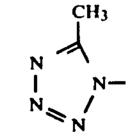 | H | H | O | 500 (0.73) | 0.6 | 510 (86) | ($CDCl_3$) 0.90(t, J=6Hz, 3H), 2.4-2.75(m, 2H), 2.58(s, 3H), 2.95-3.15(m, 2H), 3.4-3.8(m, 2H), 3.6-3.95(m, 2H), 4.25-4.6(m, 2H), 4.85-5.1(m, 1H), 5.25-5.55(m, 3H), 6.9-7.15(m, 1H), 7.94(t, J=7.6Hz, 1H), 8.1-8.4(m, 3H), 8.68(d, J=9Hz, 1H), 9.05(d, J=8. 4Hz, 1H), 9.88(d, J =5.8Hz, 1H). | ($CHCl_3$) 1729, 1334. | 77~87 |
| 56 | $-CONHC_{18}H_{37}$ | 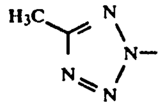 | H | H | O | 500 (0.73) | 0.6 | 440 (74) | ($CDCl_3$) 0.88(t, J=6.4Hz, 3H), 2.46(s, 3H), 2.45-2.8(m, 2H), 2.95-3.2(m, 2H), 3.5-3.75(m, 2H), 3.65-3.95(m, 2H), 4.35-4.7(m, 2H), 5.15-5.45(m, 2H), 5.35-5.7(m, 2H), 6.7-6.95(m, 1H), 7.99 (t, J=8Hz, 1H), 8.1-8.4(m, 3H), 8.70(d, J=9.4Hz, 1H), 9.04(d, J=8.2Hz, 1H), 10.04 (d, J=5.6Hz, 1H). | ($CHCl_3$) 1726, 1340. | Amorphous powder |
| 59 | $-CONHC_{18}H_{37}$ | 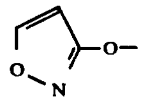 | H | H | O | 500 (0.73) | 0.6 | 440 (74) | ($CDCl_3$) 0.90(t, J=6Hz, 3H), 1.35-1.55(m, 2H), 2.6-2.7 (m, 2H), 3.10(qualtet, J=6Hz, 2H), 3.4-3.7(m, 4H), 4.28(ABX, J=12 & 6.4Hz, 1H), 4.38(ABX, J=12 & 4.4Hz), 4.85-5.0(m, 1H), 5.35(t, J=5Hz, 1H), 5.54(t, J=7Hz, 2H), 6.08(d, J=2Hz, 1H), 6.45(t, J=6Hz, 1H), 7.96(t, J=8Hz, 1H), 8.10(d, J=2Hz, 1H), 8.1-8.35(m, 3H), 8.70(d, J=10Hz, 1H), 9.01(d, J=10Hz, 1H). | ($CHCl_3$) 1721, 1330 | Amorphous powder |
| 62 | $-C_{16}H_{33}$ | $CH_3OCH_2-$ | H | H | O | 500 (0.87) | 1 | 370 (60) | ($CDCl_3$) 0.88(t, J=6Hz, 3H), 1.4-1.6(m, 2H), 2.1-2.3(m, 1H), 2.65-2.85(m, 2H), 3.32(s, 3H), 5.65(t, J=8.4Hz, 2H), 5.87(t, J=5Hz, 1H), 8.0(t, J=7Hz, 1H), 8.15-8.4(m, 3H), 8.68(d, J=8Hz, 1H), 9.03 (d, J=9Hz, 1H), 10.39(d, J=5.6Hz, 1H). | 1320 | 81~84 |
| 64 | $-CONHC_{18}H_{37}$ | $CH_3OCH_2-$ | H | H | O | 500 (0.77) | 0.8 | 460 (77) | ($CDCl_3$) 0.88(t, J=6Hz, 3H), 1.4-1.6(m, 2H), 2.1-2.35 (m, 1H), 2.6-2.85(m, 2H), 3.05-3.2(m, 2H), 3.15-3.35(m, 2H), 3.30(s, 3H), 3.44(d, J=6Hz, 2H), 3.58(t, J=6Hz, 2H), 3.95-4.25(m, 2H), 5.34(t, | 1710, 1322 | 55~60 |

TABLE 10-continued

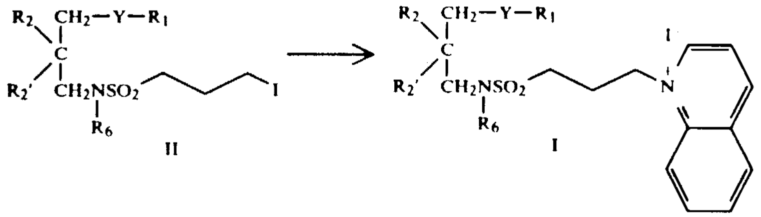

II I

| Ex. No. | $R_1$ | $R_2$ | $R_2'$ | $R_6$ | Y | S.M. [mg] ([mM]) | Quinoline [ml] | Yield [mg] (%) | | NMR δ ppm | IRνmax [cm⁻¹] | m.p. [°C.] |
|---|---|---|---|---|---|---|---|---|---|---|---|---|
| | | | | | | | | | | J=6Hz, 1H), 5.61(t, J=8Hz, 2H), 6.08(t, J=6Hz, 1H), 7.98(t, J=9Hz, 1H), 8.15-8.4(m, 3H), 8.71 (d, J=9.4Hz, 1H), 9.03(d, J=8.6Hz, 1H), 10.31(d, J=5.8Hz, 1H). | | |
| 65 | $-CONHC_{18}H_{37}$ | $CH_3OCH_2-$ | H | Ac | O | 650 (0.95) | 0.8 | 540 (70) | ($CDCl_3$) | 0.88(t, J=6Hz, 3H), 1.4-1.6(m, 2H), 2.25-2.5 (m, 1H), 2.42(s, 3H), 2.65-2.9(m, 1H), 3.13(q, J=7Hz, 2H), 3.30(s, 3H), 3.41(d, J=4Hz, 2H), 3.87(d, J=6.8Hz, 2H), 3.95-4.2(m, 4H), 5.10(t, J=7Hz, 1H), 5.68(t, J=6.5Hz, 2H), 8.01(t, J=7.4Hz, 1H), 8.15-8.4(m, 3H), 8.71(d, J=8.8Hz, 1H), 9.07(d, J=8.6Hz, 1H), 10.42(d, J=5.6Hz, 1H). | 1710 | 55~65 |
| 66 | $-CONHC_{18}H_{37}$ | $CH_3COCH_2-$ | H | H | O | 182 (0.276) | 0.26 | 204 (93.8) | ($CDCl_3$) | 0.88(t, J=6.4Hz, 3H), 1.17-1.36(m, 30H), 1.38-1.59(m, 2H), 2.16(s, 3H), 2.36-2.58(m, 2H), 2.60-2.84(m, 3H), 3.02-3.24(m, 4H), 3.47-3.64 (m, 2H), 4.04(d, J=4.8Hz, 2H), 5.21-5.33(m, 1H), 5.58(t, J=7.2Hz, 2H), 6.16-6.30(m, 1H), 8.10 (t, J=7.6Hz, 1H), 8.14-8.37(m, 3H), 8.70(d, J=9.0Hz, 1H), 9.02(d, J=8.6Hz, 1H), 10.30(d, J=6.0Hz, 1H). | 1703, 1320, 1140 | — |
| 68 | $-C_{16}H_{33}$ | $NCCH_2-$ | H | H | O | 132 (0.23) | 0.27 | 134 (82.6) | ($CDCl_3$) | 0.88(t, J=6.4Hz, 3H), 1.15-1.43(m, 26H), 1.43-1.62(m, 2H), 2.19-2.42(m, 1H), 2.42-2.87(m, 4H), 3.09-3.68(m, 8H), 5.58(t, J=7.8Hz, 2H), 6.54(t, J=6.3Hz, 1H), 7.99(t, J=7.2Hz, 1H), 8.14-8.36(m, 3H), 8.69(d, J=9.0Hz, 1H), 8.99(d, J=8.2Hz, 1H), 10.23(d, J=5.6Hz, 1H). | 2230, 1320 | — |
| 69 | $-CONHC_{18}H_{37}$ | $NCCH_2-$ | H | H | O | 140 (0.22) | 0.26 | 152 (91) | ($CDCl_3$) | 0.88(t, J=6.4Hz, 3H), 1.16-1.40(m, 30H), 1.39-1.57(m, 2H), 2.23-2.54(m, 1H), 2.51-2.65(m, 2H), 2.65-2.86(m, 2H), 3.02-3.20(m, 2H), 3.52-3.72(m, 2H), 4.14(d, J=4.8Hz, 2H), 5.13-5.28 (br., 1H), 5.56(t, J=7.8Hz, 2H), 6.56-6.74(br., 1H), 7.99(t, J=7.2Hz, 1H), 8.12-8.39(m, 3H), 8.69(d, J=9.2Hz, 1H), 8.99(d, J=9.2Hz, 1H), 10.18(d, J=6.0Hz, 1H). | 2230, 1710, 1320, 1140 | — |

TABLE 10-continued
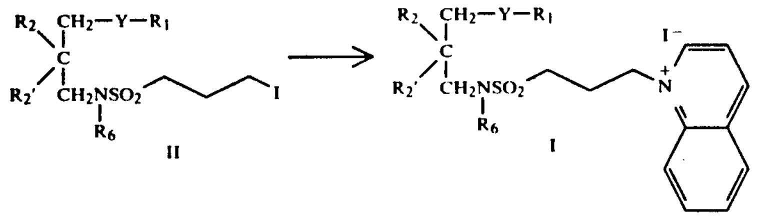
II → I
| Ex. No. | $R_1$ | $R_2$ | $R_2'$ | $R_6$ | Y | S.M. [mg] ([mM]) | Quino-line [ml] | Yield [mg] (%) | | NMR δ ppm | IRνmax [$cm^{-1}$] | m.p. [°C.] |
|---|---|---|---|---|---|---|---|---|---|---|---|---|
| 72 | $-CONHC_{18}H_{37}$ | 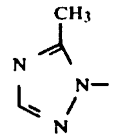 | H | H | O | 500 (0.73) | 0.6 | 450 (76) | ($CDCl_3$) | 0.88(t, J=6Hz, 3H), 2.49(s, 3H), 2.45-2.7(m, 2H), 2.9-3.2(m, 2H), 3.4-3.8(m, 4H), 4.15-4.55(m, 2H), 4.7-4.9(m, 1H), 5.35-5.6(m, 3H), 6.9-7.1(m, 1H), 7.71(s, 1H), 7.97(d, J=7.7Hz, 1H), 8.1-8.3(m, 1H), 8.29(d, J=8Hz, 1H), 8.67(d, J=9.2Hz, 1H), 9.03 (d, J=9.6Hz, 1H), 10.07(d, J=6.4Hz, 1H) | 1719, 1330 | Amorphous powder |
| 73 | $-CONHC_{18}H_{37}$ | 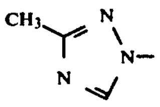 | H | H | O | 389 (0.57) | 0.68 | 393 (85) | ($CDCl_3$) | 0.88(t, J=6.4Hz, 3H), 1.12-1.38(m, 30H), 1.35-1.68(m, 2H), 2.28(s, 3H), 2.46-2.84(m, 2H), 2.97-3.20(m, 2H), 3.33-3.79(m, 4H), 4.24-4.49(m, 2H), 4.72-4.94(m, 1H), 5.34-5.60(m, 3H), 6.90-7.09(m, 1H), 7.97(t, J=7.6Hz, 1H), 8.11-8.40(m, 4H), 8.67(d, J=9.0Hz, 1H ), 8.99 (d, J=8.6Hz, 1H), 10.16(d, J=5.0Hz, 1H). | 1718, 1320, 1140. | |

EFFECT OF THE INVENTION

The compounds of the present invention are PAF analogues which serve as PAF receptor antagonist and/or antitumor agent. The compounds of the present invention inhibit the platelet from aggregation induced by PAF and may be useful agents for the treatment of physiological and pathological disorders in which PAF may participate, for example, endotoxic shock, asthma, inflammation, acute tissue transplant rejection, hypotension, gastric ulcer, and nephritis. The platelet aggregation inhibitory activities (in vitro) of the representative compounds of the present invention are shown below.

Materials Tested and Methods

Mature male rabbits (NIBS-JW, RABITON Institute Inc., weighing 2.2-2.5 kg) were used. Under sodium pentobarbital anesthesia (Somnopentyl, Pitmab Moore, about 25 mg/Kg, i.v.), blood (7.2 ml each) was successively collected from the carotid artery by cannulation and put into centrifuge tubes containing 0.8 ml each of 3.8% sodium citrate solution. (The total volume of blood sample in each tube was adjusted to 8 ml.)

The blood sample in each tube was gently shaken and then centrifuged for 10 minutes at 200 g at 22° C. to give platelet rich plasma (PRP). The remaining blood was further centrifuged at 3,000 rpm (about 1,900 g) for 10 minutes at 22° C. to give platelet-poor plasma (PPP).

PRP was diluted with PPP to prepare a blood sample whose platelet number was $50-55 \times 10^4/\mu l$. The sample was then subjected to a platelet aggregation test.

The platelet aggregation was examined by the method of Born [Born, G. V. R., Nature, 194, 927-929 (1962)], using a Type AUTO RAM-61 aggregometer, (Rika Denki Co., Ltd., Tokyo). A volume of 230 μl of PRP, whose platelet number was adjusted to $50-55 \times 10^4/\mu l$, was placed in a measuring cuvette and set in the aggregometer. PRP was warmed at 37° C. for 1 minute with stirring at 1,200 rpm, and then a solution of the test compound [dimethylsulfoxide solution (1μl) of the compound+saline (9μl)] was added thereto. Exactly 2 minutes later, 10 μl of platelet activating factor (PAF, $C_{16}$) (final concentration: 20 nM) was added as a platelet aggregating agent, and the change in light transmission caused by platelet aggregation was recorded.

The light transmissions of PRP and PPP were taken as 0% and 100% aggregation, respectively, and the maximum light transmission after addition of an aggregating agent was made the maximum aggregation. The inhibition rate of the platelet aggregation was expressed as the percentage of the maximum aggregation by a test compound to that by a control (Vehicle added group).

The results of the test are shown as follows. The results are shown as the concentration of the test compounds which inhibit 50% platelet aggregation, i.e., $IC_{50}$ (μM).

| Compound Number* | $IC_{50}$ (μM) | Compound Number* | $IC_{50}$ (μM) | Compound Number* | $IC_{50}$ (μM) |
|---|---|---|---|---|---|
| I a1 | 48.10 | I a2 | 1.89 | I a3 | 5.20 |
| I a4 | 64.2 | I a5 | 1.89 | I a6 | 45.4 |
| I a7 | 0.65 | I a8 | 82.1 | I a9 | 3.64 |
| I a10 | 79.9 | I a11 | 2.97 | I a12 | 5.95 |
| I a13 | 1.77 | I a14 | 1.29 | I a16 | 13.5 |
| I a20 | 16.0 | I a25 | 0.36 | I a26 | 1.93 |
| I a27 | 0.74 | I b2 | 0.385 | I c1 | 0.92 |

-continued

| Compound Number* | $IC_{50}$ (μM) | Compound Number* | $IC_{50}$ (μM) | Compound Number* | $IC_{50}$ (μM) |
|---|---|---|---|---|---|
| I c3 | 0.33 | I e5 | 0.533 | I e6 | 3.09 |
| I e7 | 0.85 | I e8 | 1.97 | I f3 | 0.965 |
| I f4 | 0.873 | I g2 | 14.3 | I g4 | 1.83 |
| I f5 | 0.558 | I g6 | 1.32 | I h1 | 23.2 |
| I h2 | 0.125 | I i2 | 0.63 | I j3 | 0.25 |
| I k3 | 0.60 | I k4 | 80.3 | I k5 | 0.40 |
| I k6 | 0.34 | $PGE_1$ | 0.259 | | |

*Compound Number corresponds to the number in the examples.

The reason why $PGE_1$ is chosen as a reference compound is that the activity level of the prepared novel compounds are aimed at that of $PGE_1$, since $PGE_1$ is known to potently inhibit the PAF-induced platelet aggregation. As a result, the compounds of the present invention can mostly inhibit the platelet aggregation as potent as $PGE_1$ can.

Antitumor activity is proven by various methods, e.g., the inhibition of Meth A fibrosarcama growth in Balb-c mouse (Slc), the survival effect of C3H/HeN mouse injected into MH134 (mouse heptoma) and DS mouse injected into Ehrlich (Ehrlich Ascites carinoma).

The compound (I) of the present invention can be orally or parenterally administered to humans or animals. For example, the compound (I) which is dissolved or suspended in a solvent for injection (e.g., distilled water for injection, ethanol, glycerol, propylene glycol, olive oil, peanut oil) can be administered intravenously, intramuscularly, or subcutaneously. For an injectable use, the compound (I) may be a solution or suspension which is sealed in an ampule or, preferably, may be crystals, an powder, fine crystals, or lyophilizate which are preserved in a ampule or vial. The latter formulation may be used by dissolving them with a solvent for injection. The stabilizer may be further added thereto. The compound (I) may be also formulated into powder, tablets, granules, capsules, troches, or dry syrups for oral use, together with pharmaceutical additives such as a diluent (e.g., starch, sucrose, lactose, calcium carbonate, kaolin), lubricant (e.g., stearic acid, sodium benzoate, boric acid, silica, polyethylene glycol) or the like.

The compound (I) can be administered, for example, for the treatment of endotoxic shock, asthma, inflammation, acute tissue transplant rejection, hypotension, gastric ulcer, nephritis, or tumor, at a usual dosage for an adult of about 1 mg to 5 g per day in 1 to 3 divided doses. The compound (I) should be, however, used by increasing or decreasing the recommended dosage, taking into consideration the age, body weight, severity of disease, clinical history of a patient, or the like.

What we claim is:

1. A compound represented by the formula:

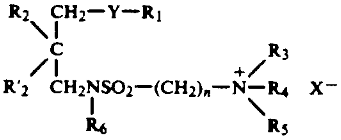

wherein $R_1$ is alkyl or alkylcarbamoyl; $R_2$ is lower alkyloxy, lower alkylcarbamoyloxy, lower alkylcarbonylamino, lower alkyloxycarbonylamino, lower alkylureido, lower alkyloxymethyl, lower alkylcarbonylmethyl, cyanomethyl, a 5-membered heterocyclic group, or a 5-membered heterocyclyloxy group, wherein one or more N, O or S heteroatoms are present; $R_2'$ is hydrogen or taken together with $R_2$ forms $—O(CH_2)_m—$ wherein m is an integer of 1 to 5; $R_3$, $R_4$, and $R_5$ each is hydrogen or lower alkyl or two or three of $R_3$, $R_4$, and $R_5$ taken together with the adjacent nitrogen atom form cyclic ammonio selected from the group consisting of 3-oxazolio, 2-isoxazolio, 3-thiazolio, 3-imidazolio, 3-benzoxazolio, 3-benzothiazolio, which are unsubstituted or substituted by a member selected from the group consisting of lower alkyl, carboxyl, lower alkyloxycarbonyl, hydroxy, lower alkyloxy, acyloxy, lower alkylamino, amino, carbamoyl and ureido; $R_6$ is hydrogen or lower alkylcarbonyl; $X^-$ is a pharmaceutically acceptable anion; Y is oxygen or sulfur; and n is an integer of 1 to 10.

2. A compound claimed in claim 1 wherein $R_1$ is $C_{12}$ to $C_{20}$ alkyl; and n is an integer of 1 to 5.

3. A compound claimed in claim 1 wherein $R_1$ is $C_{12}$ to $C_{20}$ alkylcarbamoyl; and n is an integer of 1 to 5.

4. A compound claimed in claim 2 or 3 wherein $R_2'$ is hydrogen; $R_6$ is hydrogen; and $X^-$ is halogen anion.

5. A compound claimed in any of claims 1 to 3 wherein $R_2$ is lower alkyloxy; and cyclic ammonio is 3-thiazolio.

6. A compound claimed in any of claims 1 to 3 wherein $R_2$ is lower alkyloxymethyl; and cyclic ammonio is 3-thiazolio.

7. A compound claimed in any of claims 1 to 3 wherein $R_2$ is N-containing 5 membered heterocyclic group which may contain oxygen or sulfur and optionally may be substituted and ammonio is thiazolio.

8. A compound claimed in any of claims 1 to 3 wherein $R_2$ is lower alkylcarbamoyloxy; and cyclic ammonio is thiazolio.

9. A compound claimed in any of claims 1 to 3 wherein $R_2$ is lower alkyloxymethyl; and $R_3$, $R_4$, and $R_5$ each is lower alkyl.

10. A compound claimed in claim 1, namely, 2-methoxy-1-octadecylcarbamoyloxy-3-(3-thiazoliopropylsulfonylamino)propane iodide.

11. A compound claimed in claim 1 namely, 1-hexadecyloxy-2-methoxymethyl-3-(3-trimethylammoniopropylsulfonylamino)propane iodide.

12. A compound claimed in claim 1 namely, 1-hexadecylthio-2-methoxymethyl-3-(3-trimethylammoniopropylsulfonylamino)propane iodide.

13. A compound claimed in claim 4 wherein $R_2$ is lower alkyloxy; and cyclic ammonio is 3-thiazolio.

14. A compound claimed in claim 4 wherein $R_2$ is lower alkyloxymethyl; and cyclic ammonio is 3-thiazolio.

15. A compound claimed in claim 4 wherein $R_2$ is N-containing 5-membered heterocyclic group which may contain oxygen or sulfur and optionally may be substituted; and cyclic ammonio is 3-thiazolio.

16. A compound claimed in claim 4 wherein $R_2$ is lower alkylcarbamoyloxy; and cyclic ammonio is 3-thiazolio.

17. A compound claimed in claim 4 wherein $R_2$ is lower alkyloxymethyl; and $R_3$, $R_4$, and $R_5$ each is lower alkyl.

* * * * *